US006294716B1

(12) United States Patent
Meyerowitz et al.

(10) Patent No.: US 6,294,716 B1
(45) Date of Patent: *Sep. 25, 2001

(54) PLANTS HAVING MODIFIED RESPONSE TO ETHYLENE BY TRANSFORMATION WITH AN ETR NUCLEIC ACID

(75) Inventors: Elliott M. Meyerowitz; Caren Chang, both of Pasadena, CA (US); Anthony B. Bleecker, Madison, WI (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/714,524

(22) Filed: Sep. 16, 1996

Related U.S. Application Data

(63) Continuation of application No. 08/263,480, filed on Jun. 28, 1994, now abandoned, which is a continuation-in-part of application No. 08/086,555, filed on Jul. 1, 1993, now abandoned.

(51) Int. Cl.$^7$ .............................. A01H 5/00; A01H 5/08; C12N 5/14; C12N 15/82
(52) U.S. Cl. .................................... 800/317.4; 435/320.1; 435/419; 435/440; 536/23.6; 800/283; 800/298
(58) Field of Search ..................... 536/23.6; 435/172.3, 435/320.1, 419, 69.1, 468, 440, 283; 800/205, DIG. 15, DIG. 44, 69.1, 278, 298, 317.4, 287

(56) References Cited

U.S. PATENT DOCUMENTS

| | | | |
|---|---|---|---|
| 4,743,548 | 5/1988 | Crossway et al. | 435/172.3 |
| 4,762,785 | 8/1988 | Comai | 435/172.3 |
| 4,769,061 | 9/1988 | Comai | 435/240.4 |
| 4,801,540 | 1/1989 | Hiatt et al. | 435/172.3 |
| 4,943,674 | 7/1990 | Houck et al. | 800/205 |
| 4,956,282 | 9/1990 | Goodman et al. | 435/172.3 |
| 5,068,193 | 11/1991 | Comai | 435/252.3 |
| 5,106,739 | 4/1992 | Comai et al. | 435/172.3 |
| 5,107,065 | 4/1992 | Shewmaker et al. | 800/205 |
| 5,110,728 | 5/1992 | Kridl et al. | 435/69.1 |
| 5,147,792 | 9/1992 | Perchorowicz et al. | 435/134 |
| 5,175,095 | 12/1992 | Martineau et al. | 435/69.1 |
| 5,177,011 | 1/1993 | Shewmaker et al. | 435/172.3 |
| 5,177,307 | 1/1993 | Houck et al. | 800/205 |
| 5,689,055 | * 11/1997 | Meyerowitz et al. | 800/205 |
| 5,824,868 | * 10/1998 | Meyerowitz et al. | 800/205 |

FOREIGN PATENT DOCUMENTS

| | | |
|---|---|---|
| 8 912386 | 12/1989 | (WO) . |
| 9 001260 | 2/1990 | (WO) . |
| 9 101324 | 2/1991 | (WO) . |
| 9 101373 | 2/1991 | (WO) . |
| 9 211382 | 7/1992 | (WO) . |
| 9 212249 | 7/1992 | (WO) . |
| 9307264 | 4/1993 | (WO) . |

OTHER PUBLICATIONS

Stam M, et al. "The silence of genes in transgenic plants." Ann. Bot. 79: 3–12, 1997.*
Koziel MG, et al. "Optimizing expression of transgenes with an emphasis on post–transcriptional events." Plant Mol. Biol. 32: 393–405, 1996.*
Smith CJS, et al. "Antisense RNA inhibition of polygalacturonase gene expression in transgenic tomatoes." Nature 334: 724–726, Aug. 25, 1988.*
Boswell et al. in Computational Molecular Biology Sources and Methods for Sequence Analysis (Lesk, ed.) Oxford University Press, Oxford, 1988, pp. 170–171.*
Chang et al., "Restriction fragment length polymorphism linkage map for *Arabidopsis thaliana*" *PNAS USA,* 85:6856–6860 (1988).
Pickett et al., "Recessive Mutation at the ETR–2 Locus of *Arabidopsis thaliana* Confers Resistance to Some Effects of Ethylene Exposure," *J. Cell. Biochem.*, Supp. 0 (13 part D):324 (1989). Symposium on Plant Gene Transfer, 18th Annual UCLA Symposium, Park City, Utah, USA: Apr. 1–7, 1989.
Chang, C., et al., "Arabidopsis Ethylene–Response Gene ETR1: Similarity of Product of Two–Component Regulators", *Science*, 262:539–544 (1993).
Chang, C., et al., "Eukaryotes have "two–component" signal transducers", *Res. Microb.* 1459:481–486 (1994).
Lawton, K.A., et al., "Acquired–Resistance Signal–Transduction in Arabidopsis is Ethylene Independent", *Cell*, 6(5):581–588 (1994).
Bleecker, A.B. et al. "Insensitivity to Ethylene Conferred by a Cominant Mutation in *Arabidepsis thaliana*" *Science,* 241:1086–1089 (1988).
Guzmán, P. et al. "Exploiting the Triple Response of Arabidopsis to Identify Ethylene–Related Mutants", *The Plant Cell,* 2:513–523, (1990).
Kleber, J.J. et al., "CTRI, a Negative Regulator of the Ethylene Response Pathway in Arabidopsis, Encodes a Member of the Raf Family of Protein Kinases" *Cell,* 72:427–441, (1993).

(List continued on next page.)

*Primary Examiner*—Amy J. Nelson
(74) *Attorney, Agent, or Firm*—Richard F. Trecartin; Flehr Hohbach Test Albritton & Herbert LLP

(57) ABSTRACT

The invention includes transformed plants having at least one cell transformed with a modified ETR nucleic acid. Such plants have a phenotype characterized by a decrease in the response of at least one transformed plant cell to ethylene as compared to a plant not containing the transformed plant cell. Tissue and/or temporal specificity for expression of the modified ETR nucleic acid is controlled by selecting appropriate expression regulation sequences to target the location and/or time of expression of the transformed nucleic acid. The plants are made by transforming at least one plant cell with an appropriate modified ETR nucleic acid, regenerating plants from one or more of the transformed plant cells and selecting at least one plant having the desired phenotype.

32 Claims, 65 Drawing Sheets

OTHER PUBLICATIONS

Harpham, N.V.J. et al., "The Effect of Ethylene on the Growth and Development of Wild–type and Mutant *Arabidopsis thaliana* (L.) Heynh", *Annals of Botany*, 68:55–61, (1991).

Oeller, P.W. et al., "Reversible Inhibition of Tomato Fruit Senescence by Antisense RNA", *Science*, 254:437–439, (1991).

*Ethylene in Plant Biology*, 2d ed., F.B. Abeles, P.W. Morgan and M.E. Saltveit, Jr., Eds. (San Diego) Academic Press, Inc., pp. 242–263.

McCormick, S. et al., "Leaf disc transformation of cultivated tomato (*L. ezculentum*) using *Agrobacterium tumefaciens*" *Plant Cell Reports*, 5:81–84 (1986).

Horsch, R.B. et al., "A Simple and General Method for Transferring Genes into Plants", *Science*, 227:1229, (1985).

Trolinder, N.L. et al., Somatic embryogenesis and plant regeneration in cotton (*Gossypium hirsutum L.*) *Plant Cell Reports*, 6:231–234, (1987).

Bollmann, J. et al., "Allelic Interactions at the nivea Locus of Antirrhinum", *The Plant Cell*, 3:1327–1336 (1991).

Matzke, M.A. et al., "A variety of epistatic interactions can occur between partially homologous transgene loci brought together by sexual crossing", *Mol. Gen. Genet.*, 236:379–386 (1993).

McBride, K.E., et al., "Improved binary vectors for Agrobacterium–mediated plant transformation", *Plant Molecular Biology*, 14:269–276, (1990).

Jorgensen, R., "Beyond antisense—How do transgenes interact with homologous plant genes?", *Tibtech*, 9:266–267, (1991).

Matzke, M.A., et al., "Differential inactivation and methylation of a transgene in plants by two suppressor loci containing homologous sequences", *Plant Molecular Biology*, 16:821–830, (1991).

Chang, C., et al., "The TMKI Gene from Arabidopsis Codes for a Protein with Structural and Biochemical Characteristics of a Receptor Protein Kinase,", *Plant Cell*, 4:1263 (1992).

Bleeker, A.B., et al., "Genetic Analysis of Ethylene Responses in *Arabidopsis thaliana*, ", *Great Britain Society for Experimental Biology*, (1991).

Chang C., et al., "Molecular Cloning Approach for a Putative Ethylene Receptor Gene in Arabidopsis, ", *Biochem. Soc. Trans.*, 20:73 (1992).

Arondel, V., et al., "Map–Based Cloning of a Gene Controlling Omega–3 Fatty Acid Desaturation in Arabidopsis, ", *Science*, 258:1353 (1992).

Giraudat, J. et al., "Isolation of the Arabidopsis AB13 Gene by Positional Cloning,", *Plant Cell*, 4:1251 (1992).

* cited by examiner

| | |
|---|---|
| AAAGATAGTA TTTGTTGATA AATATGGGGA TATTTATCCT ATATTATCTG | 50 |
| TATTTTTCTT ACCATTTTTA CTCTATTCCT TTATCTACAT TACGTCATTA | 100 |
| CACTATCATA AGATATTTGA ATGAACAAAT TCATGCACCC ACCAGCTATA | 150 |
| TTACCCTTTT TTATTAAAAA AAAACATCTG ATAATAATAA CAAAAAAATT | 200 |
| AGAGAAATGA CGTCGAAAAA AAAAGTAAGA ACGAAGAAGA AGTGTTAAAC | 250 |
| CCAACCAATT TTGACTTGAA AAAAAGCTTC AACGCTCCCC TTTTCTCCTT | 300 |
| CTCCGTCGCT CTCCGCCGCG TCCCAAATCC CCAATTCCTC CTCTTCTCCG | 350 |
| ATCAATTCTT CCCAAGTAAG CTTCTTCTTC CTCGATTCTC TCCTCAGATT | 400 |
| GTTTCGTGAC TTCTTTATAT ATATTCTTCA CTTCCACAGT TTTCTTCTGT | 450 |
| TGTTGTCGTC GATCTCAAAT CATAGAGATT GATTAACCTA ATTGGTCTTT | 500 |
| ATCTAGTGTA ATGCATCGTT ATTAGGAACT TTAAATTAAG ATTTAATCGT | 550 |
| TAATTTCATG ATTCGGATTC GAATTTTACT GTTCTCGAGA CTGAAATATG | 600 |
| CAACCTATTT TTTCGTAATC GTTGTGATCG AATTCGATTC TTCAGAATTT | 650 |
| ATAGCAATTT TGATGCTCAT GATCTGTCTA CGCTACGTTC TCGTCGTAAA | 700 |
| TCGAAGTTGA TAATGCTATG TGTTTGTTAC ACAGGTGTGT GTATGTGTGA | 750 |
| GAGAGGAACT ATAGTGTAAA AAATTCATAA TGGAAGTCTG CAATTGTATT | 800 |
| GAACCGCAAT GGCCAGCGGA TGAATTGTTA ATGAAATACC AATACATCTC | 850 |
| CGATTTCTTC ATTGCGATTG CGTATTTTTC GATTCCTCTT GAGTTGATTT | 900 |
| ACTTTGTGAA GAAATCAGCC GTGTTTCCGT ATAGATGGGT ACTTGTTCAG | 950 |
| TTTGGTGCTT TTATCGTTCT TTGTGGAGCA ACTCATCTTA TTAACTTATG | 1000 |
| GACTTTCACT ACGCATTCGA GAACCGTGGC GCTTGTGATG ACTACCGCGA | 1050 |
| AGGTGTTAAC CGCTGTTGTC TCGTGTGCTA CTGCGTTGAT GCTTGTTCAT | 1100 |
| ATTATTCCTG ATCTTTTGAG TGTTAAGACT CGGGAGCTTT TCTTGAAAAA | 1150 |
| TAAAGCTGCT GAGCTCGATA GAGAAATGGG ATTGATTCGA ACTCAGGAAG | 1200 |
| AAACCGGAAG GCATGTGAGA ATGTTGACTC ATGAGATTAG AAGCACTTTA | 1250 |
| GATAGACATA CTATTTTAAA GACTACACTT GTTGAGCTTG GTAGGACATT | 1300 |
| AGCTTTGGAG GAGTGTGCAT TGTGGATGCC TACTAGAACT GGGTTAGAGC | 1350 |
| TACAGCTTTC TTATACACTT CGTCATCAAC ATCCCGTGGA GTATACGGTT | 1400 |
| CCTATTCAAT TACCGGTGAT TAACCAAGTG TTTGGTACTA GTAGGGCTGT | 1450 |
| AAAAATATCT CCTAATTCTC CTGTGGCTAG GTTGAGACCT GTTTCTGGGA | 1500 |
| AATATATGCT AGGGGAGGTG GTCGCTGTGA GGGTTCCGCT CTCCACCTT | 1550 |

FIG. 2A

| | | | | |
|---|---|---|---|---|
| TCTAATTTTC | AGATTAATGA | CTGGCCTGAG | CTTTCAACAA | AGAGATATGC | 1600 |
| TTTGATGGTT | TTGATGCTTC | CTTCAGATAG | TGCAAGGCAA | TGGCATGTCC | 1650 |
| ATGAGTTGGA | ACTCGTTGAA | GTCGTCGCTG | ATCAGGTTTT | ACATTGCTGA | 1700 |
| GAATTTCTCT | TCTTTGCTAT | GTTCATGATC | TTGTCTATAA | CTTTTCTTCT | 1750 |
| CTTATTATAG | GTGGCTGTAG | CTCTCTCACA | TGCTGCGATC | CTAGAAGAGT | 1800 |
| CGATGCGAGC | TAGGGACCTT | CTCATGGAGC | AGAATGTTGC | TCTTGATCTA | 1850 |
| GCTAGACGAG | AAGCAGAAAC | AGCAATCCGT | GCCCGCAATG | ATTTCCTAGC | 1900 |
| GGTTATGAAC | CATGAAATGC | GAACACCGAT | GCATGCGATT | ATTGCACTCT | 1950 |
| CTTCCTTACT | CCAAGAAACG | GAACTAACCC | CTGAACAAAG | ACTGATGGTG | 2000 |
| GAAACAATAC | TTAAAAGTAG | TAACCTTTTG | GCAACTTTGA | TGAATGATGT | 2050 |
| CTTAGATCTT | TCAAGGTTAG | AAGATGGAAG | TCTTCAACTT | GAACTTGGGA | 2100 |
| CATTCAATCT | TCATACATTA | TTTAGAGAGG | TAACTTTTGA | ACAGCTCTAT | 2150 |
| GTTTCATAAG | TTTATACTAT | TTGTGTACTT | GATTGTCATA | TTGAATCTTG | 2200 |
| TTGCAGGTCC | TCAATCTGAT | AAAGCCTATA | GCGGTTGTTA | AGAAATTACC | 2250 |
| CATCACACTA | AATCTTGCAC | CAGATTTGCC | AGAATTTGTT | GTTGGGGATG | 2300 |
| AGAAACGGCT | AATGCAGATA | ATATTAAATA | TAGTTGGTAA | TGCTGTGAAA | 2350 |
| TTCTCCAAAC | AAGGTAGTAT | CTCCGTAACC | GCTCTTGTCA | CCAAGTCAGA | 2400 |
| CACACGAGCT | GCTGACTTTT | TTGTCGTGCC | AACTGGGAGT | CATTTCTACT | 2450 |
| TGAGAGTGAA | GGTTATTATC | TTGTATCTTG | GGATCTTATA | CCATAGCTGA | 2500 |
| AAGTATTTCT | TAGGTCTTAA | TTTTGATGAT | TATTCAAATA | TAGGTAAAAG | 2550 |
| ACTCTGGAGC | AGGAATAAAT | CCTCAAGACA | TTCCAAAGAT | TTTCACTAAA | 2600 |
| TTTGCTCAAA | CACAATCTTT | AGCGACGAGA | AGCTCGGGTG | GTAGTGGGCT | 2650 |
| TGGCCTCGCC | ATCTCCAAGA | GGTTTGAGCC | TTATTAAAAG | ACGTTTTTT | 2700 |
| CCAACTTTTT | CTTGTCTTCT | GTGTTGTTAA | AAGTTTACTC | ATAAGCGTTT | 2750 |
| AATATGACAA | GGTTTGTGAA | TCTGATGGAG | GGTAACATTT | GGATTGAGAG | 2800 |
| CGATGGTCTT | GGAAAAGGAT | GCACGGCTAT | CTTTGATGTT | AAACTTGGGA | 2850 |
| TCTCAGAACG | TTCAAACGAA | TCTAAACAGT | CGGGCATACC | GAAAGTTCCA | 2900 |
| GCCATTCCCC | GACATTCAAA | TTTCACTGGA | CTTAAGGTTC | TTGTCATGGA | 2950 |
| TGAGAACGGG | TTAGTATAAG | CTTCTCACCT | TTCTCTTTGC | AAAATCTCTC | 3000 |
| GCCTTACTTC | TTGCAAATGC | AGATATTGGC | GTTTAGAAAA | AACGCAAATT | 3050 |
| TAATCTTATG | AGAAACCGAT | GATTATTTTG | GTTGCAGGGT | AAGTAGAATG | 3100 |

*FIG. 2B*

```
GTGACGAAGG GACTTCTTGT ACACCTTGGG TGCGAAGTGA CCACGGTGAG    3150
TTCAAACGAG GAGTGTCTCC GAGTTGTGTC CCATGAGCAC AAAGTGGTCT    3200
TCATGGACGT GTGCATGCCC GGGGTCGAAA ACTACCAAAT CGCTCTCCGT    3250
ATTCACGAGA AATTCACAAA ACAACGCCAC CAACGGCCAC TACTTGTGGC    3300
ACTCAGTGGT AACACTGACA AATCCACAAA AGAGAAATGC ATGAGCTTTG    3350
GTCTAGACGG TGTGTTGCTC AAACCCGTAT CACTAGACAA CATAAGAGAT    3400
GTTCTGTCTG ATCTTCTCGA GCCCCGGGTA CTGTACGAGG GCATGTAAAG    3450
GCGATGGATG CCCCATGCCC CAGAGGAGTA ATTCCGCTCC CGCCTTCTTC    3500
TCCCGTAAAA CATCGGAAGC TGATGTTCTC TGGTTTAATT GTGTACATAT    3550
CAGAGATTGT CGGAGCGTTT TGGATGATAT CTTAAAACAG AAAGGGAATA    3600
ACAAAATAGA AACTCTAAAC CGGTATGTGT CCGTGGCGAT TTCGGTTATA    3650
GAGGAACAAG ATGGTGGTGG TATAATCATA CCATTTCAGA TTACATGTTT    3700
GACTAATGTT GTATCCTTAT ATATGTAGTT ACATTCTTAT AAGAATTTGG    3750
ATCGAGTTAT GGATGCTTGT TGCGTGCATG TATGACATTG ATGCAGTATT    3800
ATGGCGTCAG CTTTGCGCCG CTTAGTAGAA CAACAACAAT GGCGTTACTT    3850
AGTTTCTCAA TCAACCCGAT CTCCAAAAC                          3879
```

FIG. 2C

```
AGTAAGAACG AAGAAGAAGT GTTAAACCCA ACCAATTTTG ACTTGAAAAA      50

AAGCTTCAAC GCTCCCCTTT TCTCCTTCTC CGTCGCTCTC CGCCGCGTCC     100

CAAATCCCCA ATTCCTCCTC TTCTCCGATC AATTCTTCCC AAGTGTGTGT     150

ATGTGTGAGA GAGGAACTAT AGTGTAAAAA ATTCATA ATG GAA GTC TGC   199
                                         Met Glu Val Cys
                                         1
```

| | | | | | | | | | | | | |
|---|---|---|---|---|---|---|---|---|---|---|---|---|
| AAT | TGT | ATT | GAA | CCG | CAA | TGG | CCA | GCG | GAT | GAA | TTG TTA ATG | 241 |
| Asn | Cys | Ile | Glu | Pro | Gln | Trp | Pro | Ala | Asp | Glu | Leu Leu Met | |
| 5 | | | | 10 | | | | | 15 | | | |

| AAA | TAC | CAA | TAC | ATC | TCC | GAT | TTC | TTC | ATT | GCG | ATT GCG TAT | 283 |
|---|---|---|---|---|---|---|---|---|---|---|---|---|
| Lys | Tyr | Gln | Tyr | Ile | Ser | Asp | Phe | Phe | Ile | Ala | Ile Ala Tyr | |
| | 20 | | | | 25 | | | | | 30 | | |

| TTT | TCG | ATT | CCT | CTT | GAG | TTG | ATT | TAC | TTT | GTG | AAG AAA TCA | 325 |
|---|---|---|---|---|---|---|---|---|---|---|---|---|
| Phe | Ser | Ile | Pro | Leu | Glu | Leu | Ile | Tyr | Phe | Val | Lys Lys Ser | |
| | | 35 | | | | | 40 | | | | 45 | |

| GCC | GTG | TTT | CCG | TAT | AGA | TGG | GTA | CTT | GTT | CAG | TTT GGT GCT | 367 |
|---|---|---|---|---|---|---|---|---|---|---|---|---|
| Ala | Val | Phe | Pro | Tyr | Arg | Trp | Val | Leu | Val | Gln | Phe Gly Ala | |
| | | | 50 | | | | | 55 | | | | 60 |

| TTT | ATC | GTT | CTT | TGT | GGA | GCA | ACT | CAT | CTT | ATT | AAC TTA TGG | 409 |
|---|---|---|---|---|---|---|---|---|---|---|---|---|
| Phe | Ile | Val | Leu | Cys | Gly | Ala | Thr | His | Leu | Ile | Asn Leu Trp | |
| | | | | 65 | | | | | 70 | | | |

| ACT | TTC | ACT | ACG | CAT | TCG | AGA | ACC | GTG | GCG | CTT | GTG ATG ACT | 451 |
|---|---|---|---|---|---|---|---|---|---|---|---|---|
| Thr | Phe | Thr | Thr | His | Ser | Arg | Thr | Val | Ala | Leu | Val Met Thr | |
| 75 | | | | | 80 | | | | | 85 | | |

| ACC | GCG | AAG | GTG | TTA | ACC | GCT | GTT | GTC | TCG | TGT | GCT ACT GCG | 493 |
|---|---|---|---|---|---|---|---|---|---|---|---|---|
| Thr | Ala | Lys | Val | Leu | Thr | Ala | Val | Val | Ser | Cys | Ala Thr Ala | |
| | 90 | | | | 95 | | | | | 100 | | |

| TTG | ATG | CTT | GTT | CAT | ATT | ATT | CCT | GAT | CTT | TTG | AGT GTT AAG | 535 |
|---|---|---|---|---|---|---|---|---|---|---|---|---|
| Leu | Met | Leu | Val | His | Ile | Ile | Pro | Asp | Leu | Leu | Ser Val Lys | |
| | | 105 | | | | | 110 | | | | 115 | |

| ACT | CGG | GAG | CTT | TTC | TTG | AAA | AAT | AAA | GCT | GCT | GAG CTC GAT | 577 |
|---|---|---|---|---|---|---|---|---|---|---|---|---|
| Thr | Arg | Glu | Leu | Phe | Leu | Lys | Asn | Lys | Ala | Ala | Glu Leu Asp | |
| | | | 120 | | | | | 125 | | | | 130 |

| AGA | GAA | ATG | GGA | TTG | ATT | CGA | ACT | CAG | GAA | GAA | ACC GGA AGG | 619 |
|---|---|---|---|---|---|---|---|---|---|---|---|---|
| Arg | Glu | Met | Gly | Leu | Ile | Arg | Thr | Gln | Glu | Glu | Thr Gly Arg | |
| | | | | 135 | | | | | 140 | | | |

| CAT | GTG | AGA | ATG | TTG | ACT | CAT | GAG | ATT | AGA | AGC | ACT TTA GAT | 661 |
|---|---|---|---|---|---|---|---|---|---|---|---|---|
| His | Val | Arg | Met | Leu | Thr | His | Glu | Ile | Arg | Ser | Thr Leu Asp | |
| 145 | | | | | 150 | | | | | 155 | | |

| AGA | CAT | ACT | ATT | TTA | AAG | ACT | ACA | CTT | GTT | GAG | CTT GGT AGG | 703 |
|---|---|---|---|---|---|---|---|---|---|---|---|---|
| Arg | His | Thr | Ile | Leu | Lys | Thr | Thr | Leu | Val | Glu | Leu Gly Arg | |
| | 160 | | | | | 165 | | | | | 170 | |

| ACA | TTA | GCT | TTG | GAG | GAG | TGT | GCA | TTG | TGG | ATG | CCT ACT AGA | 745 |
|---|---|---|---|---|---|---|---|---|---|---|---|---|
| Thr | Leu | Ala | Leu | Glu | Glu | Cys | Ala | Leu | Trp | Met | Pro Thr Arg | |
| | | | 175 | | | | | 180 | | | | 185 |

*FIG. 3A*

| | | | | | | | | | | | | | |
|---|---|---|---|---|---|---|---|---|---|---|---|---|---|
| ACT | GGG | TTA | GAG | CTA | CAG | CTT | TCT | TAT | ACA | CTT | CGT | CAT | CAA | 787 |
| Thr | Gly | Leu | Glu 190 | Leu | Gln | Leu | Ser | Tyr 195 | Thr | Leu | Arg | His | Gln 200 | |
| CAT | CCC | GTG | GAG | TAT | ACG | GTT | CCT | ATT | CAA | TTA | CCG | GTG | ATT | 829 |
| His | Pro | Val | Glu | Tyr 205 | Thr | Val | Pro | Ile | Gln 210 | Leu | Pro | Val | Ile | |
| AAC | CAA | GTG | TTT | GGT | ACT | AGT | AGG | GCT | GTA | AAA | ATA | TCT | CCT | 871 |
| Asn 215 | Gln | Val | Phe | Gly | Thr 220 | Ser | Arg | Ala | Val | Lys 225 | Ile | Ser | Pro | |
| AAT | TCT | CCT | GTG | GCT | AGG | TTG | AGA | CCT | GTT | TCT | GGG | AAA | TAT | 913 |
| Asn | Ser 230 | Pro | Val | Ala | Arg | Leu 235 | Arg | Pro | Val | Ser | Gly 240 | Lys | Tyr | |
| ATG | CTA | GGG | GAG | GTG | GTC | GCT | GTG | AGG | GTT | CCG | CTT | CTC | CAC | 955 |
| Met | Leu | Gly 245 | Glu | Val | Val | Ala | Val 250 | Arg | Val | Pro | Leu | Leu 255 | His | |
| CTT | TCT | AAT | TTT | CAG | ATT | AAT | GAC | TGG | CCT | GAG | CTT | TCA | ACA | 997 |
| Leu | Ser | Asn | Phe 260 | Gln | Ile | Asn | Asp | Trp 265 | Pro | Glu | Leu | Ser | Thr 270 | |
| AAG | AGA | TAT | GCT | TTG | ATG | GTT | TTG | ATG | CTT | CCT | TCA | GAT | AGT | 1039 |
| Lys | Arg | Tyr | Ala | Leu 275 | Met | Val | Leu | Met | Leu 280 | Pro | Ser | Asp | Ser | |
| GCA | AGG | CAA | TGG | CAT | GTC | CAT | GAG | TTG | GAA | CTC | GTT | GAA | GTC | 1081 |
| Ala 285 | Arg | Gln | Trp | His | Val 290 | His | Glu | Leu | Glu | Leu 295 | Val | Glu | Val | |
| GTC | GCT | GAT | CAG | GTG | GCT | GTA | GCT | CTC | TCA | CAT | GCT | GCG | ATC | 1123 |
| Val | Ala | Asp 300 | Gln | Val | Ala | Val | Ala 305 | Leu | Ser | His | Ala | Ala 310 | Ile | |
| CTA | GAA | GAG | TCG | ATG | CGA | GCT | AGG | GAC | CTT | CTC | ATG | GAG | CAG | 1165 |
| Leu | Glu | Glu 315 | Ser | Met | Arg | Ala | Arg 320 | Asp | Leu | Leu | Met | Glu 325 | Gln | |
| AAT | GTT | GCT | CTT | GAT | CTA | GCT | AGA | CGA | GAA | GCA | GAA | ACA | GCA | 1207 |
| Asn | Val | Ala | Leu 330 | Asp | Leu | Ala | Arg | Arg 335 | Glu | Ala | Glu | Thr | Ala 340 | |
| ATC | CGT | GCC | CGC | AAT | GAT | TTC | CTA | GCG | GTT | ATG | AAC | CAT | GAA | 1249 |
| Ile | Arg | Ala | Arg | Asn 345 | Asp | Phe | Leu | Ala | Val 350 | Met | Asn | His | Glu | |
| ATG | CGA | ACA | CCG | ATG | CAT | GCG | ATT | ATT | GCA | CTC | TCT | TCC | TTA | 1291 |
| Met 355 | Arg | Thr | Pro | Met | His 360 | Ala | Ile | Ile | Ala | Leu 365 | Ser | Ser | Leu | |
| CTC | CAA | GAA | ACG | GAA | CTA | ACC | CCT | GAA | CAA | AGA | CTG | ATG | GTG | 1333 |
| Leu | Gln | Glu | Thr 370 | Glu | Leu | Thr | Pro 375 | Glu | Gln | Arg | Leu 380 | Met | Val | |
| GAA | ACA | ATA | CTT | AAA | AGT | AGT | AAC | CTT | TTG | GCA | ACT | TTG | ATG | 1375 |
| Glu | Thr | Ile 385 | Leu | Lys | Ser | Ser | Asn 390 | Leu | Leu | Ala | Thr | Leu 395 | Met | |

FIG. 3B

```
AAT GAT GTC TTA GAT CTT TCA AGG TTA GAA GAT GGA AGT CTT      1417
Asn Asp Val Leu Asp Leu Ser Arg Leu Glu Asp Gly Ser Leu
            400             405                     410

CAA CTT GAA CTT GGG ACA TTC AAT CTT CAT ACA TTA TTT AGA      1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA      1501
Glu Val Leu Asn Leu Ile Lys Pro Ile Ala Val Val Lys Lys
425                     430                 435

TTA CCC ATC ACA CTA AAT CTT GCA CCA GAT TTG CCA GAA TTT      1543
Leu Pro Ile Thr Leu Asn Leu Ala Pro Asp Leu Pro Glu Phe
        440                 445                 450

GTT GTT GGG GAT GAG AAA CGG CTA ATG CAG ATA ATA TTA AAT      1585
Val Val Gly Asp Glu Lys Arg Leu Met Gln Ile Ile Leu Asn
            455                 460                 465

ATA GTT GGT AAT GCT GTG AAA TTC TCC AAA CAA GGT AGT ATC      1621
Ile Val Gly Asn Ala Val Lys Phe Ser Lys Gln Gly Ser Ile
                470                 475             480

TCC GTA ACC GCT CTT GTC ACC AAG TCA GAC ACA CGA GCT GCT      1669
Ser Val Thr Ala Leu Val Thr Lys Ser Asp Thr Arg Ala Ala
                    485                 490

GAC TTT TTT GTC GTG CCA ACT GGG AGT CAT TTC TAC TTG AGA      1711
Asp Phe Phe Val Val Pro Thr Gly Ser His Phe Tyr Leu Arg
495                     500                 505

GTG AAG GTA AAA GAC TCT GGA GCA GGA ATA AAT CCT CAA GAC      1753
Val Lys Val Lys Asp Ser Gly Ala Gly Ile Asn Pro Gln Asp
        510                 515                 520

ATT CCA AAG ATT TTC ACT AAA TTT GCT CAA ACA CAA TCT TTA      1795
Ile Pro Lys Ile Phe Thr Lys Phe Ala Gln Thr Gln Ser Leu
            525                 530                 535

GCG ACG AGA AGC TCG GGT GGT AGT GGG CTT GGC CTC GCC ATC      1837
Ala Thr Arg Ser Ser Gly Gly Ser Gly Leu Gly Leu Ala Ile
                540                 545                 550

TCC AAG AGG TTT GTG AAT CTG ATG GAG GGT AAC ATT TGG ATT      1879
Ser Lys Arg Phe Val Asn Leu Met Glu Gly Asn Ile Trp Ile
                    555                 560

GAG AGC GAT GGT CTT GGA AAA GGA TGC ACG GCT ATC TTT GAT      1921
Glu Ser Asp Gly Leu Gly Lys Gly Cys Thr Ala Ile Phe Asp
565             570                     575

GTT AAA CTT GGG ATC TCA GAA CGT TCA AAC GAA TCT AAA CAG      1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT      2005
Ser Gly Ile Pro Lys Val Pro Ala Ile Pro Arg His Ser Asn
        595                 600                 605
```

FIG. 3C

| | | | | | | | | | | | | | |
|---|---|---|---|---|---|---|---|---|---|---|---|---|---|
| TTC | ACT | GGA | CTT | AAG | GTT | CTT | GTC | ATG | GAT | GAG | AAC | GGG | GTA | 2047
| Phe | Thr | Gly | Leu | Lys | Val | Leu | Val | Met | Asp | Glu | Asn | Gly | Val |
|  |  |  | 610 |  |  |  |  | 615 |  |  |  |  | 620 |
| AGT | AGA | ATG | GTG | ACG | AAG | GGA | CTT | CTT | GTA | CAC | CTT | GGG | TGC | 2089
| Ser | Arg | Met | Val | Thr | Lys | Gly | Leu | Leu | Val | His | Leu | Gly | Cys |
|  |  |  |  | 625 |  |  |  |  | 630 |  |  |  |  |
| GAA | GTG | ACC | ACG | GTG | AGT | TCA | AAC | GAG | GAG | TGT | CTC | CGA | GTT | 2131
| Glu | Val | Thr | Thr | Val | Ser | Ser | Asn | Glu | Glu | Cys | Leu | Arg | Val |
| 635 |  |  |  |  | 640 |  |  |  |  | 645 |  |  |  |
| GTG | TCC | CAT | GAG | CAC | AAA | GTG | GTC | TTC | ATG | GAC | GTG | TGC | ATG | 2173
| Val | Ser | His | Glu | His | Lys | Val | Val | Phe | Met | Asp | Val | Cys | Met |
|  | 650 |  |  |  |  | 655 |  |  |  |  | 660 |  |  |
| CCC | GGG | GTC | GAA | AAC | TAC | CAA | ATC | GCT | CTC | CGT | ATT | CAC | GAG | 2215
| Pro | Gly | Val | Glu | Asn | Tyr | Gln | Ile | Ala | Leu | Arg | Ile | His | Glu |
|  |  | 665 |  |  |  |  | 670 |  |  |  |  | 675 |  |
| AAA | TTC | ACA | AAA | CAA | CGC | CAC | CAA | CGG | CCA | CTA | CTT | GTG | GCA | 2257
| Lys | Phe | Thr | Lys | Gln | Arg | His | Gln | Arg | Pro | Leu | Leu | Val | Ala |
|  |  |  | 680 |  |  |  |  | 685 |  |  |  |  | 690 |
| CTC | AGT | GGT | AAC | ACT | GAC | AAA | TCC | ACA | AAA | GAG | AAA | TGC | ATG | 2299
| Leu | Ser | Gly | Asn | Thr | Asp | Lys | Ser | Thr | Lys | Glu | Lys | Cys | Met |
|  |  |  |  | 695 |  |  |  |  | 700 |  |  |  |  |
| AGC | TTT | GGT | CTA | GAC | GGT | GTG | TTG | CTC | AAA | CCC | GTA | TCA | CTA | 2341
| Ser | Phe | Gly | Leu | Asp | Gly | Val | Leu | Leu | Lys | Pro | Val | Ser | Leu |
| 705 |  |  |  |  | 710 |  |  |  |  | 715 |  |  |  |
| GAC | AAC | ATA | AGA | GAT | GTT | CTG | TCT | GAT | CTT | CTC | GAG | CCC | CGG | 2383
| Asp | Asn | Ile | Arg | Asp | Val | Leu | Ser | Asp | Leu | Leu | Glu | Pro | Arg |
|  | 720 |  |  |  |  | 725 |  |  |  |  | 730 |  |  |
| GTA | CTG | TAC | GAG | GGC | ATG | TAAAGGCGAT | GGATGCCCCA | | | | | | | 2421
| Val | Leu | Tyr | Glu | Gly | Met |
|  |  | 735 |

| | |
|---|---|
| TGCCCCAGAG GAGTAATTCC GCTCCCGCCT TCTTCTCCCG TAAAACATCG | 2471 |
| GAAGCTGATG TTCTCTGGTT TAATTGTGTA CATATCAGAG ATTGTCGGAG | 2521 |
| CGTTTTGGAT GATATCTTAA AACAGAAAGG GAATAACAAA ATAGAAACTC | 2571 |
| TAAACCGGTA TGTGTCCGTG GCGATTTCGG TTATAGAGGA ACAAGATGGT | 2621 |
| GGTGGTATAA TCATACCATT TCAGATTACA TGTTTGACTA ATGTTGTATC | 2671 |
| CTTATATATG TAGTTACATT CTTATAAGAA TTTGGATCGA GTTATGGATG | 2721 |
| CTTGTTGCGT GCATGTATGA CATTGATGCA GTATTATGGC GTCAGCTTTG | 2771 |
| CGCCGCTTAG TAGAAC | 2787 |

FIG. 3D

```
AGTAAGAACG AAGAAGAAGT GTTAAACCCA ACCAATTTTG ACTTGAAAAA        50
AAGCTTCAAC GCTCCCCTTT TCTCCTTCTC CGTCGCTCTC CGCCGCGTCC       100
CAAATCCCCA ATTCCTCCTC TTCTCCGATC AATTCTTCCC AAGTGTGTGT       150
ATGTGTGAGA GAGGAACTAT AGTGTAAAAA ATTCATA ATG GAA GTC TGC     199
                                         Met Glu Val Cys
                                          1

AAT TGT ATT GAA CCG CAA TGG CCA GCG GAT GAA TTG TTA ATG      241
Asn Cys Ile Glu Pro Gln Trp Pro Ala Asp Glu Leu Leu Met
 5              10                  15

AAA TAC CAA TAC ATC TCC GAT TTC TTC ATT GCG ATT GTG TAT      283
Lys Tyr Gln Tyr Ile Ser Asp Phe Phe Ile Ala Ile Val Tyr
        20              25                  30

TTT TCG ATT CCT CTT GAG TTG ATT TAC TTT GTG AAG AAA TCA      325
Phe Ser Ile Pro Leu Glu Leu Ile Tyr Phe Val Lys Lys Ser
            35                  40              45

GCC GTG TTT CCG TAT AGA TGG GTA CTT GTT CAG TTT GGT GCT      367
Ala Val Phe Pro Tyr Arg Trp Val Leu Val Gln Phe Gly Ala
                50                  55                  60

TTT ATC GTT CTT TGT GGA GCA ACT CAT CTT ATT AAC TTA TGG      409
Phe Ile Val Leu Cys Gly Ala Thr His Leu Ile Asn Leu Trp
                    65                  70

ACT TTC ACT ACG CAT TCG AGA ACC GTG GCG CTT GTG ATG ACT      451
Thr Phe Thr Thr His Ser Arg Thr Val Ala Leu Val Met Thr
75                  80                  85

ACC GCG AAG GTG TTA ACC GCT GTT GTC TCG TGT GCT ACT GCG      493
Thr Ala Lys Val Leu Thr Ala Val Val Ser Cys Ala Thr Ala
        90                  95                  100

TTG ATG CTT GTT CAT ATT ATT CCT GAT CTT TTG AGT GTT AAG      535
Leu Met Leu Val His Ile Ile Pro Asp Leu Leu Ser Val Lys
            105                 110                 115

ACT CGG GAG CTT TTC TTG AAA AAT AAA GCT GCT GAG CTC GAT      577
Thr Arg Glu Leu Phe Leu Lys Asn Lys Ala Ala Glu Leu Asp
                120                 125                 130

AGA GAA ATG GGA TTG ATT CGA ACT CAG GAA GAA ACC GGA AGG      619
Arg Glu Met Gly Leu Ile Arg Thr Gln Glu Glu Thr Gly Arg
                    135                 140

CAT GTG AGA ATG TTG ACT CAT GAG ATT AGA AGC ACT TTA GAT      661
His Val Arg Met Leu Thr His Glu Ile Arg Ser Thr Leu Asp
145                 150                 155

AGA CAT ACT ATT TTA AAG ACT ACA CTT GTT GAG CTT GGT AGG      703
Arg His Thr Ile Leu Lys Thr Thr Leu Val Glu Leu Gly Arg
    160                 165                 170

ACA TTA GCT TTG GAG GAG TGT GCA TTG TGG ATG CCT ACT AGA      745
Thr Leu Ala Leu Glu Glu Cys Ala Leu Trp Met Pro Thr Arg
        175                 180                 185
```

*FIG. 4A*

```
ACT GGG TTA GAG CTA CAG CTT TCT TAT ACA CTT CGT CAT CAA     787
Thr Gly Leu Glu Leu Gln Leu Ser Tyr Thr Leu Arg His Gln
            190             195                     200

CAT CCC GTG GAG TAT ACG GTT CCT ATT CAA TTA CCG GTG ATT     829
His Pro Val Glu Tyr Thr Val Pro Ile Gln Leu Pro Val Ile
                205             210

AAC CAA GTG TTT GGT ACT AGT AGG GCT GTA AAA ATA TCT CCT     871
Asn Gln Val Phe Gly Thr Ser Arg Ala Val Lys Ile Ser Pro
215                     220             225

AAT TCT CCT GTG GCT AGG TTG AGA CCT GTT TCT GGG AAA TAT     913
Asn Ser Pro Val Ala Arg Leu Arg Pro Val Ser Gly Lys Tyr
    230             235                     240

ATG CTA GGG GAG GTG GTC GCT GTG AGG GTT CCG CTT CTC CAC     955
Met Leu Gly Glu Val Val Ala Val Arg Val Pro Leu Leu His
            245             250                     255

CTT TCT AAT TTT CAG ATT AAT GAC TGG CCT GAG CTT TCA ACA     997
Leu Ser Asn Phe Gln Ile Asn Asp Trp Pro Glu Leu Ser Thr
            260             265                     270

AAG AGA TAT GCT TTG ATG GTT TTG ATG CTT CCT TCA GAT AGT    1039
Lys Arg Tyr Ala Leu Met Val Leu Met Leu Pro Ser Asp Ser
            275             280

GCA AGG CAA TGG CAT GTC CAT GAG TTG GAA CTC GTT GAA GTC    1081
Ala Arg Gln Trp His Val His Glu Leu Glu Leu Val Glu Val
285             290             295

GTC GCT GAT CAG GTG GCT GTA GCT CTC TCA CAT GCT GCG ATC    1123
Val Ala Asp Gln Val Ala Val Ala Leu Ser His Ala Ala Ile
    300             305             310

CTA GAA GAG TCG ATG CGA GCT AGG GAC CTT CTC ATG GAG CAG    1165
Leu Glu Glu Ser Met Arg Ala Arg Asp Leu Leu Met Glu Gln
            315             320             325

AAT GTT GCT CTT GAT CTA GCT AGA CGA GAA GCA GAA ACA GCA    1207
Asn Val Ala Leu Asp Leu Ala Arg Arg Glu Ala Glu Thr Ala
            330             335             340

ATC CGT GCC CGC AAT GAT TTC CTA GCG GTT ATG AAC CAT GAA    1249
Ile Arg Ala Arg Asn Asp Phe Leu Ala Val Met Asn His Glu
            345             350

ATG CGA ACA CCG ATG CAT GCG ATT ATT GCA CTC TCT TCC TTA    1291
Met Arg Thr Pro Met His Ala Ile Ile Ala Leu Ser Ser Leu
355             360             365

CTC CAA GAA ACG GAA CTA ACC CCT GAA CAA AGA CTG ATG GTG    1333
Leu Gln Glu Thr Glu Leu Thr Pro Glu Gln Arg Leu Met Val
    370             375             380

GAA ACA ATA CTT AAA AGT AGT AAC CTT TTG GCA ACT TTG ATG    1375
Glu Thr Ile Leu Lys Ser Ser Asn Leu Leu Ala Thr Leu Met
            385             390             395
```

*FIG. 4B*

```
AAT GAT GTC TTA GAT CTT TCA AGG TTA GAA GAT GGA AGT CTT    1417
Asn Asp Val Leu Asp Leu Ser Arg Leu Glu Asp Gly Ser Leu
            400                 405                 410

CAA CTT GAA CTT GGG ACA TTC AAT CTT CAT ACA TTA TTT AGA    1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA    1501
Glu Val Leu Asn Leu Ile Lys Pro Ile Ala Val Val Lys Lys
425                 430                 435

TTA CCC ATC ACA CTA AAT CTT GCA CCA GAT TTG CCA GAA TTT    1543
Leu Pro Ile Thr Leu Asn Leu Ala Pro Asp Leu Pro Glu Phe
        440                 445                 450

GTT GTT GGG GAT GAG AAA CGG CTA ATG CAG ATA ATA TTA AAT    1585
Val Val Gly Asp Glu Lys Arg Leu Met Gln Ile Ile Leu Asn
            455                 460                 465

ATA GTT GGT AAT GCT GTG AAA TTC TCC AAA CAA GGT AGT ATC    1627
Ile Val Gly Asn Ala Val Lys Phe Ser Lys Gln Gly Ser Ile
                470                 475                 480

TCC GTA ACC GCT CTT GTC ACC AAG TCA GAC ACA CGA GCT GCT    1669
Ser Val Thr Ala Leu Val Thr Lys Ser Asp Thr Arg Ala Ala
                    485                 490

GAC TTT TTT GTC GTG CCA ACT GGG AGT CAT TTC TAC TTG AGA    1711
Asp Phe Phe Val Val Pro Thr Gly Ser His Phe Tyr Leu Arg
495                 500                 505

GTG AAG GTA AAA GAC TCT GGA GCA GGA ATA AAT CCT CAA GAC    1753
Val Lys Val Lys Asp Ser Gly Ala Gly Ile Asn Pro Gln Asp
        510                 515                 520

ATT CCA AAG ATT TTC ACT AAA TTT GCT CAA ACA CAA TCT TTA    1795
Ile Pro Lys Ile Phe Thr Lys Phe Ala Gln Thr Gln Ser Leu
            525                 530                 535

GCG ACG AGA AGC TCG GGT GGT AGT GGG CTT GGC CTC GCC ATC    1837
Ala Thr Arg Ser Ser Gly Gly Ser Gly Leu Gly Leu Ala Ile
                540                 545                 550

TCC AAG AGG TTT GTG AAT CTG ATG GAG GGT AAC ATT TGG ATT    1879
Ser Lys Arg Phe Val Asn Leu Met Glu Gly Asn Ile Trp Ile
                    555                 560

GAG AGC GAT GGT CTT GGA AAA GGA TGC ACG GCT ATC TTT GAT    1921
Glu Ser Asp Gly Leu Gly Lys Gly Cys Thr Ala Ile Phe Asp
565                 570                 575

GTT AAA CTT GGG ATC TCA GAA CGT TCA AAC GAA TCT AAA CAG    1963
Val Lys Leu Gly Ile Ser Glu Arg Ser Asn Glu Ser Lys Gln
        580                 585                 590

TCG GGC ATA CCG AAA GTT CCA GCC ATT CCC CGA CAT TCA AAT    2005
Ser Gly Ile Pro Lys Val Pro Ala Ile Pro Arg His Ser Asn
            595                 600                 605
```

*FIG. 4C*

| | | | | | | | | | | | | |
|---|---|---|---|---|---|---|---|---|---|---|---|---|
| TTC | ACT | GGA | CTT | AAG | GTT | CTT | GTC | ATG | GAT | GAG | AAC | GGG | GTA | 2047 |
| Phe | Thr | Gly | Leu | Lys | Val | Leu | Val | Met | Asp | Glu | Asn | Gly | Val |
| | | | 610 | | | | 615 | | | | | 620 |
| AGT | AGA | ATG | GTG | ACG | AAG | GGA | CTT | CTT | GTA | CAC | CTT | GGG | TGC | 2089 |
| Ser | Arg | Met | Val | Thr | Lys | Gly | Leu | Leu | Val | His | Leu | Gly | Cys |
| | | | | 625 | | | | 630 |
| GAA | GTG | ACC | ACG | GTG | AGT | TCA | AAC | GAG | GAG | TGT | CTC | CGA | GTT | 2131 |
| Glu | Val | Thr | Thr | Val | Ser | Ser | Asn | Glu | Glu | Cys | Leu | Arg | Val |
| 635 | | | | | 640 | | | | | 645 |
| GTG | TCC | CAT | GAG | CAC | AAA | GTG | GTC | TTC | ATG | GAC | GTG | TGC | ATG | 2173 |
| Val | Ser | His | Glu | His | Lys | Val | Val | Phe | Met | Asp | Val | Cys | Met |
| | 650 | | | | | 655 | | | | | 660 |
| CCC | GGG | GTC | GAA | AAC | TAC | CAA | ATC | GCT | CTC | CGT | ATT | CAC | GAG | 2215 |
| Pro | Gly | Val | Glu | Asn | Tyr | Gln | Ile | Ala | Leu | Arg | Ile | His | Glu |
| | | 665 | | | | | 670 | | | | | 675 |
| AAA | TTC | ACA | AAA | CAA | CGC | CAC | CAA | CGG | CCA | CTA | CTT | GTG | GCA | 2257 |
| Lys | Phe | Thr | Lys | Gln | Arg | His | Gln | Arg | Pro | Leu | Leu | Val | Ala |
| | | | 680 | | | | | 685 | | | | | 690 |
| CTC | AGT | GGT | AAC | ACT | GAC | AAA | TCC | ACA | AAA | GAG | AAA | TGC | ATG | 2299 |
| Leu | Ser | Gly | Asn | Thr | Asp | Lys | Ser | Thr | Lys | Glu | Lys | Cys | Met |
| | | | | 695 | | | | | 700 |
| AGC | TTT | GGT | CTA | GAC | GGT | GTG | TTG | CTC | AAA | CCC | GTA | TCA | CTA | 2341 |
| Ser | Phe | Gly | Leu | Asp | Gly | Val | Leu | Leu | Lys | Pro | Val | Ser | Leu |
| 705 | | | | | 710 | | | | | 715 |
| GAC | AAC | ATA | AGA | GAT | GTT | CTG | TCT | GAT | CTT | CTC | GAG | CCC | CGG | 2383 |
| Asp | Asn | Ile | Arg | Asp | Val | Leu | Ser | Asp | Leu | Leu | Glu | Pro | Arg |
| | 720 | | | | | 725 | | | | | 730 |
| GTA | CTG | TAC | GAG | GGC | ATG | TAAAGGCGAT | GGATGCCCCA | | | | | | | 2421 |
| Val | Leu | Tyr | Glu | Gly | Met |
| | | 735 |

TGCCCCAGAG GAGTAATTCC GCTCCCGCCT TCTTCTCCCG TAAAACATCG 2471

GAAGCTGATG TTCTCTGGTT TAATTGTGTA CATATCAGAG ATTGTCGGAG 2521

CGTTTTGGAT GATATCTTAA AACAGAAAGG GAATAACAAA ATAGAAACTC 2571

TAAACCGGTA TGTGTCCGTG GCGATTTCGG TTATAGAGGA ACAAGATGGT 2621

GGTGGTATAA TCATACCATT TCAGATTACA TGTTTGACTA ATGTTGTATC 2671

CTTATATATG TAGTTACATT CTTATAAGAA TTTGGATCGA GTTATGGATG 2721

CTTGTTGCGT GCATGTATGA CATTGATGCA GTATTATGGC GTCAGCTTTG 2771

CGCCGCTTAG TAGAAC 2787

FIG. 4D

```
AGTAAGAACG AAGAAGAAGT GTTAAACCCA ACCAATTTTG ACTTGAAAAA          50

AAGCTTCAAC GCTCCCCTTT TCTCCTTCTC CGTCGCTCTC CGCCGCGTCC         100

CAAATCCCCA ATTCCTCCTC TTCTCCGATC AATTCTTCCC AAGTGTGTGT         150

ATGTGTGAGA GAGGAACTAT AGTGTAAAAA ATTCATA ATG GAA GTC TGC       199
                                         Met Glu Val Cys
                                          1
```

| | | | | | | | | | | | | | |
|---|---|---|---|---|---|---|---|---|---|---|---|---|---|
| AAT | TGT | ATT | GAA | CCG | CAA | TGG | CCA | GCG | GAT | GAA | TTG | TTA | ATG | 241 |
| Asn | Cys | Ile | Glu | Pro | Gln | Trp | Pro | Ala | Asp | Glu | Leu | Leu | Met | |
| 5 | | | | 10 | | | | | 15 | | | | | |

```
AAA TAC CAA TAC ATC TCC GAT TTC TTC ATT GCG ATT GCG TAT        283
Lys Tyr Gln Tyr Ile Ser Asp Phe Phe Ile Ala Ile Ala Tyr
     20              25              30

TTT TCG ATT CCT CTT GAG TTG ATT TAC TTT GTG AAG AAA TCA        325
Phe Ser Ile Pro Leu Glu Leu Ile Tyr Phe Val Lys Lys Ser
         35              40              45

GCC GTG TTT CCG TAT AGA TGG GTA CTT GTT CAG TTT GGT GCT        367
Ala Val Phe Pro Tyr Arg Trp Val Leu Val Gln Phe Gly Ala
             50              55              60

TTT TTC GTT CTT TGT GGA GCA ACT CAT CTT ATT AAC TTA TGG        409
Phe Phe Val Leu Cys Gly Ala Thr His Leu Ile Asn Leu Trp
                 65              70

ACT TTC ACT ACG CAT TCG AGA ACC GTG GCG CTT GTG ATG ACT        451
Thr Phe Thr Thr His Ser Arg Thr Val Ala Leu Val Met Thr
75              80              85

ACC GCG AAG GTG TTA ACC GCT GTT GTC TCG TGT GCT ACT GCG        493
Thr Ala Lys Val Leu Thr Ala Val Val Ser Cys Ala Thr Ala
     90              95              100

TTG ATG CTT GTT CAT ATT ATT CCT GAT CTT TTG AGT GTT AAG        535
Leu Met Leu Val His Ile Ile Pro Asp Leu Leu Ser Val Lys
         105             110             115

ACT CGG GAG CTT TTC TTG AAA AAT AAA GCT GCT GAG CTC GAT        577
Thr Arg Glu Leu Phe Leu Lys Asn Lys Ala Ala Glu Leu Asp
             120             125             130

AGA GAA ATG GGA TTG ATT CGA ACT CAG GAA GAA ACC GGA AGG        619
Arg Glu Met Gly Leu Ile Arg Thr Gln Glu Glu Thr Gly Arg
                 135             140

CAT GTG AGA ATG TTG ACT CAT GAG ATT AGA AGC ACT TTA GAT        661
His Val Arg Met Leu Thr His Glu Ile Arg Ser Thr Leu Asp
145             150             155

AGA CAT ACT ATT TTA AAG ACT ACA CTT GTT GAG CTT GGT AGG        703
Arg His Thr Ile Leu Lys Thr Thr Leu Val Glu Leu Gly Arg
     160             165             170

ACA TTA GCT TTG GAG GAG TGT GCA TTG TGG ATG CCT ACT AGA        745
Thr Leu Ala Leu Glu Glu Cys Ala Leu Trp Met Pro Thr Arg
         175             180             185
```

FIG. 5A

```
ACT GGG TTA GAG CTA CAG CTT TCT TAT ACA CTT CGT CAT CAA    787
Thr Gly Leu Glu Leu Gln Leu Ser Tyr Thr Leu Arg His Gln
            190                 195                 200

CAT CCC GTG GAG TAT ACG GTT CCT ATT CAA TTA CCG GTG ATT    829
His Pro Val Glu Tyr Thr Val Pro Ile Gln Leu Pro Val Ile
                205                 210

AAC CAA GTG TTT GGT ACT AGT AGG GCT GTA AAA ATA TCT CCT    871
Asn Gln Val Phe Gly Thr Ser Arg Ala Val Lys Ile Ser Pro
215             220                 225

AAT TCT CCT GTG GCT AGG TTG AGA CCT GTT TCT GGG AAA TAT    913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC    955
Met Leu Gly Glu Val Val Ala Val Arg Val Pro Leu Leu His
            245                 250                 255

CTT TCT AAT TTT CAG ATT AAT GAC TGG CCT GAG CTT TCA ACA    997
Leu Ser Asn Phe Gln Ile Asn Asp Trp Pro Glu Leu Ser Thr
                260                 265                 270

AAG AGA TAT GCT TTG ATG GTT TTG ATG CTT CCT TCA GAT AGT   1039
Lys Arg Tyr Ala Leu Met Val Leu Met Leu Pro Ser Asp Ser
                    275                 280

GCA AGG CAA TGG CAT GTC CAT GAG TTG GAA CTC GTT GAA GTC   1081
Ala Arg Gln Trp His Val His Glu Leu Glu Leu Val Glu Val
285             290                 295

GTC GCT GAT CAG GTG GCT GTA GCT CTC TCA CAT GCT GCG ATC   1123
Val Ala Asp Gln Val Ala Val Ala Leu Ser His Ala Ala Ile
        300                 305                 310

CTA GAA GAG TCG ATG CGA GCT AGG GAC CTT CTC ATG GAG CAG   1165
Leu Glu Glu Ser Met Arg Ala Arg Asp Leu Leu Met Glu Gln
            315                 320                 325

AAT GTT GCT CTT GAT CTA GCT AGA CGA GAA GCA GAA ACA GCA   1207
Asn Val Ala Leu Asp Leu Ala Arg Arg Glu Ala Glu Thr Ala
                330                 335                 340

ATC CGT GCC CGC AAT GAT TTC CTA GCG GTT ATG AAC CAT GAA   1249
Ile Arg Ala Arg Asn Asp Phe Leu Ala Val Met Asn His Glu
                    345                 350

ATG CGA ACA CCG ATG CAT GCG ATT ATT GCA CTC TCT TCC TTA   1291
Met Arg Thr Pro Met His Ala Ile Ile Ala Leu Ser Ser Leu
355                 360                 365

CTC CAA GAA ACG GAA CTA ACC CCT GAA CAA AGA CTG ATG GTG   1333
Leu Gln Glu Thr Glu Leu Thr Pro Glu Gln Arg Leu Met Val
        370                 375                 380

GAA ACA ATA CTT AAA AGT AGT AAC CTT TTG GCA ACT TTG ATG   1375
Glu Thr Ile Leu Lys Ser Ser Asn Leu Leu Ala Thr Leu Met
            385                 390                 395
```

FIG. 5B

| | |
|---|---|
| AAT GAT GTC TTA GAT CTT TCA AGG TTA GAA GAT GGA AGT CTT<br>Asn Asp Val Leu Asp Leu Ser Arg Leu Glu Asp Gly Ser Leu<br>            400                      405                    410 | 1417 |
| CAA CTT GAA CTT GGG ACA TTC AAT CTT CAT ACA TTA TTT AGA<br>Gln Leu Glu Leu Gly Thr Phe Asn Leu His Thr Leu Phe Arg<br>                    415                          420 | 1459 |
| GAG GTC CTC AAT CTG ATA AAG CCT ATA GCG GTT GTT AAG AAA<br>Glu Val Leu Asn Leu Ile Lys Pro Ile Ala Val Val Lys Lys<br>425                        430                      435 | 1501 |
| TTA CCC ATC ACA CTA AAT CTT GCA CCA GAT TTG CCA GAA TTT<br>Leu Pro Ile Thr Leu Asn Leu Ala Pro Asp Leu Pro Glu Phe<br>       440                      445                    450 | 1543 |
| GTT GTT GGG GAT GAG AAA CGG CTA ATG CAG ATA ATA TTA AAT<br>Val Val Gly Asp Glu Lys Arg Leu Met Gln Ile Ile Leu Asn<br>           455                      460                    465 | 1585 |
| ATA GTT GGT AAT GCT GTG AAA TTC TCC AAA CAA GGT AGT ATC<br>Ile Val Gly Asn Ala Val Lys Phe Ser Lys Gln Gly Ser Ile<br>                470                      475                    480 | 1627 |
| TCC GTA ACC GCT CTT GTC ACC AAG TCA GAC ACA CGA GCT GCT<br>Ser Val Thr Ala Leu Val Thr Lys Ser Asp Thr Arg Ala Ala<br>                    485                        490 | 1669 |
| GAC TTT TTT GTC GTG CCA ACT GGG AGT CAT TTC TAC TTG AGA<br>Asp Phe Phe Val Val Pro Thr Gly Ser His Phe Tyr Leu Arg<br>495                        500                      505 | 1711 |
| GTG AAG GTA AAA GAC TCT GGA GCA GGA ATA AAT CCT CAA GAC<br>Val Lys Val Lys Asp Ser Gly Ala Gly Ile Asn Pro Gln Asp<br>      510                      515                    520 | 1753 |
| ATT CCA AAG ATT TTC ACT AAA TTT GCT CAA ACA CAA TCT TTA<br>Ile Pro Lys Ile Phe Thr Lys Phe Ala Gln Thr Gln Ser Leu<br>           525                      530                    535 | 1795 |
| GCG ACG AGA AGC TCG GGT GGT AGT GGG CTT GGC CTC GCC ATC<br>Ala Thr Arg Ser Ser Gly Gly Ser Gly Leu Gly Leu Ala Ile<br>                540                      545                    550 | 1837 |
| TCC AAG AGG TTT GTG AAT CTG ATG GAG GGT AAC ATT TGG ATT<br>Ser Lys Arg Phe Val Asn Leu Met Glu Gly Asn Ile Trp Ile<br>                    555                        560 | 1879 |
| GAG AGC GAT GGT CTT GGA AAA GGA TGC ACG GCT ATC TTT GAT<br>Glu Ser Asp Gly Leu Gly Lys Gly Cys Thr Ala Ile Phe Asp<br>565                        570                      575 | 1921 |
| GTT AAA CTT GGG ATC TCA GAA CGT TCA AAC GAA TCT AAA CAG<br>Val Lys Leu Gly Ile Ser Glu Arg Ser Asn Glu Ser Lys Gln<br>      580                      585                    590 | 1963 |
| TCG GGC ATA CCG AAA GTT CCA GCC ATT CCC CGA CAT TCA AAT<br>Ser Gly Ile Pro Lys Val Pro Ala Ile Pro Arg His Ser Asn<br>           595                      600                    605 | 2005 |

*FIG. 5C*

| | |
|---|---|
| TTC ACT GGA CTT AAG GTT CTT GTC ATG GAT GAG AAC GGG GTA<br>Phe Thr Gly Leu Lys Val Leu Val Met Asp Glu Asn Gly Val<br>610                         615                    620 | 2047 |
| AGT AGA ATG GTG ACG AAG GGA CTT CTT GTA CAC CTT GGG TGC<br>Ser Arg Met Val Thr Lys Gly Leu Leu Val His Leu Gly Cys<br>625                         630 | 2089 |
| GAA GTG ACC ACG GTG AGT TCA AAC GAG GAG TGT CTC CGA GTT<br>Glu Val Thr Thr Val Ser Ser Asn Glu Glu Cys Leu Arg Val<br>635                   640                645 | 2131 |
| GTG TCC CAT GAG CAC AAA GTG GTC TTC ATG GAC GTG TGC ATG<br>Val Ser His Glu His Lys Val Val Phe Met Asp Val Cys Met<br>650                   655              660 | 2173 |
| CCC GGG GTC GAA AAC TAC CAA ATC GCT CTC CGT ATT CAC GAG<br>Pro Gly Val Glu Asn Tyr Gln Ile Ala Leu Arg Ile His Glu<br>         665                 670                  675 | 2215 |
| AAA TTC ACA AAA CAA CGC CAC CAA CGG CCA CTA CTT GTG GCA<br>Lys Phe Thr Lys Gln Arg His Gln Arg Pro Leu Leu Val Ala<br>             680                  685              690 | 2257 |
| CTC AGT GGT AAC ACT GAC AAA TCC ACA AAA GAG AAA TGC ATG<br>Leu Ser Gly Asn Thr Asp Lys Ser Thr Lys Glu Lys Cys Met<br>                     695                    700 | 2299 |
| AGC TTT GGT CTA GAC GGT GTG TTG CTC AAA CCC GTA TCA CTA<br>Ser Phe Gly Leu Asp Gly Val Leu Leu Lys Pro Val Ser Leu<br>705                      710              715 | 2341 |
| GAC AAC ATA AGA GAT GTT CTG TCT GAT CTT CTC GAG CCC CGG<br>Asp Asn Ile Arg Asp Val Leu Ser Asp Leu Leu Glu Pro Arg<br>720                       725              730 | 2383 |
| GTA CTG TAC GAG GGC ATG TAAAGGCGAT GGATGCCCCA<br>Val Leu Tyr Glu Gly Met<br>           735 | 2421 |
| TGCCCCAGAG GAGTAATTCC GCTCCCGCCT TCTTCTCCCG TAAAACATCG | 2471 |
| GAAGCTGATG TTCTCTGGTT TAATTGTGTA CATATCAGAG ATTGTCGGAG | 2521 |
| CGTTTTGGAT GATATCTTAA AACAGAAAGG GAATAACAAA ATAGAAACTC | 2571 |
| TAAACCGGTA TGTGTCCGTG GCGATTTCGG TTATAGAGGA ACAAGATGGT | 2621 |
| GGTGGTATAA TCATACCATT TCAGATTACA TGTTTGACTA ATGTTGTATC | 2671 |
| CTTATATATG TAGTTACATT CTTATAAGAA TTTGGATCGA GTTATGGATG | 2721 |
| CTTGTTGCGT GCATGTATGA CATTGATGCA GTATTATGGC GTCAGCTTTG | 2771 |
| CGCCGCTTAG TAGAAC | 2787 |

FIG. 5D

```
AGTAAGAACG AAGAAGAAGT GTTAAACCCA ACCAATTTTG ACTTGAAAAA            50
AAGCTTCAAC GCTCCCCTTT TCTCCTTCTC CGTCGCTCTC CGCCGCGTCC           100
CAAATCCCCA ATTCCTCCTC TTCTCCGATC AATTCTTCCC AAGTGTGTGT           150
ATGTGTGAGA GAGGAACTAT AGTGTAAAAA ATTCATA ATG GAA GTC TGC         199
                                         Met Glu Val Cys
                                          1
```

| AAT TGT ATT GAA CCG CAA TGG CCA GCG GAT GAA TTG TTA ATG | 241 |
|---|---|
| Asn Cys Ile Glu Pro Gln Trp Pro Ala Asp Glu Leu Leu Met | |
|   5           10              15                       | |

| AAA TAC CAA TAC ATC TCC GAT TTC TTC ATT GCG ATT GCG TAT | 283 |
|---|---|
| Lys Tyr Gln Tyr Ile Ser Asp Phe Phe Ile Ala Ile Ala Tyr | |
|     20              25              30                  | |

| TTT TCG ATT CCT CTT GAG TTG ATT TAC TTT GTG AAG AAA TCA | 325 |
|---|---|
| Phe Ser Ile Pro Leu Glu Leu Ile Tyr Phe Val Lys Lys Ser | |
|         35              40              45              | |

| GCC GTG TTT CCG TAT AGA TGG GTA CTT GTT CAG TTT GGT GCT | 367 |
|---|---|
| Ala Val Phe Pro Tyr Arg Trp Val Leu Val Gln Phe Gly Ala | |
|             50              55              60          | |

| TTT ATC GTT CTT TAT GGA GCA ACT CAT CTT ATT AAC TTA TGG | 409 |
|---|---|
| Phe Ile Val Leu Tyr Gly Ala Thr His Leu Ile Asn Leu Trp | |
|                 65              70                      | |

| ACT TTC ACT ACG CAT TCG AGA ACC GTG GCG CTT GTG ATG ACT | 451 |
|---|---|
| Thr Phe Thr Thr His Ser Arg Thr Val Ala Leu Val Met Thr | |
| 75              80              85                      | |

| ACC GCG AAG GTG TTA ACC GCT GTT GTC TCG TGT GCT ACT GCG | 493 |
|---|---|
| Thr Ala Lys Val Leu Thr Ala Val Val Ser Cys Ala Thr Ala | |
|     90              95              100                 | |

| TTG ATG CTT GTT CAT ATT ATT CCT GAT CTT TTG AGT GTT AAG | 535 |
|---|---|
| Leu Met Leu Val His Ile Ile Pro Asp Leu Leu Ser Val Lys | |
|         105             110             115             | |

| ACT CGG GAG CTT TTC TTG AAA AAT AAA GCT GCT GAG CTC GAT | 577 |
|---|---|
| Thr Arg Glu Leu Phe Leu Lys Asn Lys Ala Ala Glu Leu Asp | |
|             120             125             130         | |

| AGA GAA ATG GGA TTG ATT CGA ACT CAG GAA GAA ACC GGA AGG | 619 |
|---|---|
| Arg Glu Met Gly Leu Ile Arg Thr Gln Glu Glu Thr Gly Arg | |
|                 135             140                     | |

| CAT GTG AGA ATG TTG ACT CAT GAG ATT AGA AGC ACT TTA GAT | 661 |
|---|---|
| His Val Arg Met Leu Thr His Glu Ile Arg Ser Thr Leu Asp | |
| 145             150             155                     | |

| AGA CAT ACT ATT TTA AAG ACT ACA CTT GTT GAG CTT GGT AGG | 703 |
|---|---|
| Arg His Thr Ile Leu Lys Thr Thr Leu Val Glu Leu Gly Arg | |
|     160             165             170                 | |

| ACA TTA GCT TTG GAG GAG TGT GCA TTG TGG ATG CCT ACT AGA | 745 |
|---|---|
| Thr Leu Ala Leu Glu Glu Cys Ala Leu Trp Met Pro Thr Arg | |
|         175             180             185             | |

*FIG. 6A*

```
ACT GGG TTA GAG CTA CAG CTT TCT TAT ACA CTT CGT CAT CAA      787
Thr Gly Leu Glu Leu Gln Leu Ser Tyr Thr Leu Arg His Gln
            190             195                     200

CAT CCC GTG GAG TAT ACG GTT CCT ATT CAA TTA CCG GTG ATT      829
His Pro Val Glu Tyr Thr Val Pro Ile Gln Leu Pro Val Ile
                205                 210

AAC CAA GTG TTT GGT ACT AGT AGG GCT GTA AAA ATA TCT CCT      871
Asn Gln Val Phe Gly Thr Ser Arg Ala Val Lys Ile Ser Pro
215                 220                 225

AAT TCT CCT GTG GCT AGG TTG AGA CCT GTT TCT GGG AAA TAT      913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC      955
Met Leu Gly Glu Val Val Ala Val Arg Val Pro Leu Leu His
        245                 250                 255

CTT TCT AAT TTT CAG ATT AAT GAC TGG CCT GAG CTT TCA ACA      997
Leu Ser Asn Phe Gln Ile Asn Asp Trp Pro Glu Leu Ser Thr
            260                 265                 270

AAG AGA TAT GCT TTG ATG GTT TTG ATG CTT CCT TCA GAT AGT     1039
Lys Arg Tyr Ala Leu Met Val Leu Met Leu Pro Ser Asp Ser
                275                 280

GCA AGG CAA TGG CAT GTC CAT GAG TTG GAA CTC GTT GAA GTC     1081
Ala Arg Gln Trp His Val His Glu Leu Glu Leu Val Glu Val
285                 290                 295

GTC GCT GAT CAG GTG GCT GTA GCT CTC TCA CAT GCT GCG ATC     1123
Val Ala Asp Gln Val Ala Val Ala Leu Ser His Ala Ala Ile
    300                 305                 310

CTA GAA GAG TCG ATG CGA GCT AGG GAC CTT CTC ATG GAG CAG     1165
Leu Glu Glu Ser Met Arg Ala Arg Asp Leu Leu Met Glu Gln
        315                 320                 325

AAT GTT GCT CTT GAT CTA GCT AGA CGA GAA GCA GAA ACA GCA     1207
Asn Val Ala Leu Asp Leu Ala Arg Arg Glu Ala Glu Thr Ala
            330                 335                 340

ATC CGT GCC CGC AAT GAT TTC CTA GCG GTT ATG AAC CAT GAA     1249
Ile Arg Ala Arg Asn Asp Phe Leu Ala Val Met Asn His Glu
                345                 350

ATG CGA ACA CCG ATG CAT GCG ATT ATT GCA CTC TCT TCC TTA     1291
Met Arg Thr Pro Met His Ala Ile Ile Ala Leu Ser Ser Leu
355                 360                 365

CTC CAA GAA ACG GAA CTA ACC CCT GAA CAA AGA CTG ATG GTG     1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG     1375
Glu Thr Ile Leu Lys Ser Ser Asn Leu Leu Ala Thr Leu Met
        385                 390                 395
```

*FIG. 6B*

| | | | | | | | | | | | | |
|---|---|---|---|---|---|---|---|---|---|---|---|---|
| AAT | GAT | GTC | TTA | GAT | CTT | TCA | AGG | TTA | GAA | GAT | GGA | AGT | CTT | 1417 |
| Asn | Asp | Val | Leu | Asp | Leu | Ser | Arg | Leu | Glu | Asp | Gly | Ser | Leu | |
| | | | 400 | | | | | 405 | | | | | 410 | |
| CAA | CTT | GAA | CTT | GGG | ACA | TTC | AAT | CTT | CAT | ACA | TTA | TTT | AGA | 1459 |
| Gln | Leu | Glu | Leu | Gly | Thr | Phe | Asn | Leu | His | Thr | Leu | Phe | Arg | |
| | | | | 415 | | | | | 420 | | | | | |
| GAG | GTC | CTC | AAT | CTG | ATA | AAG | CCT | ATA | GCG | GTT | GTT | AAG | AAA | 1501 |
| Glu | Val | Leu | Asn | Leu | Ile | Lys | Pro | Ile | Ala | Val | Val | Lys | Lys | |
| 425 | | | | | 430 | | | | | 435 | | | | |
| TTA | CCC | ATC | ACA | CTA | AAT | CTT | GCA | CCA | GAT | TTG | CCA | GAA | TTT | 1543 |
| Leu | Pro | Ile | Thr | Leu | Asn | Leu | Ala | Pro | Asp | Leu | Pro | Glu | Phe | |
| | | 440 | | | | | 445 | | | | | 450 | | |
| GTT | GTT | GGG | GAT | GAG | AAA | CGG | CTA | ATG | CAG | ATA | ATA | TTA | AAT | 1585 |
| Val | Val | Gly | Asp | Glu | Lys | Arg | Leu | Met | Gln | Ile | Ile | Leu | Asn | |
| | | 455 | | | | | 460 | | | | | 465 | | |
| ATA | GTT | GGT | AAT | GCT | GTG | AAA | TTC | TCC | AAA | CAA | GGT | AGT | ATC | 1627 |
| Ile | Val | Gly | Asn | Ala | Val | Lys | Phe | Ser | Lys | Gln | Gly | Ser | Ile | |
| | | | 470 | | | | | 475 | | | | | 480 | |
| TCC | GTA | ACC | GCT | CTT | GTC | ACC | AAG | TCA | GAC | ACA | CGA | GCT | GCT | 1669 |
| Ser | Val | Thr | Ala | Leu | Val | Thr | Lys | Ser | Asp | Thr | Arg | Ala | Ala | |
| | | | | 485 | | | | | 490 | | | | | |
| GAC | TTT | TTT | GTC | GTG | CCA | ACT | GGG | AGT | CAT | TTC | TAC | TTG | AGA | 1711 |
| Asp | Phe | Phe | Val | Val | Pro | Thr | Gly | Ser | His | Phe | Tyr | Leu | Arg | |
| 495 | | | | | 500 | | | | | 505 | | | | |
| GTG | AAG | GTA | AAA | GAC | TCT | GGA | GCA | GGA | ATA | AAT | CCT | CAA | GAC | 1753 |
| Val | Lys | Val | Lys | Asp | Ser | Gly | Ala | Gly | Ile | Asn | Pro | Gln | Asp | |
| | 510 | | | | | 515 | | | | | 520 | | | |
| ATT | CCA | AAG | ATT | TTC | ACT | AAA | TTT | GCT | CAA | ACA | CAA | TCT | TTA | 1795 |
| Ile | Pro | Lys | Ile | Phe | Thr | Lys | Phe | Ala | Gln | Thr | Gln | Ser | Leu | |
| | | 525 | | | | | 530 | | | | | 535 | | |
| GCG | ACG | AGA | AGC | TCG | GGT | GGT | AGT | GGG | CTT | GGC | CTC | GCC | ATC | 1837 |
| Ala | Thr | Arg | Ser | Ser | Gly | Gly | Ser | Gly | Leu | Gly | Leu | Ala | Ile | |
| | | | 540 | | | | | 545 | | | | | 550 | |
| TCC | AAG | AGG | TTT | GTG | AAT | CTG | ATG | GAG | GGT | AAC | ATT | TGG | ATT | 1879 |
| Ser | Lys | Arg | Phe | Val | Asn | Leu | Met | Glu | Gly | Asn | Ile | Trp | Ile | |
| | | | | 555 | | | | | 560 | | | | | |
| GAG | AGC | GAT | GGT | CTT | GGA | AAA | GGA | TGC | ACG | GCT | ATT | TTT | GAT | 1921 |
| Glu | Ser | Asp | Gly | Leu | Gly | Lys | Gly | Cys | Thr | Ala | Ile | Phe | Asp | |
| 565 | | | | | 570 | | | | | 575 | | | | |
| GTT | AAA | CTT | GGG | ATC | TCA | GAA | CGT | TCA | AAC | GAA | TCT | AAA | CAG | 1963 |
| Val | Lys | Leu | Gly | Ile | Ser | Glu | Arg | Ser | Asn | Glu | Ser | Lys | Gln | |
| | 580 | | | | | 585 | | | | | 590 | | | |
| TCG | GGC | ATA | CCG | AAA | GTT | CCA | GCC | ATT | CCC | CGA | CAT | TCA | AAT | 2005 |
| Ser | Gly | Ile | Pro | Lys | Val | Pro | Ala | Ile | Pro | Arg | His | Ser | Asn | |
| | | 595 | | | | | 600 | | | | | 605 | | |

*FIG. 6C*

```
TTC ACT GGA CTT AAG GTT CTT GTC ATG GAT GAG AAC GGG GTA    2047
Phe Thr Gly Leu Lys Val Leu Val Met Asp Glu Asn Gly Val
            610             615                     620

AGT AGA ATG GTG ACG AAG GGA CTT CTT GTA CAC CTT GGG TGC    2089
Ser Arg Met Val Thr Lys Gly Leu Leu Val His Leu Gly Cys
            625             630

GAA GTG ACC ACG GTG AGT TCA AAC GAG GAG TGT CTC CGA GTT    2131
Glu Val Thr Thr Val Ser Ser Asn Glu Glu Cys Leu Arg Val
635             640                     645

GTG TCC CAT GAG CAC AAA GTG GTC TTC ATG GAC GTG TGC ATG    2173
Val Ser His Glu His Lys Val Val Phe Met Asp Val Cys Met
        650             655             660

CCC GGG GTC GAA AAC TAC CAA ATC GCT CTC CGT ATT CAC GAG    2215
Pro Gly Val Glu Asn Tyr Gln Ile Ala Leu Arg Ile His Glu
            665             670             675

AAA TTC ACA AAA CAA CGC CAC CAA CGG CCA CTA CTT GTG GCA    2257
Lys Phe Thr Lys Gln Arg His Gln Arg Pro Leu Leu Val Ala
            680             685                     690

CTC AGT GGT AAC ACT GAC AAA TCC ACA AAA GAG AAA TGC ATG    2299
Leu Ser Gly Asn Thr Asp Lys Ser Thr Lys Glu Lys Cys Met
                695             700

AGC TTT GGT CTA GAC GGT GTG TTG CTC AAA CCC GTA TCA CTA    2341
Ser Phe Gly Leu Asp Gly Val Leu Leu Lys Pro Val Ser Leu
705             710             715

GAC AAC ATA AGA GAT GTT CTG TCT GAT CTT CTC GAG CCC CGG    2383
Asp Asn Ile Arg Asp Val Leu Ser Asp Leu Leu Glu Pro Arg
        720             725             730

GTA CTG TAC GAG GGC ATG TAAAGGCGAT GGATGCCCCA TGCCCCAGAG   2431
Val Leu Tyr Glu Gly Met
            735

GAGTAATTCC GCTCCCGCCT TCTTCTCCCG TAAAACATCG GAAGCTGATG    2481
TTCTCTGGTT TAATTGTGTA CATATCAGAG ATTGTCGGAG CGTTTTGGAT    2531
GATATCTTAA AACAGAAAGG GAATAACAAA ATAGAAACTC TAAACCGGTA    2581
TGTGTCCGTG GCGATTTCGG TTATAGAGGA ACAAGATGGT GGTGGTATAA    2631
TCATACCATT TCAGATTACA TGTTTGACTA ATGTTGTATC CTTATATATG    2681
TAGTTACATT CTTATAAGAA TTTGGATCGA GTTATGGATG CTTGTTGCGT    2731
GCATGTATGA CATTGATGCA GTATTATGGC GTCAGCTTTG CGCCGCTTAG    2781
TAGAAC                                                    2787
```

*FIG. 6D*

```
AGTAAGAACG AAGAAGAAGT GTTAAACCCA ACCAATTTTG ACTTGAAAAA        50

AAGCTTCAAC GCTCCCCTTT TCTCCTTCTC CGTCGCTCTC CGCCGCGTCC       100

CAAATCCCCA ATTCCTCCTC TTCTCCGATC AATTCTTCCC AAGTGTGTGT       150

ATGTGTGAGA GAGGAACTAT AGTGTAAAAA ATTCATA ATG GAA GTC TGC     199
                                         Met Glu Val Cys
                                          1

AAT TGT ATT GAA CCG CAA TGG CCA GCG GAT GAA TTG TTA ATG      241
Asn Cys Ile Glu Pro Gln Trp Pro Ala Asp Glu Leu Leu Met
 5              10                  15

AAA TAC CAA TAC ATC TCC GAT TTC TTC ATT GCG ATT GCG TAT      283
Lys Tyr Gln Tyr Ile Ser Asp Phe Phe Ile Ala Ile Ala Tyr
    20              25                  30

TTT TCG ATT CCT CTT GAG TTG ATT TAC TTT GTG AAG AAA TCA      325
Phe Ser Ile Pro Leu Glu Leu Ile Tyr Phe Val Lys Lys Ser
        35              40                  45

GCC GTG TTT CCG TAT AGA TGG GTA CTT GTT CAG TTT GGT GCT      367
Ala Val Phe Pro Tyr Arg Trp Val Leu Val Gln Phe Gly Ala
            50              55                  60

TTT ATC GTT CTT TGT GGA GCA ACT CAT CTT ATT AAC TTA TGG      409
Phe Ile Val Leu Cys Gly Ala Thr His Leu Ile Asn Leu Trp
                65              70

ACT TTC ACT ACG CAT TCG AGA ACC GTG GCG CTT GTG ATG ACT      451
Thr Phe Thr Thr His Ser Arg Thr Val Ala Leu Val Met Thr
 75              80                  85

ACC GCG AAG GTG TTA ACC GCT GTT GTC TCG TGT GCT ACT ACG      493
Thr Ala Lys Val Leu Thr Ala Val Val Ser Cys Ala Thr Thr
    90              95                  100

TTG ATG CTT GTT CAT ATT ATT CCT GAT CTT TTG AGT GTT AAG      535
Leu Met Leu Val His Ile Ile Pro Asp Leu Leu Ser Val Lys
        105             110                 115

ACT CGG GAG CTT TTC TTG AAA AAT AAA GCT GCT GAG CTC GAT      577
Thr Arg Glu Leu Phe Leu Lys Asn Lys Ala Ala Glu Leu Asp
            120             125                 130

AGA GAA ATG GGA TTG ATT CGA ACT CAG GAA GAA ACC GGA AGG      619
Arg Glu Met Gly Leu Ile Arg Thr Gln Glu Glu Thr Gly Arg
                135             140

CAT GTG AGA ATG TTG ACT CAT GAG ATT AGA AGC ACT TTA GAT      661
His Val Arg Met Leu Thr His Glu Ile Arg Ser Thr Leu Asp
145             150                 155

AGA CAT ACT ATT TTA AAG ACT ACA CTT GTT GAG CTT GGT AGG      703
Arg His Thr Ile Leu Lys Thr Thr Leu Val Glu Leu Gly Arg
    160             165                 170

ACA TTA GCT TTG GAG GAG TGT GCA TTG TGG ATG CCT ACT AGA      745
Thr Leu Ala Leu Glu Glu Cys Ala Leu Trp Met Pro Thr Arg
        175             180                 185
```

FIG. 7A

```
ACT GGG TTA GAG CTA CAG CTT TCT TAT ACA CTT CGT CAT CAA    787
Thr Gly Leu Glu Leu Gln Leu Ser Tyr Thr Leu Arg His Gln
            190             195                     200

CAT CCC GTG GAG TAT ACG GTT CCT ATT CAA TTA CCG GTG ATT    829
His Pro Val Glu Tyr Thr Val Pro Ile Gln Leu Pro Val Ile
                205                 210

AAC CAA GTG TTT GGT ACT AGT AGG GCT GTA AAA ATA TCT CCT    871
Asn Gln Val Phe Gly Thr Ser Arg Ala Val Lys Ile Ser Pro
215                     220                 225

AAT TCT CCT GTG GCT AGG TTG AGA CCT GTT TCT GGG AAA TAT    913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC    955
Met Leu Gly Glu Val Val Ala Val Arg Val Pro Leu Leu His
        245                 250                 255

CTT TCT AAT TTT CAG ATT AAT GAC TGG CCT GAG CTT TCA ACA    997
Leu Ser Asn Phe Gln Ile Asn Asp Trp Pro Glu Leu Ser Thr
            260                 265                 270

AAG AGA TAT GCT TTG ATG GTT TTG ATG CTT CCT TCA GAT AGT   1039
Lys Arg Tyr Ala Leu Met Val Leu Met Leu Pro Ser Asp Ser
                275                 280

GCA AGG CAA TGG CAT GTC CAT GAG TTG GAA CTC GTT GAA GTC   1081
Ala Arg Gln Trp His Val His Glu Leu Glu Leu Val Glu Val
285                     290                 295

GTC GCT GAT CAG GTG GCT GTA GCT CTC TCA CAT GCT GCG ATC   1123
Val Ala Asp Gln Val Ala Val Ala Leu Ser His Ala Ala Ile
        300                 305                 310

CTA GAA GAG TCG ATG CGA GCT AGG GAC CTT CTC ATG GAG CAG   1165
Leu Glu Glu Ser Met Arg Ala Arg Asp Leu Leu Met Glu Gln
            315                 320                 325

AAT GTT GCT CTT GAT CTA GCT AGA CGA GAA GCA GAA ACA GCA   1207
Asn Val Ala Leu Asp Leu Ala Arg Arg Glu Ala Glu Thr Ala
                330                 335                 340

ATC CGT GCC CGC AAT GAT TTC CTA GCG GTT ATG AAC CAT GAA   1249
Ile Arg Ala Arg Asn Asp Phe Leu Ala Val Met Asn His Glu
                    345                 350

ATG CGA ACA CCG ATG CAT GCG ATT ATT GCA CTC TCT TCC TTA   1291
Met Arg Thr Pro Met His Ala Ile Ile Ala Leu Ser Ser Leu
355                     360                 365

CTC CAA GAA ACG GAA CTA ACC CCT GAA CAA AGA CTG ATG GTG   1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG   1375
Glu Thr Ile Leu Lys Ser Ser Asn Leu Leu Ala Thr Leu Met
            385                 390                 395
```

*FIG. 7B*

```
AAT GAT GTC TTA GAT CTT TCA AGG TTA GAA GAT GGA AGT CTT    1417
Asn Asp Val Leu Asp Leu Ser Arg Leu Glu Asp Gly Ser Leu
            400                 405                 410

CAA CTT GAA CTT GGG ACA TTC AAT CTT CAT ACA TTA TTT AGA    1459
Gln Leu Glu Leu Gly Thr Phe Asn Leu His Thr Leu Phe Arg
            415                 420

GAG GTC CTC AAT CTG ATA AAG CCT ATA GCG GTT GTT AAG AAA    1501
Glu Val Leu Asn Leu Ile Lys Pro Ile Ala Val Val Lys Lys
425             430                 435

TTA CCC ATC ACA CTA AAT CTT GCA CCA GAT TTG CCA GAA TTT    1543
Leu Pro Ile Thr Leu Asn Leu Ala Pro Asp Leu Pro Glu Phe
    440                 445                 450

GTT GTT GGG GAT GAG AAA CGG CTA ATG CAG ATA ATA TTA AAT    1585
Val Val Gly Asp Glu Lys Arg Leu Met Gln Ile Ile Leu Asn
            455                 460                 465

ATA GTT GGT AAT GCT GTG AAA TTC TCC AAA CAA GGT AGT ATC    1627
Ile Val Gly Asn Ala Val Lys Phe Ser Lys Gln Gly Ser Ile
            470                 475                 480

TCC GTA ACC GCT CTT GTC ACC AAG TCA GAC ACA CGA GCT GCT    1669
Ser Val Thr Ala Leu Val Thr Lys Ser Asp Thr Arg Ala Ala
            485                 490

GAC TTT TTT GTC GTG CCA ACT GGG AGT CAT TTC TAC TTG AGA    1711
Asp Phe Phe Val Val Pro Thr Gly Ser His Phe Tyr Leu Arg
495             500                 505

GTG AAG GTA AAA GAC TCT GGA GCA GGA ATA AAT CCT CAA GAC    1753
Val Lys Val Lys Asp Ser Gly Ala Gly Ile Asn Pro Gln Asp
    510                 515                 520

ATT CCA AAG ATT TTC ACT AAA TTT GCT CAA ACA CAA TCT TTA    1795
Ile Pro Lys Ile Phe Thr Lys Phe Ala Gln Thr Gln Ser Leu
        525                 530                 535

GCG ACG AGA AGC TCG GGT GGT AGT GGG CTT GGC CTC GCC ATC    1837
Ala Thr Arg Ser Ser Gly Gly Ser Gly Leu Gly Leu Ala Ile
            540                 545                 550

TCC AAG AGG TTT GTG AAT CTG ATG GAG GGT AAC ATT TGG ATT    1879
Ser Lys Arg Phe Val Asn Leu Met Glu Gly Asn Ile Trp Ile
            555                 560

GAG AGC GAT GGT CTT GGA AAA GGA TGC ACG GCT ATC TTT GAT    1921
Glu Ser Asp Gly Leu Gly Lys Gly Cys Thr Ala Ile Phe Asp
565             570                 575

GTT AAA CTT GGG ATC TCA GAA CGT TCA AAC GAA TCT AAA CAG    1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT    2005
Ser Gly Ile Pro Lys Val Pro Ala Ile Pro Arg His Ser Asn
        595                 600                 605
```

*FIG. 7C*

| | | | | | | | | | | | | | |
|---|---|---|---|---|---|---|---|---|---|---|---|---|---|
| TTC | ACT | GGA | CTT | AAG | GTT | CTT | GTC | ATG | GAT | GAG | AAC | GGG | GTA | 2047 |
| Phe | Thr | Gly | Leu 610 | Lys | Val | Leu | Val | Met 615 | Asp | Glu | Asn | Gly | Val 620 | |

AGT AGA ATG GTG ACG AAG GGA CTT CTT GTA CAC CTT GGG TGC 2089
Ser Arg Met Val Thr Lys Gly Leu Leu Val His Leu Gly Cys
          625                  630

GAA GTG ACC ACG GTG AGT TCA AAC GAG GAG TGT CTC CGA GTT 2131
Glu Val Thr Thr Val Ser Ser Asn Glu Glu Cys Leu Arg Val
635              640              645

GTG TCC CAT GAG CAC AAA GTG GTC TTC ATG GAC GTG TGC ATG 2173
Val Ser His Glu His Lys Val Val Phe Met Asp Val Cys Met
      650                655              660

CCC GGG GTC GAA AAC TAC CAA ATC GCT CTC CGT ATT CAC GAG 2215
Pro Gly Val Glu Asn Tyr Gln Ile Ala Leu Arg Ile His Glu
          665              670              675

AAA TTC ACA AAA CAA CGC CAC CAA CGG CCA CTA CTT GTG GCA 2257
Lys Phe Thr Lys Gln Arg His Gln Arg Pro Leu Leu Val Ala
              680              685              690

CTC AGT GGT AAC ACT GAC AAA TCC ACA AAA GAG AAA TGC ATG 2299
Leu Ser Gly Asn Thr Asp Lys Ser Thr Lys Glu Lys Cys Met
                  695              700

AGC TTT GGT CTA GAC GGT GTG TTG CTC AAA CCC GTA TCA CTA 2341
Ser Phe Gly Leu Asp Gly Val Leu Leu Lys Pro Val Ser Leu
705                      710              715

GAC AAC ATA AGA GAT GTT CTG TCT GAT CTT CTC GAG CCC CGG 2383
Asp Asn Ile Arg Asp Val Leu Ser Asp Leu Leu Glu Pro Arg
        720              725              730

GTA CTG TAC GAG GGC ATG TAAAGGCGAT GGATGCCCCA TGCCCCAGAG 2431
Val Leu Tyr Glu Gly Met
            735

GAGTAATTCC GCTCCCGCCT TCTTCTCCCG TAAAACATCG GAAGCTGATG 2481

TTCTCTGGTT TAATTGTGTA CATATCAGAG ATTGTCGGAG CGTTTTGGAT 2531

GATATCTTAA AACAGAAAGG GAATAACAAA ATAGAAACTC TAAACCGGTA 2581

TGTGTCCGTG GCGATTTCGG TTATAGAGGA ACAAGATGGT GGTGGTATAA 2631

TCATACCATT TCAGATTACA TGTTTGACTA ATGTTGTATC CTTATATATG 2681

TAGTTACATT CTTATAAGAA TTTGGATCGA GTTATGGATG CTTGTTGCGT 2731

GCATGTATGA CATTGATGCA GTATTATGGC GTCAGCTTTG CGCCGCTTAG 2781

TAGAAC 2787

FIG. 7D

```
ETR1  QNVALDLARREAETAIRARNDFLAV MNHEMRTPM HAIIALSLLQETELTPEQRL      380
BARA  QNVELDLAKKRAQEAARIKSEFLAN MSHELRTPL NGVIGFTRLTLKTELTPTQRD     329
LEMA  QNIELDLARKEALEASRIKSEFLAN MSHEIRTPL NGILGFTHLLQKSELTPRQFD     311
RPFC  RAVREARHANQAKSRFLAN MSHEFRTPL NGLSGMTEVLATTRLDAEQKE           176

ETR1  MVETILKSSNLLATLMNDVLDLSRLEDGSLQELGTFNLHTLFREVLNLIKPIAVV       436
BARA  HLNTIERSANNLLAIINDVLDFSKLEAGKLILESIPFPLRSTLDEVVTLLAHSSHD      385
LEMA  YLGTIEKSADNLLSIINEILDFSKIEAGKLVLDNIPFNLRDLLQDTLTILAPAAHA      367
RPFC  CLNTIQASARSLLSLVEEVLDISAIEAGKIRIDRRDFSLREMIGSVNLILQPQARG      232

ETR1  KKLPITLNLAPDLPEFVVGDEKR LMQIILNLIVGNA VKFSKQGSI (26) LRVK      510
BARA  KGLELTLNIKSDVPDNVIGDPLR LQQIITNLVGNA  IKFTENGNI (15) IEVQ      448
LEMA  KQLEIVSLVYRDTPLALSGDPLR LRQILTNLVSNA  IKFTREGTI (15) LRIS      430
RPFC  RRLEYGTQVADDVPLLLKGDTAH LRQVLLNLVGNA  VKFTEHGHV (16) LRFD      296

ETR1  VKDSGAGIN PQDIPK IFTKF AQTQSLATRSSG GSGLGL AISKRFVNLMEGNI      562
BARA  IRDTGIGIP ERDQSR LFQAF RQADASISRRHG GTGLGL VITQKLVNEMGGDI     500
LEMA  VQDTGIGLS SQDVRA LFQAF SQADNSLSRQPG GTGLGL VISKRLIEQMGGEI     482
RPFC  VEDTGIGVP MDMRPR LFEAF EQADVGLSRRYE GTGLGT TIAKGLVEAMGGSI     348
```

FIG. 9A

```
ETR1  LKVLVM DE NGVSRMVTKGLLVHLGCEVTTVSSNEECLRV                    648
BVGS  LRVLVV DD HKPNLMLLRQQLDYLGQRVVAADSGEAALAL                   1011
RCSC  MMILVV DD HPINRLLADQLGSLGYQCKTANDGVDALNV                     847
LEMA  PRVLCV DD NPANLLLVQTLLEDMGAEVVAVEGGYAAVNA                    695

ETR1  VSHEH-KVVFM D VCMPGVENYQIALRIH (10) PLLVA                     690
BVGS  WHEHAFDVVIT D CNMPGINGYELARRIR (12) CILFG                    1056
RCSC  LSKNHIDIVLS D VNMPNMDGYRLTQRIR  (5) LPVIG                     885
LEMA  VQQEAFDLVLM D VQMPGMDGRQATEAIR (10) LPIVA                     738

ETR1  LSGNTDKSTKEKCMSFGLDGVLL K PVSLDNIRDVLSDLL                     729
BVGS  FTASAQMDEAHACRAAGMDDCLF K PIGVDALRQRLNEAA                   1095
RCSC  VTANALAEEKQRCLESGMDSCLS K PVTLDVIKQSLTLYA                    924
LEMA  LTAHAMANEKRSLLQSGMDDYLT K PISERQLAQVVLKWT                    777
```

FIG. 9B

```
TOMATO        1 ATGGAATCCTGTGATTGCATTGAGGCTTTACTGCCAACTGGTGACCTGCT    50
                ||||  |||||| ||||||||  | |||| |||| ||||||||  |||| 
ARABIDOPSIS 157 ATGGAAGTCTGCAATTGTATTGAACCGCAATGGCCAGCGGATGAATTGTT   206

51 GGTTAAATACCAATACCTCTCAGATTTCTTCATTGCTGTAGCCTACTTTT   100
                ||||||||||||||| |||||||||||||  |||| ||| |||| || |
            207 AATGAAATACCAATACATCTCCGATTTCTTCATTGCGATTGCGTATTTTT   256

101 CCATTCCGTTGGAGCTTTATTATTTTGTCCACAAATCTGCATGCTTCCCA   150
                |   ||| ||||| |||  |||||||||| | ||| |||| || ||||
            257 CGATTCCCTCTTGAGTTGATTACTTGTGAAGAAATCAGCCGTGTTTTCCG   306

151 TACAGATGGGTCCTCATGCAATTTGGTGCTTTTATTGTGCTCTGCGGAGC   200
                || ||||||||||  ||| |||||||||||| | ||| ||   |||||| 
            307 TATAGATGGGTACTTGTTCAGTTTGGTGCTTTTAT CGTTCTTTGTGGAGC   356

201 AACACACTTTATTAGCTTGTGGACCTTCTTTATGCACTCTAAGACGGTCG   250
                |  | |||||| ||||  ||| | |||  | ||| | ||| |||| | |
            357 AACTCATCTTATTAACTTATGGACTTTCACTACGCCATTCGAGAACCGTGG   406

251 CTGTGGTTATGACCATATCAAAAATGTTGACAGCTGCCGTCCTCCTGTATC   300
                |  ||| || || | || || || | | | |||||| ||||| |||| |
            407 CGCTTGTGATGACTACCGCGAAGGTGTTAACCGCTGTTGTCTCGTGTGCT   456

301 ACAGCTTTGATGCTTGTTCACATTATTCCTGATTTGCTAAGTGTTAAAAC   350
                | |||||||| ||||||   ||| |||||||| || ||| ||||| ||| 
            457 ACTGCGGTTGATGCTTGTTCATATTATTCCTGATCTTTTGAGTGTTAAGAC   506

351 GCGAGAGTTGTTCTTGAAA    369
                |   |||  ||| ||||||
            507 TCGGGAGCTTTTTCTTGAAA    525
                                       Lys
                                       123

FIG. 10A
```

```
              Ala
              306
TOMATO      1 GCTCTTTCACATGCTGCAATTTTTAGAAGATTCCATGCGAGCCCATGATCA   50
              ||||||||||||||||||||||||  || || ||||||| ||| ||||
ARABIDOPSIS 1072 GCTCTCTCACATGCTGCGATCCTGCGATGCCGAGCTAGGAGCTAGGGACCT 1121

51 GCTCATGGAACAGAATATTGCTTTTGGATGTAGCTCGACAAGAAGCAGAGA  100
              ||||||||| ||||| |||||| ||| ||| || || || ||||||||||
         1122 GCTCATGGAGCAGAATGTTGCTCTTGAATCTAGACGAGAAGCAGAAA    1171

101 TGGCCATCCGTGCACGTAACGACTTCCTTGCTGTGATGAACCATGAAATG  150
              ||| ||||| ||  |  || ||||| || |  | ||||||||||||||||
         1172 CAGCAATCCGTGCCCGCAATGATTTCCTAGCGGTTATGAACCATGAAATG 1221

151 AGAACGCCCATGCATGCAGTTATTGCTCTGTGCTCTCTGCTTTTAGAAAC  200
              ||||| ||||||||||| |||||||| || || || || ||||||||||
         1222 CGAACACCGATGCATGCCATTATTGCACTCTCTTCCTTACTCCAAGAAAC 1271

201 AGACTTAACTCCAGAGCAGAGTTATGATTGAGACCATATTGAAGAGCA    250
              ||| |||||| || |  |||  |||||| ||| || || ||||||| |
         1272 CGAAACTAACCCCTGAACAACAAGACTGATGGTGGAAACAATACTTAAAGTA 1321

251 GCAATCTTCTTGCAACACTGATAAAATGATGTTCTAGATCTTTCTAG     296
              | |||| || ||||| ||| ||| ||||||| || || ||||||||
         1322 GTAACCTTTTGGCAACTTTGATGAATGATGTCTTAGATCTTTCAAG     1367

Ser
                                                               403
```

*FIG. 10B*

```
TOMATO       1 MESCDCIEALLPTGDLLVKYQYLSDFFIAVAYFSIPLELIYFVHKSACFP  50
               ||·|·||||· ·|·||·|||||·||||||||||||||||·||||·||·||
ARABIDOPSIS  1 MEVCNCIEPQWPADELLMKYQYISDFFIAIAYFSIPLELIYFVKKSAVFP  50

51 YRWVLMQFGAFIVLCGATHFISLWTFFMHSKTVAVVMTISKMLTAAVSCI 100
               ||||||·||||||||||||||·||||||·|||||·||·||·||||·|||
            51 YRWVLVQFGAFIVLCGATHLINLWTFTTHSRTVALVMTTAKVLTAVVSCA 100

101 TALMLVHIIPDLLSVKTRELFLK 123
               |||||||||||||||||||||||
           101 TALMLVHIIPDLLSVKTRELFLK 123
```

FIG. 11A

```
ARABIDOPSIS 306 ALSHAAILEESMRARDLLMEQNVALDLARREAETAIRARNDFLAVMNHEM 355
                |||||||||·||||||||||||·||||·||·||·|||||||||||||||
TOMATO        1 ALSHAAILEDSMRAHDQLMEQNIALDVARQEAEMAIRARNDFLAVMNHEM  50

356 RTPMHAIIAISSLLQETELTPEQRLMVETILKSSNLLATLMNDVLDLS 403
                ||||||·||·||·|·|||·|||||·||||||||||||||·|||·|||
             51 RTPMHAVIALCSLLLETDLTPEQRVMIETILKSSNLLATLINDVLDLS  93
```

FIG. 11B

```
ACTTTTAAAA TTTCTTTATT TCATTGTCAG AAAAAGAGAG CTAATAATAT         50
TATTATTTAA ATGTAACAAG TAGGCCTATA ACACGTGAAC TTCCCTCTTT        100
GCAAAAAAAA AATCATCAAA AACTTTTACC TCTCATTGGT TTCTTCTTTA        150
TCACACTGTT ACGCTTGGAT TCTCATTTCT TCAAGTTCAT AACGCTCGGA        200
TCAATCAGGA AGACGAACTT GAACTTTCTT TTTTTCATCA TTACCCAAAG        250
CTATGAGGCT CACACCACCA ATACGTCCGC CGTCATGAAT CCTTCTCTTC        300
CAGGTACTGT GCCGTCTCGG GATAACAAAC TTTCTATTTA TTCTCTTCTG        350
ATCGGATCTA TCTATCGATG AAGATTGATT TCACTACTTT AGTAACATTT        400
CATCTGATCG ATCTGTGTTG TGTTATCGAG GAATCAATCT CATTTGTAG         450
ATTCAATTTT CTGGATAGAT TTTGTATCTC TTTTCCATAG CTCTAGTCCA        500
AATCTAGTCT CCACTGATAT CTGAGTTTTG TTGACCAGGT CAACACAAGT        550
CAGAGCTCCA AAA ATG GAG TCA TGC GAT TGT TTT GAG ACG CAT        593
            Met Glu Ser Cys Asp Cys Phe Glu Thr His
             1           5                      10
```

GTG AAT CAA GAT GAT CTG TTA GTG AAG TAC CAA TAC ATC TCA         635
Val Asn Gln Asp Asp Leu Leu Val Lys Tyr Gln Tyr Ile Ser
             15                      20

GAT GCG TTG ATT GCT CTT GCA TAC TTC TCA ATC CCA CTC GAG         677
Asp Ala Leu Ile Ala Leu Ala Tyr Phe Ser Ile Pro Leu Glu
25                  30                      35

CTT ATC TAT TTC GTG CAA AAG TCT GCT TTC TTC CCT TAC AAA         719
Leu Ile Tyr Phe Val Gln Lys Ser Ala Phe Phe Pro Tyr Lys
        40                      45                  50

TGG GTG CTT ATG CAG TTT GGA GCC TTT ATC ATT CTC TGT GGA         761
Trp Val Leu Met Gln Phe Gly Ala Phe Ile Ile Leu Cys Gly
            55                      60                  65

GCT ACG CAT TTC ATC AAC CTA TGG ATG TTC TTC ATG CAT TCC         803
Ala Thr His Phe Ile Asn Leu Trp Met Phe Phe Met His Ser
                70                      75              80

AAA GCC GTT GCC ATT GTC ATG ACT ATT GCT AAA GTC TCT TGC         845
Lys Ala Val Ala Ile Val Met Thr Ile Ala Lys Val Ser Cys
                    85                      90

GCG GTT GTG TCG TGT GCT ACC GCG TTG ATG TTG GTT CAT ATT         887
Ala Val Val Ser Cys Ala Thr Ala Leu Met Leu Val His Ile
95                  100                     105

ATT CCT GAT CTT CTC AGT GTT AAG AAC AGG GAA TTG TTT CTC         929
Ile Pro Asp Leu Leu Ser Val Lys Asn Arg Glu Leu Phe Leu
    110                     115                     120

AAG AAG AAA GCT GAT GAG TTA GAT AGA GAA ATG GGT CTT ATT         971
Lys Lys Lys Ala Asp Glu Leu Asp Arg Glu Met Gly Leu Ile
        125                     130                     135

FIG. 12A

| | | | | | | | | | | | | |
|---|---|---|---|---|---|---|---|---|---|---|---|---|
| TTA | ACA | CAA | GAG | GAG | ACT | GGT | AGG | CAT | GTT | AGG | ATG | CTT | ACT | 1013 |
| Leu | Thr | Gln | Glu 140 | Glu | Thr | Gly | Arg | His 145 | Val | Arg | Met | Leu | Thr 150 | |

```
TTA ACA CAA GAG GAG ACT GGT AGG CAT GTT AGG ATG CTT ACT    1013
Leu Thr Gln Glu Glu Thr Gly Arg His Val Arg Met Leu Thr
            140             145             150

CAT GGA ATT AGA AGA ACT CTT GAT AGG CAT ACT ATT TTA AGA    1055
His Gly Ile Arg Arg Thr Leu Asp Arg His Thr Ile Leu Arg
            155             160

ACC ACT CTT GTT GAG CTT GGT AAA ACT CTT TGT CTT GAG GAA    1097
Thr Thr Leu Val Glu Leu Gly Lys Thr Leu Cys Leu Glu Glu
165         170             175

TGT GCG TTG TGG ATG CCT TCT CAA AGT GGT TTA TAT TTG CAG    1139
Cys Ala Leu Trp Met Pro Ser Gln Ser Gly Leu Tyr Leu Gln
        180         185             190

CTT TCT CAT ACT TTG AGT CAT AAA ATA CAA GTT GGA AGC AGT    1181
Leu Ser His Thr Leu Ser His Lys Ile Gln Val Gly Ser Ser
            195             200             205

GTG CCG ATA AAT CTC CCG ATT ATT AAT GAA CTC TTC AAT AGC    1223
Val Pro Ile Asn Leu Pro Ile Ile Asn Glu Leu Phe Asn Ser
                210             215             220

GCT CAA GCT ATG CAC ATA CCT CAT TCT TGT CCT TTG GCT AAG    1265
Ala Gln Ala Met His Ile Pro His Ser Cys Pro Leu Ala Lys
                225             230

ATT GGG CCT CCG GTT GGG AGA TAT TCA CCT CCT GAG GTT GTT    1307
Ile Gly Pro Pro Val Gly Arg Tyr Ser Pro Pro Glu Val Val
235             240             245

TCT GTC CGT GTT CCT CTT TTA CAT CTC TCT AAT TTC CAA GGC    1349
Ser Val Arg Val Pro Leu Leu His Leu Ser Asn Phe Gln Gly
    250             255             260

AGT GAC TGG TCG GAT CTC TCT GGC AAA GGT TAC GCT ATC ATG    1391
Ser Asp Trp Ser Asp Leu Ser Gly Lys Gly Tyr Ala Ile Met
            265             270             275

GTC CTG ATT CTC CCA ACC GAT GGT GCA AGA AAA TGG AGA GAC    1433
Val Leu Ile Leu Pro Thr Asp Gly Ala Arg Lys Trp Arg Asp
            280             285             290

CAT GAG TTA GAG CTT GTA GAA AAC GTG GCG GAT CAG            1469
His Glu Leu Glu Leu Val Glu Asn Val Ala Asp Gln
            295             300

GTCCATCTCT TTACTTGTAT ATGTTTGGTT GTGTGTCAAG TTGCTTTACC    1519

AGCTTTTAGT GTTTTGTTTT GTCCCCTGAC TCTCACTTCA TTCAG          1564

GTG GCT GTG GCT CTC TCA CAT GCT GCA ATT TTG GAA GAA TCC    1606
Val Ala Val Ala Leu Ser His Ala Ala Ile Leu Glu Glu Ser
            305             310             315

ATG CAC GCT CGT GAC CAG CTT ATG GAG CAG AAT TTT GCT TTA    1648
Met His Ala Arg Asp Gln Leu Met Glu Gln Asn Phe Ala Leu
            320             325             330

GAC AAG GCT CGT CAA GAG GCT GAG ATG GCA GTA CAT GCT CGA    1690
Asp Lys Ala Arg Gln Glu Ala Glu Met Ala Val His Ala Arg
            335             340
```

FIG. 12B

| | | | | | | | | | | | | |
|---|---|---|---|---|---|---|---|---|---|---|---|---|
| AAT | GAT | TTC | CTA | GCT | GTT | ATG | AAC | CAC | GAG | ATG | AGG | ACA CCG | 1732
| Asn | Asp | Phe | Leu | Ala | Val | Met | Asn | His | Glu | Met | Arg | Thr Pro |
| 345 | | | | | 350 | | | | | 355 | | |

| ATG | CAT | GCC | ATC | ATC | TCT | CTT | TCT | TCT | CTT | CTC | CTT | GAG ACT | 1774
| Met | His | Ala | Ile | Ile | Ser | Leu | Ser | Ser | Leu | Leu | Leu | Glu Thr |
| | 360 | | | | | 365 | | | | | 370 | |

| GAG | CTG | TCT | CCA | GAG | CAA | AGA | GTT | ATG | ATC | GAG | ACA | ATA CTG | 1816
| Glu | Leu | Ser | Pro | Glu | Gln | Arg | Val | Met | Ile | Glu | Thr | Ile Leu |
| | | 375 | | | | | 380 | | | | | 385 |

| AAA | AGC | AGC | AAT | CTT | GTG | GCT | ACA | CTA | ATC | AGC | GAC | GTT CTG | 1858
| Lys | Ser | Ser | Asn | Leu | Val | Ala | Thr | Leu | Ile | Ser | Asp | Val Leu |
| | | | 390 | | | | | 395 | | | | 400 |

| GAT | CTT | TCG | AGA | TTG | GAA | GAT | GGG | AGC | TTA | CTC | TTG | GAA AAT | 1900
| Asp | Leu | Ser | Arg | Leu | Glu | Asp | Gly | Ser | Leu | Leu | Leu | Glu Asn |
| | | | | 405 | | | | | 410 | | | |

| GAA | CCA | TTC | AGT | CTA | CAA | GCG | ATC | TTT | GAA | GAG | GTAACTAAAT | | 1943
| Glu | Pro | Phe | Ser | Leu | Gln | Ala | Ile | Phe | Glu | Glu | | |
| 415 | | | | | 420 | | | | | 425 | | |

CCCCCTGATT AACCAGTGAA GTCCATTATA TATGTCTTAC ATGAATAACA    1993

TGGGCGCTTT GAATCTGCAG GTC ATC TCT TTG ATA AAG CCA ATC    2037
                     Val Ile Ser Leu Ile Lys Pro Ile
                                     430

| GCA | TCA | GTG | AAG | AAA | CTA | TCA | ACG | AAT | CTG | ATT | CTG | TCT GCA | 2079
| Ala | Ser | Val | Lys | Lys | Leu | Ser | Thr | Asn | Leu | Ile | Leu | Ser Ala |
| | 435 | | | | | 440 | | | | | 445 | |

| GAC | TTA | CCA | ACT | TAT | GCT | ATT | GGT | GAT | GAG | AAA | CGT | CTG ATG | 2121
| Asp | Leu | Pro | Thr | Tyr | Ala | Ile | Gly | Asp | Glu | Lys | Arg | Leu Met |
| | | 450 | | | | | 455 | | | | | 460 |

| CAA | ACA | ATT | CTT | AAC | ATC | ATG | GGC | AAC | GCT | GTG | AAA | TTT ACT | 2163
| Gln | Thr | Ile | Leu | Asn | Ile | Met | Gly | Asn | Ala | Val | Lys | Phe Thr |
| | | | 465 | | | | | 470 | | | | 475 |

| AAG | GAA | GGC | TAC | ATC | TCC | ATA | ATA | GCC | TCT | ATC | ATG | AAA CCC | 2205
| Lys | Glu | Gly | Tyr | Ile | Ser | Ile | Ile | Ala | Ser | Ile | Met | Lys Pro |
| | | | | 480 | | | | | 485 | | | |

| GAG | TCC | TTA | CAA | GAA | TTA | CCA | TCT | CCA | GAA | TTT | TTT | CCA GTT | 2247
| Glu | Ser | Leu | Gln | Glu | Leu | Pro | Ser | Pro | Glu | Phe | Phe | Pro Val |
| 490 | | | | | 495 | | | | | 500 | | |

| CTC | AGT | GAC | AGT | CAC | TTC | TAC | CTA | TGT | GTG | CAG | GTTAGACCCA | | 2290
| Leu | Ser | Asp | Ser | His | Phe | Tyr | Leu | Cys | Val | Gln | | |
| | 505 | | | | | 510 | | | | | | |

ATCTACAAAT TACTAAACTA CAAAGTTAAG CTTCTTACTG TGTTCTTACT    2340

GTTATAATCA TGGTGCAG GTG AAG GAC ACA GGG TGT GGA ATT CAC    2385
                   Val Lys Asp Thr Gly Cys Gly Ile His
                        515              520

| ACA | CAA | GAC | ATT | CCT | TTG | CTC | TTT | ACC | AAA | TTT | GTA | CAG CCT | 2427
| Thr | Gln | Asp | Ile | Pro | Leu | Leu | Phe | Thr | Lys | Phe | Val | Gln Pro |
| | 525 | | | | | 530 | | | | | 535 | |

*FIG. 12C*

```
CGG ACC GGA ACT CAG AGG AAC CAT TCC GGT GGA GGA CTC GGG    2469
Arg Thr Gly Thr Gln Arg Asn His Ser Gly Gly Gly Leu Gly
        540                 545                 550

CTA GCT CTC TGT AAA CGG TAACAACCC AAAAGTATAT ATAAGTTATA    2516
Leu Ala Leu Cys Lys Arg
            555

AGCAGATGGT GTTACAAATA GCTAAAAGGC AAGTTTCTGT TGATGGATGT    2566

CTCTGGTTAG G TTT GTC GGG CTA ATG GGA GGA TAC ATG TGG      2607
             Phe Val Gly Leu Met Gly Gly Tyr Met Trp
                     560             565

ATA GAA AGT GAA GGC CTA GAG AAA GGC TGC ACA GCT TCG TTC    2649
Ile Glu Ser Glu Gly Leu Glu Lys Gly Cys Thr Ala Ser Phe
        570                 575                 580

ATC ATC AGG CTT GGT ATC TGC AAC GGT CCA AGC AGT AGC AGT    2691
Ile Ile Arg Leu Gly Ile Cys Asn Gly Pro Ser Ser Ser Ser
            585                 590                 595

GGT TCA ATG GCG CTA CAT CTT GCA GCT AAA TCA CAA ACC AGA    2733
Gly Ser Met Ala Leu His Leu Ala Ala Lys Ser Gln Thr Arg
                600                 605

CCG TGG AAC TGG TGATACTTAC GTTGGAAAGA CTTGTATTGA           2775
Pro Trp Asn Trp
610

GGTGAGACTT TTAACTACA CAGCAGCAAG AGAAAGAAGA AAATACATGA      2825

CCGGACGGTG TGATCTAACT TATTGGATTT TGTTGGATGT AATATGTAAA     2875

ATAAAAATCC TATATACGGG GAGAGGTACC TTATCTGTTC TCACTATATT     2925

TTATTGAACA TTACTTTAGA GAATATGTTT TGGAATTCAC TACTAAATAA     2975

ACGATATAAA TCTTCACGAA AAGAGCAACA TTTT                      3009
```

FIG. 12D

```
AAAAAAATCA TCAAAAACTT TTACCTCTCA TTGGTTTCTT CTTTATCACA        50
CTGTTACGCT TGGATTCTCA TTTCTTCAAG TTCATAACGC TCGGATCAAT       100
CAGGAAGACG AACTTGAACT TTCTTTTTTT CATCATTACC CAAAGCTATG       150
AGGCTCACAC CACCAATACG TCCGCCGTCA TGAATCCTTC TCTTCCAGGT       200
CAACACAAGT CAGAGCTCCA AAA ATG GAG TCA TGC GAT TGT TTT        244
                         Met Glu Ser Cys Asp Cys Phe
                          1               5

GAG ACG CAT GTG AAT CAA GAT GAT CTG TTA GTG AAG TAC CAA       286
Glu Thr His Val Asn Gln Asp Asp Leu Leu Val Lys Tyr Gln
         10              15              20

TAC ATC TCA GAT GCG TTG ATT GCT CTT GCA TAC TTC TCA ATC       328
Tyr Ile Ser Asp Ala Leu Ile Ala Leu Ala Tyr Phe Ser Ile
             25              30              35

CCA CTC GAG CTT ATC TAT TTC GTG CAA AAG TCT GCT TTC TTC       370
Pro Leu Glu Leu Ile Tyr Phe Val Gln Lys Ser Ala Phe Phe
                 40              45

CCT TAC AAA TGG GTG CTT ATG CAG TTT GGA GCC TTT ATC ATT       412
Pro Tyr Lys Trp Val Leu Met Gln Phe Gly Ala Phe Ile Ile
 50              55              60

CTC TGT GGA GCT ACG CAT TTC ATC AAC CTA TGG ATG TTC TTC       454
Leu Cys Gly Ala Thr His Phe Ile Asn Leu Trp Met Phe Phe
     65              70              75

ATG CAT TCC AAA GCC GTT GCC ATT GTC ATG ACT ATT GCT AAA       496
Met His Ser Lys Ala Val Ala Ile Val Met Thr Ile Ala Lys
             80              85              90

GTC TCT TGC GCG GTT GTG TCG TGT GCT ACC GCG TTG ATG TTG       538
Val Ser Cys Ala Val Val Ser Cys Ala Thr Ala Leu Met Leu
                 95             100             105

GTT CAT ATT ATT CCT GAT CTT CTC AGT GTT AAG AAC AGG GAA       580
Val His Ile Ile Pro Asp Leu Leu Ser Val Lys Asn Arg Glu
                    110             115

TTG TTT CTC AAG AAG AAA GCT GAT GAG TTA GAT AGA GAA ATG       622
Leu Phe Leu Lys Lys Lys Ala Asp Glu Leu Asp Arg Glu Met
120             125             130

GGT CTT ATT TTA ACA CAA GAG GAG ACT GGT AGG CAT GTT AGG       664
Gly Leu Ile Leu Thr Gln Glu Glu Thr Gly Arg His Val Arg
    135             140             145

ATG CTT ACT CAT GGA ATT AGA AGA ACT CTT GAT AGG CAT ACT       706
Met Leu Thr His Gly Ile Arg Arg Thr Leu Asp Arg His Thr
        150             155             160

ATT TTA AGA ACC ACT CTT GTT GAG CTT GGT AAA ACT CTT TGT       748
Ile Leu Arg Thr Thr Leu Val Glu Leu Gly Lys Thr Leu Cys
            165             170             175
```

FIG. 13A

```
CTT GAG GAA TGT GCG TTG TGG ATG CCT TCT CAA AGT GGT TTA        790
Leu Glu Glu Cys Ala Leu Trp Met Pro Ser Gln Ser Gly Leu
            180                     185

TAT TTG CAG CTT TCT CAT ACT TTG AGT CAT AAA ATA CAA GTT        832
Tyr Leu Gln Leu Ser His Thr Leu Ser His Lys Ile Gln Val
190                     195                 200

GGA AGC AGT GTG CCG ATA AAT CTC CCG ATT ATT AAT GAA CTC        874
Gly Ser Ser Val Pro Ile Asn Leu Pro Ile Ile Asn Glu Leu
    205                     210                 215

TTC AAT AGC GCT CAA GCT ATG CAC ATA CCT CAT TCT TGT CCT        916
Phe Asn Ser Ala Gln Ala Met His Ile Pro His Ser Cys Pro
        220                     225             230

TTG GCT AAG ATT GGG CCT CCG GTT GGG AGA TAT TCA CCT CCT        958
Leu Ala Lys Ile Gly Pro Pro Val Gly Arg Tyr Ser Pro Pro
            235                     240             245

GAG GTT GTT TCT GTC CGT GTT CCT CTT TTA CAT CTC TCT AAT       1000
Glu Val Val Ser Val Arg Val Pro Leu Leu His Leu Ser Asn
                250                     255

TTC CAA GGC AGT GAC TGG TCG GAT CTC TCT GGC AAA GGT TAC       1042
Phe Gln Gly Ser Asp Trp Ser Asp Leu Ser Gly Lys Gly Tyr
260                     265             270

GCT ATC ATG GTC CTG ATT CTC CCA ACC GAT GGT GCA AGA AAA       1084
Ala Ile Met Val Leu Ile Leu Pro Thr Asp Gly Ala Arg Lys
        275                     280             285

TGG AGA GAC CAT GAG TTA GAG CTT GTA GAA AAC GTG GCG GAT       1126
Trp Arg Asp His Glu Leu Glu Leu Val Glu Asn Val Ala Asp
            290                     295             300

CAG GTG GCT GTG GCT CTC TCA CAT GCT GCA ATT TTG GAA GAA       1168
Gln Val Ala Val Ala Leu Ser His Ala Ala Ile Leu Glu Glu
                305                     310             315

TCC ATG CAC GCT CGT GAC CAG CTT ATG GAG CAG AAT TTT GCT       1210
Ser Met His Ala Arg Asp Gln Leu Met Glu Gln Asn Phe Ala
                    320                     325

TTA GAC AAG GCT CGT CAA GAG GCT GAG ATG GCA GTA CAT GCT       1252
Leu Asp Lys Ala Arg Gln Glu Ala Glu Met Ala Val His Ala
330                     335                 340

CGA AAT GAT TTC CTA GCT GTT ATG AAC CAC GAG ATG AGG ACA       1294
Arg Asn Asp Phe Leu Ala Val Met Asn His Glu Met Arg Thr
    345                     350                 355

CCG ATG CAT GCC ATC ATC TCT CTT TCT TCT CTT CTC CTT GAG       1336
Pro Met His Ala Ile Ile Ser Leu Ser Ser Leu Leu Leu Glu
        360                     365                 370

ACT GAG CTG TCT CCA GAG CAA AGA GTT ATG ATC GAG ACA ATA       1378
Thr Glu Leu Ser Pro Glu Gln Arg Val Met Ile Glu Thr Ile
            375                     380             385
```

*FIG. 13B*

```
CTG AAA AGC AGC AAT CTT GTG GCT ACA CTA ATC AGC GAC GTT    1420
Leu Lys Ser Ser Asn Leu Val Ala Thr Leu Ile Ser Asp Val
            390                 395

CTG GAT CTT TCG AGA TTG GAA GAT GGG AGC TTA CTC TTG GAA    1462
Leu Asp Leu Ser Arg Leu Glu Asp Gly Ser Leu Leu Leu Glu
400                 405                 410

AAT GAA CCA TTC AGT CTA CAA GCG ATC TTT GAA GAG GTC ATC    1504
Asn Glu Pro Phe Ser Leu Gln Ala Ile Phe Glu Glu Val Ile
    415                 420                 425

TCT TTG ATA AAG CCA ATC GCA TCA GTG AAG AAA CTA TCA ACG    1546
Ser Leu Ile Lys Pro Ile Ala Ser Val Lys Lys Leu Ser Thr
        430                 435                 440

AAT CTG ATT CTG TCT GCA GAC TTA CCA ACT TAT GCT ATT GGT    1588
Asn Leu Ile Leu Ser Ala Asp Leu Pro Thr Tyr Ala Ile Gly
            445                 450                 455

GAT GAG AAA CGT CTG ATG CAA ACA ATT CTT AAC ATC ATG GGC    1630
Asp Glu Lys Arg Leu Met Gln Thr Ile Leu Asn Ile Met Gly
                460                 465

AAC GCT GTG AAA TTT ACT AAG GAA GGC TAC ATC TCC ATA ATA    1672
Asn Ala Val Lys Phe Thr Lys Glu Gly Tyr Ile Ser Ile Ile
470                 475                 480

GCC TCT ATC ATG AAA CCC GAG TCC TTA CAA GAA TTA CCA TCT    1714
Ala Ser Ile Met Lys Pro Glu Ser Leu Gln Glu Leu Pro Ser
    485                 490                 495

CCA GAA TTT TTT CCA GTT CTC AGT GAC AGT CAC TTC TAC CTA    1756
Pro Glu Phe Phe Pro Val Leu Ser Asp Ser His Phe Tyr Leu
        500                 505                 510

TGT GTG CAG GTG AAG GAC ACA GGG TGT GGA ATT CAC ACA CAA    1798
Cys Val Gln Val Lys Asp Thr Gly Cys Gly Ile His Thr Gln
            515                 520                 525

GAC ATT CCT TTG CTC TTT ACC AAA TTT GTA CAG CCT CGG ACC    1840
Asp Ile Pro Leu Leu Phe Thr Lys Phe Val Gln Pro Arg Thr
                530                 535

GGA ACT CAG AGG AAC CAT TCC GGT GGA GGA CTC GGG CTA GCT    1882
Gly Thr Gln Arg Asn His Ser Gly Gly Gly Leu Gly Leu Ala
540                 545                 550

CTC TGT AAA CGG TTT GTC GGG CTA ATG GGA GGA TAC ATG TGG    1924
Leu Cys Lys Arg Phe Val Gly Leu Met Gly Gly Tyr Met Trp
    555                 560                 565

ATA GAA AGT GAA GGC CTA GAG AAA GGC TGC ACA GCT TCG TTC    1966
Ile Glu Ser Glu Gly Leu Glu Lys Gly Cys Thr Ala Ser Phe
        570                 575                 580

ATC ATC AGG CTT GGT ATC TGC AAC GGT CCA AGC AGT AGC AGT    2008
Ile Ile Arg Leu Gly Ile Cys Asn Gly Pro Ser Ser Ser Ser
            585                 590                 595
```

FIG. 13C

| | |
|---|---|
| GGT TCA ATG GCG CTA CAT CTT GCA GCT AAA TCA CAA ACC AGA<br>Gly Ser Met Ala Leu His Leu Ala Ala Lys Ser Gln Thr Arg<br>600                    605 | 2050 |
| CCG TGG AAC TGG TGATACTTAC GTTGGAAAGA CTTGTATTGA<br>Pro Trp Asn Trp<br>610 | 2092 |
| GGTGAGACTT TTTAACTACA CAGCAGCAAG AGAAAGAAGA AAATACATGA | 2142 |
| CCGGACGGTG TGATCTAACT TATTGGATTT TGTTGGATGT AATATGTAAA | 2192 |
| ATAAAAATCC TATATACGGG GAGAGGTACC TTATCTGTTC TCACTATATT | 2242 |
| TTATTGAACA TTACTTTAGA GAATATGTTT TGGAATTCAC TACTAAATAA | 2292 |
| ACGATATAAA TCTTCACGAA AA | 2314 |

FIG. 13D

```
GAATTCGAAC TGCAATGGGA TAAACATTAT ATGCGTTTTA ATAATAGGTT      50
GGTGAAGTTT ATAATTTACA CCATTTGAAA AGCCTTCCAA ATTTAGAAAC     100
TACATTTTTG CAGACCCATG TGAGCTCATA TGAATCAATC ATAGCCTTGA     150
TGTTGTAAAA CAAATTATGA TTATAAAAAT GTGATAGTAT ATTACATGCA     200
TAAAAAATAA AGGAGAGTAA ATGAAAGTCA ATCTGGGTT TTATGAACTG      250
AAAGTTGAAG TTTAGAAGTA GAAGTAGCGA TCAAAGTATG ACCAGTTAAA     300
AGGCCCAATA TCATTTGGAG GTTTGATTTT TGGGTTCGTA AATTTCAAGA     350
GCCAGATTAT GATTTGCTGG GCTTAAAAAT CATGGAAAAA TTGAAATGAC     400
GGTGTTAAAA TATATAACTC AAATTAAAGA TTTTAATTGG GTGTAGTAGG     450
CTGATTTTTT TATAAGAATC TTGTCTATAG ATGCTTCAAG GTTATGCCTT     500
ATAGTACTGG TTGTAAAACA CCACTATCTA ATTTGAAGC TGGTCAGAAC      550
TATAAGGTAT GTTGTTGTTC GCCTTGTTGC TAATGAAGAT TATAACATTC     600
TGTTGTTGCA TTTTTTTTTT TTTTTTGTG TTAAATATAT ATATTTTTT       650
TGCATATTTA TTGTTGCATA TTGTGTTGCA TATTTAGTAA TGGTTACATT     700
CCCTGTTATC GGAGACCAAG ATAATACGGC TCTGTGGCAT GGACTACTAC     750
TCCATGGATT CTTCCAAGTA ATCTTGCTTT GTGTGTCAAT GCAAAGTTTG     800
TTTATCTTAA GGTTCGTCAA CAACACTGGA AAAGTCTACA TTGTTGCTGA     850
ATCTCGGTTG TCATCGCTTC CTAGTGATAA GCCTAAGGCC GGCTTAACTA     900
ATGGAACTTA CTAGTGATAC CATAATGCGA AAGGTGCTAA TTAAGCTTGA     950
CAGTGAAGAG GATTCTTATC AAGTTTTGGA AAATTTTAAT GGAGATTCCT    1000
TGGTTGGGAA GAAGTATGAA CCTTTGTTTG ATTACTTTTA GCGATTTCTC    1050
AAGTGTGACT TTTCGACTAG TAGCAGATGA TTATGTCATG AATGATAGTG    1100
GTACTGGTAT TGTCCATTGT GCTCCTGTCT TTGGTGCAGA TGACTATCGT    1150
GTTTGTCTTG AGAACGAGAT AATTAAGAAG GTTAGATTTG ACAACATCTT    1200
CCTTATATCA CCACCTTTAA CATTAAGTTT ATTTTCTTTC TTGTTTAAGT    1250
TTACAGTATC TTCAAGAACC CATGTTCATG ACACATTTTG TTCATGTGTT    1300
GTTTAGATTG TCAGAGATTT CAAACGTCCA GATGGTTTGA AAGATACAGA    1350
GATTGATGCA GCTGTAGATA GTACATATCT TAATTAAAAA TACCACTTCT    1400
CTATGCTCTA TTGTTGAGGA AACATATAAT ATTTGCATTC GTTCATGGTT    1450
CAGATATGAT GTTATGGTAA TTCTTGATCT ACGAGAAGAT GAATCTTTGA    1500
AAAACGAAGG TGTTGCCCGT GAGGTAAATA AATGTAACCG AAGCGATTAA    1550
TGGTCATATA TAAGTTGTAT ATTTGATATA TGGGTTTCCT TCTCATTGTG    1600
```

FIG. 14A

| | |
|---|---|
| CTCATGCATT GAAAAGCACC CTGTTATGAC TGTGGTTCTA GGAGAACATT | 1650 |
| TGCATTTGAC AGTCGGTGAC TAATTGTTAA GCAAGAAGAA CGCATGAGAG | 1700 |
| CCTTTTAAAG TGTTTTCTTC TAGATCGTTG CAAAAAGTTA AATGTCTCTT | 1750 |
| GAGACTTTGT ACTCATTCTA TAGATAAAGA TGGGATTTAT TACAAAAACA | 1800 |
| ACAAGAAACT TGTTACTTG TGGAAATTCA AAATTATCCG AACTAGCTTC | 1850 |
| ACAAAATATG CTCAAGAGTT TCAATGTATT TTTTTTTGTT CTGTAATTGT | 1900 |
| ATGACTCCGT TGAAGCATC AAGATTATGG TTATAGGTAG TGATGCTAAA | 1950 |
| ACTCTCTGTT GTTACAGTGA CCACTAAAAA CACCAACAAA AAAAACTTAG | 2000 |
| GTAACGTGTC GTCTAAAAAC TTCTAGGTTC AATTTCTTTA GATAGTACTA | 2050 |
| TCAATAAATA AAATAAATAT GTACAAAGGC TTTAAACAAT GATGTTTTC | 2100 |
| AAAGATGATT GGTAGATACT AATTAGAGCT TCAATATAAA AGAACACATG | 2150 |
| CGATTCTGAC ATTCTGTGGT CTAACATGGT TTCTTCTAGA GTCAAAACCA | 2200 |
| TACAATTAAA AGTTAGGAAA GTAATAGCAA TGTGGTTTCA AATATATACT | 2250 |
| CATTACTCTT TAGATTCATG TATGGTGAAG GAAACATTAT AATAAAATCA | 2300 |
| AAGATCACAG TTTTGTAGGT CCCTCATATT AATCAACATC TTAAGGCGTT | 2350 |
| ATACATATCT TCTTTTTGTA AATATTTGAC TAATTAAAAT ATCTAATTAG | 2400 |
| AGTATTAGAC TAATCTCATC AAATATCCGA CTACTTGTGT CAGTTCAAAA | 2450 |
| CACAGTGATT ACGTTAGATT TTGTGCTCTT TGTTTATAA ACAAAGCTAA | 2500 |
| TTAAGAAAT ATATGATCTA TTTGCCTCCT TGGTCTTAAT TTTATACTTT | 2550 |
| CTTGGAATAA AACACATTTA TTAAAATAAT TTTTAGGGTC CTAGATTCAT | 2600 |
| GTCATGTGGC TTGATAGTTT CCAACAATTA TACCAATATT TTACTCATTC | 2650 |
| ATATACAAAT AAACAAGCTT TATTCTATTC TTCAGTCTCA TGATATACGG | 2700 |
| GATTTGATA AAATTCAGAG TACCCATTAA TTATTCTATG TTACAGCTTG | 2750 |
| TAATAAGTTA AATTTATAAA ACGTACAAGT TGAGGAAATA ACAAATGTTT | 2800 |
| TCAATATTAA ATGATTTATT AATACATTAG TGACCAAAAA ATTATTAAGT | 2850 |
| GTAAGAAAAA AAACACAACT CAGAAAAAAT TCAAAAGACC GTCTAAGTTC | 2900 |
| GGTTCATGTA AGAACAAGTG GGACCTCTTT AAGTTTCTAA ATCAGAGAAT | 2950 |
| AAAGAAGAAG AAAAAATCTC AAAACCTTCC TCTAAAACCA ACGGCTCCTA | 3000 |
| CCTTTACTTA CACCCTATAC ATACACTTCT CTTTTTATCC TCCATCGGCG | 3050 |
| GCTTATGGCG GTTTTCCGGC ACTAATCATC TCCGGCATAT ATAAATAAAC | 3100 |
| GTACTTCACG TTTTTTTATA TAACTTCAAA GTAGTTTCAG ATTTGTCTCT | 3150 |
| ATCTCTTCAC TTTTAAGTCT TCTGGTTTTG TCATCACCAG CTTTTTTTGT | 3200 |
| TCTCTCTCTG TCTCTGTCTC TGTCTTTCTC TTTGTGTATT TTATTCTCG | 3250 |

FIG. 14B

```
TCATCGTTGT TCTTCTATGA GAGGAAGATC GGAATGTCGA AGAGAATTAG         3300

AAGATTCTCG TACATCACTT CGTTGGAATT TCACAGGTCG ATGAGAGATC         3350

TGAGAACTGT TTCATTTTGA TCCAAACTCA TCTCTTTCAG GTATTCCAAA         3400

TTTGTCTTTC TCTGTTCTTT CTACTATTAC CCAAATTAAA GTTTTGATTT         3450

TTATTTCTCA CTCTGTTTCT TGTTTTTCTA ATTGCAGAGT ATAATGGACT         3500

AAGCATTTTT TTTCTCCGAA G ATG GTT AAA GAA ATA GCT TCT TGG        3545
                        Met Val Lys Glu Ile Ala Ser Trp
                         1                5
```

| | | | | | | | | | | | | | | |
|---|---|---|---|---|---|---|---|---|---|---|---|---|---|---|
| TTA | TTG | ATA | CTA | TCA | ATG | GTG | GTG | TTT | GTT | TCT | CCG | GTT | TTA | 3587 |
| Leu | Leu | Ile | Leu | Ser | Met | Val | Val | Phe | Val | Ser | Pro | Val | Leu | |
| | | 10 | | | 15 | | | | 20 | | | | | |
| GCT | ATA | AAC | GGC | GGT | GGT | TAT | CCA | CGA | TGT | AAC | TGC | GAA | GAC | 3629 |
| Ala | Ile | Asn | Gly | Gly | Gly | Tyr | Pro | Arg | Cys | Asn | Cys | Glu | Asp | |
| | | 25 | | | | 30 | | | | | 35 | | | |
| GAA | GGA | AAC | AGT | TTC | TGG | AGT | ACA | GAG | AAC | ATT | CTA | GAA | ACT | 3671 |
| Glu | Gly | Asn | Ser | Phe | Trp | Ser | Thr | Glu | Asn | Ile | Leu | Glu | Thr | |
| | | | 40 | | | | | 45 | | | | | 50 | |
| CAA | AGA | GTA | AGC | GAT | TTC | TTA | ATC | GCA | GTA | GCT | TAT | TTC | TCA | 3713 |
| Gln | Arg | Val | Ser | Asp | Phe | Leu | Ile | Ala | Val | Ala | Tyr | Phe | Ser | |
| | | | | 55 | | | | | 60 | | | | | |
| ATC | CCT | ATT | GAG | TTA | CTT | TAC | TTC | GTG | AGT | TGT | TCC | AAT | GTT | 3755 |
| Ile | Pro | Ile | Glu | Leu | Leu | Tyr | Phe | Val | Ser | Cys | Ser | Asn | Val | |
| 65 | | | | | 70 | | | | | 75 | | | | |
| CCA | TTC | AAA | TGG | GTT | CTC | TTT | GAG | TTT | ATC | GCC | TTC | ATT | GTT | 3797 |
| Pro | Phe | Lys | Trp | Val | Leu | Phe | Glu | Phe | Ile | Ala | Phe | Ile | Val | |
| | 80 | | | | | 85 | | | | | 90 | | | |
| CTT | TGT | GGT | ATG | ACT | CAT | CTT | CTT | CAT | GGT | TGG | ACT | TAC | TCT | 3839 |
| Leu | Cys | Gly | Met | Thr | His | Leu | Leu | His | Gly | Trp | Thr | Tyr | Ser | |
| | | 95 | | | | | 100 | | | | | 105 | | |
| GCT | CAT | CCA | TTT | AGA | TTA | ATG | ATG | GCG | TTT | ACT | GTT | TTC | AAG | 3881 |
| Ala | His | Pro | Phe | Arg | Leu | Met | Met | Ala | Phe | Thr | Val | Phe | Lys | |
| | | | 110 | | | | | 115 | | | | | 120 | |
| ATG | TTG | ACT | GCT | TTA | GTC | TCT | TGT | GCT | ACT | GCG | ATT | ACG | CTT | 3923 |
| Met | Leu | Thr | Ala | Leu | Val | Ser | Cys | Ala | Thr | Ala | Ile | Thr | Leu | |
| | | | | 125 | | | | | 130 | | | | | |
| ATT | ACT | TTG | ATT | CCT | CTG | CTT | TTG | AAA | GTT | AAA | GTT | AGA | GAG | 3965 |
| Ile | Thr | Leu | Ile | Pro | Leu | Leu | Leu | Lys | Val | Lys | Val | Arg | Glu | |
| 135 | | | | | 140 | | | | | 145 | | | | |
| TTT | ATG | CTT | AAG | AAG | AAA | GCT | CAT | GAG | CTT | GGT | CGT | GAA | GTT | 4007 |
| Phe | Met | Leu | Lys | Lys | Lys | Ala | His | Glu | Leu | Gly | Arg | Glu | Val | |
| | 150 | | | | | 155 | | | | | 160 | | | |
| GGT | TTG | ATT | TTG | ATT | AAG | AAA | GAG | ACT | GGC | TTT | CAT | GTT | CGT | 4049 |
| Gly | Leu | Ile | Leu | Ile | Lys | Lys | Glu | Thr | Gly | Phe | His | Val | Arg | |
| | | 165 | | | | | 170 | | | | | 175 | | |

FIG. 14C

```
ATG CTT ACT CAA GAG ATT CGT AAG TCT TTG GAT CGT CAT ACG    4091
Met Leu Thr Gln Glu Ile Arg Lys Ser Leu Asp Arg His Thr
        180                 185                     190

ATT CTT TAT ACT ACT TTG GTT GAG CTT TCG AAG ACT TTA GGG    4133
Ile Leu Tyr Thr Thr Leu Val Glu Leu Ser Lys Thr Leu Gly
                195                 200

TTG CAG AAT TGT GCG GTT TGG ATG CCG AAT GAC GGT GGA ACG    4175
Leu Gln Asn Cys Ala Val Trp Met Pro Asn Asp Gly Gly Thr
205                 210                 215

GAG ATG GAT TTG ACT CAT GAG TTG AGA GGG AGA GGT GGT TAT    4217
Glu Met Asp Leu Thr His Glu Leu Arg Gly Arg Gly Gly Tyr
    220                 225                 230

GGT GGT TGT TCT GTT TCT ATG GAG GAT TTG GAT GTT GTT AGG    4259
Gly Gly Cys Ser Val Ser Met Glu Asp Leu Asp Val Val Arg
            235                 240                 245

ATT AGG GAG AGT GAT GAA GTG AAT GTG TTG AGT GTT GAC TCG    4301
Ile Arg Glu Ser Asp Glu Val Asn Val Leu Ser Val Asp Ser
                250                 255                 260

TCC ATT GCT CGA GCT AGT GGT GGT GGG GAT GTT AGT GAG        4343
Ser Ile Ala Arg Ala Ser Gly Gly Gly Gly Asp Val Ser Glu
            265                 270

ATT GGT GCC GTG GCT GCT ATT AGA ATG CCG ATG CTT CGT GTT    4385
Ile Gly Ala Val Ala Ala Ile Arg Met Pro Met Leu Arg Val
275                 280                 285

TCG GAT TTT AAT GGA GAG CTA AGT TAT GCG ATA CTT GTT TGT    4427
Ser Asp Phe Asn Gly Glu Leu Ser Tyr Ala Ile Leu Val Cys
    290                 295                 300

GTT TTA CCG GGC GGG ACC CGT CGG GAT TGG ACT TAT CAG GAG    4469
Val Leu Pro Gly Gly Thr Arg Arg Asp Trp Thr Tyr Gln Glu
        305                 310                 315

ATT GAG ATT GTT AAA GTT GTG GCG GAT CAA GTA ACC GTT GCG    4511
Ile Glu Ile Val Lys Val Val Ala Asp Gln Val Thr Val Ala
                320                 325                 330

TTA GAT CAT GCA GCG GTT CTT GAA GAG TCT CAG CTT ATG AGG    4553
Leu Asp His Ala Ala Val Leu Glu Glu Ser Gln Leu Met Arg
                335                 340

GAG AAG CTG GCG GAA CAG AAC AGG GCG TTG CAG ATG GCG AAG    4595
Glu Lys Leu Ala Glu Gln Asn Arg Ala Leu Gln Met Ala Lys
345                 350                 355

AGA GAC GCG TTG AGA GCG AGC CAA GCG AGG AAT GCG TTT CAG    4637
Arg Asp Ala Leu Arg Ala Ser Gln Ala Arg Asn Ala Phe Gln
        360                 365                 370

AAA ACG ATG AGC GAA GGG ATG AGG CGT CCT ATG CAT TCG ATA    4679
Lys Thr Met Ser Glu Gly Met Arg Arg Pro Met His Ser Ile
                375                 380                 385

CTC GGT CTT TTG TCG ATG ATT CAG GAC GAG AAG TTG AGT GAC    4721
Leu Gly Leu Leu Ser Met Ile Gln Asp Glu Lys Leu Ser Asp
                390                 395                 400
```

FIG. 14D

| | | | | | | | | | | | | |
|---|---|---|---|---|---|---|---|---|---|---|---|---|
| GAG | CAG | AAA | ATG | ATT | GTT | GAT | ACG | ATG | GTT | AAA | ACA | GGG | AAT | 4763 |
| Glu | Gln | Lys | Met | Ile 405 | Val | Asp | Thr | Met | Val 410 | Lys | Thr | Gly | Asn | |
| GTT | ATG | TCG | AAT | TTG | GTG | GGG | GAC | TCT | ATG | GAT | GTG | CCT | GAC | 4805 |
| Val 415 | Met | Ser | Asn | Leu | Val 420 | Gly | Asp | Ser | Met | Asp 425 | Val | Pro | Asp | |
| GGT | AGA | TTT | GGT | ACG | GAG | ATG | AAA | CCG | TTT | AGT | CTG | CAT | CGT | 4847 |
| Gly | Arg 430 | Phe | Gly | Thr | Glu | Met 435 | Lys | Pro | Phe | Ser | Leu 440 | His | Arg | |
| ACG | ATC | CAT | GAA | GCA | GCT | TGT | ATG | GCG | AGA | TGT | TTG | TGT | CTA | 4889 |
| Thr | Ile | His 445 | Glu | Ala | Ala | Cys | Met 450 | Ala | Arg | Cys | Leu | Cys 455 | Leu | |
| TGC | AAT | GGA | ATT | AGG | TTC | TTG | GTT | GAC | GCG | GAG | AAG | TCT | CTA | 4931 |
| Cys | Asn | Gly | Ile 460 | Arg | Phe | Leu | Val | Asp 465 | Ala | Glu | Lys | Ser | Leu 470 | |
| CCT | GAT | AAT | GTA | GTA | GGT | GAT | GAA | AGA | AGG | GTC | TTT | CAA | GTG | 4973 |
| Pro | Asp | Asn | Val | Val 475 | Gly | Asp | Glu | Arg | Arg 480 | Val | Phe | Gln | Val | |
| ATA | CTT | CAT | ATG | GTT | GGT | AGT | TTA | GTA | AAG | CCT | AGA | AAA | CGT | 5015 |
| Ile 485 | Leu | His | Met | Val | Gly 490 | Ser | Leu | Val | Lys | Pro 495 | Arg | Lys | Arg | |
| CAA | GAA | GGA | TCT | TCA | TTG | ATG | TTT | AAG | GTT | TTG | AAA | GAA | AGA | 5057 |
| Gln | Glu 500 | Gly | Ser | Ser | Leu | Met 505 | Phe | Lys | Val | Leu | Lys 510 | Glu | Arg | |
| GGA | AGC | TTG | GAT | AGG | AGT | GAT | CAT | AGA | TGG | GCT | GCT | TGG | AGA | 5099 |
| Gly | Ser | Leu 515 | Asp | Arg | Ser | Asp | His 520 | Arg | Trp | Ala | Ala | Trp 525 | Arg | |
| TCA | CCG | GCT | TCT | TCA | GCA | GAT | GGA | GAT | GTG | TAT | ATA | AGA | TTT | 5141 |
| Ser | Pro | Ala | Ser 530 | Ser | Ala | Asp | Gly | Asp 535 | Val | Tyr | Ile | Arg | Phe 540 | |
| GAA | ATG | AAT | GTA | GAG | AAT | GAT | GAT | TCA | AGT | TCT | CAA | TCA | TTT | 5183 |
| Glu | Met | Asn | Val | Glu 545 | Asn | Asp | Asp | Ser | Ser 550 | Ser | Gln | Ser | Phe | |
| GCT | TCT | GTT | TCC | TCC | AGA | GAT | CAA | GAA | GTT | GGT | GAT | GTT | AGA | 5225 |
| Ala | Ser | Val | Ser | Ser 560 | Arg | Asp | Gln | Glu | Val 565 | Gly | Asp | Val | Arg | |
| | | | | 555 | | | | | | | | | | |
| TTC | TCC | GGC | GGC | TAT | GGG | TTA | GGA | CAA | GAT | CTA | AGC | TTT | GGT | 5266 |
| Phe | Ser | Gly | Gly | Tyr | Gly 575 | Leu | Gly | Gln | Asp | Leu 580 | Ser | Phe | Gly | |
| | | 570 | | | | | | | | | | | | |
| GTT | TGT | AAG | AAA | GTG | GTG | CAG | GTGAGTTTCC | TTACATATCT | | | | | | 5316 |
| Val | Cys | Lys 585 | Lys | Val | Val | Gln | | | | | | | | |

CTTTCTAAAG TTCCTGTCAT TAGTCTGAGT TTCTGTTTAG GAGTTCTTTG        5359

FIG. 14E

```
ATAATGTGTG CAG TTG ATT CAT GGG AAT ATC TCG GTG GTC CCT    5401
            Leu Ile His Gly Asn Ile Ser Val Val Pro
            590                 595

GGC TCG GAT GGT TCA CCG GAG ACC ATG TCG TTG CTC CTT CGG    5443
Gly Ser Asp Gly Ser Pro Glu Thr Met Ser Leu Leu Leu Arg
600             605                 610

TTT CGA CGT AGA CCC TCC ATA TCT GTC CAT GGA TCC AGC GAG    5485
Phe Arg Arg Arg Pro Ser Ile Ser Val His Gly Ser Ser Glu
        615             620                 625

TCG CCA GCT CCT GAC CAC CAC GCT CAC CCA CAT TCG AAT TCT    5527
Ser Pro Ala Pro Asp His His Ala His Pro His Ser Asn Ser
            630             635                 640

CTG TTA CGT GGC TTA CAA GTT TTA TTG GTA GAC ACC AAC GAT    5569
Leu Leu Arg Gly Leu Gln Val Leu Leu Val Asp Thr Asn Asp
                645             650                 655

TCG AAC CGG GCA GTT ACA CGT AAA CTC TTA GAG AAA CTC GGG    5611
Ser Asn Arg Ala Val Thr Arg Lys Leu Leu Glu Lys Leu Gly
                660             665

TGC GAT GTA ACC GCG GTT TCC TCT GGA TTC GAT TGC CTT ACC    5653
Cys Asp Val Thr Ala Val Ser Ser Gly Phe Asp Cys Leu Thr
670             675                 680

GCC ATT GCT CCC GGC TCG TCC TCG CCT TCT ACT TCG TTT CAA    5695
Ala Ile Ala Pro Gly Ser Ser Ser Pro Ser Thr Ser Phe Gln
    685             690                 695

GTG GTG GTG CTT GAT CTT CAA ATG GCA GAG ATG GAC GGT TAT    5737
Val Val Val Leu Asp Leu Gln Met Ala Glu Met Asp Gly Tyr
            700             705                 710

GAA GTG GCC ATG AGG ATC AGG AGT CGA TCT TGG CCG TTG ATT    5779
Glu Val Ala Met Arg Ile Arg Ser Arg Ser Trp Pro Leu Ile
                715             720                 725

GTG GCG ACG ACA GTG AGC TTG GAT GAA GAA ATG TGG GAC AAG    5821
Val Ala Thr Thr Val Ser Leu Asp Glu Glu Met Trp Asp Lys
                730             735

TGT GCA CAG ATT GGA ATC AAT GGA GTT GTG AGA AAG CCA GTG    5863
Cys Ala Gln Ile Gly Ile Asn Gly Val Val Arg Lys Pro Val
740             745                 750

GTG TTA AGA GCT ATG GAG AGT GAG CTC CGA AGA GTA TTG TTG    5905
Val Leu Arg Ala Met Glu Ser Glu Leu Arg Arg Val Leu Leu
    755             760                 765

CAA GCT GAC CAA CTT CTC TAAGTTGTTA TCTCAACTTC TCTTCTACAT   5953
Gln Ala Asp Gln Leu Leu
            770

TCAAAATTTT TACACCATAG ATTTATGTCA AATATATCAA AATGAAATTT     6003

CGAAATTGTT ATTATATATA CCACCCATAT CTCTATGATT TGTACATCCT     6053

GTTTTTTTTT GTTCTTTTTC TCATTTTGAA CCCCACGAAA TTGCATTGAA     6103

TCTTAGTATT TCGTAGGGTC AAGAAGGAGT CAGTTTCGTA GTTTTTTGTT     6153

TTCTTTATGT TACGAACTTA CGAAACTGAA TATGGCATTA TAGAGTTTT      6202
```

FIG. 14F

```
ATG GTT AAA GAA ATA GCT TCT TGG TTA TTG ATA CTA TCA ATG            42
Met Val Lys Glu Ile Ala Ser Trp Leu Leu Ile Leu Ser Met
 1               5                   10

GTG GTG TTT GTT TCT CCG GTT TTA GCT ATA AAC GGC GGT GGT            84
Val Val Phe Val Ser Pro Val Leu Ala Ile Asn Gly Gly Gly
 15              20                  25

TAT CCA CGA TGT AAC TGC GAA GAC GAA GGA AAC AGT TTC TGG           126
Tyr Pro Arg Cys Asn Cys Glu Asp Glu Gly Asn Ser Phe Trp
         30              35                  40

AGT ACA GAG AAC ATT CTA GAA ACT CAA AGA GTA AGC GAT TTC           168
Ser Thr Glu Asn Ile Leu Glu Thr Gln Arg Val Ser Asp Phe
             45                  50                  55

TTA ATC GCA GTA GCT TAT TTC TCA ATC CCT ATT GAG TTA CTT           210
Leu Ile Ala Val Ala Tyr Phe Ser Ile Pro Ile Glu Leu Leu
                 60                  65                  70

TAC TTC GTG AGT TGT TCC AAT GTT CCA TTC AAA TGG GTT CTC           252
Tyr Phe Val Ser Cys Ser Asn Val Pro Phe Lys Trp Val Leu
                 75                  80

TTT GAG TTT ATC GCC TTC ATT GTT CTT TGT GGT ATG ACT CAT           294
Phe Glu Phe Ile Ala Phe Ile Val Leu Cys Gly Met Thr His
 85                  90                  95

CTT CTT CAT GGT TGG ACT TAC TCT GCT CAT CCA TTT AGA TTA           336
Leu Leu His Gly Trp Thr Tyr Ser Ala His Pro Phe Arg Leu
     100                 105                 110

ATG ATG GCG TTT ACT GTT TTC AAG ATG TTG ACT GCT TTA GTC           378
Met Met Ala Phe Thr Val Phe Lys Met Leu Thr Ala Leu Val
         115                 120                 125

TCT TGT GCT ACT GCG ATT ACG CTT ATT ACT TTG ATT CCT CTG           420
Ser Cys Ala Thr Ala Ile Thr Leu Ile Thr Leu Ile Pro Leu
             130                 135                 140

CTT TTG AAA GTT AAA GTT AGA GAG TTT ATG CTT AAG AAG AAA           462
Leu Leu Lys Val Lys Val Arg Glu Phe Met Leu Lys Lys Lys
                 145                 150

GCT CAT GAG CTT GGT CGT GAA GTT GGT TTG ATT TTG ATT AAG           504
Ala His Glu Leu Gly Arg Glu Val Gly Leu Ile Leu Ile Lys
 155                 160                 165

AAA GAG ACT GGC TTT CAT GTT CGT ATG CTT ACT CAA GAG ATT           546
Lys Glu Thr Gly Phe His Val Arg Met Leu Thr Gln Glu Ile
     170                 175                 180

CGT AAG TCT TTG GAT CGT CAT ACG ATT CTT TAT ACT ACT TTG           588
Arg Lys Ser Leu Asp Arg His Thr Ile Leu Tyr Thr Thr Leu
         185                 190                 195

GTT GAG CTT TCG AAG ACT TTA GGG TTG CAG AAT TGT GCG GTT           630
Val Glu Leu Ser Lys Thr Leu Gly Leu Gln Asn Cys Ala Val
             200                 205                 210

TGG ATG CCG AAT GAC GGT GGA ACG GAG ATG GAT TTG ACT CAT           672
Trp Met Pro Asn Asp Gly Gly Thr Glu Met Asp Leu Thr His
                 215                 220
```

FIG. 15A

| | | | | | | | | | | | | | |
|---|---|---|---|---|---|---|---|---|---|---|---|---|---|
| GAG | TTG | AGA | GGG | AGA | GGT | GGT | TAT | GGT | GGT | TGT | TCT | GTT | TCT | 714 |
| Glu | Leu | Arg | Gly | Arg | Gly | Gly | Tyr | Gly | Gly | Cys | Ser | Val | Ser |
| 225 | | | | | 230 | | | | | 235 | | | |

ATG GAG GAT TTG GAT GTT GTT AGG ATT AGG GAG AGT GAT GAA  756
Met Glu Asp Leu Asp Val Val Arg Ile Arg Glu Ser Asp Glu
    240              245              250

GTG AAT GTG TTG AGT GTT GAC TCG TCC ATT GCT CGA GCT AGT  798
Val Asn Val Leu Ser Val Asp Ser Ser Ile Ala Arg Ala Ser
        255              260              265

GGT GGT GGT GGG GAT GTT AGT GAG ATT GGT GCC GTG GCT GCT  840
Gly Gly Gly Gly Asp Val Ser Glu Ile Gly Ala Val Ala Ala
            270              275              280

ATT AGA ATG CCG ATG CTT CGT GTT TCG GAT TTT AAT GGA GAG  882
Ile Arg Met Pro Met Leu Arg Val Ser Asp Phe Asn Gly Glu
                285              290

CTA AGT TAT GCG ATA CTT GTT TGT GTT TTA CCG GGC GGG ACC  924
Leu Ser Tyr Ala Ile Leu Val Cys Val Leu Pro Gly Gly Thr
295              300              305

CGT CGG GAT TGG ACT TAT CAG GAG ATT GAG ATT GTT AAA GTT  966
Arg Arg Asp Trp Thr Tyr Gln Glu Ile Glu Ile Val Lys Val
    310              315              320

GTG GCG GAT CAA GTA ACC GTT GCG TTA GAT CAT GCA GCG GTT  1008
Val Ala Asp Gln Val Thr Val Ala Leu Asp His Ala Ala Val
        325              330              335

CTT GAA GAG TCT CAG CTT ATG AGG GAG AAG CTG GCG GAA CAG  1050
Leu Glu Glu Ser Gln Leu Met Arg Glu Lys Leu Ala Glu Gln
            340              345              350

AAC AGG GCG TTG CAG ATG GCG AAG AGA GAC GCG TTG AGA GCG  1092
Asn Arg Ala Leu Gln Met Ala Lys Arg Asp Ala Leu Arg Ala
                355              360

AGC CAA GCG AGG AAT GCG TTT CAG AAA ACG ATG AGC GAA GGG  1134
Ser Gln Ala Arg Asn Ala Phe Gln Lys Thr Met Ser Glu Gly
365              370              375

ATG AGG CGT CCT ATG CAT TCG ATA CTC GGT CTT TTG TCG ATG  1176
Met Arg Arg Pro Met His Ser Ile Leu Gly Leu Leu Ser Met
    380              385              390

ATT CAG GAC GAG AAG TTG AGT GAC GAG CAG AAA ATG ATT GTT  1218
Ile Gln Asp Glu Lys Leu Ser Asp Glu Gln Lys Met Ile Val
        395              400              405

GAT ACG ATG GTT AAA ACA GGG AAT GTT ATG TCG AAT TTG GTG  1260
Asp Thr Met Val Lys Thr Gly Asn Val Met Ser Asn Leu Val
            410              415              420

GGG GAC TCT ATG GAT GTG CCT GAC GGT AGA TTT GGT ACG GAG  1302
Gly Asp Ser Met Asp Val Pro Asp Gly Arg Phe Gly Thr Glu
                425              430

ATG AAA CCG TTT AGT CTG CAT CGT ACG ATC CAT GAA GCA GCT  1344
Met Lys Pro Phe Ser Leu His Arg Thr Ile His Glu Ala Ala
435              440              445

FIG. 15B

| | |
|---|---|
| TGT ATG GCG AGA TGT TTG TGT CTA TGC AAT GGA ATT AGG TTC<br>Cys Met Ala Arg Cys Leu Cys Leu Cys Asn Gly Ile Arg Phe<br>    450                 455                 460 | 1386 |
| TTG GTT GAC GCG GAG AAG TCT CTA CCT GAT AAT GTA GTA GGT<br>Leu Val Asp Ala Glu Lys Ser Leu Pro Asp Asn Val Val Gly<br>        465                 470                 475 | 1428 |
| GAT GAA AGA AGG GTC TTT CAA GTG ATA CTT CAT ATG GTT GGT<br>Asp Glu Arg Arg Val Phe Gln Val Ile Leu His Met Val Gly<br>            480                 485                 490 | 1470 |
| AGT TTA GTA AAG CCT AGA AAA CGT CAA GAA GGA TCT TCA TTG<br>Ser Leu Val Lys Pro Arg Lys Arg Gln Glu Gly Ser Ser Leu<br>                495                 500 | 1512 |
| ATG TTT AAG GTT TTG AAA GAA AGA GGA AGC TTG GAT AGG AGT<br>Met Phe Lys Val Leu Lys Glu Arg Gly Ser Leu Asp Arg Ser<br>505                 510                 515 | 1554 |
| GAT CAT AGA TGG GCT GCT TGG AGA TCA CCG GCT TCT TCA GCA<br>Asp His Arg Trp Ala Ala Trp Arg Ser Pro Ala Ser Ser Ala<br>        520                 525                 530 | 1596 |
| GAT GGA GAT GTG TAT ATA AGA TTT GAA ATG AAT GTA GAG AAT<br>Asp Gly Asp Val Tyr Ile Arg Phe Glu Met Asn Val Glu Asn<br>            535                 540                 545 | 1636 |
| GAT GAT TCA AGT TCT CAA TCA TTT GCT TCT GTT TCC TCC AGA<br>Asp Asp Ser Ser Ser Gln Ser Phe Ala Ser Val Ser Ser Arg<br>                550                 555                 560 | 1680 |
| GAT CAA GAA GTT GGT GAT GTT AGA TTC TCC GGC GGC TAT GGG<br>Asp Gln Glu Val Gly Asp Val Arg Phe Ser Gly Gly Tyr Gly<br>                    565                 570 | 1722 |
| TTA GGA CAA GAT CTA AGC TTT GGT GTT TGT AAG AAA GTG GTG<br>Leu Gly Gln Asp Leu Ser Phe Gly Val Cys Lys Lys Val Val<br>575                 580                 585 | 1764 |
| CAG TTG ATT CAT GGG AAT ATC TCG GTG GTC CCT GGC TCG GAT<br>Gln Leu Ile His Gly Asn Ile Ser Val Val Pro Gly Ser Asp<br>        590                 595                 600 | 1806 |
| GGT TCA CCG GAG ACC ATG TCG TTG CTC CTT CGG TTT CGA CGT<br>Gly Ser Pro Glu Thr Met Ser Leu Leu Leu Arg Phe Arg Arg<br>            605                 610                 615 | 1848 |
| AGA CCC TCC ATA TCT GTC CAT GGA TCC AGC GAG TCG CCA GCT<br>Arg Pro Ser Ile Ser Val His Gly Ser Ser Glu Ser Pro Ala<br>                620                 625                 630 | 1890 |
| CCT GAC CAC CAC GCT CAC CCA CAT TCG AAT TCT CTG TTA CGT<br>Pro Asp His His Ala His Pro His Ser Asn Ser Leu Leu Arg<br>                    635                 640 | 1932 |
| GGC TTA CAA GTT TTA TTG GTA GAC ACC AAC GAT TCG AAC CGG<br>Gly Leu Gln Val Leu Leu Val Asp Thr Asn Asp Ser Asn Arg<br>645                 650                 655 | 1974 |
| GCA GTT ACA CGT AAA CTC TTA GAG AAA CTC GGG TGC GAT GTA<br>Ala Val Thr Arg Lys Leu Leu Glu Lys Leu Gly Cys Asp Val<br>        660                 665                 670 | 2016 |

FIG. 15C

```
ACC GCG GTT TCC TCT GGA TTC GAT TGC CTT ACC GCC ATT GCT              2058
Thr Ala Val Ser Ser Gly Phe Asp Cys Leu Thr Ala Ile Ala
        675                 680                 685

CCC GGC TCG TCC TCG CCT TCT ACT TCG TTT CAA GTG GTG GTG              2100
Pro Gly Ser Ser Ser Pro Ser Thr Ser Phe Gln Val Val Val
        690                 695                 700

CTT GAT CTT CAA ATG GCA GAG ATG GAC GGT TAT GAA GTG GCC              2142
Leu Asp Leu Gln Met Ala Glu Met Asp Gly Tyr Glu Val Ala
        705                 710

ATG AGG ATC AGG AGT CGA TCT TGG CCG TTG ATT GTG GCG ACG              2184
Met Arg Ile Arg Ser Arg Ser Trp Pro Leu Ile Val Ala Thr
715                 720                 725

ACA GTG AGC TTG GAT GAA GAA ATG TGG GAC AAG TGT GCA CAG              2226
Thr Val Ser Leu Asp Glu Glu Met Trp Asp Lys Cys Ala Gln
        730                 735                 740

ATT GGA ATC AAT GGA GTT GTG AGA AAG CCA GTG GTG TTA AGA              2268
Ile Gly Ile Asn Gly Val Val Arg Lys Pro Val Val Leu Arg
        745                 750                 755

GCT ATG GAG AGT GAG CTC CGA AGA GTA TTG TTG CAA GCT GAC              2310
Ala Met Glu Ser Glu Leu Arg Arg Val Leu Leu Gln Ala Asp
        760                 765                 770

CAA CTT CTC TAAGTTGTTA TCTCAACTTC TCTTCTACAT TCAAAATTTT              2259
Gln Leu Leu

TACACCATAG ATTTATGTCA AATATATCAA AATGAAATTT CGAAA                    2404
```

FIG. 15D

```
TTTTTTTTTT GTCAAAAGCT CGATGTAAAA ATCCGATGGC CACAAGCAAA         50

ACGACAGGTT CCAACTTCAC GGAGATTGTG AAAATGGAGT AGTAGTTCAG        100

TGAAGTAGTA GATACTGAGA TCGCATTCTC CGGCGTCGTT TTTCACATCG        150

AAATAGTCGT GTAAAAAAAT GAAAAATTG CTGCGAGACA GGTATGTGTC         200

GCAGCAGGAA ATAGCATCTT AAAGGAAGGA AGGAAGGAAA CTCGAAAGTT        250

ACTAAAAATT TTTGATTCTT TGGGACGAAA CGAGATA ATG GAA TCC          296
                                          Met Glu Ser
                                           1

TGT GAT TGC ATT GAG GCT TTA CTG CCA ACT GGT GAC CTG CTG       338
Cys Asp Cys Ile Glu Ala Leu Leu Pro Thr Gly Asp Leu Leu
     5               10                  15

GTT AAA TAC CAA TAC CTC TCA GAT TTC TTC ATT GCT GTA GCC       380
Val Lys Tyr Gln Tyr Leu Ser Asp Phe Phe Ile Ala Val Ala
        20              25                  30

TAC TTT TCC ATT CCG TTG GAG CTT ATT TAT TTT GTC CAC AAA       422
Tyr Phe Ser Ile Pro Leu Glu Leu Ile Tyr Phe Val His Lys
            35              40                  45

TCT GCA TGC TTC CCA TAC AGA TGG GTC CTC ATG CAA TTT GGT       464
Ser Ala Cys Phe Pro Tyr Arg Trp Val Leu Met Gln Phe Gly
                50              55

GCT TTT ATT GTG CTC TGT GGA GCA ACA CAC TTT ATT AGC TTG       506
Ala Phe Ile Val Leu Cys Gly Ala Thr His Phe Ile Ser Leu
 60              65                  70

TGG ACC TTC TTT ATG CAC TCT AAG ACG GTC GCT GTG GTT ATG       548
Trp Thr Phe Phe Met His Ser Lys Thr Val Ala Val Val Met
     75                  80              85

ACC ATA TCA AAA ATG TTG ACA GCT GCC GTG TCC TGT ATC ACA       590
Thr Ile Ser Lys Met Leu Thr Ala Ala Val Ser Cys Ile Thr
        90                  95                 100

GCT TTG ATG CTT GTT CAC ATT ATT CCT GAT TTG CTA AGT GTT       632
Ala Leu Met Leu Val His Ile Ile Pro Asp Leu Leu Ser Val
           105                 110                 115

AAA ACG CGA GAG TTG TTC TTG AAA ACT CGA GCT GAA GAG CTT       674
Lys Thr Arg Glu Leu Phe Leu Lys Thr Arg Ala Glu Glu Leu
               120                 125

GAC AAG GAA ATG GGC CTA ATA ATA AGA CAA GAA GAA ACT GGC       716
Asp Lys Glu Met Gly Leu Ile Ile Arg Gln Glu Glu Thr Gly
130             135                 140

AGA CAT GTC AGG ATG CTG ACT CAT GAG ATA AGA AGC ACA CTC       758
Arg His Val Arg Met Leu Thr His Glu Ile Arg Ser Thr Leu
145                 150                 155

GAC AGA CAC ACA ATC TTG AAG ACT ACT CTT GTG GAG CTA GGT       800
Asp Arg His Thr Ile Leu Lys Thr Thr Leu Val Glu Leu Gly
         160                 165                 170
```

*FIG. 16A*

```
AGG ACC TTA GAC CTG GCA GAA TGT GCT TTG TGG ATG CCA TGC    842
Arg Thr Leu Asp Leu Ala Glu Cys Ala Leu Trp Met Pro Cys
            175                 180                 185

CAA GGA GGC CTG ACT TTG CAA CTT TCC CAT AAT TTA AAC AAT    884
Gln Gly Gly Leu Thr Leu Gln Leu Ser His Asn Leu Asn Asn
                190                 195

CTA ATA CCT CTG GGA TCT ACT GTG CCA ATT AAT CTT CCT ATT    926
Leu Ile Pro Leu Gly Ser Thr Val Pro Ile Asn Leu Pro Ile
200                 205                 210

ATC AAT GAA ATT TTT AGT AGC CCT GAA GCA ATA CAA ATT CCA    968
Ile Asn Glu Ile Phe Ser Ser Pro Glu Ala Ile Gln Ile Pro
        215                 220                 225

CAT ACA AAT CCT TTG GCA AGG ATG AGG AAT ACT GTT GGT AGA   1010
His Thr Asn Pro Leu Ala Arg Met Arg Asn Thr Val Gly Arg
            230                 235                 240

TAT ATT CCA CCA GAA GTA GTT GCT GTT CGT GTA CCG CTT TTA   1052
Tyr Ile Pro Pro Glu Val Val Ala Val Arg Val Pro Leu Leu
                245                 250                 255

CAC CTC TCA AAT TTT ACT AAT GAC TGG GCT GAA CTG TCT ACT   1094
His Leu Ser Asn Phe Thr Asn Asp Trp Ala Glu Leu Ser Thr
                    260                 265

AGA AGT TAT GCG GTT ATG GTT CTG GTT CTC CCG ATG AAT GGC   1136
Arg Ser Tyr Ala Val Met Val Leu Val Leu Pro Met Asn Gly
270                 275                 280

TTA AGA AAG TGG CGT GAA CAT GAG TTA GAA CTT GTG CAA GTT   1178
Leu Arg Lys Trp Arg Glu His Glu Leu Glu Leu Val Gln Val
        285                 290                 295

GTC GCA GAT CAG GTT GCT GTC GCT CTT TCA CAT GCT GCA ATT   1220
Val Ala Asp Gln Val Ala Val Ala Leu Ser His Ala Ala Ile
            300                 305                 310

TTA GAA GAT TCC ATG CGA GCC CAT GAT CAG CTC ATG GAA CAG   1262
Leu Glu Asp Ser Met Arg Ala His Asp Gln Leu Met Glu Gln
                315                 320                 325

AAT ATT GCT TTG GAT GTA GCT CGA CAA GAA GCA GAG ATG GCC   1304
Asn Ile Ala Leu Asp Val Ala Arg Gln Glu Ala Glu Met Ala
                    330                 335

ATC CGT GCA CGT AAC GAC TTC CTT GCT GTG ATG AAC CAT GAA   1346
Ile Arg Ala Arg Asn Asp Phe Leu Ala Val Met Asn His Glu
340                 345                 350

ATG AGA ACG CCC ATG CAT GCA GTT ATT GCT CTG TGC TCT CTG   1388
Met Arg Thr Pro Met His Ala Val Ile Ala Leu Cys Ser Leu
        355                 360                 365

CTT TTA GAA ACA GAC TTA ACT CCA GAG CAG AGA GTT ATG ATT   1430
Leu Leu Glu Thr Asp Leu Thr Pro Glu Gln Arg Val Met Ile
            370                 375                 380

GAG ACC ATA TTG AAG AGC AGC AAT CTT CTT GCA ACA CTG ATA   1472
Glu Thr Ile Leu Lys Ser Ser Asn Leu Leu Ala Thr Leu Ile
                385                 390                 395
```

FIG. 16B

| | | | | | | | | | | | | | |
|---|---|---|---|---|---|---|---|---|---|---|---|---|---|
| AAT | GAT | GTT | CTA | GAT | CTT | TCT | AGA | CTT | GAA | GAT | GGT | ATT | CTT | 1514 |
| Asn | Asp | Val | Leu | Asp<br>400 | Leu | Ser | Arg | Leu | Glu<br>405 | Asp | Gly | Ile | Leu | |

```
AAT GAT GTT CTA GAT CTT TCT AGA CTT GAA GAT GGT ATT CTT   1514
Asn Asp Val Leu Asp Leu Ser Arg Leu Glu Asp Gly Ile Leu
            400             405

GAA CTA GAA AAC GGA ACA TTC AAT CTT CAT GGC ATC TTA AGA   1556
Glu Leu Glu Asn Gly Thr Phe Asn Leu His Gly Ile Leu Arg
410             415             420

GAG GCC GTT AAT TTG ATA AAG CCA ATT GCA TCT TTG AAG AAA   1598
Glu Ala Val Asn Leu Ile Lys Pro Ile Ala Ser Leu Lys Lys
        425             430             435

TTA TCT ATA ACT CTT GCT TTG GCT CTG GAT TTA CCT ATT CTT   1640
Leu Ser Ile Thr Leu Ala Leu Ala Leu Asp Leu Pro Ile Leu
            440             445             450

GCT GTG GGT GAT GCA AAA CGT CTT ATC CAA ACT CTC TTA AAC   1682
Ala Val Gly Asp Ala Lys Arg Leu Ile Gln Thr Leu Leu Asn
                455             460             465

GTG GTG GGA AAT GCT GTG AAG TTC ACT AAA GAA GGA CAT ATT   1724
Val Val Gly Asn Ala Val Lys Phe Thr Lys Glu Gly His Ile
                470             475

TCA ATT GAG GCT TCA GTT GCC AAA CCA GAG TAT GCG AGA GAT   1766
Ser Ile Glu Ala Ser Val Ala Lys Pro Glu Tyr Ala Arg Asp
480             485             490

TGT CAT CCT CCT GAA ATG TTC CCT ATG CCA AGT GAT GGC CAG   1808
Cys His Pro Pro Glu Met Phe Pro Met Pro Ser Asp Gly Gln
    495             500             505

TTT TAT TTG CGT GTC CAG GTT AGA GAT ACT GGG TGT GGA ATT   1850
Phe Tyr Leu Arg Val Gln Val Arg Asp Thr Gly Cys Gly Ile
            510             515             520

AGC CCA CAA GAT ATA CCA CTA GTA TTC ACC AAA TTT GCA GAG   1892
Ser Pro Gln Asp Ile Pro Leu Val Phe Thr Lys Phe Ala Glu
            525             530             535

TCA CGG CCT ACG TCA AAT CGA AGT ACT GGA GGG GAA GGT CTA   1934
Ser Arg Pro Thr Ser Asn Arg Ser Thr Gly Gly Glu Gly Leu
                540             545

GGG CTT GCC ATT TGG AGA CGA TTT ATT CAA CTT ATG AAA GGT   1976
Gly Leu Ala Ile Trp Arg Arg Phe Ile Gln Leu Met Lys Gly
550             555             560

AAC ATT TGG ATT GAG AGT GAG GGC CCT GGA AAG GGA ACC ACT   2018
Asn Ile Trp Ile Glu Ser Glu Gly Pro Gly Lys Gly Thr Thr
        565             570             575

GTC ACG TTT GTA GTG AAA CTC GGA ATC TGT CAC CAT CCA AAT   2060
Val Thr Phe Val Val Lys Leu Gly Ile Cys His His Pro Asn
            580             585             590

GCA TTA CCT CTG CTA CCT ATG CCT CCC AGA GGC AGA TTG AAC   2102
Ala Leu Pro Leu Leu Pro Met Pro Pro Arg Gly Arg Leu Asn
            595             600             605

AAA GGT AGC GAT GAT CTC TTC AGG TAT AGA CAG TTC CGT GGA   2144
Lys Gly Ser Asp Asp Leu Phe Arg Tyr Arg Gln Phe Arg Gly
                610             615
```

FIG. 16C

| | |
|---|---|
| GAT GAT GGT GGG ATG TCT GTG AAT GCT CAA CGC TAT CAA AGA<br>Asp Asp Gly Gly Met Ser Val Asn Ala Gln Arg Tyr Gln Arg<br>620                       625                    630 | 2186 |
| AGT ATG TAA A TGACAAAGG ACATTGGTGT GACAAAGAAC<br>Ser Met  *<br>      635 | 2226 |
| ATTAAATCAT GACTAGTGAA TTTGAGATTT CTTCACTGTT CTGTACACTC | 2276 |
| CAAATGGCAC AGTTTGTCTT GTAACTAACC TAATTCAATG CTCGTAAAGT | 2326 |
| GAGTACTGGA GTATCTTGAA AATGTAACTA TCGAATTTAT ACATCGAGCT | 2376 |
| TTTGACAAAA AAAAAAAAAA AAAAAAAA | 2405 |

*FIG. 16D*

```
Tetr    1  MESCDCIEALLPTGDLLVKYQYLSDFFIAVAYFSIPLELIYFVHKSACFP        50
           ||| |:.|||:..|.::|||::|||||||||||||||||||||.||||.||
Etr1    1  MEVCNCIEPQWPADELLMKYQYISDFFIAVAYFSIPLELIYFVKKSAVFP        50

51  YRWVLMQFGAFIVLCGATHFISLWTFFMHSKTVAVVMTISKMLTAAVSCI       100
           |||||:|||||||||||||||..|||.|..||||.||||:|.|||.||.|
       51  YRWVLVQFGAFIVLCGATHLINLWTFTTHSRTVALVMTTAKVLTAVVSCA       100

101  TALMLVHIIPDLLSVKTRELFLKTRAEELDKEMGLIIRQEETGRHVRMLT       150
           ||||||||||||||||||||||||.|:.||:|.||:|||||||||||||||
      101  TALMLVHIIPDLLSVKTRELFLKNKAAELDREMGLIRTQEETGRHVRMLT       150

151  HEIRSTLDRHTILKTTLVELGRTLDLAECALWMPCQGGLTLQLSHNLNNI       200
           |||||||||||||||||||||||||..:.||||||..:...|..:.||.:
      151  HEIRSTLDRHTILKTTLVELGRTLALEECALWMPTRTGLELQLSYTLRHQ       200

201  IPLGSTVPINLPIINEIFSSPEAIQIPHTNPLARMRNTVGRYIPPEVVAV       250
           .|:|.||||:|:..:|:..::.|:|:|..||||||||||:|||||||||||
      201  HPVEYTVPIQLPVINQVFGTSRAVKISPNSPVARLRPVSGKYMLGEVVAV       250

251  RVPLLHLSNF.TNDWAELSTRSYAVMVLVLPMNGLRKWREHELELVQVVA       299
           |||||||||||.|:|||||||:||:|||:||:::.||||:.|||||:|||
      251  RVPLLHLSNFQINDWPELSTKRYALMVLMLPSDSARQWHVHELELVEVVA       300

300  DQVAVALSHAAILEDS                                      315
           ||||||||||||||:|
      301  DQVAVALSHAAILEES                                      316
```

FIG. 17

| | | | |
|---|---|---|---|
| AGATCTGGTA | CTACCAAAAG | GTATCCAATT | AATCCATGCT | TGGCCTCCCA | 50 |
| TTACAATGCC | TGTAAGAAAT | AATTGTTCTT | TCCACCTCCA | CAACTAATTG | 100 |
| TCGAACTATT | ATATCTATCT | TTATTCCCTT | AAATGTGAAA | CGAATTACAC | 150 |
| AGACTATTTG | GCGCTACTTT | TTTCCTAGAT | ATATTGAAGA | CCTAGTTTCT | 200 |
| TATATTTGTG | GGAAGCATTT | GGAAGTTCTA | TAAGAACTAT | ATCATGTTCG | 250 |
| AAAACATTCT | TATAATTTTC | GACAAGATTG | CTGAAGGAGT | GTCTTATCTT | 300 |
| TTATGTATTC | TTGACTAGAG | GAGTTTAATA | AAAAGAAAAT | AGAAAGGAAC | 350 |
| AAAGAAACGT | ACAAGTGTAT | AAAAGGAGTT | GGGGCAAAGA | CATCAGAAAC | 400 |
| ATTTAGACCT | ACGATTTCAT | CCTACATGTT | ATGGTTTTAG | TTCGTTAGAG | 450 |
| GTTTTAACAT | ATTAAATCAG | CAAAGTTGTG | ACATACATAA | AGTGCATAAC | 500 |
| ATAAAGATGA | AATTCACAAT | TTGCTGGATC | TTTTGGTGCA | AGGGAACTAT | 550 |
| TTTTTACACT | ATAAGTTAGC | TGTTAATTTC | AATATTGGCT | CTTCTACACC | 600 |
| TTGTTGTTCT | TGAGTATAAT | TCTATTTTGC | ATCAAACATA | TGTCAGAACT | 650 |
| TATGCTGCAA | TTAAATATAT | TCAGGTTGTT | TAACTCTTGT | ACAGCTTGTT | 700 |
| ATTCTTCTGA | GGTCTATTTC | CTTCTCCTTA | TTTGCTAACT | TGTGCTGCAG | 750 |

```
TTATCTTCCA TC GTG GAG TCA TGT AAC TGC ATC ATT GAC CCA          792
            Val Glu Ser Cys Asn Cys Ile Ile Asp Pro
            1             5                       10

CAG TTG CCT GCT GAC GAC TTG CTA ATG AAG TAT CAG TAC ATT        834
Gln Leu Pro Ala Asp Asp Leu Leu Met Lys Tyr Gln Tyr Ile
            15              20

TCT GAT TTT TTC ATA GCA CTT GCT TAT TTC TCC ATT CCA GTG        876
Ser Asp Phe Phe Ile Ala Leu Ala Tyr Phe Ser Ile Pro Val
25              30                  35

GAG TTG ATA TAC TTC GTT AAG AAG TCT GCT GTC TTT CCA TAT        918
Glu Leu Ile Tyr Phe Val Lys Lys Ser Ala Val Phe Pro Tyr
        40              45              50

AGA TGG GTT CTT GTG CAG TTC GGT GCT TTC ATA GTT CTT TGT        960
Arg Trp Val Leu Val Gln Phe Gly Ala Phe Ile Val Leu Cys
        55              60              65

GGA GCA ACC CAT CTT ATC AAC TTA TGG ACA TTT AAT ATG CAT       1002
Gly Ala Thr His Leu Ile Asn Leu Trp Thr Phe Asn Met His
        70              75              80

ACA AGG AAT GTG GCA ATA GTA ATG ACT ACT GCA AAG GCC TTG       1044
Thr Arg Asn Val Ala Ile Val Met Thr Thr Ala Lys Ala Leu
                85              90

ACT GCA CTG GTG TCA TGT ATA ACT GCT CTC ATG CTT GTC CAC       1086
Thr Ala Leu Val Ser Cys Ile Thr Ala Leu Met Leu Val His
95              100                 105
```

*FIG. 18A*

| | | | | | | | | | | | | | | |
|---|---|---|---|---|---|---|---|---|---|---|---|---|---|---|
| ATC | ATT | CCT | GAT | TTA | TTA | AGT | GTC | AAA | ACT | AGA | GAA | CTG | TTC | 1128 |
| Ile | Ile | Pro | Asp | Leu | Leu | Ser | Val | Lys | Thr | Arg | Glu | Leu | Phe | |
| | 110 | | | | 115 | | | | | 120 | | | | |
| TTG | AAA | AAG | AAA | GCT | GCA | CAG | CTT | GAC | CGT | GAA | ATG | GGT | ATT | 1170 |
| Leu | Lys | Lys | Lys | Ala | Ala | Gln | Leu | Asp | Arg | Glu | Met | Gly | Ile | |
| | | 125 | | | | 130 | | | | | 135 | | | |
| ATT | CGG | ACT | CAG | GAG | GAG | ACA | GGT | AGA | CAT | GTT | AGA | ATG | CTA | 1212 |
| Ile | Arg | Thr | Gln | Glu | Glu | Thr | Gly | Arg | His | Val | Arg | Met | Leu | |
| | | | 140 | | | | 145 | | | | | 150 | | |
| ACT | CAT | GAA | ATC | CGA | AGC | ACT | CTT | GAT | AGA | CAT | ACT | ATT | TTA | 1254 |
| Thr | His | Glu | Ile | Arg | Ser | Thr | Leu | Asp | Arg | His | Thr | Ile | Leu | |
| | | | | 155 | | | | | 160 | | | | | |
| AAG | ACT | ACA | CTT | GTT | GAG | CTA | GGA | AGA | ACA | TTG | GCA | TTG | GAA | 1296 |
| Lys | Thr | Thr | Leu | Val | Glu | Leu | Gly | Arg | Thr | Leu | Ala | Leu | Glu | |
| 165 | | | | | 170 | | | | | 175 | | | | |
| GAG | TGT | GCA | TTA | TGG | ATG | CCA | ACA | CGT | ACT | GGA | CTA | GAG | CTT | 1338 |
| Glu | Cys | Ala | Leu | Trp | Met | Pro | Thr | Arg | Thr | Gly | Leu | Glu | Leu | |
| | | 180 | | | | 185 | | | | | 190 | | | |
| CAG | CTT | TCT | TAC | ACT | TTA | CGA | CAC | CAA | AAT | CCA | GTT | GGA | TTA | 1380 |
| Gln | Leu | Ser | Tyr | Thr | Leu | Arg | His | Gln | Asn | Pro | Val | Gly | Leu | |
| | | | 195 | | | | | 200 | | | | | 205 | |
| ACT | GTA | CCC | ATT | CAA | CTT | CCT | GTA | ATC | AAT | CAA | GTT | TTC | GGT | 1422 |
| Thr | Val | Pro | Ile | Gln | Leu | Pro | Val | Ile | Asn | Gln | Val | Phe | Gly | |
| | | | | 210 | | | | | 215 | | | | | 220 |
| ACA | AAT | CAT | GTC | GTG | AAA | ATA | TCA | CCA | AAT | TCT | CCT | GTC | GCA | 1464 |
| Thr | Asn | His | Val | Val | Lys | Ile | Ser | Pro | Asn | Ser | Pro | Val | Ala | |
| | | | | | 225 | | | | | 230 | | | | |
| AGA | CTT | CGA | CCT | GCT | GGG | AAA | TAC | ATG | CCT | GGT | GAG | GTG | GTT | 1506 |
| Arg | Leu | Arg | Pro | Ala | Gly | Lys | Tyr | Met | Pro | Gly | Glu | Val | Val | |
| 235 | | | | | 240 | | | | | 245 | | | | |
| GCT | GTC | AGG | GTT | CCA | CTT | CTG | CAT | CTG | TCG | AAC | TTT | CAG | ATT | 1548 |
| Ala | Val | Arg | Val | Pro | Leu | Leu | His | Leu | Ser | Asn | Phe | Gln | Ile | |
| | | 250 | | | | | 255 | | | | | 260 | | |
| AAT | GAT | TGG | CCT | GAA | CTT | TCA | ACA | AAG | CGC | TAT | GCT | TTA | ATG | 1590 |
| Asn | Asp | Trp | Pro | Glu | Leu | Ser | Thr | Lys | Arg | Tyr | Ala | Leu | Met | |
| | | 265 | | | | | 270 | | | | | 275 | | |
| GTT | CTG | ATG | CTT | CCT | TCA | GAC | AGT | GCA | AGA | CAA | TGG | CAT | GTT | 1632 |
| Val | Leu | Met | Leu | Pro | Ser | Asp | Ser | Ala | Arg | Gln | Trp | His | Val | |
| | | | 280 | | | | | 285 | | | | | 290 | |
| CAT | GAG | CTG | GAG | CTT | GTT | GAA | GTG | GTA | GCT | GAT | CAG | GTT | | 1671 |
| His | Glu | Leu | Glu | Leu | Val | Glu | Val | Val | Ala | Asp | Gln | Val | | |
| | | | | 295 | | | | | 300 | | | | | |

| | | | | |
|---|---|---|---|---|
| TGATTTTTGT | TATTGAAAAT | TCCTTAATAT | AATGTTAAAA | TTTCTCTTTT | 1721 |
| ATATATTTTT | GGGTTGAACA | CAACCACGTT | GACATACTGA | GTTCTGGGTG | 1771 |
| TAAAATTAGA | CATGGAGAAG | ACCAATTACA | AAAATCTGAG | AATCTGCTAG | 1821 |
| CAGAATCACA | AGGCTTAGTT | GTTCTTAGTA | TTATGGTTTT | ATCCATTGGA | 1871 |

FIG. 18B

| | |
|---|---|
| ATTGCACAGC AGAATTGTTA TTACTGTTAT TTTTTTTTAA AATTTTCAAA | 1921 |
| GATAAATCAA AAGCTGAACT ATATGACTTT TTGCATACTT CGTCTGCTGA | 1971 |
| TTGCTTTTTG GTGATGGAAT AGTTAGGCTG GGTTGTGGAT GAGTATATCA | 2021 |
| TAGTAGATTT TCTGATAGGA TCTTAACTCC TTGGCTTTTG TTTTCTATAG | 2071 |
| ATGATCCCTT GTATTAGAAG CACGGGAAAT AGGATCGATG GTATATAGAA | 2121 |
| ATATTAGGAA CAGCTTTCTG AATCATTTGA ATATTCCTTT TATGGAACAT | 2171 |
| AGAACTCTTG ACGTGTATGT AGTTTTCTTA GTACTTTTAT CATATGAAGT | 2221 |
| GAAAATAACG TTTTGCGATA ATGTATTTGA GTGTGTAAAA TTAAATACTA | 2271 |
| CTGAGTTTTA CAAAAATAAT TCTTCAACGG AAGCCATTTA TTTTTTTTAC | 2321 |
| ATATCTGGCA TCTTACTTCT CCATCAAAGA CTTTAGAGAA CTTTAACTTT | 2371 |
| TTCATTCTGT CTCTCGTAGT GTACTGTTCT CTGATGTATG TAATTAGCTC | 2421 |
| ACTGGCAAGT AGCACACCTA GTCTTTGTTT GACTTGTTTA AAAATCATGA | 2471 |
| TGTATCATCA GTTACGGTGA AGTGTCCAAG TTTTACTGCT TTTTGCTATT | 2521 |
| TGCATTGCAG AGTCTTAAAA CATTTCAGTT ATTCCTGGAT TTCTCCTGTT | 2571 |
| TATCAATGGA AAATTCAACT ATCAACTATG CCTCAATCAA TAAATGAAAC | 2621 |
| CTCTATATCT AACCACTCCA ACTCAGATCC AGAAATCAGA TTTCAAAGAA | 2671 |
| ATTCATCATA ACTCAACTAT AGGATTGCTG TTAACCAAGA GTAATCCTCA | 2721 |
| TTTGTCCAGA CAGGCGACCA GCTATTATGC TTTCATTATG GGAAAAATTG | 2771 |
| ACAATTAATT AAAGGAAGGA ACAACTGAAG AAAAGACATC CTTGTCAGCT | 2821 |
| TCCTCTCCCA ACCCTTGCCT GAATAAGACA AAAAGTTTCT TGGAGAAAAC | 2871 |
| TCTGAATATT GGTATCCACC TCCTTTCTCC TAATTTAGGA TGCTCTATTT | 2921 |
| CTAGACATAT AGGGGAATAC TCTATTCTAG TGGTCGGTGT CTGGTTGCAA | 2971 |
| CTAGTTTTAG ATGTTTATAT GTCTTATTTG ATTTAATAAG AGCTATCCTT | 3021 |
| GAGTGCCCAA TGTGATTTAA TCTACGCTTC GGCATTTCAG GTT GCT GTT<br>                                                                                   Val Ala Val<br>                                                                                      305 | 3070 |
| GCT CTT TCA CAT GCT GCT ATA TTA GAA GAA TCA ATG AGG GCT<br>Ala Leu Ser His Ala Ala Ile Leu Glu Glu Ser Met Arg Ala<br>           310                     315                   320 | 3112 |
| AGG GAT CTT CTT ATG GAG CAG AAT GTG GCT CTT GAT CTG GCA<br>Arg Asp Leu Leu Met Glu Gln Asn Val Ala Leu Asp Leu Ala<br>                   325                             330 | 3154 |
| AGA AGA GAA GCA GAA ATG GCT GTT CGT GCA CGT AAT GAT TTC<br>Arg Arg Glu Ala Glu Met Ala Val Arg Ala Arg Asn Asp Phe<br>335                     340                       345 | 3196 |

FIG. 18C

| | |
|---|---|
| TTG GCT GTT ATG AAT CAT GAA ATG AGA ACT CCC ATG CAT GCA<br>Leu Ala Val Met Asn His Glu Met Arg Thr Pro Met His Ala<br>350                 355                 360 | 3238 |
| ATA ATT GCA CTT TCT TCC TTA CTA CAA GAA ATC GAT CTA ACT<br>Ile Ile Ala Leu Ser Ser Leu Leu Gln Glu Ile Asp Leu Thr<br>    365                 370                 375 | 3280 |
| CCA GAG CAA CGT CTG ATG GTT GAA ACA ATC CTC AAA AGC AGC<br>Pro Glu Gln Arg Leu Met Val Glu Thr Ile Leu Lys Ser Ser<br>            380                 385                 390 | 3322 |
| AAC CTT TTA GCA ACG CTC ATC AAC GAT GTC TTG GAT CTT TCA<br>Asn Leu Leu Ala Thr Leu Ile Asn Asp Val Leu Asp Leu Ser<br>                395                 400 | 3364 |
| AGG CTA GAG GAT GGA AGT CTT CAA CTT GAT ATT GGC ACT TTC<br>Arg Leu Glu Asp Gly Ser Leu Gln Leu Asp Ile Gly Thr Phe<br>405                 410                 415 | 3406 |
| AAT CTC CAT GCT TTA TTT AGA GAG GTG CCCTTCATCA CCCTCTTTTC<br>Asn Leu His Ala Leu Phe Arg Glu Val<br>    420                 425 | 3453 |
| TTTTTTACTT GCAAATTCTA GATTACCTGT CAGAAAAAAA GTGTCATTAC | 3503 |
| AGATATTTTG CACTTCAATA TGTTTGCTGG ACCTGCTGAC TGATATATGT | 3553 |
| GTCTGCTTAT TCCTGTAG GTC CAT AGC TTA ATC AAG CCT ATT GCA<br>                        Val His Ser Leu Ile Lys Pro Ile Ala<br>                                        430                 435 | 3598 |
| TCT GTG AAA AAG TCT GTT GCT CAA CTT AGT TTG TCG TCA GAT<br>Ser Val Lys Lys Ser Val Ala Gln Leu Ser Leu Ser Ser Asp<br>            440                 445                 450 | 3640 |
| TTG CCG GAA TAT GTA ATT GGG GAT GAA AAA CGG TTA ATG CAA<br>Leu Pro Glu Tyr Val Ile Gly Asp Glu Lys Arg Leu Met Gln<br>                455                 460 | 3682 |
| ATT CTC TTA AAC GTT GTT GGC AAT GCT GTA AAG TTC TCA AAG<br>Ile Leu Leu Asn Val Val Gly Asn Ala Val Lys Phe Ser Lys<br>465                 470                 475 | 3724 |
| GAA GGC AAC GTA TCA ATC TCC GCT TTT GTT GCA AAA TCA GAC<br>Glu Gly Asn Val Ser Ile Ser Ala Phe Val Ala Lys Ser Asp<br>    480                 485                 490 | 3766 |
| TCT TTA AGA GAT CCT AGA GCC CCT GAA TTT TTT GCT GTG CCT<br>Ser Leu Arg Asp Pro Arg Ala Pro Glu Phe Phe Ala Val Pro<br>            495                 500                 505 | 3808 |
| AGT GAA AAT CAC TTC TAT TTA CGG GTG CAG<br>Ser Glu Asn His Phe Tyr Leu Arg Val Gln<br>                510                 515 | 3838 |
| GTATATTTTT ACAAGCTTGA TATACTATCT TCGTAGGTTA AGGATAGTCA | 3888 |
| CAAATATGAT ATTTTAGACT TATAACTGTC AGATGTTCTG TTCTTGATAT | 3938 |
| TTGTAATATT CTAAGTAATA CTTTCTGTAG | 3968 |

FIG. 18D

| | |
|---|---|
| ATA AAA GAT ACG GGG ATA GGA ATT ACA CCA CAG GAT ATT CCC<br>Ile Lys Asp Thr Gly Ile Gly Ile Thr Pro Gln Asp Ile Pro<br>               520                        525                       530 | 4010 |
| AAC CTG TTT AGC AAG TTT ACA CAA AGC CAA GCG CTA GCA ACT<br>Asn Leu Phe Ser Lys Phe Thr Gln Ser Gln Ala Leu Ala Thr<br>               535                        540 | 4052 |
| ACA AAT TCT GGT GGC ACT GGG CTT GGT CTT GCA ATT TGT AAG<br>Thr Asn Ser Gly Gly Thr Gly Leu Gly Leu Ala Ile Cys Lys<br>545                       550                       555 | 4094 |
| AG GTACGGGTAC CAGTTCCTTA GTGTTCTTTT TCCGACTCTG<br>Arg | 4136 |
| ATTTTCATTC TACGTGAACT TGGTAACTGC TTCATATTCA ATTTCTTTCT | 4186 |
| CTTACTGTAT TTACGTATTG ACACATCTCC TGATGGGACA CAAAAAG G | 4234 |
| TTT GTG AAT CTT ATG GAA GGA CAT ATT TGG ATT GAA AGT GAA<br>Phe Val Asn Leu Met Glu Gly His Ile Trp Ile Glu Ser Glu<br>560                       565                       570 | 4276 |
| GGT CTT GGC AAG GGG TCT ACT GCT ATA TTT ATC ATT AAA CTT<br>Gly Leu Gly Lys Gly Ser Thr Ala Ile Phe Ile Ile Lys Leu<br>               575                        580                       585 | 4318 |
| GGA CTT CCT GGA CGT GCA AAT GAA TCT AAG CTC CCC TTT GTG<br>Gly Leu Pro Gly Arg Ala Asn Glu Ser Lys Leu Pro Phe Val<br>               590                        595                       600 | 4360 |
| ACC AAA TTG CCA GCA AAT CAC ACG CAG ATG AGT TTT AAG GAT<br>Thr Lys Leu Pro Ala Asn His Thr Gln Met Ser Phe Lys Asp<br>               605                        610                       615 | 4402 |
| TAAAGGTTTT GGTGATGGAT GAGAATGGGT GAGTACTATC TGGACCCCTT | 4452 |
| TATCCTCGAC TCTTGTCTTG CCATGCTGTT TAATGATCCA TCTGATTGCG | 4502 |
| TGATTTCTCA TCTTATATGT ATTGAGCTGT CTTACTCACT TTACATGAGA | 4552 |
| CTACAGTAAT ACTT | 4566 |

FIG. 18E

```
AAGATAAGAG TGATTCATTA AGGAGTTTGT TC ATC ATG GAT TGT AAC            47
                                    Ile Met Asp Cys Asn
                                     1                5

TGC TTC GAT CCA CTG TTG CCT GCC GAT GAG TTG TTA ATG AAG           89
Cys Phe Asp Pro Leu Leu Pro Ala Asp Glu Leu Leu Met Lys
             10                  15

TAT CAG TAC ATT TCT GAT TTT TTC ATT GCA GTT GCT TAT TTT          131
Tyr Gln Tyr Ile Ser Asp Phe Phe Ile Ala Val Ala Tyr Phe
 20              25                  30

TCC ATC CCA ATC GAA CTG GTA TTC TTT GTC CAG AAA TCA GCT          173
Ser Ile Pro Ile Glu Leu Val Phe Phe Val Gln Lys Ser Ala
     35              40                  45

GTT TTT CCG TAT CGA TGG GTG CTT GTG CAG TTT GGT GCT TTC          215
Val Phe Pro Tyr Arg Trp Val Leu Val Gln Phe Gly Ala Phe
         50                  55                  60

ATA GTT CTT TGT GGA GCA ACA CAC CTT ATC AAT TTG TGG ACT          257
Ile Val Leu Cys Gly Ala Thr His Leu Ile Asn Leu Trp Thr
                 65              70                  75

TCT ACT CCT CAT ACA AGG ACT GTG GCA ATG GTG ATG ACT ACG          299
Ser Thr Pro His Thr Arg Thr Val Ala Met Val Met Thr Thr
                     80                  85

GCG AAG TTC TCC ACT GCT GCG GTA TCA TGT GCA ACT GCT GTC          341
Ala Lys Phe Ser Thr Ala Ala Val Ser Cys Ala Thr Ala Val
 90                  95                 100

ATG CTT GTC GCA ATT ATT CCG GAT TTA TTA AGT GTC AAA ACT          383
Met Leu Val Ala Ile Ile Pro Asp Leu Leu Ser Val Lys Thr
    105                 110                 115

AGG GAG CTA TTC TTG AAA AAC AAA GCG GCG GAA CTT GAT CGT          425
Arg Glu Leu Phe Leu Lys Asn Lys Ala Ala Glu Leu Asp Arg
        120                 125                 130

GAA ATG GGT CTT ATT CGG ACA CAG GAG GAG ACG GGT AGA TAT          467
Glu Met Gly Leu Ile Arg Thr Gln Glu Glu Thr Gly Arg Tyr
            135                 140                 145

GTT AGA ATG CTA ACA CAT GAA ATC AGA AGT ACT CTG GAT AGA          509
Val Arg Met Leu Thr His Glu Ile Arg Ser Thr Leu Asp Arg
                150                 155

CAT ACT ATT TTG AAG ACT ACA CTT GTT GAA CTT GGA AGA GCA          551
His Thr Ile Leu Lys Thr Thr Leu Val Glu Leu Gly Arg Ala
160                 165                 170

TTG CAA CTG GAA GAG TGT GCT TTG TGG ATG CCG ACT CGA ACT          593
Leu Gln Leu Glu Glu Cys Ala Leu Trp Met Pro Thr Arg Thr
    175                 180                 185

GGA GTG GAG CTT CAA CTT TCT TAC ACT TTA CAT CAT CAA AAT          635
Gly Val Glu Leu Gln Leu Ser Tyr Thr Leu His His Gln Asn
        190                 195                 200

CCA GTT GGA TTT ACA GTA CCT ATA CAA CTC CCT GTA ATT AAT          677
Pro Val Gly Phe Thr Val Pro Ile Gln Leu Pro Val Ile Asn
            201                 210                 215
```

FIG. 19A

```
CAA GTT TTC AGT GCA AAT TGT GCT GTT AAA ATT TCA CCT         716
Gln Val Phe Ser Ala Asn Cys Ala Val Lys Ile Ser Pro
                220                 225
TAATCTGCCG TTGCAAGGCT T                                     737
```

FIG. 19B

```
Tgetr1    1 VESCNCIIDPQLPADDLLMKYQVISDFFIALAYFSIPVELIYFVKKSAVF  50
            :|||:||||  :|||:|||||||||||||||||:|:||||||||||||
Etr1      1 MEVCNCI.EPQWPADELLMKYQVISDFFIAIAYFSIPLELIYFVKKSAVF  49

51 PYRWLVQFGAFIVLCGATHLINLWTFNMHTRNVAIVMTTAKALTALVSC  100
            ||||||||||||||||||||||||| |:|:|||:|:|||||:|||:|||
         50 PYRWLVQFGAFIVLCGATHLINLWTFTTHSRTVALVMTTAKVLTAVVSC   99

101 ITALMLVHIIPDLLSVKTRELFLKKKAAQLDREMGIIRTQEETGRHVRML 150
            :|||||||||||||||||||||||||:||||||||||||||||||||||
        100 ATALMLVHIIPDLLSVKTRELFLKNKAAELDREMGLIRTQEETGRHVRML 149

151 THEIRSTLDRHTILKTTLVELGRTLALEECALWMPTRTGLELQLSYTLRH 200
            |||||||||||||||||||||||||||||||||||||||||||||||||
        150 THEIRSTLDRHTILKTTLVELGRTLALEECALWMPTRTGLELQLSYTLRH 199

201 QNPVGLTVPIQLPVINQVFGTNHVVKISPNSPVARLRP.AGKYMPGEVVA 249
            |:|:|:||||||||||||||||:|||||||||:|:|||   :||:||||
        200 QHPVEYTVPIQLPVINQVFGTSRAVKISPNSPVARLRPVSGKYMLGEVVA 249

250 VRVPLLHLSNFQINDWPELSTKRYALMVLMLPSDSARQWHVHELELVEVV 298
            |||||||||||||||||||||||||||||||||||||||||||||||:|
        250 VRVPLLHLSNFQINDWPELSTKRYALMVLMLPSDSARQWHVHELELVEVV 298

300 ADQVAVALSHAAILEES 316
            |||||||||||||||||
        300 ADQVAVALSHAAILEES 316
```

FIG. 20

```
Tgetr2   11  IMDCNCFDPLLPADELLMKYQYISDFFIAVAYFSIPIELVFFVQKSAVFP  60
             ..  ||::.|||::.||||||||||||||||||.||:.||.||::.||||||
Etr1      1  MEVCNCIEPQWPADELLMKYQYISDFFIAIAYFSIPLELIYFVKKSAVFP  50

61  YRWVLVQFGAFIVLCGATHLINLWTSTPHTRTVAMVMTTAKFSTAAVVSCA 110
             ||||||||||||||||||||||||||.|.|.|||:|||||:.|||.|||||
         51  YRWVLVQFGAFIVLCGATHLINLWTFTHSRTVALVMTTAKVLTAVVSCA  100

111  TAVMLVAIIPDLLSVKTRELFLKNKAAELDREMGLIRTQEETGRYVRMLT 160
             ||:|||.||||||||||||||||||||||||||||||||||||||.|||||
        101  TALMLVHIIPDLLSVKTRELFLKNKAAELDREMGLIRTQEETGRHVRMLT 150

161  HEIRSTLDRHTILKTTLVELGRALQLEECALWMPTRTGVELQLSYTLHHQ 210
             |||||||||||||||||||||||.|||||||||||||||:|||||||:|||
        151  HEIRSTLDRHTILKTTLVELGRTLALEECALWMPTRTGLELQLSYTLRHQ 200

211  NPVGFTVPIQLPVINQVFSANCAVKISP*SAVARL  245
             .:||.||||||||||||||:.  |||  |:||||
        201  HPVEYTVPIQLPVINQVFGTSRAVKISPNSPVARL  235
```

FIG. 21

```
TTTTTTTTTT GTCAAAAGCT CGATGTAAAA ATCCGATGGC CACAAGCAAA        50

ACGACAGGTT CCAACTTCAC GGAGATTGTG AAAATGGAGT AGTAGTTCAG        100

TGAAGTAGTA GATACTGAGA TCGCATTCTC CGGCGTCGTT TTTCACATCG        150

AAATAGTCGT GTAAAAAAAT GAAAAAATTG CTGCGAGACA GGTATGTGTC        200

GCAGCAGGAA ATAGCATCTT AAAGGAAGGA AGGAAGGAAA CTCGAAAGTT        250

ACTAAAAATT TTTGATTCTT TGGGACGAAA CGAGATA ATG GAA TCC TGT      299
                                         Met Glu Ser Cys
                                          1

GAT TGC ATT GAG GCT TTA CTG CCA ACT GGT GAC CTG CTG GTT       341
Asp Cys Ile Glu Ala Leu Leu Pro Thr Gly Asp Leu Leu Val
 5              10                  15

AAA TAC CAA TAC CTC TCA GAT TTC TTC ATT GCT GTA GCC TAC       383
Lys Tyr Gln Tyr Leu Ser Asp Phe Phe Ile Ala Val Ala Tyr
     20              25                  30

TTT TCC ATT CTG TTG GAG CTT ATT TAT TTT GTC CAC AAA TCT       425
Phe Ser Ile Leu Leu Glu Leu Ile Tyr Phe Val His Lys Ser
         35              40                  45

GCA TGC TTC CCA TAC AGA TGG GTC CTC ATG CAA TTT GGT GCT       467
Ala Cys Phe Pro Tyr Arg Trp Val Leu Met Gln Phe Gly Ala
             50              55                      60

TTT ATT GTG CTC TGT GGA GCA ACA CAC TTT ATT AGC TTG TGG       509
Phe Ile Val Leu Cys Gly Ala Thr His Phe Ile Ser Leu Trp
                 65              70

ACC TTC TTT ATG CAC TCT AAG ACG GTC GCT GTG GTT ATG ACC       551
Thr Phe Phe Met His Ser Lys Thr Val Ala Val Val Met Thr
75          Phe Met     80                  85

ATA TCA AAA ATG TTG ACA GCT GCC GTG TCC TGT ATC ACA GCT       593
Ile Ser Lys Met Leu Thr Ala Ala Val Ser Cys Ile Thr Ala
        90              95                  100

TTG ATG CTT GTT CAC ATT ATT CCT GAT TTG CTA AGT GTT AAA       635
Leu Met Leu Val His Ile Ile Pro Asp Leu Leu Ser Val Lys
            105             110             115

ACG CGA GAG TTG TTC TTG AAA ACT CGA GCT GAA GAG CTT GAC       677
Thr Arg Glu Leu Phe Leu Lys Thr Arg Ala Glu Glu Leu Asp
                120             125                 130

AAG GAA ATG GGC CTA ATA ATA AGA CAA GAA GAA ACT GGC AGA       719
Lys Glu Met Gly Leu Ile Ile Arg Gln Glu Glu Thr Gly Arg
                    135             140

CAT GTC AGG ATG CTG ACT CAT GAG ATA AGA AGC ACA CTC GAC       761
His Val Arg Met Leu Thr His Glu Ile Arg Ser Thr Leu Asp
145             150             155

AGA CAC ACA ATC TTG AAG ACT ACT CTT GTG GAG CTA GGT AGG       803
Arg His Thr Ile Leu Lys Thr Thr Leu Val Glu Leu Gly Arg
    160             165             170
```

FIG. 22A

```
ACC TTA GAC CTG GCA GAA TGT GCT TTG TGG ATG CCA TGC CAA         845
Thr Leu Asp Leu Ala Glu Cys Ala Leu Trp Met Pro Cys Gln
        175                 180                 185

GGA GGC CTG ACT TTG CAA CTT TCC CAT AAT TTA AAC AAT CTA         887
Gly Gly Leu Thr Leu Gln Leu Ser His Asn Leu Asn Asn Leu
                190                 195                 200

ATA CCT CTG GGA TCT ACT GTG CCA ATT AAT CTT CCT ATT ATC         929
Ile Pro Leu Gly Ser Thr Val Pro Ile Asn Leu Pro Ile Ile
                    205                 210

AAT GAA ATT TTT AGT AGC CCT GAA GCA ATA CAA ATT CCA CAT         971
Asn Glu Ile Phe Ser Ser Pro Glu Ala Ile Gln Ile Pro His
215                     220                 225

ACA AAT CCT TTG GCA AGG ATG AGG AAT ACT GTT GGT AGA TAT        1013
Thr Asn Pro Leu Ala Arg Met Arg Asn Thr Val Gly Arg Tyr
    230                     235                 240

ATT CCA CCA GAA GTA GTT GCT GTT CGT GTA CCG CTT TTA CAC        1055
Ile Pro Pro Glu Val Val Ala Val Arg Val Pro Leu Leu His
            245                 250                 255

CTC TCA AAT TTT ACT AAT GAC TGG GCT GAA CTG TCT ACT AGA        1097
Leu Ser Asn Phe Thr Asn Asp Trp Ala Glu Leu Ser Thr Arg
                260                 265                 270

AGT TAT GCG GTT ATG GTT CTG GTT CTC CCG ATG AAT GGC TTA        1139
Ser Tyr Ala Val Met Val Leu Val Leu Pro Met Asn Gly Leu
                    275                 280

AGA AAG TGG CGT GAA CAT GAG TTA GAA CTT GTG CAA GTT GTC        1181
Arg Lys Trp Arg Glu His Glu Leu Glu Leu Val Gln Val Val
285                     290                 295

GCA GAT CAG GTT GCT GTC GCT CTT TCA CAT GCT GCA ATT TTA        1223
Ala Asp Gln Val Ala Val Ala Leu Ser His Ala Ala Ile Leu
        300                 305                 310

GAA GAT TCC ATG CGA GCC CAT GAT CAG CTC ATG GAA CAG AAT        1265
Glu Asp Ser Met Arg Ala His Asp Gln Leu Met Glu Gln Asn
                315                 320                 325

ATT GCT TTG GAT GTA GCT CGA CAA GAA GCA GAG ATG GCC ATC        1307
Ile Ala Leu Asp Val Ala Arg Gln Glu Ala Glu Met Ala Ile
                    330                 335                 340

CGT GCA CGT AAC GAC TTC CTT GCT GTG ATG AAC CAT GAA ATG        1349
Arg Ala Arg Asn Asp Phe Leu Ala Val Met Asn His Glu Met
                    345                 350

AGA ACG CCC ATG CAT GCA GTT ATT GCT CTG TGC TCT CTG CTT        1391
Arg Thr Pro Met His Ala Val Ile Ala Leu Cys Ser Leu Leu
355                     360                 365

TTA GAA ACA GAC TTA ACT CCA GAG CAG AGA GTT ATG ATT GAG        1433
Leu Glu Thr Asp Leu Thr Pro Glu Gln Arg Val Met Ile Glu
    370                 375                 380
```

*FIG. 22B*

| | | | | | | | | | | | | | |
|---|---|---|---|---|---|---|---|---|---|---|---|---|---|
| ACC | ATA | TTG | AAG | AGC | AGC | AAT | CTT | CTT | GCA | ACA | CTG | ATA | AAT | 1475 |
| Thr | Ile | Leu | Lys | Ser | Ser | Asn | Leu | Leu | Ala | Thr | Leu | Ile | Asn | |
| | | 385 | | | | | 390 | | | | | 395 | | |
| GAT | GTT | CTA | GAT | CTT | TCT | AGA | CTT | GAA | GAT | GGT | ATT | CTT | GAA | 1517 |
| Asp | Val | Leu | Asp | Leu | Ser | Arg | Leu | Glu | Asp | Gly | Ile | Leu | Glu | |
| | | | 400 | | | | | 405 | | | | | 410 | |
| CTA | GAA | AAC | GGA | ACA | TTC | AAT | CTT | CAT | GGC | ATC | TTA | AGA | GAG | 1559 |
| Leu | Glu | Asn | Gly | Thr | Phe | Asn | Leu | His | Gly | Ile | Leu | Arg | Glu | |
| | | | | 415 | | | | | 420 | | | | | |
| GCC | GTT | AAT | TTG | ATA | AAG | CCA | ATT | GCA | TCT | TTG | AAG | AAA | TTA | 1601 |
| Ala | Val | Asn | Leu | Ile | Lys | Pro | Ile | Ala | Ser | Leu | Lys | Lys | Leu | |
| 425 | | | | | 430 | | | | | 435 | | | | |
| TCT | ATA | ACT | CTT | GCT | TTG | GCT | CTG | GAT | TTA | CCT | ATT | CTT | GCT | 1643 |
| Ser | Ile | Thr | Leu | Ala | Leu | Ala | Leu | Asp | Leu | Pro | Ile | Leu | Ala | |
| | 440 | | | | | 445 | | | | | 450 | | | |
| GTG | GGT | GAT | GCA | AAA | CGT | CTT | ATC | CAA | ACT | CTC | TTA | AAC | GTG | 1685 |
| Val | Gly | Asp | Ala | Lys | Arg | Leu | Ile | Gln | Thr | Leu | Leu | Asn | Val | |
| | | 455 | | | | | 460 | | | | | 465 | | |
| GTG | GGA | AAT | GCT | GTG | AAG | TTC | ACT | AAA | GAA | GGA | CAT | ATT | TCA | 1727 |
| Val | Gly | Asn | Ala | Val | Lys | Phe | Thr | Lys | Glu | Gly | His | Ile | Ser | |
| | | | 470 | | | | | 475 | | | | | 480 | |
| ATT | GAG | GCT | TCA | GTT | GCC | AAA | CCA | GAG | TAT | GCG | AGA | GAT | TGT | 1769 |
| Ile | Glu | Ala | Ser | Val | Ala | Lys | Pro | Glu | Tyr | Ala | Arg | Asp | Cys | |
| | | | | 485 | | | | | 490 | | | | | |
| CAT | CCT | CCT | GAA | ATG | TTC | CCT | ATG | CCA | AGT | GAT | GGC | CAG | TTT | 1811 |
| His | Pro | Pro | Glu | Met | Phe | Pro | Met | Pro | Ser | Asp | Gly | Gln | Phe | |
| 495 | | | | | 500 | | | | | 505 | | | | |
| TAT | TTG | CGT | GTC | CAG | GTT | AGA | GAT | ACT | GGG | TGT | GGA | ATT | AGC | 1853 |
| Tyr | Leu | Arg | Val | Gln | Val | Arg | Asp | Thr | Gly | Cys | Gly | Ile | Ser | |
| | 510 | | | | | 515 | | | | | 520 | | | |
| CCA | CAA | GAT | ATA | CCA | CTA | GTA | TTC | ACC | AAA | TTT | GCA | GAG | TCA | 1895 |
| Pro | Gln | Asp | Ile | Pro | Leu | Val | Phe | Thr | Lys | Phe | Ala | Glu | Ser | |
| | | 525 | | | | | 530 | | | | | 535 | | |
| CGG | CCT | ACG | TCA | AAT | CGA | AGT | ACT | GGA | GGG | GAA | GGT | CTA | GGG | 1937 |
| Arg | Pro | Thr | Ser | Asn | Arg | Ser | Thr | Gly | Gly | Glu | Gly | Leu | Gly | |
| | | | 540 | | | | | 545 | | | | | 550 | |
| CTT | GCC | ATT | TGG | AGA | CGA | TTT | ATT | CAA | CTT | ATG | AAA | GGT | AAC | 1979 |
| Leu | Ala | Ile | Trp | Arg | Arg | Phe | Ile | Gln | Leu | Met | Lys | Gly | Asn | |
| | | | | 555 | | | | | 560 | | | | | |
| ATT | TGG | ATT | GAG | AGT | GAG | GGC | CCT | GGA | AAG | GGA | ACC | ACT | GTC | 2021 |
| Ile | Trp | Ile | Glu | Ser | Glu | Gly | Pro | Gly | Lys | Gly | Thr | Thr | Val | |
| 565 | | | | | 570 | | | | | 575 | | | | |
| ACG | TTT | GTA | GTG | AAA | CTC | GGA | ATC | TGT | CAC | CAT | CCA | AAT | GCA | 2063 |
| Thr | Phe | Val | Val | Lys | Leu | Gly | Ile | Cys | His | His | Pro | Asn | Ala | |
| | | | 580 | | | | | 585 | | | | | 590 | |

FIG. 22C

| | |
|---|---|
| TTA CCT CTG CTA CCT ATG CCT CCC AGA GGC AGA TTG AAC AAA<br>Leu Pro Leu Leu Pro Met Pro Pro Arg Gly Arg Leu Asn Lys<br>595                     600                     605 | 2105 |
| GGT AGC GAT GAT CTC TTC AGG TAT AGA CAG TTC CGT GGA GAT<br>Gly Ser Asp Asp Leu Phe Arg Tyr Arg Gln Phe Arg Gly Asp<br>610                    615                  620 | 2147 |
| GAT GGT GGG ATG TCT GTG AAT GCT CAA CGC TAT CAA AGA AGT<br>Asp Gly Gly Met Ser Val Asn Ala Gln Arg Tyr Gln Arg Ser<br>             625                  630 | 2189 |
| ATG TAA A TGACAAAGG ACATTGGTGT GACAAGAAC ATTAAATCAT<br>Met *<br>635 | 2236 |
| GACTAGTGAA TTTGAGATTT CTTCACTGTT CTGTACACTC CAAATGGCAC | 2286 |
| AGTTTGTCTT GTAACTAACC TAATTCAATG CTCGTAAAGT GAGTACTGGA | 2336 |
| GTATCTTGAA AATGTAACTA TCGAATTTAT ACATCGAGCT TTTGACAAAA | 2386 |
| AAAAAAAAAA AAAAAAAA | 2405 |

FIG. 22D

SEQUENCE LISTING

<160> NUMBER OF SEQ ID NOS: 56

<210> SEQ ID NO 1
<211> LENGTH: 3879
<212> TYPE: DNA
<213> ORGANISM: Arabidopsis thaliana

<400> SEQUENCE: 1

```
aaagatagta tttgttgata aatatgggga tatttatcct atattatctg tatttttctt        60
accatttta ctctattcct ttatctacat tacgtcatta cactatcata agatatttga       120
atgaacaaat tcatgcaccc accagctata ttacccttt ttattaaaaa aaaacatctg       180
ataataataa caaaaaaatt agagaaatga cgtcgaaaaa aaaagtaaga acgaagaaga       240
agtgttaaac ccaaccaatt ttgacttgaa aaaaagcttc aacgctcccc ttttctcctt       300
ctccgtcgct ctccgccgcg tcccaaatcc ccaattcctc ctcttctccg atcaattctt       360
cccaagtaag cttcttcttc ctcgattctc tcctcagatt gtttcgtgac ttctttatat       420
atattcttca cttccacagt tttcttctgt tgttgtcgtc gatctcaaat catagagatt       480
gattaaccta attggtcttt atctagtgta atgcatcgtt attaggaact ttaaattaag       540
atttaatcgt taatttcatg attcggattc gaattttact gttctcgaga ctgaaatatg       600
caacctattt tttcgtaatc gttgtgatcg aattcgattc ttcagaattt atagcaattt       660
tgatgctcat gatctgtcta cgctacgttc tcgtcgtaaa tcgaagttga taatgctatg       720
tgtttgttac acaggtgtgt gtatgtgtga gagaggaact atagtgtaaa aaattcataa       780
tggaagtctg caattgtatt gaaccgcaat ggccagcgga tgaattgtta atgaaatacc       840
aatacatctc cgatttcttc attgcgattg cgtatttttc gattcctctt gagttgattt       900
actttgtgaa gaaatcagcc gtgtttccgt atagatgggt acttgttcag tttggtgctt       960
ttatcgttct ttgtggagca actcatctta ttaacttatg gactttcact acgcattcga      1020
gaaccgtggc gcttgtgatg actaccgcga aggtgttaac cgctgttgtc tcgtgtgcta      1080
ctgcgttgat gcttgttcat attattcctg atcttttgag tgttaagact cgggagcttt      1140
tcttgaaaaa taaagctgct gagctcgata gagaaatggg attgattcga actcaggaag      1200
aaaccggaag gcatgtgaga atgttgactc atgagattag aagcacttta gatagacata      1260
ctatttaaa gactacactt gttgagcttg gtaggacatt agctttggag gagtgtgcat      1320
tgtggatgcc tactagaact gggttagagc tacagctttc ttatacactt cgtcatcaac      1380
atcccgtgga gtatacggtt cctattcaat taccggtgat taaccaagtg tttggtacta      1440
gtagggctgt aaaaatatct cctaattctc ctgtggctag gttgagacct gtttctggga      1500
aatatatgct agggagggtg gtcgctgtga gggttccgct tctccacctt tctaattttc      1560
agattaatga ctggcctgag ctttcaacaa agagatatgc tttgatggtt tgatgcttc      1620
```

-continued

```
cttcagatag tgcaaggcaa tggcatgtcc atgagttgga actcgttgaa gtcgtcgctg    1680
atcaggtttt acattgctga gaatttctct tctttgctat gttcatgatc ttgtctataa    1740
cttttcttct cttattatag gtggctgtag ctctctcaca tgctgcgatc ctagaagagt    1800
cgatgcgagc tagggacctt ctcatggagc agaatgttgc tcttgatcta gctagacgag    1860
aagcagaaac agcaatccgt gcccgcaatg atttcctagc ggttatgaac catgaaatgc    1920
gaacaccgat gcatgcgatt attgcactct cttccttact ccaagaaacg gaactaaccc    1980
ctgaacaaag actgatggtg gaaacaatac ttaaaagtag taacctttg gcaactttga    2040 tgaatgatgt cttagatctt tcaaggttag aagatggaag tcttcaactt gaacttggga    2100
cattcaatct tcatacatta tttagagagg taacttttga acagctctat gtttcataag    2160
tttatactat ttgtgtactt gattgtcata ttgaatcttg ttgcaggtcc tcaatctgat    2220
aaagcctata gcggttgtta agaaattacc catcacacta atcttgcac cagatttgcc     2280 agaatttgtt gttggggatg agaaacggct aatgcagata atattaaata tagttggtaa    2340
tgctgtgaaa ttctccaaac aaggtagtat ctccgtaacc gctcttgtca ccaagtcaga    2400
cacacgagct gctgactttt ttgtcgtgcc aactgggagt catttctact tgagagtgaa    2460
ggttattatc ttgtatcttg ggatcttata ccatagctga aagtatttct taggtcttaa    2520
ttttgatgat tattcaaata taggtaaaag actctggagc aggaataaat cctcaagaca    2580
ttccaaagat tttcactaaa tttgctcaaa cacaatcttt agcgacgaga agctcgggtg    2640
gtagtgggct tggcctcgcc atctccaaga ggtttgagcc ttattaaaag acgttttttt    2700 ccaactttt cttgtcttct gtgttgttaa agtttactc ataagcgttt aatatgacaa      2760
ggtttgtgaa tctgatggag ggtaacattt ggattgagag cgatggtctt ggaaaaggat    2820
gcacggctat ctttgatgtt aaacttggga tctcagaacg ttcaaacgaa tctaaacagt    2880
cgggcatacc gaaagttcca gccattcccc gacattcaaa tttcactgga cttaaggttc    2940
ttgtcatgga tgagaacggg ttagtataag cttctcacct ttctctttgc aaaatctctc    3000
gccttacttc ttgcaaatgc agatattggc gtttagaaaa aacgcaaatt taatcttatg    3060
agaaaccgat gattattttg gttgcagggt aagtagaatg gtgacgaagg gacttcttgt    3120
acaccttggg tgcgaagtga ccacggtgag ttcaaacgag gagtgtctcc gagttgtgtc    3180
ccatgagcac aaagtggtct tcatggacgt gtgcatgccc gggtcgaaa actaccaaat    3240 cgctctccgt attcacgaga aattcacaaa acaacgccac caacgccac tacttgtggc     3300 actcagtggt aacactgaca atccacaaa agagaaatgc atgagctttg gtctagacgg     3360
tgtgttgctc aaacccgtat cactagacaa cataagagat gttctgtctg atcttctcga    3420
gccccgggta ctgtacgagg gcatgtaaag gcgatggatg ccccatgccc cagaggagta    3480
attccgctcc cgccttcttc tcccgtaaaa catcggaagc tgatgttctc tggtttaatt    3540
gtgtacatat cagagattgt cggagcgttt tggatgatat cttaaaacag aaagggaata    3600
acaaaataga aactctaaac cggtatgtgt ccgtggcgat ttcggttata gaggaacaag    3660
atggtggtgg tataatcata ccatttcaga ttacatgttt gactaatgtt gtatccttat    3720
atatgtagtt acattcttat aagaatttgg atcgagttat ggatgcttgt tgcgtgcatg    3780
tatgacattg atgcagtatt atggcgtcag cttttcgccg cttagtagaa caacaacaat    3840
ggcgttactt agtttctcaa tcaacccgat ctccaaaac                           3879
```

<210> SEQ ID NO 2

```
<211> LENGTH: 2787
<212> TYPE: DNA
<213> ORGANISM: Arabidopsis thaliana
<220> FEATURE:
<221> NAME/KEY: CDS
<222> LOCATION: (188)..(2401)

<400> SEQUENCE: 2
agtaagaacg aagaagaagt gttaaaccca accaattttg acttgaaaaa aagcttcaac      60
gctccccttt tctccttctc cgtcgctctc cgccgcgtcc caaatcccca attcctcctc     120
ttctccgatc aattcttccc aagtgtgtgt atgtgtgaga gaggaactat agtgtaaaaa     180 attcata atg gaa gtc tgc aat tgt att gaa ccg caa tgg cca gcg gat      229
        Met Glu Val Cys Asn Cys Ile Glu Pro Gln Trp Pro Ala Asp
         1               5                  10 gaa ttg tta atg aaa tac caa tac atc tcc gat ttc ttc att gcg att      277
Glu Leu Leu Met Lys Tyr Gln Tyr Ile Ser Asp Phe Phe Ile Ala Ile
 15              20                  25                  30 gcg tat ttt tcg att cct ctt gag ttg att tac ttt gtg aag aaa tca      325
Ala Tyr Phe Ser Ile Pro Leu Glu Leu Ile Tyr Phe Val Lys Lys Ser
                 35                  40                  45 gcc gtg ttt ccg tat aga tgg gta ctt gtt cag ttt ggt gct ttt atc      373
Ala Val Phe Pro Tyr Arg Trp Val Leu Val Gln Phe Gly Ala Phe Ile
         50                  55                  60 gtt ctt tgt gga gca act cat ctt att aac tta tgg act ttc act acg      421
Val Leu Cys Gly Ala Thr His Leu Ile Asn Leu Trp Thr Phe Thr Thr
 65                  70                  75 cat tcg aga acc gtg gcg ctt gtg atg act acc gcg aag gtg tta acc      469
His Ser Arg Thr Val Ala Leu Val Met Thr Thr Ala Lys Val Leu Thr
 80                  85                  90 gct gtt gtc tcg tgt gct act gcg ttg atg ctt gtt cat att att cct      517
Ala Val Val Ser Cys Ala Thr Ala Leu Met Leu Val His Ile Ile Pro
 95                 100                 105                 110 gat ctt ttg agt gtt aag act cgg gag ctt ttc ttg aaa aat aaa gct      565
Asp Leu Leu Ser Val Lys Thr Arg Glu Leu Phe Leu Lys Asn Lys Ala
                115                 120                 125 gct gag ctc gat aga gaa atg gga ttg att cga act cag gaa gaa acc      613
Ala Glu Leu Asp Arg Glu Met Gly Leu Ile Arg Thr Gln Glu Glu Thr
        130                 135                 140 gga agg cat gtg aga atg ttg act cat gag att aga agc act tta gat      661
Gly Arg His Val Arg Met Leu Thr His Glu Ile Arg Ser Thr Leu Asp
    145                 150                 155 aga cat act att tta aag act aca ctt gtt gag ctt ggt agg aca tta      709
Arg His Thr Ile Leu Lys Thr Thr Leu Val Glu Leu Gly Arg Thr Leu
160                 165                 170 gct ttg gag gag tgt gca ttg tgg atg cct act aga act ggg tta gag      757
Ala Leu Glu Glu Cys Ala Leu Trp Met Pro Thr Arg Thr Gly Leu Glu
175                 180                 185                 190 cta cag ctt tct tat aca ctt cgt cat caa cat ccc gtg gag tat acg      805
Leu Gln Leu Ser Tyr Thr Leu Arg His Gln His Pro Val Glu Tyr Thr
                195                 200                 205 gtt cct att caa tta ccg gtg att aac caa gtg ttt ggt act agt agg      853
Val Pro Ile Gln Leu Pro Val Ile Asn Gln Val Phe Gly Thr Ser Arg
        210                 215                 220 gct gta aaa ata tct cct aat tct cct gtg gct agg ttg aga cct gtt      901
Ala Val Lys Ile Ser Pro Asn Ser Pro Val Ala Arg Leu Arg Pro Val
    225                 230                 235 tct ggg aaa tat atg cta ggg gag gtg gtc gct gtg agg gtt ccg ctt      949
Ser Gly Lys Tyr Met Leu Gly Glu Val Val Ala Val Arg Val Pro Leu
240                 245                 250
```

-continued

| | | |
|---|---|---|
| ctc cac ctt tct aat ttt cag att aat gac tgg cct gag ctt tca aca<br>Leu His Leu Ser Asn Phe Gln Ile Asn Asp Trp Pro Glu Leu Ser Thr<br>255                    260                    265                    270 | 997 |
| aag aga tat gct ttg atg gtt ttg atg ctt cct tca gat agt gca agg<br>Lys Arg Tyr Ala Leu Met Val Leu Met Leu Pro Ser Asp Ser Ala Arg<br>                    275                    280                    285 | 1045 |
| caa tgg cat gtc cat gag ttg gaa ctc gtt gaa gtc gtc gct gat cag<br>Gln Trp His Val His Glu Leu Glu Leu Val Glu Val Val Ala Asp Gln<br>                290                    295                    300 | 1093 |
| gtg gct gta gct ctc tca cat gct gcg atc cta gaa gag tcg atg cga<br>Val Ala Val Ala Leu Ser His Ala Ala Ile Leu Glu Glu Ser Met Arg<br>      305                    310                    315 | 1141 |
| gct agg gac ctt ctc atg gag cag aat gtt gct ctt gat cta gct aga<br>Ala Arg Asp Leu Leu Met Glu Gln Asn Val Ala Leu Asp Leu Ala Arg<br>      320                    325                    330 | 1189 |
| cga gaa gca gaa aca gca atc cgt gcc cgc aat gat ttc cta gcg gtt<br>Arg Glu Ala Glu Thr Ala Ile Arg Ala Arg Asn Asp Phe Leu Ala Val<br>335                    340                    345                    350 | 1237 |
| atg aac cat gaa atg cga aca ccg atg cat gcg att att gca ctc tct<br>Met Asn His Glu Met Arg Thr Pro Met His Ala Ile Ile Ala Leu Ser<br>                    355                    360                    365 | 1285 |
| tcc tta ctc caa gaa acg gaa cta acc cct gaa caa aga ctg atg gtg<br>Ser Leu Leu Gln Glu Thr Glu Leu Thr Pro Glu Gln Arg Leu Met Val<br>              370                    375                    380 | 1333 |
| gaa aca ata ctt aaa agt agt aac ctt ttg gca act ttg atg aat gat<br>Glu Thr Ile Leu Lys Ser Ser Asn Leu Leu Ala Thr Leu Met Asn Asp<br>385                    390                    395 | 1381 |
| gtc tta gat ctt tca agg tta gaa gat gga agt ctt caa ctt gaa ctt<br>Val Leu Asp Leu Ser Arg Leu Glu Asp Gly Ser Leu Gln Leu Glu Leu<br>      400                    405                    410 | 1429 |
| ggg aca ttc aat ctt cat aca tta ttt aga gag gtc ctc aat ctg ata<br>Gly Thr Phe Asn Leu His Thr Leu Phe Arg Glu Val Leu Asn Leu Ile<br>415                    420                    425                    430 | 1477 |
| aag cct ata gcg gtt gtt aag aaa tta ccc atc aca cta aat ctt gca<br>Lys Pro Ile Ala Val Val Lys Lys Leu Pro Ile Thr Leu Asn Leu Ala<br>                    435                    440                    445 | 1525 |
| cca gat ttg cca gaa ttt gtt gtt ggg gat gag aaa cgg cta atg cag<br>Pro Asp Leu Pro Glu Phe Val Val Gly Asp Glu Lys Arg Leu Met Gln<br>              450                    455                    460 | 1573 |
| ata ata tta aat ata gtt ggt aat gct gtg aaa ttc tcc aaa caa ggt<br>Ile Ile Leu Asn Ile Val Gly Asn Ala Val Lys Phe Ser Lys Gln Gly<br>                    465                    470                    475 | 1621 |
| agt atc tcc gta acc gct ctt gtc acc aag tca gac aca cga gct gct<br>Ser Ile Ser Val Thr Ala Leu Val Thr Lys Ser Asp Thr Arg Ala Ala<br>480                    485                    490 | 1669 |
| gac ttt ttt gtc gtg cca act ggg agt cat ttc tac ttg aga gtg aag<br>Asp Phe Phe Val Val Pro Thr Gly Ser His Phe Tyr Leu Arg Val Lys<br>495                    500                    505                    510 | 1717 |
| gta aaa gac tct gga gca gga ata aat cct caa gac att cca aag att<br>Val Lys Asp Ser Gly Ala Gly Ile Asn Pro Gln Asp Ile Pro Lys Ile<br>                    515                    520                    525 | 1765 |
| ttc act aaa ttt gct caa aca caa tct tta gcg acg aga agc tcg ggt<br>Phe Thr Lys Phe Ala Gln Thr Gln Ser Leu Ala Thr Arg Ser Ser Gly<br>              530                    535                    540 | 1813 |
| ggt agt ggg ctt ggc ctc gcc atc tcc aag agg ttt gtg aat ctg atg<br>Gly Ser Gly Leu Gly Leu Ala Ile Ser Lys Arg Phe Val Asn Leu Met<br>      545                    550                    555 | 1861 |
| gag ggt aac att tgg att gag agc gat ggt ctt gga aaa gga tgc acg<br>Glu Gly Asn Ile Trp Ile Glu Ser Asp Gly Leu Gly Lys Gly Cys Thr<br>      560                    565                    570 | 1909 |

| | | |
|---|---|---|
| gct atc ttt gat gtt aaa ctt ggg atc tca gaa cgt tca aac gaa tct<br>Ala Ile Phe Asp Val Lys Leu Gly Ile Ser Glu Arg Ser Asn Glu Ser<br>575                      580                  585                590 | | 1957 |
| aaa cag tcg ggc ata ccg aaa gtt cca gcc att ccc cga cat tca aat<br>Lys Gln Ser Gly Ile Pro Lys Val Pro Ala Ile Pro Arg His Ser Asn<br>                  595                  600                  605 | | 2005 |
| ttc act gga ctt aag gtt ctt gtc atg gat gag aac ggg gta agt aga<br>Phe Thr Gly Leu Lys Val Leu Val Met Asp Glu Asn Gly Val Ser Arg<br>            610                  615                  620 | | 2053 |
| atg gtg acg aag gga ctt ctt gta cac ctt ggg tgc gaa gtg acc acg<br>Met Val Thr Lys Gly Leu Leu Val His Leu Gly Cys Glu Val Thr Thr<br>625                      630                  635 | | 2101 |
| gtg agt tca aac gag gag tgt ctc cga gtt gtg tcc cat gag cac aaa<br>Val Ser Ser Asn Glu Glu Cys Leu Arg Val Val Ser His Glu His Lys<br>640                      645                  650 | | 2149 |
| gtg gtc ttc atg gac gtg tgc atg ccc ggg gtc gaa aac tac caa atc<br>Val Val Phe Met Asp Val Cys Met Pro Gly Val Glu Asn Tyr Gln Ile<br>655                      660                  665                670 | | 2197 |
| gct ctc cgt att cac gag aaa ttc aca aaa caa cgc cac caa cgg cca<br>Ala Leu Arg Ile His Glu Lys Phe Thr Lys Gln Arg His Gln Arg Pro<br>                  675                  680                  685 | | 2245 |
| cta ctt gtg gca ctc agt ggt aac act gac aaa tcc aca aaa gag aaa<br>Leu Leu Val Ala Leu Ser Gly Asn Thr Asp Lys Ser Thr Lys Glu Lys<br>            690                  695                  700 | | 2293 |
| tgc atg agc ttt ggt cta gac ggt gtg ttg ctc aaa ccc gta tca cta<br>Cys Met Ser Phe Gly Leu Asp Gly Val Leu Leu Lys Pro Val Ser Leu<br>705                      710                  715 | | 2341 |
| gac aac ata aga gat gtt ctg tct gat ctt ctc gag ccc cgg gta ctg<br>Asp Asn Ile Arg Asp Val Leu Ser Asp Leu Leu Glu Pro Arg Val Leu<br>720                      725                  730 | | 2389 |
| tac gag ggc atg taaaggcgat ggatgcccca tgcccagag gagtaattcc<br>Tyr Glu Gly Met<br>735 | | 2441 |
| gctcccgcct tcttctcccg taaaacatcg gaagctgatg ttctctggtt taattgtgta | | 2501 |
| catatcagag attgtcggag cgttttggat gatatcttaa aacagaaagg gaataacaaa | | 2561 |
| atagaaactc taaaccggta tgtgtccgtg gcgatttcgg ttatagagga acaagatggt | | 2621 |
| ggtggtataa tcataccatt tcagattaca tgtttgacta atgttgtatc cttatatatg | | 2681 |
| tagttacatt cttataagaa tttggatcga gttatggatg cttgttgcgt gcatgtatga | | 2741 |
| cattgatgca gtattatggc gtcagctttg cgccgcttag tagaac | | 2787 |

<210> SEQ ID NO 3
<211> LENGTH: 738
<212> TYPE: PRT
<213> ORGANISM: Arabidopsis thaliana

<400> SEQUENCE: 3

Met Glu Val Cys Asn Cys Ile Glu Pro Gln Trp Pro Ala Asp Glu Leu
1                  5                    10                  15

Leu Met Lys Tyr Gln Tyr Ile Ser Asp Phe Phe Ile Ala Ile Ala Tyr
                  20                    25                  30

Phe Ser Ile Pro Leu Glu Leu Ile Tyr Phe Val Lys Lys Ser Ala Val
        35                    40                  45

Phe Pro Tyr Arg Trp Val Leu Val Gln Phe Gly Ala Phe Ile Val Leu
50                      55                    60

Cys Gly Ala Thr His Leu Ile Asn Leu Trp Thr Phe Thr Thr His Ser
65                  70                    75                  80

-continued

```
Arg Thr Val Ala Leu Val Met Thr Thr Ala Lys Val Leu Thr Ala Val
                85                  90                  95
Val Ser Cys Ala Thr Ala Leu Met Leu Val His Ile Ile Pro Asp Leu
            100                 105                 110
Leu Ser Val Lys Thr Arg Glu Leu Phe Leu Lys Asn Lys Ala Ala Glu
        115                 120                 125
Leu Asp Arg Glu Met Gly Leu Ile Arg Thr Gln Glu Thr Gly Arg
    130                 135                 140
His Val Arg Met Leu Thr His Glu Ile Arg Ser Thr Leu Asp Arg His
145                 150                 155                 160
Thr Ile Leu Lys Thr Thr Leu Val Glu Leu Gly Arg Thr Leu Ala Leu
                165                 170                 175
Glu Glu Cys Ala Leu Trp Met Pro Thr Arg Thr Gly Leu Glu Leu Gln
            180                 185                 190
Leu Ser Tyr Thr Leu Arg His Gln His Pro Val Glu Tyr Thr Val Pro
        195                 200                 205
Ile Gln Leu Pro Val Ile Asn Gln Val Phe Gly Thr Ser Arg Ala Val
    210                 215                 220
Lys Ile Ser Pro Asn Ser Pro Val Ala Arg Leu Arg Pro Val Ser Gly
225                 230                 235                 240
Lys Tyr Met Leu Gly Glu Val Val Ala Val Arg Val Pro Leu Leu His
                245                 250                 255
Leu Ser Asn Phe Gln Ile Asn Asp Trp Pro Glu Leu Ser Thr Lys Arg
            260                 265                 270
Tyr Ala Leu Met Val Leu Met Leu Pro Ser Asp Ser Ala Arg Gln Trp
        275                 280                 285
His Val His Glu Leu Glu Leu Val Glu Val Val Ala Asp Gln Val Ala
    290                 295                 300
Val Ala Leu Ser His Ala Ala Ile Leu Glu Glu Ser Met Arg Ala Arg
305                 310                 315                 320
Asp Leu Leu Met Glu Gln Asn Val Ala Leu Asp Leu Ala Arg Arg Glu
                325                 330                 335
Ala Glu Thr Ala Ile Arg Ala Arg Asn Asp Phe Leu Ala Val Met Asn
            340                 345                 350
His Glu Met Arg Thr Pro Met His Ala Ile Ile Ala Leu Ser Ser Leu
        355                 360                 365
Leu Gln Glu Thr Glu Leu Thr Pro Glu Gln Arg Leu Met Val Glu Thr
    370                 375                 380
Ile Leu Lys Ser Ser Asn Leu Leu Ala Thr Leu Met Asn Asp Val Leu
385                 390                 395                 400
Asp Leu Ser Arg Leu Glu Asp Gly Ser Leu Gln Leu Glu Leu Gly Thr
                405                 410                 415
Phe Asn Leu His Thr Leu Phe Arg Glu Val Leu Asn Leu Ile Lys Pro
            420                 425                 430
Ile Ala Val Val Lys Lys Leu Pro Ile Thr Leu Asn Leu Ala Pro Asp
        435                 440                 445
Leu Pro Glu Phe Val Val Gly Asp Glu Lys Arg Leu Met Gln Ile Ile
    450                 455                 460
Leu Asn Ile Val Gly Asn Ala Val Lys Phe Ser Lys Gln Gly Ser Ile
465                 470                 475                 480
Ser Val Thr Ala Leu Val Thr Lys Ser Asp Thr Arg Ala Ala Asp Phe
                485                 490                 495
```

-continued

```
Phe Val Val Pro Thr Gly Ser His Phe Tyr Leu Arg Val Lys Val Lys
            500                 505                 510

Asp Ser Gly Ala Gly Ile Asn Pro Gln Asp Ile Pro Lys Ile Phe Thr
        515                 520                 525

Lys Phe Ala Gln Thr Gln Ser Leu Ala Thr Arg Ser Ser Gly Gly Ser
    530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
        595                 600                 605

Gly Leu Lys Val Leu Val Met Asp Glu Asn Gly Val Ser Arg Met Val
    610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
                645                 650                 655

Phe Met Asp Val Cys Met Pro Gly Val Glu Asn Tyr Gln Ile Ala Leu
            660                 665                 670

Arg Ile His Glu Lys Phe Thr Lys Gln Arg His Gln Arg Pro Leu Leu
        675                 680                 685

Val Ala Leu Ser Gly Asn Thr Asp Lys Ser Thr Lys Glu Lys Cys Met
    690                 695                 700

Ser Phe Gly Leu Asp Gly Val Leu Leu Lys Pro Val Ser Leu Asp Asn
705                 710                 715                 720

Ile Arg Asp Val Leu Ser Asp Leu Leu Glu Pro Arg Val Leu Tyr Glu
                725                 730                 735

Gly Met

<210> SEQ ID NO 4
<211> LENGTH: 2787
<212> TYPE: DNA
<213> ORGANISM: Arabidopsis thaliana
<220> FEATURE:
<221> NAME/KEY: CDS
<222> LOCATION: (188)..(2401)

<400> SEQUENCE: 4
agtaagaacg aagaagaagt gttaaaccca accaattttg acttgaaaaa aagcttcaac      60
gctccccttt tctccttctc cgtcgctctc cgccgcgtcc caaatcccca attcctcctc     120
ttctccgatc aattcttccc aagtgtgtgt atgtgtgaga gaggaactat agtgtaaaaa     180 attcata atg gaa gtc tgc aat tgt att gaa ccg caa tgg cca gcg gat      229
        Met Glu Val Cys Asn Cys Ile Glu Pro Gln Trp Pro Ala Asp
          1               5                  10 gaa ttg tta atg aaa tac caa tac atc tcc gat ttc ttc att gcg att      277
Glu Leu Leu Met Lys Tyr Gln Tyr Ile Ser Asp Phe Phe Ile Ala Ile
 15              20                  25                  30 gcg tat ttt tcg att cct ctt gag ttg att tac ttt gtg aag aaa tca      325
Ala Tyr Phe Ser Ile Pro Leu Glu Leu Ile Tyr Phe Val Lys Lys Ser
                 35                  40                  45 gcc gtg ttt ccg tat aga tgg gta ctt gtt cag ttt ggt gct ttt atc      373
Ala Val Phe Pro Tyr Arg Trp Val Leu Val Gln Phe Gly Ala Phe Ile
             50                  55                  60
```

```
gtt ctt tat gga gca act cat ctt att aac tta tgg act ttc act acg    421
Val Leu Tyr Gly Ala Thr His Leu Ile Asn Leu Trp Thr Phe Thr Thr
             65                  70                  75 cat tcg aga acc gtg gcg ctt gtg atg act acc gcg aag gtg tta acc    469
His Ser Arg Thr Val Ala Leu Val Met Thr Thr Ala Lys Val Leu Thr
 80                  85                  90 gct gtt gtc tcg tgt gct act gcg ttg atg ctt gtt cat att att cct    517
Ala Val Val Ser Cys Ala Thr Ala Leu Met Leu Val His Ile Ile Pro
 95                 100                 105                 110 gat ctt ttg agt gtt aag act cgg gag ctt ttc ttg aaa aat aaa gct    565
Asp Leu Leu Ser Val Lys Thr Arg Glu Leu Phe Leu Lys Asn Lys Ala
                115                 120                 125 gct gag ctc gat aga gaa atg gga ttg att cga act cag gaa gaa acc    613
Ala Glu Leu Asp Arg Glu Met Gly Leu Ile Arg Thr Gln Glu Glu Thr
            130                 135                 140 gga agg cat gtg aga atg ttg act cat gag att aga agc act tta gat    661
Gly Arg His Val Arg Met Leu Thr His Glu Ile Arg Ser Thr Leu Asp
        145                 150                 155 aga cat act att tta aag act aca ctt gtt gag ctt ggt agg aca tta    709
Arg His Thr Ile Leu Lys Thr Thr Leu Val Glu Leu Gly Arg Thr Leu
    160                 165                 170 gct ttg gag gag tgt gca ttg tgg atg cct act aga act ggg tta gag    757
Ala Leu Glu Glu Cys Ala Leu Trp Met Pro Thr Arg Thr Gly Leu Glu
175                 180                 185                 190 cta cag ctt tct tat aca ctt cgt cat caa cat ccc gtg gag tat acg    805
Leu Gln Leu Ser Tyr Thr Leu Arg His Gln His Pro Val Glu Tyr Thr
                195                 200                 205 gtt cct att caa tta ccg gtg att aac caa gtg ttt ggt act agt agg    853
Val Pro Ile Gln Leu Pro Val Ile Asn Gln Val Phe Gly Thr Ser Arg
            210                 215                 220 gct gta aaa ata tct cct aat tct cct gtg gct agg ttg aga cct gtt    901
Ala Val Lys Ile Ser Pro Asn Ser Pro Val Ala Arg Leu Arg Pro Val
        225                 230                 235 tct ggg aaa tat atg cta ggg gag gtg gtc gct gtg agg gtt ccg ctt    949
Ser Gly Lys Tyr Met Leu Gly Glu Val Val Ala Val Arg Val Pro Leu
    240                 245                 250 ctc cac ctt tct aat ttt cag att aat gac tgg cct gag ctt tca aca    997
Leu His Leu Ser Asn Phe Gln Ile Asn Asp Trp Pro Glu Leu Ser Thr
255                 260                 265                 270 aag aga tat gct ttg atg gtt ttg atg ctt cct tca gat agt gca agg   1045
Lys Arg Tyr Ala Leu Met Val Leu Met Leu Pro Ser Asp Ser Ala Arg
                275                 280                 285 caa tgg cat gtc cat gag ttg gaa ctc gtt gaa gtc gtc gct gat cag   1093
Gln Trp His Val His Glu Leu Glu Leu Val Glu Val Val Ala Asp Gln
            290                 295                 300 gtg gct gta gct ctc tca cat gct gcg atc cta gaa gag tcg atg cga   1141
Val Ala Val Ala Leu Ser His Ala Ala Ile Leu Glu Glu Ser Met Arg
        305                 310                 315 gct agg gac ctt ctc atg gag cag aat gtt gct ctt gat cta gct aga   1189
Ala Arg Asp Leu Leu Met Glu Gln Asn Val Ala Leu Asp Leu Ala Arg
    320                 325                 330 cga gaa gca gaa aca gca atc cgt gcc cgc aat gat ttc cta gcg gtt   1237
Arg Glu Ala Glu Thr Ala Ile Arg Ala Arg Asn Asp Phe Leu Ala Val
335                 340                 345                 350 atg aac cat gaa atg cga aca ccg atg cat gcg att att gca ctc tct   1285
Met Asn His Glu Met Arg Thr Pro Met His Ala Ile Ile Ala Leu Ser
                355                 360                 365 tcc tta ctc caa gaa acg gaa cta acc cct gaa caa aga ctg atg gtg   1333
Ser Leu Leu Gln Glu Thr Glu Leu Thr Pro Glu Gln Arg Leu Met Val
```

```
                    370                 375                 380
gaa aca ata ctt aaa agt agt aac ctt ttg gca act ttg atg aat gat    1381
Glu Thr Ile Leu Lys Ser Ser Asn Leu Leu Ala Thr Leu Met Asn Asp
            385                 390                 395 gtc tta gat ctt tca agg tta gaa gat gga agt ctt caa ctt gaa ctt    1429
Val Leu Asp Leu Ser Arg Leu Glu Asp Gly Ser Leu Gln Leu Glu Leu
    400                 405                 410 ggg aca ttc aat ctt cat aca tta ttt aga gag gtc ctc aat ctg ata    1477
Gly Thr Phe Asn Leu His Thr Leu Phe Arg Glu Val Leu Asn Leu Ile
415                 420                 425                 430 aag cct ata gcg gtt gtt aag aaa tta ccc atc aca cta aat ctt gca    1525
Lys Pro Ile Ala Val Val Lys Lys Leu Pro Ile Thr Leu Asn Leu Ala
                435                 440                 445 cca gat ttg cca gaa ttt gtt gtt ggg gat gag aaa cgg cta atg cag    1573
Pro Asp Leu Pro Glu Phe Val Val Gly Asp Glu Lys Arg Leu Met Gln
            450                 455                 460 ata ata tta aat ata gtt ggt aat gct gtg aaa ttc tcc aaa caa ggt    1621
Ile Ile Leu Asn Ile Val Gly Asn Ala Val Lys Phe Ser Lys Gln Gly
    465                 470                 475 agt atc tcc gta acc gct ctt gtc acc aag tca gac aca cga gct gct    1669
Ser Ile Ser Val Thr Ala Leu Val Thr Lys Ser Asp Thr Arg Ala Ala
        480                 485                 490 gac ttt ttt gtc gtg cca act ggg agt cat ttc tac ttg aga gtg aag    1717
Asp Phe Phe Val Val Pro Thr Gly Ser His Phe Tyr Leu Arg Val Lys
495                 500                 505                 510 gta aaa gac tct gga gca gga ata aat cct caa gac att cca aag att    1765
Val Lys Asp Ser Gly Ala Gly Ile Asn Pro Gln Asp Ile Pro Lys Ile
                515                 520                 525 ttc act aaa ttt gct caa aca caa tct tta gcg acg aga agc tcg ggt    1813
Phe Thr Lys Phe Ala Gln Thr Gln Ser Leu Ala Thr Arg Ser Ser Gly
            530                 535                 540 ggt agt ggg ctt ggc ctc gcc atc tcc aag agg ttt gtg aat ctg atg    1861
Gly Ser Gly Leu Gly Leu Ala Ile Ser Lys Arg Phe Val Asn Leu Met
    545                 550                 555 gag ggt aac att tgg att gag agc gat ggt ctt gga aaa gga tgc acg    1909
Glu Gly Asn Ile Trp Ile Glu Ser Asp Gly Leu Gly Lys Gly Cys Thr
        560                 565                 570 gct atc ttt gat gtt aaa ctt ggg atc tca gaa cgt tca aac gaa tct    1957
Ala Ile Phe Asp Val Lys Leu Gly Ile Ser Glu Arg Ser Asn Glu Ser
575                 580                 585                 590 aaa cag tcg ggc ata ccg aaa gtt cca gcc att ccc cga cat tca aat    2005
Lys Gln Ser Gly Ile Pro Lys Val Pro Ala Ile Pro Arg His Ser Asn
                595                 600                 605 ttc act gga ctt aag gtt ctt gtc atg gat gag aac ggg gta agt aga    2053
Phe Thr Gly Leu Lys Val Leu Val Met Asp Glu Asn Gly Val Ser Arg
            610                 615                 620 atg gtg acg aag gga ctt ctt gta cac ctt ggg tgc gaa gtg acc acg    2101
Met Val Thr Lys Gly Leu Leu Val His Leu Gly Cys Glu Val Thr Thr
    625                 630                 635 gtg agt tca aac gag gag tgt ctc cga gtt gtg tcc cat gag cac aaa    2149
Val Ser Ser Asn Glu Glu Cys Leu Arg Val Val Ser His Glu His Lys
        640                 645                 650 gtg gtc ttc atg gac gtg tgc atg ccc ggg gtc gaa aac tac caa atc    2197
Val Val Phe Met Asp Val Cys Met Pro Gly Val Glu Asn Tyr Gln Ile
655                 660                 665                 670 gct ctc cgt att cac gag aaa ttc aca aaa caa cgc cac caa cgg cca    2245
Ala Leu Arg Ile His Glu Lys Phe Thr Lys Gln Arg His Gln Arg Pro
                675                 680                 685 cta ctt gtg gca ctc agt ggt aac act gac aaa tcc aca aaa gag aaa    2293
Leu Leu Val Ala Leu Ser Gly Asn Thr Asp Lys Ser Thr Lys Glu Lys
```

```
Leu Leu Val Ala Leu Ser Gly Asn Thr Asp Lys Ser Thr Lys Glu Lys
            690                 695                 700 tgc atg agc ttt ggt cta gac ggt gtg ttg ctc aaa ccc gta tca cta    2341
Cys Met Ser Phe Gly Leu Asp Gly Val Leu Leu Lys Pro Val Ser Leu
        705                 710                 715 gac aac ata aga gat gtt ctg tct gat ctt ctc gag ccc cgg gta ctg    2389
Asp Asn Ile Arg Asp Val Leu Ser Asp Leu Leu Glu Pro Arg Val Leu
    720                 725                 730 tac gag ggc atg taaaggcgat ggatgcccca tgccccagag gagtaattcc        2441
Tyr Glu Gly Met
735 gctcccgcct tcttctcccg taaaacatcg gaagctgatg ttctctggtt taattgtgta  2501 catatcagag attgtcggag cgttttggat gatatcttaa aacagaaagg gaataacaaa  2561 atagaaactc taaaccggta tgtgtccgtg gcgatttcgg ttatagagga acaagatggt  2621 ggtggtataa tcataccatt tcagattaca tgtttgacta atgttgtatc cttatatatg  2681 tagttacatt cttataagaa tttggatcga gttatggatg cttgttgcgt gcatgtatga  2741 cattgatgca gtattatggc gtcagctttg cgccgcttag tagaac                2787

<210> SEQ ID NO 5
<211> LENGTH: 738
<212> TYPE: PRT
<213> ORGANISM: Arabidopsis thaliana

<400> SEQUENCE: 5

Met Glu Val Cys Asn Cys Ile Glu Pro Gln Trp Pro Ala Asp Glu Leu
  1               5                  10                  15

Leu Met Lys Tyr Gln Tyr Ile Ser Asp Phe Phe Ile Ala Ile Ala Tyr
             20                  25                  30

Phe Ser Ile Pro Leu Glu Leu Ile Tyr Phe Val Lys Lys Ser Ala Val
         35                  40                  45

Phe Pro Tyr Arg Trp Val Leu Gln Phe Gly Ala Phe Ile Val Leu
     50                  55                  60

Tyr Gly Ala Thr His Leu Ile Asn Leu Trp Thr Phe Thr Thr His Ser
 65                  70                  75                  80

Arg Thr Val Ala Leu Val Met Thr Thr Ala Lys Val Leu Thr Ala Val
                 85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220

Lys Ile Ser Pro Asn Ser Pro Val Ala Arg Leu Arg Pro Val Ser Gly
225                 230                 235                 240
```

```
Lys Tyr Met Leu Gly Glu Val Ala Val Arg Val Pro Leu Leu His
                245                 250                 255

Leu Ser Asn Phe Gln Ile Asn Asp Trp Pro Glu Leu Ser Thr Lys Arg
            260                 265                 270

Tyr Ala Leu Met Val Leu Met Leu Pro Ser Asp Ser Ala Arg Gln Trp
            275                 280             285

His Val His Glu Leu Glu Leu Val Glu Val Val Ala Asp Gln Val Ala
        290                 295             300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Thr Ala Ile Arg Ala Arg Asn Asp Phe Leu Ala Val Met Asn
                340                 345                 350

His Glu Met Arg Thr Pro Met His Ala Ile Ile Ala Leu Ser Ser Leu
                355                 360                 365

Leu Gln Glu Thr Glu Leu Thr Pro Glu Gln Arg Leu Met Val Glu Thr
            370                 375                 380

Ile Leu Lys Ser Ser Asn Leu Leu Ala Thr Leu Met Asn Asp Val Leu
385                 390                 395                 400

Asp Leu Ser Arg Leu Glu Asp Gly Ser Leu Gln Leu Glu Leu Gly Thr
                    405                 410                 415

Phe Asn Leu His Thr Leu Phe Arg Glu Val Leu Asn Leu Ile Lys Pro
                420                 425                 430

Ile Ala Val Val Lys Lys Leu Pro Ile Thr Leu Asn Leu Ala Pro Asp
                435                 440                 445

Leu Pro Glu Phe Val Val Gly Asp Glu Lys Arg Leu Met Gln Ile Ile
            450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495

Phe Val Val Pro Thr Gly Ser His Phe Tyr Leu Arg Val Lys Val Lys
                500                 505                 510

Asp Ser Gly Ala Gly Ile Asn Pro Gln Asp Ile Pro Lys Ile Phe Thr
            515                 520                 525

Lys Phe Ala Gln Thr Gln Ser Leu Ala Thr Arg Ser Ser Gly Gly Ser
            530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
            595                 600                 605

Gly Leu Lys Val Leu Val Met Asp Glu Asn Gly Val Ser Arg Met Val
        610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
                645                 650                 655
```

-continued

```
Phe Met Asp Val Cys Met Pro Gly Val Glu Asn Tyr Gln Ile Ala Leu
        660                 665                 670

Arg Ile His Glu Lys Phe Thr Lys Gln Arg His Gln Arg Pro Leu Leu
    675                 680                 685

Val Ala Leu Ser Gly Asn Thr Asp Lys Ser Thr Lys Glu Lys Cys Met
690                 695                 700

Ser Phe Gly Leu Asp Gly Val Leu Leu Lys Pro Val Ser Leu Asp Asn
705                 710                 715                 720

Ile Arg Asp Val Leu Ser Asp Leu Leu Glu Pro Arg Val Leu Tyr Glu
                725                 730                 735

Gly Met

<210> SEQ ID NO 6
<211> LENGTH: 2787
<212> TYPE: DNA
<213> ORGANISM: Arabidopsis thaliana
<220> FEATURE:
<221> NAME/KEY: CDS
<222> LOCATION: (188)..(2401)

<400> SEQUENCE: 6
agtaagaacg aagaagaagt gttaaaccca accaattttg acttgaaaaa aagcttcaac      60
gctccccttt tctccttctc cgtcgctctc cgccgcgtcc caaatcccca attcctcctc     120
ttctccgatc aattcttccc aagtgtgtgt atgtgtgaga gaggaactat agtgtaaaaa     180 attcata atg gaa gtc tgc aat tgt att gaa ccg caa tgg cca gcg gat     229
        Met Glu Val Cys Asn Cys Ile Glu Pro Gln Trp Pro Ala Asp
          1               5                  10 gaa ttg tta atg aaa tac caa tac atc tcc gat ttc ttc att gcg att     277
Glu Leu Leu Met Lys Tyr Gln Tyr Ile Ser Asp Phe Phe Ile Ala Ile
 15              20                  25                  30 gcg tat ttt tcg att cct ctt gag ttg att tac ttt gtg aag aaa tca     325
Ala Tyr Phe Ser Ile Pro Leu Glu Leu Ile Tyr Phe Val Lys Lys Ser
                35                  40                  45 gcc gtg ttt ccg tat aga tgg gta ctt gtt cag ttt ggt gct ttt atc     373
Ala Val Phe Pro Tyr Arg Trp Val Leu Val Gln Phe Gly Ala Phe Ile
            50                  55                  60 gtt ctt tgt gga gca act cat ctt att aac tta tgg act ttc act acg     421
Val Leu Cys Gly Ala Thr His Leu Ile Asn Leu Trp Thr Phe Thr Thr
         65                  70                  75 cat tcg aga acc gtg gcg ctt gtg atg act acc gcg aag gtg tta acc     469
His Ser Arg Thr Val Ala Leu Val Met Thr Thr Ala Lys Val Leu Thr
     80                  85                  90 gct gtt gtc tcg tgt gct act acg ttg atg ctt gtt cat att att cct     517
Ala Val Val Ser Cys Ala Thr Thr Leu Met Leu Val His Ile Ile Pro
 95                 100                 105                 110 gat ctt ttg agt gtt aag act cgg gag ctt ttc ttg aaa aat aaa gct     565
Asp Leu Leu Ser Val Lys Thr Arg Glu Leu Phe Leu Lys Asn Lys Ala
                115                 120                 125 gct gag ctc gat aga gaa atg gga ttg att cga act cag gaa gaa acc     613
Ala Glu Leu Asp Arg Glu Met Gly Leu Ile Arg Thr Gln Glu Glu Thr
            130                 135                 140 gga agg cat gtg aga atg ttg act cat gag att aga agc act tta gat     661
Gly Arg His Val Arg Met Leu Thr His Glu Ile Arg Ser Thr Leu Asp
        145                 150                 155 aga cat act att tta aag act aca ctt gtt gag ctt ggt agg aca tta     709
Arg His Thr Ile Leu Lys Thr Thr Leu Val Glu Leu Gly Arg Thr Leu
    160                 165                 170 gct ttg gag gag tgt gca ttg tgg atg cct act aga act ggg tta gag     757
```

```
                                                           -continued

Ala Leu Glu Glu Cys Ala Leu Trp Met Pro Thr Arg Thr Gly Leu Glu
175                 180                 185                 190 cta cag ctt tct tat aca ctt cgt cat caa cat ccc gtg gag tat acg         805
Leu Gln Leu Ser Tyr Thr Leu Arg His Gln His Pro Val Glu Tyr Thr
                195                 200                 205 gtt cct att caa tta ccg gtg att aac caa gtg ttt ggt act agt agg         853
Val Pro Ile Gln Leu Pro Val Ile Asn Gln Val Phe Gly Thr Ser Arg
                210                 215                 220 gct gta aaa ata tct cct aat tct cct gtg gct agg ttg aga cct gtt         901
Ala Val Lys Ile Ser Pro Asn Ser Pro Val Ala Arg Leu Arg Pro Val
                225                 230                 235 tct ggg aaa tat atg cta ggg gag gtg gtc gct gtg agg gtt ccg ctt         949
Ser Gly Lys Tyr Met Leu Gly Glu Val Val Ala Val Arg Val Pro Leu
240                 245                 250 ctc cac ctt tct aat ttt cag att aat gac tgg cct gag ctt tca aca         997
Leu His Leu Ser Asn Phe Gln Ile Asn Asp Trp Pro Glu Leu Ser Thr
255                 260                 265                 270 aag aga tat gct ttg atg gtt ttg atg ctt cct tca gat agt gca agg        1045
Lys Arg Tyr Ala Leu Met Val Leu Met Leu Pro Ser Asp Ser Ala Arg
                275                 280                 285 caa tgg cat gtc cat gag ttg gaa ctc gtt gaa gtc gtc gct gat cag        1093
Gln Trp His Val His Glu Leu Glu Leu Val Glu Val Val Ala Asp Gln
                290                 295                 300 gtg gct gta gct ctc tca cat gct gcg atc cta gaa gag tcg atg cga        1141
Val Ala Val Ala Leu Ser His Ala Ala Ile Leu Glu Glu Ser Met Arg
                305                 310                 315 gct agg gac ctt ctc atg gag cag aat gtt gct ctt gat cta gct aga        1189
Ala Arg Asp Leu Leu Met Glu Gln Asn Val Ala Leu Asp Leu Ala Arg
320                 325                 330 cga gaa gca gaa aca gca atc cgt gcc cgc aat gat ttc cta gcg gtt        1237
Arg Glu Ala Glu Thr Ala Ile Arg Ala Arg Asn Asp Phe Leu Ala Val
335                 340                 345                 350 atg aac cat gaa atg cga aca ccg atg cat gcg att att gca ctc tct        1285
Met Asn His Glu Met Arg Thr Pro Met His Ala Ile Ile Ala Leu Ser
                355                 360                 365 tcc tta ctc caa gaa acg gaa cta acc cct gaa caa aga ctg atg gtg        1333
Ser Leu Leu Gln Glu Thr Glu Leu Thr Pro Glu Gln Arg Leu Met Val
                370                 375                 380 gaa aca ata ctt aaa agt agt aac ctt ttg gca act ttg atg aat gat        1381
Glu Thr Ile Leu Lys Ser Ser Asn Leu Leu Ala Thr Leu Met Asn Asp
                385                 390                 395 gtc tta gat ctt tca agg tta gaa gat gga agt ctt caa ctt gaa ctt        1429
Val Leu Asp Leu Ser Arg Leu Glu Asp Gly Ser Leu Gln Leu Glu Leu
    400                 405                 410 ggg aca ttc aat ctt cat aca tta ttt aga gag gtc ctc aat ctg ata        1477
Gly Thr Phe Asn Leu His Thr Leu Phe Arg Glu Val Leu Asn Leu Ile
415                 420                 425                 430 aag cct ata gcg gtt gtt aag aaa tta ccc atc aca cta aat ctt gca        1525
Lys Pro Ile Ala Val Val Lys Lys Leu Pro Ile Thr Leu Asn Leu Ala
                435                 440                 445 cca gat ttg cca gaa ttt gtt gtt ggg gat gag aaa cgg cta atg cag        1573
Pro Asp Leu Pro Glu Phe Val Val Gly Asp Glu Lys Arg Leu Met Gln
                450                 455                 460 ata ata tta aat ata gtt ggt aat gct gtg aaa ttc tcc aaa caa ggt        1621
Ile Ile Leu Asn Ile Val Gly Asn Ala Val Lys Phe Ser Lys Gln Gly
                465                 470                 475 agt atc tcc gta acc gct ctt gtc acc aag tca gac aca cga gct gct        1669
Ser Ile Ser Val Thr Ala Leu Val Thr Lys Ser Asp Thr Arg Ala Ala
480                 485                 490
```

```
gac ttt ttt gtc gtg cca act ggg agt cat ttc tac ttg aga gtg aag      1717
Asp Phe Phe Val Val Pro Thr Gly Ser His Phe Tyr Leu Arg Val Lys
495                 500                 505                 510 gta aaa gac tct gga gca gga ata aat cct caa gac att cca aag att      1765
Val Lys Asp Ser Gly Ala Gly Ile Asn Pro Gln Asp Ile Pro Lys Ile
                515                 520                 525 ttc act aaa ttt gct caa aca caa tct tta gcg acg aga agc tcg ggt      1813
Phe Thr Lys Phe Ala Gln Thr Gln Ser Leu Ala Thr Arg Ser Ser Gly
        530                 535                 540 ggt agt ggg ctt ggc ctc gcc atc tcc aag agg ttt gtg aat ctg atg      1861
Gly Ser Gly Leu Gly Leu Ala Ile Ser Lys Arg Phe Val Asn Leu Met
545                 550                 555 gag ggt aac att tgg att gag agc gat ggt ctt gga aaa gga tgc acg      1909
Glu Gly Asn Ile Trp Ile Glu Ser Asp Gly Leu Gly Lys Gly Cys Thr
            560                 565                 570 gct atc ttt gat gtt aaa ctt ggg atc tca gaa cgt tca aac gaa tct      1957
Ala Ile Phe Asp Val Lys Leu Gly Ile Ser Glu Arg Ser Asn Glu Ser
575                 580                 585                 590 aaa cag tcg ggc ata ccg aaa gtt cca gcc att ccc cga cat tca aat      2005
Lys Gln Ser Gly Ile Pro Lys Val Pro Ala Ile Pro Arg His Ser Asn
                595                 600                 605 ttc act gga ctt aag gtt ctt gtc atg gat gag aac ggg gta agt aga      2053
Phe Thr Gly Leu Lys Val Leu Val Met Asp Glu Asn Gly Val Ser Arg
        610                 615                 620 atg gtg acg aag gga ctt ctt gta cac ctt ggg tgc gaa gtg acc acg      2101
Met Val Thr Lys Gly Leu Leu Val His Leu Gly Cys Glu Val Thr Thr
625                 630                 635 gtg agt tca aac gag gag tgt ctc cga gtt gtg tcc cat gag cac aaa      2149
Val Ser Ser Asn Glu Glu Cys Leu Arg Val Val Ser His Glu His Lys
            640                 645                 650 gtg gtc ttc atg gac gtg tgc atg ccc ggg gtc gaa aac tac caa atc      2197
Val Val Phe Met Asp Val Cys Met Pro Gly Val Glu Asn Tyr Gln Ile
655                 660                 665                 670 gct ctc cgt att cac gag aaa ttc aca aaa caa cgc cac caa cgg cca      2245
Ala Leu Arg Ile His Glu Lys Phe Thr Lys Gln Arg His Gln Arg Pro
                675                 680                 685 cta ctt gtg gca ctc agt ggt aac act gac aaa tcc aca aaa gag aaa      2293
Leu Leu Val Ala Leu Ser Gly Asn Thr Asp Lys Ser Thr Lys Glu Lys
        690                 695                 700 tgc atg agc ttt ggt cta gac ggt gtg ttg ctc aaa ccc gta tca cta      2341
Cys Met Ser Phe Gly Leu Asp Gly Val Leu Leu Lys Pro Val Ser Leu
705                 710                 715 gac aac ata aga gat gtt ctg tct gat ctt ctc gag ccc cgg gta ctg      2389
Asp Asn Ile Arg Asp Val Leu Ser Asp Leu Leu Glu Pro Arg Val Leu
            720                 725                 730 tac gag ggc atg taaaggcgat ggatgcccca tgccccagag gagtaattcc          2441
Tyr Glu Gly Met
735 gctcccgcct tcttctcccg taaaacatcg gaagctgatg ttctctggtt taattgtgta    2501 catatcagag attgtcggag cgttttggat gatatcttaa aacagaaagg gaataacaaa    2561 atagaaactc taaaccggta tgtgtccgtg gcgatttcgg ttatagagga acaagatggt    2621 ggtggtataa tcataccatt tcagattaca tgtttgacta atgttgtatc cttatatatg    2681 tagttacatt cttataagaa tttggatcga gttatggatg cttgttgcgt gcatgtatga    2741 cattgatgca gtattatggc gtcagctttg cgccgcttag tagaac                   2787
```

<210> SEQ ID NO 7
<211> LENGTH: 738

```
<212> TYPE: PRT
<213> ORGANISM: Arabidopsis thaliana

<400> SEQUENCE: 7

Met Glu Val Cys Asn Cys Ile Glu Pro Gln Trp Pro Ala Asp Glu Leu
  1               5                  10                  15

Leu Met Lys Tyr Gln Tyr Ile Ser Asp Phe Phe Ile Ala Ile Ala Tyr
             20                  25                  30

Phe Ser Ile Pro Leu Glu Leu Ile Tyr Phe Val Lys Lys Ser Ala Val
         35                  40                  45

Phe Pro Tyr Arg Trp Val Leu Val Gln Phe Gly Ala Phe Ile Val Leu
     50                  55                  60

Cys Gly Ala Thr His Leu Ile Asn Leu Trp Thr Phe Thr Thr His Ser
 65                  70                  75                  80

Arg Thr Val Ala Leu Val Met Thr Thr Ala Lys Val Leu Thr Ala Val
                 85                  90                  95

Val Ser Cys Ala Thr Thr Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220

Lys Ile Ser Pro Asn Ser Pro Val Ala Arg Leu Arg Pro Val Ser Gly
225                 230                 235                 240

Lys Tyr Met Leu Gly Glu Val Val Ala Val Arg Val Pro Leu Leu His
                245                 250                 255

Leu Ser Asn Phe Gln Ile Asn Asp Trp Pro Glu Leu Ser Thr Lys Arg
            260                 265                 270

Tyr Ala Leu Met Val Leu Met Leu Pro Ser Asp Ser Ala Arg Gln Trp
        275                 280                 285

His Val His Glu Leu Glu Leu Val Glu Val Val Ala Asp Gln Val Ala
    290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Thr Ala Ile Arg Ala Arg Asn Asp Phe Leu Ala Val Met Asn
            340                 345                 350

His Glu Met Arg Thr Pro Met His Ala Ile Ile Ala Leu Ser Ser Leu
        355                 360                 365

Leu Gln Glu Thr Glu Leu Thr Pro Gly Gln Arg Leu Met Val Glu Thr
    370                 375                 380

Ile Leu Lys Ser Ser Asn Leu Leu Ala Thr Leu Met Asn Asp Val Leu
385                 390                 395                 400
```

-continued

```
Asp Leu Ser Arg Leu Glu Asp Gly Ser Leu Gln Leu Glu Leu Gly Thr
            405                 410                 415

Phe Asn Leu His Thr Leu Phe Arg Glu Val Leu Asn Leu Ile Lys Pro
        420                 425                 430

Ile Ala Val Val Lys Lys Leu Pro Ile Thr Leu Asn Leu Ala Pro Asp
    435                 440                 445

Leu Pro Glu Phe Val Val Gly Asp Glu Lys Arg Leu Met Gln Ile Ile
450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495

Phe Val Val Pro Thr Gly Ser His Phe Tyr Leu Arg Val Lys Val Lys
            500                 505                 510

Asp Ser Gly Ala Gly Ile Asn Pro Gln Asp Ile Pro Lys Ile Phe Thr
        515                 520                 525

Lys Phe Ala Gln Thr Gln Ser Leu Ala Thr Arg Ser Ser Gly Gly Ser
    530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
        595                 600                 605

Gly Leu Lys Val Leu Val Met Asp Glu Asn Gly Val Ser Arg Met Val
    610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
                645                 650                 655

Phe Met Asp Val Cys Met Pro Gly Val Glu Asn Tyr Gln Ile Ala Leu
            660                 665                 670

Arg Ile His Glu Lys Phe Thr Lys Gln Arg His Gln Arg Pro Leu Leu
        675                 680                 685

Val Ala Leu Ser Gly Asn Thr Asp Lys Ser Thr Lys Glu Lys Cys Met
    690                 695                 700

Ser Phe Gly Leu Asp Gly Val Leu Leu Lys Pro Val Ser Leu Asp Asn
705                 710                 715                 720

Ile Arg Asp Val Leu Ser Asp Leu Leu Glu Pro Arg Val Leu Tyr Glu
                725                 730                 735

Gly Met
```

<210> SEQ ID NO 8
<211> LENGTH: 2787
<212> TYPE: DNA
<213> ORGANISM: Arabidopsis thaliana
<220> FEATURE:
<221> NAME/KEY: CDS
<222> LOCATION: (188)..(2401)

<400> SEQUENCE: 8
agtaagaacg aagaagaagt gttaaaccca accaattttg acttgaaaaa aagcttcaac    60

```
gctcccttt tctccttctc cgtcgctctc cgccgcgtcc caaatcccca attcctcctc      120
ttctccgatc aattcttccc aagtgtgtgt atgtgtgaga gaggaactat agtgtaaaaa      180 attcata atg gaa gtc tgc aat tgt att gaa ccg caa tgg cca gcg gat         229
        Met Glu Val Cys Asn Cys Ile Glu Pro Gln Trp Pro Ala Asp
        1               5                   10 gaa ttg tta atg aaa tac caa tac atc tcc gat ttc ttc att gcg att         277
Glu Leu Leu Met Lys Tyr Gln Tyr Ile Ser Asp Phe Phe Ile Ala Ile
15                  20                  25                  30 gtg tat ttt tcg att cct ctt gag ttg att tac ttt gtg aag aaa tca         325
Val Tyr Phe Ser Ile Pro Leu Glu Leu Ile Tyr Phe Val Lys Lys Ser
                35                  40                  45 gcc gtg ttt ccg tat aga tgg gta ctt gtt cag ttt ggt gct ttt atc         373
Ala Val Phe Pro Tyr Arg Trp Val Leu Val Gln Phe Gly Ala Phe Ile
            50                  55                  60 gtt ctt tgt gga gca act cat ctt att aac tta tgg act ttc act acg         421
Val Leu Cys Gly Ala Thr His Leu Ile Asn Leu Trp Thr Phe Thr Thr
65                  70                  75 cat tcg aga acc gtg gcg ctt gtg atg act acc gcg aag gtg tta acc         469
His Ser Arg Thr Val Ala Leu Val Met Thr Thr Ala Lys Val Leu Thr
        80                  85                  90 gct gtt gtc tcg tgt gct act gcg ttg atg ctt gtt cat att att cct         517
Ala Val Val Ser Cys Ala Thr Ala Leu Met Leu Val His Ile Ile Pro
95                  100                 105                 110 gat ctt ttg agt gtt aag act cgg gag ctt ttc ttg aaa aat aaa gct         565
Asp Leu Leu Ser Val Lys Thr Arg Glu Leu Phe Leu Lys Asn Lys Ala
                115                 120                 125 gct gag ctc gat aga gaa atg gga ttg att cga act cag gaa gaa acc         613
Ala Glu Leu Asp Arg Glu Met Gly Leu Ile Arg Thr Gln Glu Glu Thr
            130                 135                 140 gga agg cat gtg aga atg ttg act cat gag att aga agc act tta gat         661
Gly Arg His Val Arg Met Leu Thr His Glu Ile Arg Ser Thr Leu Asp
145                 150                 155 aga cat act att tta aag act aca ctt gtt gag ctt ggt agg aca tta         709
Arg His Thr Ile Leu Lys Thr Thr Leu Val Glu Leu Gly Arg Thr Leu
        160                 165                 170 gct ttg gag gag tgt gca ttg tgg atg cct act aga act ggg tta gag         757
Ala Leu Glu Glu Cys Ala Leu Trp Met Pro Thr Arg Thr Gly Leu Glu
175                 180                 185                 190 cta cag ctt tct tat aca ctt cgt cat caa cat ccc gtg gag tat acg         805
Leu Gln Leu Ser Tyr Thr Leu Arg His Gln His Pro Val Glu Tyr Thr
                195                 200                 205 gtt cct att caa tta ccg gtg att aac caa gtg ttt ggt act agt agg         853
Val Pro Ile Gln Leu Pro Val Ile Asn Gln Val Phe Gly Thr Ser Arg
            210                 215                 220 gct gta aaa ata tct cct aat tct cct gtg gct agg ttg aga cct gtt         901
Ala Val Lys Ile Ser Pro Asn Ser Pro Val Ala Arg Leu Arg Pro Val
225                 230                 235 tct ggg aaa tat atg cta ggg gag gtg gtc gct gtg agg gtt ccg ctt         949
Ser Gly Lys Tyr Met Leu Gly Glu Val Val Ala Val Arg Val Pro Leu
240                 245                 250 ctc cac ctt tct aat ttt cag att aat gac tgg cct gag ctt tca aca         997
Leu His Leu Ser Asn Phe Gln Ile Asn Asp Trp Pro Glu Leu Ser Thr
255                 260                 265                 270 aag aga tat gct ttg atg gtt ttg atg ctt cct tca gat agt gca agg         1045
Lys Arg Tyr Ala Leu Met Val Leu Met Leu Pro Ser Asp Ser Ala Arg
                275                 280                 285 caa tgg cat gtc cat gag ttg gaa ctc gtt gaa gtc gtc gct gat cag         1093
Gln Trp His Val His Glu Leu Glu Leu Val Glu Val Val Ala Asp Gln
            290                 295                 300
```

```
gtg gct gta gct ctc tca cat gct gcg atc cta gaa gag tcg atg cga      1141
Val Ala Val Ala Leu Ser His Ala Ala Ile Leu Glu Glu Ser Met Arg
        305                 310                 315 gct agg gac ctt ctc atg gag cag aat gtt gct ctt gat cta gct aga      1189
Ala Arg Asp Leu Leu Met Glu Gln Asn Val Ala Leu Asp Leu Ala Arg
320                 325                 330 cga gaa gca gaa aca gca atc cgt gcc cgc aat gat ttc cta gcg gtt      1237
Arg Glu Ala Glu Thr Ala Ile Arg Ala Arg Asn Asp Phe Leu Ala Val
335                 340                 345                 350 atg aac cat gaa atg cga aca ccg atg cat gcg att att gca ctc tct      1285
Met Asn His Glu Met Arg Thr Pro Met His Ala Ile Ile Ala Leu Ser
                355                 360                 365 tcc tta ctc caa gaa acg gaa cta acc cct gaa caa aga ctg atg gtg      1333
Ser Leu Leu Gln Glu Thr Glu Leu Thr Pro Glu Gln Arg Leu Met Val
        370                 375                 380 gaa aca ata ctt aaa agt agt aac ctt ttg gca act ttg atg aat gat      1381
Glu Thr Ile Leu Lys Ser Ser Asn Leu Leu Ala Thr Leu Met Asn Asp
                385                 390                 395 gtc tta gat ctt tca agg tta gaa gat gga agt ctt caa ctt gaa ctt      1429
Val Leu Asp Leu Ser Arg Leu Glu Asp Gly Ser Leu Gln Leu Glu Leu
400                 405                 410 ggg aca ttc aat ctt cat aca tta ttt aga gag gtc ctc aat ctg ata      1477
Gly Thr Phe Asn Leu His Thr Leu Phe Arg Glu Val Leu Asn Leu Ile
415                 420                 425                 430 aag cct ata gcg gtt gtt aag aaa tta ccc atc aca cta aat ctt gca      1525
Lys Pro Ile Ala Val Val Lys Lys Leu Pro Ile Thr Leu Asn Leu Ala
                435                 440                 445 cca gat ttg cca gaa ttt gtt gtt ggg gat gag aaa cgg cta atg cag      1573
Pro Asp Leu Pro Glu Phe Val Val Gly Asp Glu Lys Arg Leu Met Gln
        450                 455                 460 ata ata tta aat ata gtt ggt aat gct gtg aaa ttc tcc aaa caa ggt      1621
Ile Ile Leu Asn Ile Val Gly Asn Ala Val Lys Phe Ser Lys Gln Gly
                465                 470                 475 agt atc tcc gta acc gct ctt gtc acc aag tca gac aca cga gct gct      1669
Ser Ile Ser Val Thr Ala Leu Val Thr Lys Ser Asp Thr Arg Ala Ala
        480                 485                 490 gac ttt ttt gtc gtg cca act ggg agt cat ttc tac ttg aga gtg aag      1717
Asp Phe Phe Val Val Pro Thr Gly Ser His Phe Tyr Leu Arg Val Lys
495                 500                 505                 510 gta aaa gac tct gga gca gga ata aat cct caa gac att cca aag att      1765
Val Lys Asp Ser Gly Ala Gly Ile Asn Pro Gln Asp Ile Pro Lys Ile
                515                 520                 525 ttc act aaa ttt gct caa aca caa tct tta gcg acg aga agc tcg ggt      1813
Phe Thr Lys Phe Ala Gln Thr Gln Ser Leu Ala Thr Arg Ser Ser Gly
        530                 535                 540 ggt agt ggg ctt ggc ctc gcc atc tcc aag agg ttt gtg aat ctg atg      1861
Gly Ser Gly Leu Gly Leu Ala Ile Ser Lys Arg Phe Val Asn Leu Met
        545                 550                 555 gag ggt aac att tgg att gag agc gat ggt ctt gga aaa gga tgc acg      1909
Glu Gly Asn Ile Trp Ile Glu Ser Asp Gly Leu Gly Lys Gly Cys Thr
        560                 565                 570 gct atc ttt gat gtt aaa ctt ggg atc tca gaa cgt tca aac gaa tct      1957
Ala Ile Phe Asp Val Lys Leu Gly Ile Ser Glu Arg Ser Asn Glu Ser
575                 580                 585                 590 aaa cag tcg ggc ata ccg aaa gtt cca gcc att ccc cga cat tca aat      2005
Lys Gln Ser Gly Ile Pro Lys Val Pro Ala Ile Pro Arg His Ser Asn
                595                 600                 605 ttc act gga ctt aag gtt ctt gtc atg gat gag aac ggg gta agt aga      2053
Phe Thr Gly Leu Lys Val Leu Val Met Asp Glu Asn Gly Val Ser Arg
```

-continued

```
            610                 615                 620
atg gtg acg aag gga ctt ctt gta cac ctt ggg tgc gaa gtg acc acg    2101
Met Val Thr Lys Gly Leu Leu Val His Leu Gly Cys Glu Val Thr Thr
            625                 630                 635 gtg agt tca aac gag gag tgt ctc cga gtt gtg tcc cat gag cac aaa    2149
Val Ser Ser Asn Glu Glu Cys Leu Arg Val Val Ser His Glu His Lys
640                 645                 650 gtg gtc ttc atg gac gtg tgc atg ccc ggg gtc gaa aac tac caa atc    2197
Val Val Phe Met Asp Val Cys Met Pro Gly Val Glu Asn Tyr Gln Ile
655                 660                 665                 670 gct ctc cgt att cac gag aaa ttc aca aaa caa cgc cac caa cgg cca    2245
Ala Leu Arg Ile His Glu Lys Phe Thr Lys Gln Arg His Gln Arg Pro
                675                 680                 685 cta ctt gtg gca ctc agt ggt aac act gac aaa tcc aca aaa gag aaa    2293
Leu Leu Val Ala Leu Ser Gly Asn Thr Asp Lys Ser Thr Lys Glu Lys
                690                 695                 700 tgc atg agc ttt ggt cta gac ggt gtg ttg ctc aaa ccc gta tca cta    2341
Cys Met Ser Phe Gly Leu Asp Gly Val Leu Leu Lys Pro Val Ser Leu
            705                 710                 715 gac aac ata aga gat gtt ctg tct gat ctt ctc gag ccc cgg gta ctg    2389
Asp Asn Ile Arg Asp Val Leu Ser Asp Leu Leu Glu Pro Arg Val Leu
720                 725                 730 tac gag ggc atg taaaggcgat ggatgcccca tgccccagag gagtaattcc        2441
Tyr Glu Gly Met
735 gctcccgcct tcttctcccg taaaacatcg gaagctgatg ttctctggtt taattgtgta  2501 catatcagag attgtcggag cgttttggat gatatcttaa aacagaaagg gaataacaaa  2561 atagaaactc taaaccggta tgtgtccgtg gcgatttcgg ttatagagga acaagatggt  2621 ggtggtataa tcataccatt tcagattaca tgtttgacta atgttgtatc cttatatatg  2681 tagttacatt cttataagaa tttggatcga gttatggatg cttgttgcgt gcatgtatga  2741 cattgatgca gtattatggc gtcagctttg cgccgcttag tagaac               2787
```

<210> SEQ ID NO 9
<211> LENGTH: 738
<212> TYPE: PRT
<213> ORGANISM: Arabidopsis thaliana

<400> SEQUENCE: 9

```
Met Glu Val Cys Asn Cys Ile Glu Pro Gln Trp Pro Ala Asp Glu Leu
1               5                   10                  15

Leu Met Lys Tyr Gln Tyr Ile Ser Asp Phe Phe Ile Ala Ile Val Tyr
            20                  25                  30

Phe Ser Ile Pro Leu Glu Leu Ile Tyr Phe Val Lys Lys Ser Ala Val
        35                  40                  45

Phe Pro Tyr Arg Trp Val Leu Val Gln Phe Gly Ala Phe Ile Val Leu
    50                  55                  60

Cys Gly Ala Thr His Leu Ile Asn Leu Trp Thr Phe Thr Thr His Ser
65                  70                  75                  80

Arg Thr Val Ala Leu Val Met Thr Thr Ala Lys Val Leu Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
```

```
                130                 135                 140
His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
                180                 185                 190

Leu Ser Tyr Thr Leu Arg His Gln His Pro Val Glu Tyr Thr Val Pro
                195                 200                 205

Ile Gln Leu Pro Val Ile Asn Gln Val Phe Gly Thr Ser Arg Ala Val
                210                 215                 220

Lys Ile Ser Pro Asn Ser Pro Val Ala Arg Leu Arg Pro Val Ser Gly
225                 230                 235                 240

Lys Tyr Met Leu Gly Glu Val Ala Val Arg Val Pro Leu Leu His
                245                 250                 255

Leu Ser Asn Phe Gln Ile Asn Asp Trp Pro Glu Leu Ser Thr Lys Arg
                260                 265                 270

Tyr Ala Leu Met Val Leu Met Leu Pro Ser Asp Ser Ala Arg Gln Trp
                275                 280                 285

His Val His Glu Leu Glu Leu Val Glu Val Val Ala Asp Gln Val Ala
                290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Thr Ala Ile Arg Ala Arg Asn Asp Phe Leu Ala Val Met Asn
                340                 345                 350

His Glu Met Arg Thr Pro Met His Ala Ile Ile Ala Leu Ser Ser Leu
                355                 360                 365

Leu Gln Glu Thr Glu Leu Thr Pro Glu Gln Arg Leu Met Val Glu Thr
                370                 375                 380

Ile Leu Lys Ser Ser Asn Leu Leu Ala Thr Leu Met Asn Asp Val Leu
385                 390                 395                 400

Asp Leu Ser Arg Leu Glu Asp Gly Ser Leu Gln Leu Glu Leu Gly Thr
                405                 410                 415

Phe Asn Leu His Thr Leu Phe Arg Glu Val Leu Asn Leu Ile Lys Pro
                420                 425                 430

Ile Ala Val Val Lys Lys Leu Pro Ile Thr Leu Asn Leu Ala Pro Asp
                435                 440                 445

Leu Pro Glu Phe Val Val Gly Asp Glu Lys Arg Leu Met Gln Ile Ile
                450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495

Phe Val Val Pro Thr Gly Ser His Phe Tyr Leu Arg Val Lys Val Lys
                500                 505                 510

Asp Ser Gly Ala Gly Ile Asn Pro Gln Asp Ile Pro Lys Ile Phe Thr
                515                 520                 525

Lys Phe Ala Gln Thr Gln Ser Leu Ala Thr Arg Ser Ser Gly Ser
                530                 535                 540

Gly Leu Gly Leu Ala Ile Ser Lys Arg Phe Val Asn Leu Met Glu Gly
545                 550                 555                 560
```

```
Asn Ile Trp Ile Glu Ser Asp Gly Leu Gly Lys Gly Cys Thr Ala Ile
            565                 570                 575
Phe Asp Val Lys Leu Gly Ile Ser Glu Arg Ser Asn Glu Ser Lys Gln
        580                 585                 590
Ser Gly Ile Pro Lys Val Pro Ala Ile Pro Arg His Ser Asn Phe Thr
    595                 600                 605
Gly Leu Lys Val Leu Val Met Asp Glu Asn Gly Val Ser Arg Met Val
610                 615                 620
Thr Lys Gly Leu Leu Val His Leu Gly Cys Glu Val Thr Thr Val Ser
625                 630                 635                 640
Ser Asn Glu Glu Cys Leu Arg Val Val Ser His Glu His Lys Val Val
                645                 650                 655
Phe Met Asp Val Cys Met Pro Gly Val Glu Asn Tyr Gln Ile Ala Leu
            660                 665                 670
Arg Ile His Glu Lys Phe Thr Lys Gln Arg His Gln Arg Pro Leu Leu
        675                 680                 685
Val Ala Leu Ser Gly Asn Thr Asp Lys Ser Thr Lys Glu Lys Cys Met
    690                 695                 700
Ser Phe Gly Leu Asp Gly Val Leu Leu Lys Pro Val Ser Leu Asp Asn
705                 710                 715                 720
Ile Arg Asp Val Leu Ser Asp Leu Leu Glu Pro Arg Val Leu Tyr Glu
                725                 730                 735
Gly Met

<210> SEQ ID NO 10
<211> LENGTH: 2787
<212> TYPE: DNA
<213> ORGANISM: Arabidopsis thaliana
<220> FEATURE:
<221> NAME/KEY: CDS
<222> LOCATION: (188)..(2401)

<400> SEQUENCE: 10
agtaagaacg aagaagaagt gttaaaccca accaattttg acttgaaaaa aagcttcaac      60
gctccccttt tctccttctc cgtcgctctc cgccgcgtcc caaatcccca attcctcctc     120
ttctccgatc aattcttccc aagtgtgtgt atgtgtgaga gaggaactat agtgtaaaaa     180 attcata atg gaa gtc tgc aat tgt att gaa ccg caa tgg cca gcg gat       229
        Met Glu Val Cys Asn Cys Ile Glu Pro Gln Trp Pro Ala Asp
        1               5                   10 gaa ttg tta atg aaa tac caa tac atc tcc gat ttc ttc att gcg att      277
Glu Leu Leu Met Lys Tyr Gln Tyr Ile Ser Asp Phe Phe Ile Ala Ile
15                  20                  25                  30 gcg tat ttt tcg att cct ctt gag ttg att tac ttt gtg aag aaa tca      325
Ala Tyr Phe Ser Ile Pro Leu Glu Leu Ile Tyr Phe Val Lys Lys Ser
                35                  40                  45 gcc gtg ttt ccg tat aga tgg gta ctt gtt cag ttt ggt gct ttt ttc      373
Ala Val Phe Pro Tyr Arg Trp Val Leu Val Gln Phe Gly Ala Phe Phe
            50                  55                  60 gtt ctt tgt gga gca act cat ctt att aac tta tgg act ttc act acg      421
Val Leu Cys Gly Ala Thr His Leu Ile Asn Leu Trp Thr Phe Thr Thr
        65                  70                  75 cat tcg aga acc gtg gcg ctt gtg atg act acc gcg aag gtg tta acc      469
His Ser Arg Thr Val Ala Leu Val Met Thr Thr Ala Lys Val Leu Thr
    80                  85                  90 gct gtt gtc tcg tgt gct act gcg ttg atg ctt gtt cat att att cct      517
Ala Val Val Ser Cys Ala Thr Ala Leu Met Leu Val His Ile Ile Pro
```

-continued

|  |  |  |  |
|---|---|---|---|
| 95 | 100 | 105 | 110 |

| gat | ctt | ttg | agt | gtt | aag | act | cgg | gag | ctt | ttc | ttg | aaa | aat | aaa | gct | 565 |
|-----|-----|-----|-----|-----|-----|-----|-----|-----|-----|-----|-----|-----|-----|-----|-----|-----|
| Asp | Leu | Leu | Ser | Val | Lys | Thr | Arg | Glu | Leu | Phe | Leu | Lys | Asn | Lys | Ala | |
| | | | | 115 | | | | | 120 | | | | | 125 | | |

| gct | gag | ctc | gat | aga | gaa | atg | gga | ttg | att | cga | act | cag | gaa | gaa | acc | 613 |
| Ala | Glu | Leu | Asp | Arg | Glu | Met | Gly | Leu | Ile | Arg | Thr | Gln | Glu | Glu | Thr | |
| | | | 130 | | | | | 135 | | | | | 140 | | | |

| gga | agg | cat | gtg | aga | atg | ttg | act | cat | gag | att | aga | agc | act | tta | gat | 661 |
| Gly | Arg | His | Val | Arg | Met | Leu | Thr | His | Glu | Ile | Arg | Ser | Thr | Leu | Asp | |
| | | | 145 | | | | | 150 | | | | | 155 | | | |

| aga | cat | act | att | tta | aag | act | aca | ctt | gtt | gag | ctt | ggt | agg | aca | tta | 709 |
| Arg | His | Thr | Ile | Leu | Lys | Thr | Thr | Leu | Val | Glu | Leu | Gly | Arg | Thr | Leu | |
| | | | 160 | | | | | 165 | | | | | 170 | | | |

| gct | ttg | gag | gag | tgt | gca | ttg | tgg | atg | cct | act | aga | act | ggg | tta | gag | 757 |
| Ala | Leu | Glu | Glu | Cys | Ala | Leu | Trp | Met | Pro | Thr | Arg | Thr | Gly | Leu | Glu | |
| 175 | | | | | 180 | | | | | 185 | | | | | 190 | |

| cta | cag | ctt | tct | tat | aca | ctt | cgt | cat | caa | cat | ccc | gtg | gag | tat | acg | 805 |
| Leu | Gln | Leu | Ser | Tyr | Thr | Leu | Arg | His | Gln | His | Pro | Val | Glu | Tyr | Thr | |
| | | | | 195 | | | | | 200 | | | | | 205 | | |

| gtt | cct | att | caa | tta | ccg | gtg | att | aac | caa | gtg | ttt | ggt | act | agt | agg | 853 |
| Val | Pro | Ile | Gln | Leu | Pro | Val | Ile | Asn | Gln | Val | Phe | Gly | Thr | Ser | Arg | |
| | | | | 210 | | | | | 215 | | | | | 220 | | |

| gct | gta | aaa | ata | tct | cct | aat | tct | cct | gtg | gct | agg | ttg | aga | cct | gtt | 901 |
| Ala | Val | Lys | Ile | Ser | Pro | Asn | Ser | Pro | Val | Ala | Arg | Leu | Arg | Pro | Val | |
| | | | | 225 | | | | | 230 | | | | | 235 | | |

| tct | ggg | aaa | tat | atg | cta | ggg | gag | gtg | gtc | gct | gtg | agg | gtt | ccg | ctt | 949 |
| Ser | Gly | Lys | Tyr | Met | Leu | Gly | Glu | Val | Val | Ala | Val | Arg | Val | Pro | Leu | |
| | | | | 240 | | | | | 245 | | | | | 250 | | |

| ctc | cac | ctt | tct | aat | ttt | cag | att | aat | gac | tgg | cct | gag | ctt | tca | aca | 997 |
| Leu | His | Leu | Ser | Asn | Phe | Gln | Ile | Asn | Asp | Trp | Pro | Glu | Leu | Ser | Thr | |
| 255 | | | | | 260 | | | | | 265 | | | | | 270 | |

| aag | aga | tat | gct | ttg | atg | gtt | ttg | atg | ctt | cct | tca | gat | agt | gca | agg | 1045 |
| Lys | Arg | Tyr | Ala | Leu | Met | Val | Leu | Met | Leu | Pro | Ser | Asp | Ser | Ala | Arg | |
| | | | | 275 | | | | | 280 | | | | | 285 | | |

| caa | tgg | cat | gtc | cat | gag | ttg | gaa | ctc | gtt | gaa | gtc | gtc | gct | gat | cag | 1093 |
| Gln | Trp | His | Val | His | Glu | Leu | Glu | Leu | Val | Glu | Val | Val | Ala | Asp | Gln | |
| | | | | 290 | | | | | 295 | | | | | 300 | | |

| gtg | gct | gta | gct | ctc | tca | cat | gct | gcg | atc | cta | gaa | gag | tcg | atg | cga | 1141 |
| Val | Ala | Val | Ala | Leu | Ser | His | Ala | Ala | Ile | Leu | Glu | Glu | Ser | Met | Arg | |
| | | | | 305 | | | | | 310 | | | | | 315 | | |

| gct | agg | gac | ctt | ctc | atg | gag | cag | aat | gtt | gct | ctt | gat | cta | gct | aga | 1189 |
| Ala | Arg | Asp | Leu | Leu | Met | Glu | Gln | Asn | Val | Ala | Leu | Asp | Leu | Ala | Arg | |
| | | | 320 | | | | | 325 | | | | | 330 | | | |

| cga | gaa | gca | gaa | aca | gca | atc | cgt | gcc | cgc | aat | gat | ttc | cta | gcg | gtt | 1237 |
| Arg | Glu | Ala | Glu | Thr | Ala | Ile | Arg | Ala | Arg | Asn | Asp | Phe | Leu | Ala | Val | |
| 335 | | | | | 340 | | | | | 345 | | | | | 350 | |

| atg | aac | cat | gaa | atg | cga | aca | ccg | atg | cat | gcg | att | att | gca | ctc | tct | 1285 |
| Met | Asn | His | Glu | Met | Arg | Thr | Pro | Met | His | Ala | Ile | Ile | Ala | Leu | Ser | |
| | | | | 355 | | | | | 360 | | | | | 365 | | |

| tcc | tta | ctc | caa | gaa | acg | gaa | cta | acc | cct | gaa | caa | aga | ctg | atg | gtg | 1333 |
| Ser | Leu | Leu | Gln | Glu | Thr | Glu | Leu | Thr | Pro | Glu | Gln | Arg | Leu | Met | Val | |
| | | | 370 | | | | | 375 | | | | | 380 | | | |

| gaa | aca | ata | ctt | aaa | agt | agt | aac | ctt | ttg | gca | act | ttg | atg | aat | gat | 1381 |
| Glu | Thr | Ile | Leu | Lys | Ser | Ser | Asn | Leu | Leu | Ala | Thr | Leu | Met | Asn | Asp | |
| | | 385 | | | | | 390 | | | | | 395 | | | | |

| gtc | tta | gat | ctt | tca | agg | tta | gaa | gat | gga | agt | ctt | caa | ctt | gaa | ctt | 1429 |
| Val | Leu | Asp | Leu | Ser | Arg | Leu | Glu | Asp | Gly | Ser | Leu | Gln | Leu | Glu | Leu | |
| | | 400 | | | | | 405 | | | | | 410 | | | | |

| ggg | aca | ttc | aat | ctt | cat | aca | tta | ttt | aga | gag | gtc | ctc | aat | ctg | ata | 1477 |

```
Gly Thr Phe Asn Leu His Thr Leu Phe Arg Glu Val Leu Asn Leu Ile
415                 420                 425                 430 aag cct ata gcg gtt gtt aag aaa tta ccc atc aca cta aat ctt gca    1525
Lys Pro Ile Ala Val Val Lys Lys Leu Pro Ile Thr Leu Asn Leu Ala
                    435                 440                 445 cca gat ttg cca gaa ttt gtt gtt ggg gat gag aaa cgg cta atg cag    1573
Pro Asp Leu Pro Glu Phe Val Val Gly Asp Glu Lys Arg Leu Met Gln
                450                 455                 460 ata ata tta aat ata gtt ggt aat gct gtg aaa ttc tcc aaa caa ggt    1621
Ile Ile Leu Asn Ile Val Gly Asn Ala Val Lys Phe Ser Lys Gln Gly
            465                 470                 475 agt atc tcc gta acc gct ctt gtc acc aag tca gac aca cga gct gct    1669
Ser Ile Ser Val Thr Ala Leu Val Thr Lys Ser Asp Thr Arg Ala Ala
        480                 485                 490 gac ttt ttt gtc gtg cca act ggg agt cat ttc tac ttg aga gtg aag    1717
Asp Phe Phe Val Val Pro Thr Gly Ser His Phe Tyr Leu Arg Val Lys
495                 500                 505                 510 gta aaa gac tct gga gca gga ata aat cct caa gac att cca aag att    1765
Val Lys Asp Ser Gly Ala Gly Ile Asn Pro Gln Asp Ile Pro Lys Ile
                    515                 520                 525 ttc act aaa ttt gct caa aca caa tct tta gcg acg aga agc tcg ggt    1813
Phe Thr Lys Phe Ala Gln Thr Gln Ser Leu Ala Thr Arg Ser Ser Gly
                530                 535                 540 ggt agt ggg ctt ggc ctc gcc atc tcc aag agg ttt gtg aat ctg atg    1861
Gly Ser Gly Leu Gly Leu Ala Ile Ser Lys Arg Phe Val Asn Leu Met
            545                 550                 555 gag ggt aac att tgg att gag agc gat ggt ctt gga aaa gga tgc acg    1909
Glu Gly Asn Ile Trp Ile Glu Ser Asp Gly Leu Gly Lys Gly Cys Thr
        560                 565                 570 gct atc ttt gat gtt aaa ctt ggg atc tca gaa cgt tca aac gaa tct    1957
Ala Ile Phe Asp Val Lys Leu Gly Ile Ser Glu Arg Ser Asn Glu Ser
575                 580                 585                 590 aaa cag tcg ggc ata ccg aaa gtt cca gcc att ccc cga cat tca aat    2005
Lys Gln Ser Gly Ile Pro Lys Val Pro Ala Ile Pro Arg His Ser Asn
                    595                 600                 605 ttc act gga ctt aag gtt ctt gtc atg gat gag aac ggg gta agt aga    2053
Phe Thr Gly Leu Lys Val Leu Val Met Asp Glu Asn Gly Val Ser Arg
                610                 615                 620 atg gtg acg aag gga ctt ctt gta cac ctt ggg tgc gaa gtg acc acg    2101
Met Val Thr Lys Gly Leu Leu Val His Leu Gly Cys Glu Val Thr Thr
            625                 630                 635 gtg agt tca aac gag gag tgt ctc cga gtt gtg tcc cat gag cac aaa    2149
Val Ser Ser Asn Glu Glu Cys Leu Arg Val Val Ser His Glu His Lys
        640                 645                 650 gtg gtc ttc atg gac gtg tgc atg ccc ggg gtc gaa aac tac caa atc    2197
Val Val Phe Met Asp Val Cys Met Pro Gly Val Glu Asn Tyr Gln Ile
655                 660                 665                 670 gct ctc cgt att cac gag aaa ttc aca aaa caa cgc cac caa cgg cca    2245
Ala Leu Arg Ile His Glu Lys Phe Thr Lys Gln Arg His Gln Arg Pro
                    675                 680                 685 cta ctt gtg gca ctc agt ggt aac act gac aaa tcc aca aaa gag aaa    2293
Leu Leu Val Ala Leu Ser Gly Asn Thr Asp Lys Ser Thr Lys Glu Lys
                690                 695                 700 tgc atg agc ttt ggt cta gac ggt gtg ttg ctc aaa ccc gta tca cta    2341
Cys Met Ser Phe Gly Leu Asp Gly Val Leu Leu Lys Pro Val Ser Leu
            705                 710                 715 gac aac ata aga gat gtt ctg tct gat ctt ctc gag ccc cgg gta ctg    2389
Asp Asn Ile Arg Asp Val Leu Ser Asp Leu Leu Glu Pro Arg Val Leu
        720                 725                 730
```

-continued

```
tac gag ggc atg taaaggcgat ggatgcccca tgccccagag gagtaattcc    2441
Tyr Glu Gly Met
735 gctcccgcct tcttctcccg taaaacatcg gaagctgatg ttctctggtt taattgtgta    2501 catatcagag attgtcggag cgttttggat gatatcttaa aacagaaagg gaataacaaa    2561 atagaaactc taaaccggta tgtgtccgtg gcgatttcgg ttatagagga acaagatggt    2621 ggtggtataa tcataccatt tcagattaca tgtttgacta atgttgtatc cttatatatg    2681 tagttacatt cttataagaa tttggatcga gttatggatg cttgttgcgt gcatgtatga    2741 cattgatgca gtattatggc gtcagctttg cgccgcttag tagaac    2787
```

<210> SEQ ID NO 11
<211> LENGTH: 738
<212> TYPE: PRT
<213> ORGANISM: Arabidopsis thaliana

<400> SEQUENCE: 11

```
Met Glu Val Cys Asn Cys Ile Glu Pro Gln Trp Pro Ala Asp Glu Leu
  1               5                  10                  15

Leu Met Lys Tyr Gln Tyr Ile Ser Asp Phe Phe Ile Ala Ile Ala Tyr
             20                  25                  30

Phe Ser Ile Pro Leu Glu Leu Ile Tyr Phe Val Lys Lys Ser Ala Val
         35                  40                  45

Phe Pro Tyr Arg Trp Val Leu Val Gln Phe Gly Ala Phe Phe Val Leu
     50                  55                  60

Cys Gly Ala Thr His Leu Ile Asn Leu Trp Thr Phe Thr Thr His Ser
 65                  70                  75                  80

Arg Thr Val Ala Leu Val Met Thr Thr Ala Lys Val Leu Thr Ala Val
                 85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220

Lys Ile Ser Pro Asn Ser Pro Val Ala Arg Leu Arg Pro Val Ser Gly
225                 230                 235                 240

Lys Tyr Met Leu Gly Glu Val Val Ala Val Arg Val Pro Leu Leu His
                245                 250                 255

Leu Ser Asn Phe Gln Ile Asn Asp Trp Pro Glu Leu Ser Thr Lys Arg
            260                 265                 270

Tyr Ala Leu Met Val Leu Met Leu Pro Ser Asp Ser Ala Arg Gln Trp
        275                 280                 285

His Val His Glu Leu Glu Leu Val Glu Val Val Ala Asp Gln Val Ala
```

-continued

```
            290                 295                 300
Val Ala Leu Ser His Ala Ala Ile Leu Glu Glu Ser Met Arg Ala Arg
305                 310                 315                 320
Asp Leu Leu Met Glu Gln Asn Val Ala Leu Asp Leu Ala Arg Arg Glu
                325                 330                 335
Ala Glu Thr Ala Ile Arg Ala Arg Asn Asp Phe Leu Ala Val Met Asn
            340                 345                 350
His Glu Met Arg Thr Pro Met His Ala Ile Ile Ala Leu Ser Ser Leu
                355                 360                 365
Leu Gln Glu Thr Glu Leu Thr Pro Glu Gln Arg Leu Met Val Glu Thr
            370                 375                 380
Ile Leu Lys Ser Ser Asn Leu Leu Ala Thr Leu Met Asn Asp Val Leu
385                 390                 395                 400
Asp Leu Ser Arg Leu Glu Asp Gly Ser Leu Gln Leu Glu Leu Gly Thr
                405                 410                 415
Phe Asn Leu His Thr Leu Phe Arg Glu Val Leu Asn Leu Ile Lys Pro
            420                 425                 430
Ile Ala Val Val Lys Lys Leu Pro Ile Thr Leu Asn Leu Ala Pro Asp
                435                 440                 445
Leu Pro Glu Phe Val Val Gly Asp Glu Lys Arg Leu Met Gln Ile Ile
            450                 455                 460
Leu Asn Ile Val Gly Asn Ala Val Lys Phe Ser Lys Gln Gly Ser Ile
465                 470                 475                 480
Ser Val Thr Ala Leu Val Thr Lys Ser Asp Thr Arg Ala Ala Asp Phe
                485                 490                 495
Phe Val Val Pro Thr Gly Ser His Phe Tyr Leu Arg Val Lys Val Lys
            500                 505                 510
Asp Ser Gly Ala Gly Ile Asn Pro Gln Asp Ile Pro Lys Ile Phe Thr
                515                 520                 525
Lys Phe Ala Gln Thr Gln Ser Leu Ala Thr Arg Ser Ser Gly Gly Ser
            530                 535                 540
Gly Leu Gly Leu Ala Ile Ser Lys Arg Phe Val Asn Leu Met Glu Gly
545                 550                 555                 560
Asn Ile Trp Ile Glu Ser Asp Gly Leu Gly Lys Gly Cys Thr Ala Ile
                565                 570                 575
Phe Asp Val Lys Leu Gly Ile Ser Glu Arg Ser Asn Glu Ser Lys Gln
            580                 585                 590
Ser Gly Ile Pro Lys Val Pro Ala Ile Pro Arg His Ser Asn Phe Thr
            595                 600                 605
Gly Leu Lys Val Leu Val Met Asp Glu Asn Gly Val Ser Arg Met Val
            610                 615                 620
Thr Lys Gly Leu Leu Val His Leu Gly Cys Glu Val Thr Thr Val Ser
625                 630                 635                 640
Ser Asn Glu Glu Cys Leu Arg Val Val Ser His Glu His Lys Val Val
                645                 650                 655
Phe Met Asp Val Cys Met Pro Gly Val Glu Asn Tyr Gln Ile Ala Leu
                660                 665                 670
Arg Ile His Glu Lys Phe Thr Lys Gln Arg His Gln Arg Pro Leu Leu
                675                 680                 685
Val Ala Leu Ser Gly Asn Thr Asp Lys Ser Thr Lys Glu Lys Cys Met
            690                 695                 700
Ser Phe Gly Leu Asp Gly Val Leu Leu Lys Pro Val Ser Leu Asp Asn
705                 710                 715                 720
```

```
Ile Arg Asp Val Leu Ser Asp Leu Leu Glu Pro Arg Val Leu Tyr Glu
                725                 730                 735

Gly Met

<210> SEQ ID NO 12
<211> LENGTH: 155
<212> TYPE: PRT
<213> ORGANISM: Artificial Sequence
<220> FEATURE:
<223> OTHER INFORMATION: Description of Artificial Sequence: synthetic.

<400> SEQUENCE: 12

Gln Asn Val Ala Leu Asp Leu Ala Arg Arg Glu Ala Glu Thr Ala Ile
  1               5                  10                  15

Arg Ala Arg Asn Asp Phe Leu Ala Val Met Asn His Glu Met Arg Thr
                 20                  25                  30

Pro Met His Ala Ile Ile Ala Leu Ser Ser Leu Leu Gln Glu Thr Glu
             35                  40                  45

Leu Thr Pro Glu Gln Arg Leu Met Val Glu Thr Ile Leu Lys Ser Ser
         50                  55                  60

Asn Leu Leu Ala Thr Leu Met Asn Asp Val Leu Asp Leu Ser Arg Leu
 65                  70                  75                  80

Glu Asp Gly Ser Leu Gln Leu Glu Leu Gly Thr Phe Asn Leu His Thr
                 85                  90                  95

Leu Phe Arg Glu Val Leu Asn Leu Ile Lys Pro Ile Ala Val Val Lys
                100                 105                 110

Lys Leu Pro Ile Thr Leu Asn Leu Ala Pro Asp Leu Pro Glu Phe Val
            115                 120                 125

Val Gly Asp Glu Lys Arg Leu Met Gln Ile Ile Leu Asn Ile Val Gly
        130                 135                 140

Asn Ala Val Lys Phe Ser Lys Gln Gly Ser Ile
145                 150                 155

<210> SEQ ID NO 13
<211> LENGTH: 155
<212> TYPE: PRT
<213> ORGANISM: Escherichia coli

<400> SEQUENCE: 13

Gln Asn Val Glu Leu Asp Leu Ala Lys Lys Arg Ala Gln Glu Ala Ala
  1               5                  10                  15

Arg Ile Lys Ser Glu Phe Leu Ala Asn Met Ser His Glu Leu Arg Thr
                 20                  25                  30

Pro Leu Asn Gly Val Ile Gly Phe Thr Arg Leu Thr Leu Lys Thr Glu
             35                  40                  45

Leu Thr Pro Thr Gln Arg Asp His Leu Asn Thr Ile Glu Arg Ser Ala
         50                  55                  60

Asn Asn Leu Leu Ala Ile Ile Asn Asp Val Leu Asp Phe Ser Lys Leu
 65                  70                  75                  80

Glu Ala Gly Lys Leu Ile Leu Glu Ser Ile Pro Phe Pro Leu Arg Ser
                 85                  90                  95

Thr Leu Asp Glu Val Val Thr Leu Leu Ala His Ser Ser His Asp Lys
                100                 105                 110

Gly Leu Glu Leu Thr Leu Asn Ile Lys Ser Asp Val Pro Asp Asn Val
            115                 120                 125

Ile Gly Asp Pro Leu Arg Leu Gln Gln Ile Ile Thr Asn Leu Val Gly
```

-continued

```
                130                 135                 140

Asn Ala Ile Lys Phe Thr Glu Asn Gly Asn Ile
145                 150                 155

<210> SEQ ID NO 14
<211> LENGTH: 155
<212> TYPE: PRT
<213> ORGANISM: Pseudomonas syringae

<400> SEQUENCE: 14

Gln Asn Ile Glu Leu Asp Leu Ala Arg Lys Glu Ala Leu Glu Ala Ser
  1               5                  10                  15

Arg Ile Lys Ser Glu Phe Leu Ala Asn Met Ser His Glu Ile Arg Thr
                 20                  25                  30

Pro Leu Asn Gly Ile Leu Gly Phe Thr His Leu Leu Gln Lys Ser Glu
             35                  40                  45

Leu Thr Pro Arg Gln Phe Asp Tyr Leu Gly Thr Ile Glu Lys Ser Ala
         50                  55                  60

Asp Asn Leu Leu Ser Ile Ile Asn Glu Ile Leu Asp Phe Ser Lys Ile
 65                  70                  75                  80

Glu Ala Gly Lys Leu Val Leu Asp Asn Ile Pro Phe Asn Leu Arg Asp
                 85                  90                  95

Leu Leu Gln Asp Thr Leu Thr Ile Leu Ala Pro Ala Ala His Ala Lys
            100                 105                 110

Gln Leu Glu Leu Val Ser Leu Val Tyr Arg Asp Thr Pro Leu Ala Leu
        115                 120                 125

Ser Gly Asp Pro Leu Arg Leu Arg Gln Ile Leu Thr Asn Leu Val Ser
130                 135                 140

Asn Ala Ile Lys Phe Thr Arg Glu Gly Thr Ile
145                 150                 155

<210> SEQ ID NO 15
<211> LENGTH: 149
<212> TYPE: PRT
<213> ORGANISM: Xanthomonas campestris

<400> SEQUENCE: 15

Arg Ala Val Arg Glu Ala Arg His Ala Asn Gln Ala Lys Ser Arg Phe
  1               5                  10                  15

Leu Ala Asn Met Ser His Glu Phe Arg Thr Pro Leu Asn Gly Leu Ser
                 20                  25                  30

Gly Met Thr Glu Val Leu Ala Thr Thr Arg Leu Asp Ala Glu Gln Lys
             35                  40                  45

Glu Cys Leu Asn Thr Ile Gln Ala Ser Ala Arg Ser Leu Leu Ser Leu
         50                  55                  60

Val Glu Glu Val Leu Asp Ile Ser Ala Ile Glu Ala Gly Lys Ile Arg
 65                  70                  75                  80

Ile Asp Arg Arg Asp Phe Ser Leu Arg Glu Met Ile Gly Ser Val Asn
                 85                  90                  95

Leu Ile Leu Gln Pro Gln Ala Arg Gly Arg Arg Leu Glu Tyr Gly Thr
            100                 105                 110

Gln Val Ala Asp Asp Val Pro Asp Leu Leu Lys Gly Asp Thr Ala His
        115                 120                 125

Leu Arg Gln Val Leu Leu Asn Leu Val Gly Asn Ala Val Lys Phe Thr
130                 135                 140

Glu His Gly His Val
```

-continued

<210> SEQ ID NO 16
<211> LENGTH: 66
<212> TYPE: PRT
<213> ORGANISM: Xanthomonas campestris

<400> SEQUENCE: 16

```
Leu Lys Val Leu Val Met Asp Glu Asn Gly Val Ser Arg Met Val Thr
 1               5                  10                  15

Lys Gly Leu Leu Val His Leu Gly Cys Glu Val Thr Thr Val Ser Ser
            20                  25                  30

Asn Glu Glu Cys Leu Arg Val Val Ser His Glu His Lys Val Val Phe
        35                  40                  45

Met Asp Val Cys Met Pro Gly Val Glu Asn Tyr Gln Ile Ala Leu Arg
    50                  55                  60

Ile His
 65
```

<210> SEQ ID NO 17
<211> LENGTH: 67
<212> TYPE: PRT
<213> ORGANISM: Bordetella parapertussis

<400> SEQUENCE: 17

```
Leu Arg Val Leu Val Val Asp Asp His Lys Pro Asn Leu Met Leu Leu
 1               5                  10                  15

Arg Gln Gln Leu Asp Tyr Leu Gly Gln Arg Val Val Ala Ala Asp Ser
            20                  25                  30

Gly Glu Ala Ala Leu Ala Leu Trp His Glu His Ala Phe Asp Val Val
        35                  40                  45

Ile Thr Asp Cys Asn Met Pro Gly Ile Asn Gly Tyr Glu Leu Ala Arg
    50                  55                  60

Arg Ile Arg
 65
```

<210> SEQ ID NO 18
<211> LENGTH: 67
<212> TYPE: PRT
<213> ORGANISM: Escherichia coli

<400> SEQUENCE: 18

```
Met Met Ile Leu Val Val Asp Asp His Pro Ile Asn Arg Arg Leu Leu
 1               5                  10                  15

Ala Asp Gln Leu Gly Ser Leu Gly Tyr Gln Cys Lys Thr Ala Asn Asp
            20                  25                  30

Gly Val Asp Ala Leu Asn Val Leu Ser Lys Asn His Ile Asp Ile Val
        35                  40                  45

Leu Ser Asp Val Asn Met Pro Asn Met Asp Gly Tyr Arg Leu Thr Gln
    50                  55                  60

Arg Ile Arg
 65
```

<210> SEQ ID NO 19
<211> LENGTH: 67
<212> TYPE: PRT
<213> ORGANISM: Pseudomonas syringae

<400> SEQUENCE: 19

```
Pro Arg Val Leu Cys Val Asp Asp Asn Pro Ala Asn Leu Leu Leu Val
 1               5                  10                  15

Gln Thr Leu Leu Glu Asp Met Gly Ala Glu Val Val Ala Val Glu Gly
                 20                  25                  30

Gly Tyr Ala Ala Val Asn Ala Val Gln Gln Glu Ala Phe Asp Leu Val
             35                  40                  45

Leu Met Asp Val Gln Met Pro Gly Met Asp Gly Arg Gln Ala Thr Glu
         50                  55                  60

Ala Ile Arg
 65

<210> SEQ ID NO 20
<211> LENGTH: 369
<212> TYPE: DNA
<213> ORGANISM: Artificial Sequence
<220> FEATURE:
<223> OTHER INFORMATION: Description of Artificial Sequence: synthetic.

<400> SEQUENCE: 20
atggaatcct gtgattgcat tgaggcttta ctgccaactg gtgacctgct ggttaaatac      60
caatacctct cagatttctt cattgctgta gcctactttt ccattccgtt ggagcttatt     120
tattttgtcc acaaatctgc atgcttccca tacagatggg tcctcatgca atttggtgct     180
tttattgtgc tctgcggagc aacacacttt attagcttgt ggaccttctt tatgcactct     240
aagacggtcg ctgtggttat gaccatatca aaaatgttga cagctgccgt gtcctgtatc     300
acagctttga tgcttgttca cattattcct gatttgctaa gtgttaaaac gcgagagttg     360
ttcttgaaa                                                             369

<210> SEQ ID NO 21
<211> LENGTH: 369
<212> TYPE: DNA
<213> ORGANISM: Artificial Sequence
<220> FEATURE:
<223> OTHER INFORMATION: Description of Artificial Sequence: synthetic.

<400> SEQUENCE: 21
atggaagtct gcaattgtat tgaaccgcaa tggccagcgg atgaattgtt aatgaaatac      60
caatacatct ccgatttctt cattgcgatt gcgtattttt cgattcctct tgagttgatt     120
tactttgtga gaaatcagc cgtgtttccg tatagatggg tacttgttca gtttggtgct     180
tttatcgttc tttgtggagc aactcatctt attaacttat ggactttcac tacgcattcg     240
agaaccgtgg cgcttgtgat gactaccgcg aaggtgttaa ccgctgttgt ctcgtgtgct     300
actgcgttga tgcttgttca tattattcct gatcttttga gtgttaagac tcgggagctt     360
ttcttgaaa                                                             369

<210> SEQ ID NO 22
<211> LENGTH: 296
<212> TYPE: DNA
<213> ORGANISM: Artificial Sequence
<220> FEATURE:
<223> OTHER INFORMATION: Description of Artificial Sequence: synthetic.

<400> SEQUENCE: 22
gctctttcac atgctgcaat tttagaagat tccatgcgag cccatgatca gctcatggaa      60
cagaatattg ctttggatgt agctcgacaa gaagcagaga tggccatccg tgcacgtaac     120
gacttccttg ctgtgatgaa ccatgaaatg agaacgccca tgcatgcagt tattgctctg     180
```

```
tgctctctgc ttttagaaac agacttaact ccagagcaga gagttatgat tgagaccata      240
ttgaagagca gcaatcttct tgcaacactg ataaatgatg ttctagatct ttctag          296
```

<210> SEQ ID NO 23
<211> LENGTH: 296
<212> TYPE: DNA
<213> ORGANISM: Artificial Sequence
<220> FEATURE:
<223> OTHER INFORMATION: Description of Artificial Sequence: synthetic.

<400> SEQUENCE: 23

```
gctctctcac atgctgcgat cctagaagag tcgatgcgag ctagggacct tctcatggag      60
cagaatgttg ctcttgatct agctagacga gaagcagaaa cagcaatccg tgcccgcaat     120
gatttcctag cggttatgaa ccatgaaatg cgaacaccga tgcatgcgat tattgcactc     180
tcttccttac tccaagaaac ggaactaacc cctgaacaaa gactgatggt ggaaacaata     240
cttaaaagta gtaacctttt ggcaactttg atgaatgatg tcttagatct ttcaag         296
```

<210> SEQ ID NO 24
<211> LENGTH: 123
<212> TYPE: PRT
<213> ORGANISM: Arabidopsis thaliana

<400> SEQUENCE: 24

```
Met Glu Ser Cys Asp Cys Ile Glu Ala Leu Leu Pro Thr Gly Asp Leu
  1               5                  10                  15

Leu Val Lys Tyr Gln Tyr Leu Ser Asp Phe Phe Ile Ala Val Ala Tyr
                 20                  25                  30

Phe Ser Ile Pro Leu Glu Leu Ile Tyr Phe Val His Lys Ser Ala Cys
             35                  40                  45

Phe Pro Tyr Arg Trp Val Leu Met Gln Phe Gly Ala Phe Ile Val Leu
         50                  55                  60

Cys Gly Ala Thr His Phe Ile Ser Leu Trp Thr Phe Phe Met His Ser
 65                  70                  75                  80

Lys Thr Val Ala Val Val Met Thr Ile Ser Lys Met Leu Thr Ala Ala
                 85                  90                  95

Val Ser Cys Ile Thr Ala Leu Met Leu Val His Ile Ile Pro Asp Leu
                100                 105                 110

Leu Ser Val Lys Thr Arg Glu Leu Phe Leu Lys
            115                 120
```

<210> SEQ ID NO 25
<211> LENGTH: 123
<212> TYPE: PRT
<213> ORGANISM: Arabidopsis thaliana

<400> SEQUENCE: 25

```
Met Glu Val Cys Asn Cys Ile Glu Pro Gln Trp Pro Ala Asp Glu Leu
  1               5                  10                  15

Leu Met Lys Tyr Gln Tyr Ile Ser Asp Phe Phe Ile Ala Ile Ala Tyr
                 20                  25                  30

Phe Ser Ile Pro Leu Glu Leu Ile Tyr Phe Val Lys Lys Ser Ala Val
             35                  40                  45

Phe Pro Tyr Arg Trp Val Leu Val Gln Phe Gly Ala Phe Ile Val Leu
         50                  55                  60

Cys Gly Ala Thr His Leu Ile Asn Leu Trp Thr Phe Thr Thr His Ser
 65                  70                  75                  80
```

```
Arg Thr Val Ala Leu Val Met Thr Thr Ala Lys Val Leu Thr Ala Val
                 85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys
        115                 120

<210> SEQ ID NO 26
<211> LENGTH: 21
<212> TYPE: DNA
<213> ORGANISM: Arabidopsis thaliana

<400> SEQUENCE: 26
agtaagaacg aagaagaagt g                                        21

<210> SEQ ID NO 27
<211> LENGTH: 56
<212> TYPE: PRT
<213> ORGANISM: Arabidopsis thaliana

<400> SEQUENCE: 27

Leu Arg Val Lys Val Lys Asp Ser Gly Ala Gly Ile Asn Pro Gln Asp
  1               5                  10                  15

Ile Pro Lys Ile Phe Thr Lys Phe Ala Gln Thr Gln Ser Leu Ala Thr
             20                  25                  30

Arg Ser Ser Gly Gly Ser Gly Leu Gly Leu Ala Ile Ser Lys Arg Phe
         35                  40                  45

Val Asn Leu Met Glu Gly Asn Ile
     50                  55

<210> SEQ ID NO 28
<211> LENGTH: 56
<212> TYPE: PRT
<213> ORGANISM: Escherichia coli

<400> SEQUENCE: 28

Ile Glu Val Gln Ile Arg Asp Thr Gly Ile Gly Ile Pro Glu Arg Asp
  1               5                  10                  15

Gln Ser Arg Leu Phe Gln Ala Phe Arg Gln Ala Asp Ala Ser Ile Ser
             20                  25                  30

Arg Arg His Gly Gly Thr Gly Leu Gly Leu Val Ile Thr Gln Lys Leu
         35                  40                  45

Val Asn Glu Met Gly Gly Asp Ile
     50                  55

<210> SEQ ID NO 29
<211> LENGTH: 56
<212> TYPE: PRT
<213> ORGANISM: Pseudomonas syringae

<400> SEQUENCE: 29

Leu Arg Ile Ser Val Gln Asp Thr Gly Ile Gly Leu Ser Ser Gln Asp
  1               5                  10                  15

Val Arg Ala Leu Phe Gln Ala Phe Ser Gln Ala Asp Asn Ser Leu Ser
             20                  25                  30

Arg Gln Pro Gly Gly Thr Gly Leu Gly Leu Val Ile Ser Lys Arg Leu
         35                  40                  45

Ile Glu Gln Met Gly Gly Glu Ile
     50                  55
```

```
<210> SEQ ID NO 30
<211> LENGTH: 56
<212> TYPE: PRT
<213> ORGANISM: Xanthomonas campestris

<400> SEQUENCE: 30

Leu Arg Phe Asp Val Glu Asp Thr Gly Ile Gly Val Pro Met Asp Met
  1               5                  10                  15

Arg Pro Arg Leu Phe Glu Ala Phe Glu Gln Ala Asp Val Gly Leu Ser
             20                  25                  30

Arg Arg Tyr Glu Gly Thr Gly Leu Gly Thr Thr Ile Ala Lys Gly Leu
         35                  40                  45

Val Glu Ala Met Gly Gly Ser Ile
     50                  55

<210> SEQ ID NO 31
<211> LENGTH: 44
<212> TYPE: PRT
<213> ORGANISM: Xanthomonas campestris

<400> SEQUENCE: 31

Pro Leu Leu Val Ala Leu Ser Gly Asn Thr Asp Lys Ser Thr Lys Glu
  1               5                  10                  15

Lys Cys Met Ser Phe Gly Leu Asp Gly Val Leu Leu Lys Pro Val Ser
             20                  25                  30

Leu Asp Asn Ile Arg Asp Val Leu Ser Asp Leu Leu
         35                  40

<210> SEQ ID NO 32
<211> LENGTH: 44
<212> TYPE: PRT
<213> ORGANISM: Bordetella parapertussis

<400> SEQUENCE: 32

Cys Ile Leu Phe Gly Phe Thr Ala Ser Ala Gln Met Asp Glu Ala His
  1               5                  10                  15

Ala Cys Arg Ala Ala Gly Met Asp Asp Cys Leu Phe Lys Pro Ile Gly
             20                  25                  30

Val Asp Ala Leu Arg Gln Arg Leu Asn Glu Ala Ala
         35                  40

<210> SEQ ID NO 33
<211> LENGTH: 44
<212> TYPE: PRT
<213> ORGANISM: Escherichia coli

<400> SEQUENCE: 33

Leu Pro Val Ile Gly Val Thr Ala Asn Ala Leu Ala Glu Glu Lys Gln
  1               5                  10                  15

Arg Cys Leu Glu Ser Gly Met Asp Ser Cys Leu Ser Lys Pro Val Thr
             20                  25                  30

Leu Asp Val Ile Lys Gln Ser Leu Thr Leu Tyr Ala
         35                  40

<210> SEQ ID NO 34
<211> LENGTH: 44
<212> TYPE: PRT
<213> ORGANISM: Pseudomonas syringae

<400> SEQUENCE: 34
```

```
Leu Pro Ile Val Ala Leu Thr Ala His Ala Met Ala Asn Glu Lys Arg
 1               5                  10                  15

Ser Leu Leu Gln Ser Gly Met Asp Asp Tyr Leu Thr Lys Pro Ile Ser
             20                  25                  30

Glu Arg Gln Leu Ala Gln Val Val Leu Lys Trp Thr
         35                  40

<210> SEQ ID NO 35
<211> LENGTH: 2405
<212> TYPE: DNA
<213> ORGANISM: Lycopersicon esculentum
<220> FEATURE:
<221> NAME/KEY: CDS
<222> LOCATION: (288)..(2195)

<400> SEQUENCE: 35
tttttttttt gtcaaaagct cgatgtaaaa atccgatggc cacaagcaaa acgacaggtt      60
ccaacttcac ggagattgtg aaatggagt agtagttcag tgaagtagta gatactgaga     120
tcgcattctc cggcgtcgtt tttcacatcg aaatagtcgt gtaaaaaaat gaaaaaattg     180
ctgcgagaca ggtatgtgtc gcagcaggaa atagcatctt aaaggaagga aggaaggaaa     240
ctcgaaagtt actaaaaatt tttgattctt tgggacgaaa cgagata atg gaa tcc      296
                                                     Met Glu Ser
                                                       1 tgt gat tgc att gag gct tta ctg cca act ggt gac ctg ctg gtt aaa      344
Cys Asp Cys Ile Glu Ala Leu Leu Pro Thr Gly Asp Leu Leu Val Lys
     5                  10                  15 tac caa tac ctc tca gat ttc ttc att gct gta gcc tac ttt tcc att      392
Tyr Gln Tyr Leu Ser Asp Phe Phe Ile Ala Val Ala Tyr Phe Ser Ile
 20                  25                  30                  35 ccg ttg gag ctt att tat ttt gtc cac aaa tct gca tgc ttc cca tac      440
Pro Leu Glu Leu Ile Tyr Phe Val His Lys Ser Ala Cys Phe Pro Tyr
                 40                  45                  50 aga tgg gtc ctc atg caa ttt ggt gct ttt att gtg ctc tgt gga gca      488
Arg Trp Val Leu Met Gln Phe Gly Ala Phe Ile Val Leu Cys Gly Ala
             55                  60                  65 aca cac ttt att agc ttg tgg acc ttc ttt atg cac tct aag acg gtc      536
Thr His Phe Ile Ser Leu Trp Thr Phe Phe Met His Ser Lys Thr Val
         70                  75                  80 gct gtg gtt atg acc ata tca aaa atg ttg aca gct gcc gtg tcc tgt      584
Ala Val Val Met Thr Ile Ser Lys Met Leu Thr Ala Ala Val Ser Cys
     85                  90                  95 atc aca gct ttg atg ctt gtt cac att att cct gat ttg cta agt gtt      632
Ile Thr Ala Leu Met Leu Val His Ile Ile Pro Asp Leu Leu Ser Val
100                 105                 110                 115 aaa acg cga gag ttg ttc ttg aaa act cga gct gaa gag ctt gac aag      680
Lys Thr Arg Glu Leu Phe Leu Lys Thr Arg Ala Glu Glu Leu Asp Lys
                 120                 125                 130 gaa atg ggc cta ata ata aga caa gaa gaa act gga aga cat gtc agg      728
Glu Met Gly Leu Ile Ile Arg Gln Glu Glu Thr Gly Arg His Val Arg
             135                 140                 145 atg ctg act cat gag ata aga agc aca ctc gac aga cac aca atc ttg      776
Met Leu Thr His Glu Ile Arg Ser Thr Leu Asp Arg His Thr Ile Leu
         150                 155                 160 aag act act ctt gtg gag cta ggt agg acc tta gac ctg gca gaa tgt      824
Lys Thr Thr Leu Val Glu Leu Gly Arg Thr Leu Asp Leu Ala Glu Cys
     165                 170                 175 gct ttg tgg atg cca tgc caa gga ggc ctg act ttg caa ctt tcc cat      872
Ala Leu Trp Met Pro Cys Gln Gly Gly Leu Thr Leu Gln Leu Ser His
180                 185                 190                 195
```

```
aat tta aac aat cta ata cct ctg gga tct act gtg cca att aat ctt      920
Asn Leu Asn Asn Leu Ile Pro Leu Gly Ser Thr Val Pro Ile Asn Leu
                200                 205                 210 cct att atc aat gaa att ttt agt agc cct gaa gca ata caa att cca      968
Pro Ile Ile Asn Glu Ile Phe Ser Ser Pro Glu Ala Ile Gln Ile Pro
                215                 220                 225 cat aca aat cct ttg gca agg atg agg aat act gtt ggt aga tat att     1016
His Thr Asn Pro Leu Ala Arg Met Arg Asn Thr Val Gly Arg Tyr Ile
            230                 235                 240 cca cca gaa gta gtt gct gtt cgt gta ccg ctt tta cac ctc tca aat     1064
Pro Pro Glu Val Val Ala Val Arg Val Pro Leu Leu His Leu Ser Asn
        245                 250                 255 ttt act aat gac tgg gct gaa ctg tct act aga agt tat gcg gtt atg     1112
Phe Thr Asn Asp Trp Ala Glu Leu Ser Thr Arg Ser Tyr Ala Val Met
260                 265                 270                 275 gtt ctg gtt ctc ccg atg aat ggc tta aga aag tgg cgt gaa cat gag     1160
Val Leu Val Leu Pro Met Asn Gly Leu Arg Lys Trp Arg Glu His Glu
                280                 285                 290 tta gaa ctt gtg caa gtt gtc gca gat cag gtt gct gtc gct ctt tca     1208
Leu Glu Leu Val Gln Val Val Ala Asp Gln Val Ala Val Ala Leu Ser
                295                 300                 305 cat gct gca att tta gaa gat tcc atg cga gcc cat gat cag ctc atg     1256
His Ala Ala Ile Leu Glu Asp Ser Met Arg Ala His Asp Gln Leu Met
            310                 315                 320 gaa cag aat att gct ttg gat gta gct cga caa gaa gca gag atg gcc     1304
Glu Gln Asn Ile Ala Leu Asp Val Ala Arg Gln Glu Ala Glu Met Ala
        325                 330                 335 atc cgt gca cgt aac gac ttc ctt gct gtg atg aac cat gaa atg aga     1352
Ile Arg Ala Arg Asn Asp Phe Leu Ala Val Met Asn His Glu Met Arg
340                 345                 350                 355 acg ccc atg cat gca gtt att gct ctg tgc tct ctg ctt tta gaa aca     1400
Thr Pro Met His Ala Val Ile Ala Leu Cys Ser Leu Leu Leu Glu Thr
                360                 365                 370 gac tta act cca gag cag aga gtt atg att gag acc ata ttg aag agc     1448
Asp Leu Thr Pro Glu Gln Arg Val Met Ile Glu Thr Ile Leu Lys Ser
                375                 380                 385 agc aat ctt ctt gca aca ctg ata aat gat gtt cta gat ctt tct aga     1496
Ser Asn Leu Leu Ala Thr Leu Ile Asn Asp Val Leu Asp Leu Ser Arg
            390                 395                 400 ctt gaa gat ggt att ctt gaa cta gaa aac gga aca ttc aat ctt cat     1544
Leu Glu Asp Gly Ile Leu Glu Leu Glu Asn Gly Thr Phe Asn Leu His
        405                 410                 415 ggc atc tta aga gag gcc gtt aat ttg ata aag cca att gca tct ttg     1592
Gly Ile Leu Arg Glu Ala Val Asn Leu Ile Lys Pro Ile Ala Ser Leu
420                 425                 430                 435 aag aaa tta tct ata act ctt gct ttg gct ctg gat tta cct att ctt     1640
Lys Lys Leu Ser Ile Thr Leu Ala Leu Ala Leu Asp Leu Pro Ile Leu
                440                 445                 450 gct gtg ggt gat gca aaa cgt ctt atc caa act ctc tta aac gtg gtg     1688
Ala Val Gly Asp Ala Lys Arg Leu Ile Gln Thr Leu Leu Asn Val Val
                455                 460                 465 gga aat gct gtg aag ttc act aaa gaa gga cat att tca att gag gct     1736
Gly Asn Ala Val Lys Phe Thr Lys Glu Gly His Ile Ser Ile Glu Ala
            470                 475                 480 tca gtt gcc aaa cca gag tat gcg aga gat tgt cat cct cct gaa atg     1784
Ser Val Ala Lys Pro Glu Tyr Ala Arg Asp Cys His Pro Pro Glu Met
        485                 490                 495 ttc cct atg cca agt gat ggc cag ttt tat ttg cgt gtc cag gtt aga     1832
Phe Pro Met Pro Ser Asp Gly Gln Phe Tyr Leu Arg Val Gln Val Arg
```

```
                500                     505                     510                     515
gat act ggg tgt gga att agc cca caa gat ata cca cta gta ttc acc         1880
Asp Thr Gly Cys Gly Ile Ser Pro Gln Asp Ile Pro Leu Val Phe Thr
                520                     525                     530 aaa ttt gca gag tca cgg cct acg tca aat cga agt act gga ggg gaa         1928
Lys Phe Ala Glu Ser Arg Pro Thr Ser Asn Arg Ser Thr Gly Gly Glu
            535                     540                     545 ggt cta ggg ctt gcc att tgg aga cga ttt att caa ctt atg aaa ggt         1976
Gly Leu Gly Leu Ala Ile Trp Arg Arg Phe Ile Gln Leu Met Lys Gly
        550                     555                     560 aac att tgg att gag agt gag ggc cct gga aag gga acc act gtc acg         2024
Asn Ile Trp Ile Glu Ser Glu Gly Pro Gly Lys Gly Thr Thr Val Thr
    565                     570                     575 ttt gta gtg aaa ctc gga atc tgt cac cat cca aat gca tta cct ctg         2072
Phe Val Val Lys Leu Gly Ile Cys His His Pro Asn Ala Leu Pro Leu
580                     585                     590                     595 cta cct atg cct ccc aga ggc aga ttg aac aaa ggt agc gat gat ctc         2120
Leu Pro Met Pro Pro Arg Gly Arg Leu Asn Lys Gly Ser Asp Asp Leu
            600                     605                     610 ttc agg tat aga cag ttc cgt gga gat gat ggt ggg atg tct gtg aat         2168
Phe Arg Tyr Arg Gln Phe Arg Gly Asp Asp Gly Gly Met Ser Val Asn
        615                     620                     625 gct caa cgc tat caa aga agt atg taa atgacaaaag gacattggtg               2215
Ala Gln Arg Tyr Gln Arg Ser Met
    630                     635 tgacaaagaa cattaaatca tgactagtga atttgagatt tcttcactgt tctgtacact       2275
ccaaatggca cagtttgtct tgtaactaac ctaattcaat gctcgtaaag tgagtactgg       2335
agtatcttga aaatgtaact atcgaattta tacatcgagc ttttgacaaa aaaaaaaaaa       2395
aaaaaaaaaa                                                              2405

<210> SEQ ID NO 36
<211> LENGTH: 635
<212> TYPE: PRT
<213> ORGANISM: Lycopersicon esculentum

<400> SEQUENCE: 36

Met Glu Ser Cys Asp Cys Ile Glu Ala Leu Leu Pro Thr Gly Asp Leu
 1               5                  10                  15

Leu Val Lys Tyr Gln Tyr Leu Ser Asp Phe Phe Ile Ala Val Ala Tyr
                20                  25                  30

Phe Ser Ile Pro Leu Glu Leu Ile Tyr Phe Val His Lys Ser Ala Cys
            35                  40                  45

Phe Pro Tyr Arg Trp Val Leu Met Gln Phe Gly Ala Phe Ile Val Leu
        50                  55                  60

Cys Gly Ala Thr His Phe Ile Ser Leu Trp Thr Phe Phe Met His Ser
65                  70                  75                  80

Lys Thr Val Ala Val Met Thr Ile Ser Lys Met Leu Thr Ala Ala
                85                  90                  95

Val Ser Cys Ile Thr Ala Leu Met Leu Val His Ile Ile Pro Asp Leu
            100                 105                 110

Leu Ser Val Lys Thr Arg Glu Leu Phe Leu Lys Thr Arg Ala Glu Glu
        115                 120                 125

Leu Asp Lys Glu Met Gly Leu Ile Ile Arg Gln Glu Glu Thr Gly Arg
    130                 135                 140

His Val Arg Met Leu Thr His Glu Ile Arg Ser Thr Leu Asp Arg His
145                 150                 155                 160
```

-continued

```
Thr Ile Leu Lys Thr Thr Leu Val Glu Leu Gly Arg Thr Leu Asp Leu
            165                 170                 175
Ala Glu Cys Ala Leu Trp Met Pro Cys Gln Gly Gly Leu Thr Leu Gln
            180                 185                 190
Leu Ser His Asn Leu Asn Asn Leu Ile Pro Leu Gly Ser Thr Val Pro
            195                 200                 205
Ile Asn Leu Pro Ile Ile Asn Glu Ile Phe Ser Ser Pro Glu Ala Ile
            210                 215                 220
Gln Ile Pro His Thr Asn Pro Leu Ala Arg Met Arg Asn Thr Val Gly
225                 230                 235                 240
Arg Tyr Ile Pro Pro Glu Val Val Ala Val Arg Val Pro Leu Leu His
            245                 250                 255
Leu Ser Asn Phe Thr Asn Asp Trp Ala Glu Leu Ser Thr Arg Ser Tyr
            260                 265                 270
Ala Val Met Val Leu Val Leu Pro Met Asn Gly Leu Arg Lys Trp Arg
            275                 280                 285
Glu His Glu Leu Glu Leu Val Gln Val Val Ala Asp Gln Val Ala Val
            290                 295                 300
Ala Leu Ser His Ala Ala Ile Leu Glu Asp Ser Met Arg Ala His Asp
305                 310                 315                 320
Gln Leu Met Glu Gln Asn Ile Ala Leu Asp Val Ala Arg Gln Glu Ala
            325                 330                 335
Glu Met Ala Ile Arg Ala Arg Asn Asp Phe Leu Ala Val Met Asn His
            340                 345                 350
Glu Met Arg Thr Pro Met His Ala Val Ile Ala Leu Cys Ser Leu Leu
            355                 360                 365
Leu Glu Thr Asp Leu Thr Pro Glu Gln Arg Val Met Ile Glu Thr Ile
            370                 375                 380
Leu Lys Ser Ser Asn Leu Leu Ala Thr Leu Ile Asn Asp Val Leu Asp
385                 390                 395                 400
Leu Ser Arg Leu Glu Asp Gly Ile Leu Glu Leu Glu Asn Gly Thr Phe
            405                 410                 415
Asn Leu His Gly Ile Leu Arg Glu Ala Val Asn Leu Ile Lys Pro Ile
            420                 425                 430
Ala Ser Leu Lys Lys Leu Ser Ile Thr Leu Ala Leu Ala Leu Asp Leu
435                 440                 445
Pro Ile Leu Ala Val Gly Asp Ala Lys Arg Leu Ile Gln Thr Leu Leu
            450                 455                 460
Asn Val Val Gly Asn Ala Val Lys Phe Thr Lys Glu Gly His Ile Ser
465                 470                 475                 480
Ile Glu Ala Ser Val Ala Lys Pro Glu Tyr Ala Arg Asp Cys His Pro
            485                 490                 495
Pro Glu Met Phe Pro Met Pro Ser Asp Gly Gln Phe Tyr Leu Arg Val
            500                 505                 510
Gln Val Arg Asp Thr Gly Cys Gly Ile Ser Pro Gln Asp Ile Pro Leu
            515                 520                 525
Val Phe Thr Lys Phe Ala Glu Ser Arg Pro Thr Ser Asn Arg Ser Thr
            530                 535                 540
Gly Gly Glu Gly Leu Gly Leu Ala Ile Trp Arg Arg Phe Ile Gln Leu
545                 550                 555                 560
Met Lys Gly Asn Ile Trp Ile Glu Ser Glu Gly Pro Gly Lys Gly Thr
            565                 570                 575
```

```
Thr Val Thr Phe Val Val Lys Leu Gly Ile Cys His His Pro Asn Ala
            580                 585                 590

Leu Pro Leu Leu Pro Met Pro Pro Arg Gly Arg Leu Asn Lys Gly Ser
        595                 600                 605

Asp Asp Leu Phe Arg Tyr Arg Gln Phe Arg Gly Asp Asp Gly Gly Met
        610                 615                 620

Ser Val Asn Ala Gln Arg Tyr Gln Arg Ser Met
625                 630                 635

<210> SEQ ID NO 37
<211> LENGTH: 4567
<212> TYPE: DNA
<213> ORGANISM: Lycopersicon esculentum
<220> FEATURE:
<221> NAME/KEY: CDS
<222> LOCATION: (763)..(1671)
<221> NAME/KEY: CDS
<222> LOCATION: (3062)..(3433)
<221> NAME/KEY: CDS
<222> LOCATION: (3572)..(3838)
<221> NAME/KEY: CDS
<222> LOCATION: (3969)..(4097)
<221> NAME/KEY: CDS
<222> LOCATION: (4236)..(4403)
<221> NAME/KEY: misc_feature
<222> LOCATION: (4097)
<223> OTHER INFORMATION: the nucleic acid at position 4097 can be either
      a or g which code for Arginine.

<400> SEQUENCE: 37
agatctggta ctaccaaaag gtatccaatt aatccatgct tggcctccca ttacaatgcc      60
tgtaagaaat aattgttctt tccacctcca caactaattg tcgaactatt atatctatct    120
ttattccctt aaatgtgaaa cgaattacac agactatttg gcgctacttt tttcctagat    180
atattgaaga cctagtttct tatatttgtg ggaagcattt ggaagttcta taagaactat    240
atcatgttcg aaaacattct tataattttc gacaagattg ctgaaggagt gtcttatctt    300
ttatgtattc ttgactagag gagtttaata aaaagaaaat agaaggaac aaagaaacgt     360 acaagtgtat aaaaggagtt ggggcaaaga catcagaaac atttagacct acgatttcat    420
cctacatgtt atggttttag ttcgttagag gttttaacat attaaatcag caaagttgtg    480
acatacataa agtgcataac ataaagatga aattcacaat ttgctggatc ttttggtgca    540
agggaactat ttttttacact ataagttagc tgttaatttc aatattggct cttctacacc   600
ttgttgttct tgagtagaat tctattttgc atcaaacata tgtcagaact tatgctgcaa    660
ttaaatatat tcaggttgtt taactcttgt acagcttgtt attcttctga ggtctatttc    720
cttctcctta tttgctaact tgtgctgcag ttatcttcca tc gtg gag tca tgt        774
                                                Val Glu Ser Cys
                                                 1 aac tgc atc att gac cca cag ttg cct gct gac gac ttg cta atg aag       822
Asn Cys Ile Ile Asp Pro Gln Leu Pro Ala Asp Asp Leu Leu Met Lys
  5               10                  15                  20 tat cag tac att tct gat ttt ttc ata gca ctt gct tat ttc tcc att       870
Tyr Gln Tyr Ile Ser Asp Phe Phe Ile Ala Leu Ala Tyr Phe Ser Ile
              25                  30                  35 cca gtg gag ttg ata tac ttc gtt aag aag tct gct gtc ttt cca tat       918
Pro Val Glu Leu Ile Tyr Phe Val Lys Lys Ser Ala Val Phe Pro Tyr
          40                  45                  50 aga tgg gtt ctt gtg cag ttc ggt gct ttc ata gtt ctt tgt gga gca       966
Arg Trp Val Leu Val Gln Phe Gly Ala Phe Ile Val Leu Cys Gly Ala
      55                  60                  65
```

-continued

```
acc cat ctt atc aac tta tgg aca ttt aat atg cat aca agg aat gtg         1014
Thr His Leu Ile Asn Leu Trp Thr Phe Asn Met His Thr Arg Asn Val
         70                  75                  80 gca ata gta atg act act gca aag gcc ttg act gca ctg gtg tca tgt         1062
Ala Ile Val Met Thr Thr Ala Lys Ala Leu Thr Ala Leu Val Ser Cys
 85                  90                  95                 100 ata act gct ctc atg ctt gtc cac atc att cct gat tta tta agt gtc         1110
Ile Thr Ala Leu Met Leu Val His Ile Ile Pro Asp Leu Leu Ser Val
                    105                 110                 115 aaa act aga gaa ctg ttc ttg aaa aag aaa gct gca cag ctt gac cgt         1158
Lys Thr Arg Glu Leu Phe Leu Lys Lys Lys Ala Ala Gln Leu Asp Arg
            120                 125                 130 gaa atg ggt att att cgg act cag gag gag aca ggt aga cat gtt aga         1206
Glu Met Gly Ile Ile Arg Thr Gln Glu Glu Thr Gly Arg His Val Arg
        135                 140                 145 atg cta act cat gaa atc cga agc act ctt gat aga cat act att tta         1254
Met Leu Thr His Glu Ile Arg Ser Thr Leu Asp Arg His Thr Ile Leu
    150                 155                 160 aag act aca ctt gtt gag cta gga aga aca ttg gca ttg gaa gag tgt         1302
Lys Thr Thr Leu Val Glu Leu Gly Arg Thr Leu Ala Leu Glu Glu Cys
165                 170                 175                 180 gca tta tgg atg cca aca cgt act gga cta gag ctt cag ctt tct tac         1350
Ala Leu Trp Met Pro Thr Arg Thr Gly Leu Glu Leu Gln Leu Ser Tyr
                185                 190                 195 act tta cga cac caa aat cca gtt gga tta act gta ccc att caa ctt         1398
Thr Leu Arg His Gln Asn Pro Val Gly Leu Thr Val Pro Ile Gln Leu
            200                 205                 210 cct gta atc aat caa gtt ttc ggt aca aat cat gtc gtg aaa ata tca         1446
Pro Val Ile Asn Gln Val Phe Gly Thr Asn His Val Val Lys Ile Ser
        215                 220                 225 cca aat tct cct gtc gca aga ctt cga cct gct ggg aaa tac atg cct         1494
Pro Asn Ser Pro Val Ala Arg Leu Arg Pro Ala Gly Lys Tyr Met Pro
    230                 235                 240 ggt gag gtg gtt gct gtc agg gtt cca ctt ctg cat ctg tcg aac ttt         1542
Gly Glu Val Val Ala Val Arg Val Pro Leu Leu His Leu Ser Asn Phe
245                 250                 255                 260 cag att aat gat tgg cct gaa ctt tca aca aag cgc tat gct tta atg         1590
Gln Ile Asn Asp Trp Pro Glu Leu Ser Thr Lys Arg Tyr Ala Leu Met
                265                 270                 275 gtt ctg atg ctt cct tca gac agt gca aga caa tgg cat gtt cat gag         1638
Val Leu Met Leu Pro Ser Asp Ser Ala Arg Gln Trp His Val His Glu
            280                 285                 290 ctg gag ctt gtt gaa gtg gta gct gat cag gtt tgattttgt tattgaaaat       1691
Leu Glu Leu Val Glu Val Val Ala Asp Gln Val
        295                 300 tccttaatat aatgttaaaa tttctctttt atatatttt gggttgaaca caaccacgtt       1751
gacatactga gttctgggtg taaaattaga catggagaag accaattaca aaaatctgag      1811
aatctgctag cagaatcaca aggcttagtt gttcttagta ttatggtttt atccattgga     1871
attgcacagc agaattgtta ttactgttat ttttttttaa aattttcaaa gataaatcaa     1931
aagctgaact atatgacttt ttgcatactt cgtctgctga ttgcttttg gtgatggaat      1991 agttaggctg ggttgtggat gagtatatca tagtagattt tctgatagga tcttaactcc     2051
ttggcttttg ttttctatag atgatcccctt gtattagaag cacgggaaat aggatcgatg    2111
gtatatagaa atattaggaa cagctttctg aatcatttga atattccttt tatgaacat      2171 agaactcttg acgtgtatgt agttttctta gtactttat catatgaagt gaaaataacg      2231
ttttgcgata atgtatttga gtgtgtaaaa ttaaatacta ctgagtttta caaaaataat     2291
```

```
tcttcaacgg aagccattta ttttttttac atatctggca tcttacttct ccatcaaaga    2351
ctttagagaa ctttaacttt ttcattctgt ctctcgtagt gtactgttct ctgatgtatg    2411
taattagctc actggcaagt agcacaccta gtctttgttt gacttgttta aaaatcatga    2471
tgtatcatca gttacggtga agtgtccaag ttttactgct ttttgctatt tgcattgcag    2531
agtcttaaaa catttcagtt attcctggat ttctcctgtt tatcaatgga aaattcaact    2591
atcaactatg cctcaatcaa taaatgaaac ctctatatct aaccactcca actcagatcc    2651
agaaatcaga tttcaaagaa attcatcata actcaactat aggattgctg ttaaccaaga    2711
gtaatcctca tttgtccaga caggcgacca gctattatgc tttcattatg ggaaaaattg    2771
acaattaatt aaaggaagga acaactgaag aaaagacatc cttgtcagct tcctctccca    2831
acccttgcct gaataagaca aaagtttct tggagaaaac tctgaatatt ggtatccacc    2891
tcctttctcc taatttagga tgctctattt ctagacatat aggggaatac tctattctag    2951
tggtcggtgt ctggttgcaa ctagttttag atgtttatat gtcttatttg atttaataag    3011
agctatcctt gagtgcccaa tgtgatttaa tctacgcttc ggcatttcag gtt gct        3067
                                                         Val Ala
                                                             305 gtt gct ctt tca cat gct gct ata tta gaa gaa tca atg agg gct agg       3115
Val Ala Leu Ser His Ala Ala Ile Leu Glu Glu Ser Met Arg Ala Arg
        310                 315                 320 gat ctt ctt atg gag cag aat gtg gct ctt gat ctg gca aga aga gaa       3163
Asp Leu Leu Met Glu Gln Asn Val Ala Leu Asp Leu Ala Arg Arg Glu
    325                 330                 335 gca gaa atg gct gtt cgt gca cgt aat gat ttc ttg gct gtt atg aat       3211
Ala Glu Met Ala Val Arg Ala Arg Asn Asp Phe Leu Ala Val Met Asn
340                 345                 350 cat gaa atg aga act ccc atg cat gca ata att gca ctt tct tcc tta       3259
His Glu Met Arg Thr Pro Met His Ala Ile Ile Ala Leu Ser Ser Leu
            355                 360                 365 cta caa gaa atc gat cta act cca gag caa cgt ctg atg gtt gaa aca       3307
Leu Gln Glu Ile Asp Leu Thr Pro Glu Gln Arg Leu Met Val Glu Thr
370                 375                 380                 385 atc ctc aaa agc agc aac ctt tta gca acg ctc atc aac gat gtc ttg       3355
Ile Leu Lys Ser Ser Asn Leu Leu Ala Thr Leu Ile Asn Asp Val Leu
                390                 395                 400 gat ctt tca agg cta gag gat gga agt ctt caa ctt gat att ggc act       3403
Asp Leu Ser Arg Leu Glu Asp Gly Ser Leu Gln Leu Asp Ile Gly Thr
            405                 410                 415 ttc aat ctc cat gct tta ttt aga gag gtg cccttcatca ccctctttc          3453
Phe Asn Leu His Ala Leu Phe Arg Glu Val
            420                 425 tttttactt gcaaattcta gattacctgt cagaaaaaaa gtgtcattac agatattttg     3513
cacttcaata tgtttgctgg acctgctgac tgatatatgt gtctgcttat tcctgtag      3571 gtc cat agc tta atc aag cct att gca tct gtg aaa aag tct gtt gct       3619
Val His Ser Leu Ile Lys Pro Ile Ala Ser Val Lys Lys Ser Val Ala
        430                 435                 440 caa ctt agt ttg tcg tca gat ttg ccg gaa tat gta att ggg gat gaa       3667
Gln Leu Ser Leu Ser Ser Asp Leu Pro Glu Tyr Val Ile Gly Asp Glu
    445                 450                 455 aaa cgg tta atg caa att ctc tta aac gtt gtt ggc aat gct gta aag       3715
Lys Arg Leu Met Gln Ile Leu Leu Asn Val Val Gly Asn Ala Val Lys
460                 465                 470                 475 ttc tca aag gaa ggc aac gta tca atc tcc gct ttt gtt gca aaa tca       3763
Phe Ser Lys Glu Gly Asn Val Ser Ile Ser Ala Phe Val Ala Lys Ser
```

```
                    480              485              490
gac tct tta aga gat cct aga gcc cct gaa ttt ttt gct gtg cct agt    3811
Asp Ser Leu Arg Asp Pro Arg Ala Pro Glu Phe Phe Ala Val Pro Ser
            495              500              505 gaa aat cac ttc tat tta cgg gtg cag gtatattttt acaagcttga          3858
Glu Asn His Phe Tyr Leu Arg Val Gln
        510              515 tatactatct tcgtaggtta aggatagtca caaatatgat attttagact tataactgtc  3918
agatgttctg ttcttgatat ttgtaatatt ctaagtaata ctttctgtag ata aaa     3974
                                                        Ile Lys gat acg ggg ata gga att aca cca cag gat att ccc aac ctg ttt agc    4022
Asp Thr Gly Ile Gly Ile Thr Pro Gln Asp Ile Pro Asn Leu Phe Ser
520              525              530 aag ttt aca caa agc caa gcg cta gca act aca aat tct ggt ggc act    4070
Lys Phe Thr Gln Ser Gln Ala Leu Ala Thr Thr Asn Ser Gly Gly Thr
535              540              545              550 ggg ctt ggt ctt gca att tgt aag agg gtacgggtac cagttcctta          4117
Gly Leu Gly Leu Ala Ile Cys Lys Arg
                555 gtgttctttt tccgactctg attttcattc tacgtgaact tggtaactgc ttcatattca  4177 atttctttct cttactgtat ttacgtattg acacatctcc tgatgggaca caaaaagg    4235 ttt gtg aat ctt atg gaa gga cat att tgg att gaa agt gaa ggt ctt    4283
Phe Val Asn Leu Met Glu Gly His Ile Trp Ile Glu Ser Glu Gly Leu
560              565              570              575 ggc aag ggg tct act gct ata ttt atc att aaa ctt gga ctt cct gga    4331
Gly Lys Gly Ser Thr Ala Ile Phe Ile Ile Lys Leu Gly Leu Pro Gly
                580              585              590 cgt gca aat gaa tct aag ctc ccc ttt gtg acc aaa ttg cca gca aat    4379
Arg Ala Asn Glu Ser Lys Leu Pro Phe Val Thr Lys Leu Pro Ala Asn
            595              600              605 cac acg cag atg agt ttt aag gat taaaggtttt ggtgatggat gagaatgggt   4433
His Thr Gln Met Ser Phe Lys Asp
        610              615 gagtactatc tggaccccctt tatcctcgac tcttgtcttg ccatgctgtt taatgatcca 4493 tctgattgcg tgatttctca tcttatatgt attgagctgt cttactcact ttacatgaga  4553
ctacagtaat actt                                                    4567

<210> SEQ ID NO 38
<211> LENGTH: 615
<212> TYPE: PRT
<213> ORGANISM: Lycopersicon esculentum

<400> SEQUENCE: 38

Val Glu Ser Cys Asn Cys Ile Ile Asp Pro Gln Leu Pro Ala Asp Asp
 1               5                  10                  15

Leu Leu Met Lys Tyr Gln Tyr Ile Ser Asp Phe Ile Ala Leu Ala
                20                  25                  30

Tyr Phe Ser Ile Pro Val Glu Leu Ile Tyr Phe Val Lys Lys Ser Ala
            35                  40                  45

Val Phe Pro Tyr Arg Trp Val Leu Val Gln Phe Gly Ala Phe Ile Val
     50                  55                  60

Leu Cys Gly Ala Thr His Leu Ile Asn Leu Trp Thr Phe Asn Met His
 65                  70                  75                  80

Thr Arg Asn Val Ala Ile Val Met Thr Thr Ala Lys Ala Leu Thr Ala
                85                  90                  95
```

-continued

```
Leu Val Ser Cys Ile Thr Ala Leu Met Leu Val His Ile Ile Pro Asp
                100                 105                 110
Leu Leu Ser Val Lys Thr Arg Glu Leu Phe Lys Lys Lys Ala Ala
            115                 120                 125
Gln Leu Asp Arg Glu Met Gly Ile Ile Arg Thr Gln Glu Glu Thr Gly
        130                 135                 140
Arg His Val Arg Met Leu Thr His Glu Ile Arg Ser Thr Leu Asp Arg
145                 150                 155                 160
His Thr Ile Leu Lys Thr Thr Leu Val Glu Leu Gly Arg Thr Leu Ala
                165                 170                 175
Leu Glu Glu Cys Ala Leu Trp Met Pro Thr Arg Thr Gly Leu Glu Leu
            180                 185                 190
Gln Leu Ser Tyr Thr Leu Arg His Gln Asn Pro Val Gly Leu Thr Val
        195                 200                 205
Pro Ile Gln Leu Pro Val Ile Asn Gln Val Phe Gly Thr Asn His Val
    210                 215                 220
Val Lys Ile Ser Pro Asn Ser Pro Val Ala Arg Leu Arg Pro Ala Gly
225                 230                 235                 240
Lys Tyr Met Pro Gly Glu Val Ala Val Arg Val Pro Leu Leu His
                245                 250                 255
Leu Ser Asn Phe Gln Ile Asn Asp Trp Pro Glu Leu Ser Thr Lys Arg
            260                 265                 270
Tyr Ala Leu Met Val Leu Met Leu Pro Ser Asp Ser Ala Arg Gln Trp
        275                 280                 285
His Val His Glu Leu Glu Leu Val Glu Val Val Ala Asp Gln Val Val
    290                 295                 300
Ala Val Ala Leu Ser His Ala Ala Ile Leu Glu Glu Ser Met Arg Ala
305                 310                 315                 320
Arg Asp Leu Leu Met Glu Gln Asn Val Ala Leu Asp Leu Ala Arg Arg
                325                 330                 335
Glu Ala Glu Met Ala Val Arg Ala Arg Asn Asp Phe Leu Ala Val Met
            340                 345                 350
Asn His Glu Met Arg Thr Pro Met His Ala Ile Ile Ala Leu Ser Ser
        355                 360                 365
Leu Leu Gln Glu Ile Asp Leu Thr Pro Glu Gln Arg Leu Met Val Glu
    370                 375                 380
Thr Ile Leu Lys Ser Ser Asn Leu Leu Ala Thr Leu Ile Asn Asp Val
385                 390                 395                 400
Leu Asp Leu Ser Arg Leu Glu Asp Gly Ser Leu Gln Leu Asp Ile Gly
                405                 410                 415
Thr Phe Asn Leu His Ala Leu Phe Arg Glu Val Val His Ser Leu Ile
            420                 425                 430
Lys Pro Ile Ala Ser Val Lys Lys Ser Val Ala Gln Leu Ser Leu Ser
        435                 440                 445
Ser Asp Leu Pro Glu Tyr Val Ile Gly Asp Glu Lys Arg Leu Met Gln
    450                 455                 460
Ile Leu Leu Asn Val Val Gly Asn Ala Val Lys Phe Ser Lys Glu Gly
465                 470                 475                 480
Asn Val Ser Ile Ser Ala Phe Val Ala Lys Ser Asp Ser Leu Arg Asp
                485                 490                 495
Pro Arg Ala Pro Glu Phe Phe Ala Val Pro Ser Glu Asn His Phe Tyr
            500                 505                 510
Leu Arg Val Gln Ile Lys Asp Thr Gly Ile Gly Ile Thr Pro Gln Asp
```

```
            515                 520                 525
Ile Pro Asn Leu Phe Ser Lys Phe Thr Gln Ser Gln Ala Leu Ala Thr
        530                 535             540

Thr Asn Ser Gly Gly Thr Gly Leu Gly Leu Ala Ile Cys Lys Arg Phe
545                 550                 555                 560

Val Asn Leu Met Glu Gly His Ile Trp Ile Glu Ser Glu Gly Leu Gly
                565                 570                 575

Lys Gly Ser Thr Ala Ile Phe Ile Ile Lys Leu Gly Leu Pro Gly Arg
                580                 585                 590

Ala Asn Glu Ser Lys Leu Pro Phe Val Thr Lys Leu Pro Ala Asn His
            595                 600                 605

Thr Gln Met Ser Phe Lys Asp
    610                 615

<210> SEQ ID NO 39
<211> LENGTH: 737
<212> TYPE: DNA
<213> ORGANISM: Lycopersicon esculentum
<220> FEATURE:
<221> NAME/KEY: CDS
<222> LOCATION: (33)..(719)

<400> SEQUENCE: 39
aagataagag tgattcatta aggagtttgt tc atg gat tgt aac tgc ttc        53
                                   Ile Met Asp Cys Asn Cys Phe
                                       1               5 gat cca ctg ttg cct gcc gat gag ttg tta atg aag tat cag tac att   101
Asp Pro Leu Leu Pro Ala Asp Glu Leu Leu Met Lys Tyr Gln Tyr Ile
         10                  15                  20 tct gat ttt ttc att gca gtt gct tat ttt tcc atc cca atc gaa ctg   149
Ser Asp Phe Phe Ile Ala Val Ala Tyr Phe Ser Ile Pro Ile Glu Leu
     25                  30                  35 gta ttc ttt gtc cag aaa tca gct gtt ttt ccg tat cga tgg gtg ctt   197
Val Phe Phe Val Gln Lys Ser Ala Val Phe Pro Tyr Arg Trp Val Leu
 40                  45                  50                  55 gtg cag ttt ggt gct ttc ata gtt ctt tgt gga gca aca cac ctt atc   245
Val Gln Phe Gly Ala Phe Ile Val Leu Cys Gly Ala Thr His Leu Ile
             60                  65                  70 aat ttg tgg act tct act cct cat aca agg act gtg gca atg gtg atg   293
Asn Leu Trp Thr Ser Thr Pro His Thr Arg Thr Val Ala Met Val Met
         75                  80                  85 act acg gcg aag ttc tcc act gct gcg gta tca tgt gca act gct gtc   341
Thr Thr Ala Lys Phe Ser Thr Ala Ala Val Ser Cys Ala Thr Ala Val
     90                  95                 100 atg ctt gtc gca att att ccg gat tta tta agt gtc aaa act agg gag   389
Met Leu Val Ala Ile Ile Pro Asp Leu Leu Ser Val Lys Thr Arg Glu
105                 110                 115 cta ttc ttg aaa aac aaa gcg gcg gaa ctt gat cgt gaa atg ggt ctt   437
Leu Phe Leu Lys Asn Lys Ala Ala Glu Leu Asp Arg Glu Met Gly Leu
120                 125                 130                 135 att cgg aca cag gag gag acg ggt aga tat gtt aga atg cta aca cat   485
Ile Arg Thr Gln Glu Glu Thr Gly Arg Tyr Val Arg Met Leu Thr His
             140                 145                 150 gaa atc aga agt act ctg gat aga cat act att ttg aag act aca ctt   533
Glu Ile Arg Ser Thr Leu Asp Arg His Thr Ile Leu Lys Thr Thr Leu
         155                 160                 165 gtt gaa ctt gga aga gca ttg caa ctg gaa gag tgt gct ttg tgg atg   581
Val Glu Leu Gly Arg Ala Leu Gln Leu Glu Glu Cys Ala Leu Trp Met
    170                 175                 180
```

```
ccg act cga act gga gtg gag ctt caa ctt tct tac act tta cat cat    629
Pro Thr Arg Thr Gly Val Glu Leu Gln Leu Ser Tyr Thr Leu His His
    185                 190                 195 caa aat cca gtt gga ttt aca gta cct ata caa ctc cct gta att aat    677
Gln Asn Pro Val Gly Phe Thr Val Pro Ile Gln Leu Pro Val Ile Asn
200                 205                 210                 215 caa gtt ttc agt gca aat tgt gct gtt aaa att tca cct taa            719
Gln Val Phe Ser Ala Asn Cys Ala Val Lys Ile Ser Pro
                220                 225 tctgccgttg caaggctt                                                 737

<210> SEQ ID NO 40
<211> LENGTH: 228
<212> TYPE: PRT
<213> ORGANISM: Lycopersicon esculentum

<400> SEQUENCE: 40

Ile Met Asp Cys Asn Cys Phe Asp Pro Leu Leu Pro Ala Asp Glu Leu
 1               5                  10                  15

Leu Met Lys Tyr Gln Tyr Ile Ser Asp Phe Phe Ile Ala Val Ala Tyr
            20                  25                  30

Phe Ser Ile Pro Ile Glu Leu Val Phe Phe Val Gln Lys Ser Ala Val
        35                  40                  45

Phe Pro Tyr Arg Trp Val Leu Val Gln Phe Gly Ala Phe Ile Val Leu
    50                  55                  60

Cys Gly Ala Thr His Leu Ile Asn Leu Trp Thr Ser Thr Pro His Thr
65                  70                  75                  80

Arg Thr Val Ala Met Val Met Thr Thr Ala Lys Phe Ser Thr Ala Ala
                85                  90                  95

Val Ser Cys Ala Thr Ala Val Met Leu Val Ala Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

Tyr Val Arg Met Leu Thr His Glu Ile Arg Ser Thr Leu Asp Arg His
145                 150                 155                 160

Thr Ile Leu Lys Thr Thr Leu Val Glu Leu Gly Arg Ala Leu Gln Leu
                165                 170                 175

Glu Glu Cys Ala Leu Trp Met Pro Thr Arg Thr Gly Val Glu Leu Gln
            180                 185                 190

Leu Ser Tyr Thr Leu His His Gln Asn Pro Val Gly Phe Thr Val Pro
        195                 200                 205

Ile Gln Leu Pro Val Ile Asn Gln Val Phe Ser Ala Asn Cys Ala Val
    210                 215                 220

Lys Ile Ser Pro
225

<210> SEQ ID NO 41
<211> LENGTH: 6202
<212> TYPE: DNA
<213> ORGANISM: Arabidopsis thaliana
<220> FEATURE:
<221> NAME/KEY: CDS
<222> LOCATION: (3522)..(5288)
<221> NAME/KEY: CDS
<222> LOCATION: (5372)..(5926)

<400> SEQUENCE: 41
```

-continued

```
gaattcgaac tgcaatggga taaacattat atgcgtttta ataataggtt ggtgaagttt      60
ataatttaca ccatttgaaa agccttccaa atttagaaac tacattttg cagacccatg      120 tgagctcata tgaatcaatc atagccttga tgttgtaaaa caaattatga ttataaaaat     180
gtgatagtat attacatgca taaaaaataa aggagagtaa atgaaagtca aatctgggtt     240
ttatgaactg aaagttgaag tttagaagta gaagtagcga tcaaagtatg accagttaaa    300
aggcccaata tcatttggag gttttgatttt tgggttcgta aatttcaaga gccagattat    360
gatttgctgg gcttaaaaat catggaaaaa ttgaaatgac ggtgttaaaa tatataactc    420
aaattaaaga ttttaattgg gtgtagtagg ctgatttttt tataagaatc ttgtctatag    480
atgcttcaag gttatgcctt atagtactgg ttgtaaaaca ccactatcta attttgaagc    540
tggtcagaac tataaggtat gttgttgttc gccttgttgc taatgaagat tataacattc    600
tgttgttgca tttttttttt ttttttttgtg ttaaatatat atatttttt tgcatattta    660 ttgttgcata ttgtgttgca tatttagtaa tggttacatt ccctgttatc ggagaccaag    720
ataatacggc tctgtggcat ggactactac tccatggatt cttccaagta atcttgcttt    780
gtgtgtcaat gcaaagtttg tttatcttaa ggttcgtcaa caacactgga aaagtctaca    840
ttgttgctga atctcggttg tcatcgcttc ctagtgataa gcctaaggcc ggcttaacta    900
atggaactta ctagtgatac cataatgcga aaggtgctaa ttaagcttga cagtgaagag    960
gattcttatc aagttttgga aaattttaat ggagattcct tggttgggaa gaagtatgaa   1020
cctttgtttg attactttta gcgatttctc aagtgtgact tttcgactag tagcagatga   1080
ttatgtcatg aatgatagtg gtactggtat tgtccattgt gctcctgtct ttggtgcaga   1140
tgactatcgt gtttgtcttg agaacgagat aattaagaag gttagatttg acaacatctt   1200
ccttatatca ccacctttaa cattaagttt attttctttc ttgtttaagt ttacagtatc   1260
ttcaagaacc catgttcatg acacattttg ttcatgtgtt gtttagattg tcagagattt   1320
caaacgtcca gatggtttga agatacaga gattgatgca gctgtagata gtacatatct   1380
taattaaaaa taccacttct ctatgctcta ttgttgagga aacatataat atttgcattc   1440
gttcatggtt cagatatgat gttatggtaa ttcttgatct acgagaagat gaatctttga   1500
aaaacgaagg tgttgcccgt gaggtaaata aatgtaaccg aagcgattaa tggtcatata   1560
taagttgtat atttgatata tgggtttcct tctcattgtg ctcatgcatt gaaaagcacc   1620
ctgttatgac tgtggttcta ggagaacatt tgcatttgac agtcggtgac taattgttaa   1680
gcaagaagaa cgcatgagag cctttttaaag tgttttcttc tagatcgttg caaaagtta    1740 aatgtctctt gagactttgt actcattcta tagataaaga tgggatttat tacaaaaaca   1800
acaagaaact tgttacttg tggaaattca aaattatccg aactagcttc acaaaatatg    1860
ctcaagagtt tcaatgtatt ttttttttgtt ctgtaattgt atgactccgt ttgaagcatc   1920
aagattatgg ttataggtag tgatgctaaa actctctgtt gttacagtga ccactaaaaa   1980
caccaacaaa aaaacttag gtaacgtgtc gtctaaaaac ttctaggttc aatttcttta   2040
gatagtacta tcaataaata aaataaatat gtacaaaggc tttaaacaat gatgttttc    2100 aaagatgatt ggtagatact aattagagct tcaatataaa agaacacatg cgattctgac   2160
attctgtggt ctaacatggt ttcttctaga gtcaaaacca tacaattaaa agttaggaaa   2220
gtaatagcaa tgtggtttca aatatatact cattactctt tagattcatg tatggtgaag   2280
gaaacattat aataaaatca aagatcacag ttttgtaggt ccctcatatt aatcaacatc   2340
```

-continued

```
ttaaggcgtt atacatatct tcttttgta aatatttgac taattaaaat atctaattag    2400
agtattagac taatctcatc aaatatccga ctacttgtgt cagttcaaaa cacagtgatt    2460
acgttagatt ttgtgctctt ttgtttataa acaaagctaa tttaagaaat atatgatcta    2520
tttgcctcct tggtcttaat tttatacttt cttggaataa aacacattta ttaaaataat    2580
ttttagggtc ctagattcat gtcatgtggc ttgatagttt ccaacaatta taccaatatt    2640
ttactcattc atatacaaat aaacaagctt tattctattc ttcagtctca tgatatacgg    2700
gattttgata aaattcagag tacccattaa ttattctatg ttacagcttg taataagtta    2760
aatttataaa acgtacaagt tgaggaaata acaaatgttt tcaatattaa atgatttatt    2820
aatacattag tgaccaaaaa attattaagt gtaagaaaaa aaacacaact cagaaaaaat    2880
tcaaaagacc gtctaagttc ggttcatgta agaacaagtg ggacctcttt aagtttctaa    2940
atcagagaat aaagaagaag aaaaaatctc aaaaccttcc tctaaaacca acggctccta    3000
cctttactta caccctatac atacacttct ctttttatcc tccatcggcg gcttatggcg    3060
gttttccggc actaatcatc tccggcatat ataaataaac gtacttcacg ttttttata    3120 taacttcaaa gtagtttcag atttgtctct atctcttcac ttttaagtct tctggttttg    3180
tcatcaccag cttttttgt tctctctctg tctctgtctc tgtctttctc tttgtgtatt    3240
tttattctcg tcatcgttgt tcttctatga gaggaagatc ggaatgtcga agagaattag    3300
aagattctcg tacatcactt cgttggaatt tcacaggtcg atgagagatc tgagaactgt    3360
ttcattttga tccaaactca tctctttcag gtattccaaa tttgtctttc tctgttcttt    3420
ctactattac ccaaattaaa gttttgattt ttatttctca ctctgtttct tgttttcta    3480 attgcagagt ataatggact aagcattttt tttctccgaa g atg gtt aaa gaa ata    3536
                                              Met Val Lys Glu Ile
                                               1               5 gct tct tgg tta ttg ata cta tca atg gtg gtg ttt gtt tct ccg gtt    3584
Ala Ser Trp Leu Leu Ile Leu Ser Met Val Val Phe Val Ser Pro Val
           10                  15                  20 tta gct ata aac ggc ggt ggt tat cca cga tgt aac tgc gaa gac gaa    3632
Leu Ala Ile Asn Gly Gly Gly Tyr Pro Arg Cys Asn Cys Glu Asp Glu
       25                  30                  35 gga aac agt ttc tgg agt aca gag aac att cta gaa act caa aga gta    3680
Gly Asn Ser Phe Trp Ser Thr Glu Asn Ile Leu Glu Thr Gln Arg Val
   40                  45                  50 agc gat ttc tta atc gca gta gct tat ttc tca atc cct att gag tta    3728
Ser Asp Phe Leu Ile Ala Val Ala Tyr Phe Ser Ile Pro Ile Glu Leu
55                  60                  65 ctt tac ttc gtg agt tgt tcc aat gtt cca ttc aaa tgg gtt ctc ttt    3776
Leu Tyr Phe Val Ser Cys Ser Asn Val Pro Phe Lys Trp Val Leu Phe
       70                  75                  80                85 gag ttt atc gcc ttc att gtt ctt tgt ggt atg act cat ctt ctt cat    3824
Glu Phe Ile Ala Phe Ile Val Leu Cys Gly Met Thr His Leu Leu His
               90                  95                 100 ggt tgg act tac tct gct cat cca ttt aga tta atg atg gcg ttt act    3872
Gly Trp Thr Tyr Ser Ala His Pro Phe Arg Leu Met Met Ala Phe Thr
           105                 110                 115 gtt ttc aag atg ttg act gct tta gtc tct tgt gct act gcg att acg    3920
Val Phe Lys Met Leu Thr Ala Leu Val Ser Cys Ala Thr Ala Ile Thr
       120                 125                 130 ctt att act ttg att cct ctg ctt tgt aaa gtt aaa gtt aga gag ttt    3968
Leu Ile Thr Leu Ile Pro Leu Leu Cys Lys Val Lys Val Arg Glu Phe
   135                 140                 145 atg ctt aag aag aaa gct cat gag ctt ggt cgt gaa gtt ggt ttg att    4016
```

```
                                                          -continued

Met Leu Lys Lys Lys Ala His Glu Leu Gly Arg Glu Val Gly Leu Ile
150                 155                 160                 165 ttg att aag aaa gag act ggc ttt cat gtt cgt atg ctt act caa gag      4064
Leu Ile Lys Lys Glu Thr Gly Phe His Val Arg Met Leu Thr Gln Glu
                170                 175                 180 att cgt aag tct ttg gat cgt cat acg att ctt tat act act ttg gtt      4112
Ile Arg Lys Ser Leu Asp Arg His Thr Ile Leu Tyr Thr Thr Leu Val
            185                 190                 195 gag ctt tcg aag act tta ggg ttg cag aat tgt gcg gtt tgg atg ccg      4160
Glu Leu Ser Lys Thr Leu Gly Leu Gln Asn Cys Ala Val Trp Met Pro
        200                 205                 210 aat gac ggt gga acg gag atg gat ttg act cat gag ttg aga ggg aga      4208
Asn Asp Gly Gly Thr Glu Met Asp Leu Thr His Glu Leu Arg Gly Arg
    215                 220                 225 ggt ggt tat ggt ggt tgt tct gtt tct atg gag gat ttg gat gtt gtt      4256
Gly Gly Tyr Gly Gly Cys Ser Val Ser Met Glu Asp Leu Asp Val Val
230                 235                 240                 245 agg att agg gag agt gat gaa gtg aat gtg ttg agt gtt gac tcg tcc      4304
Arg Ile Arg Glu Ser Asp Glu Val Asn Val Leu Ser Val Asp Ser Ser
                250                 255                 260 att gct cga gct agt ggt ggt ggt ggg gat gtt agt gag att ggt gcc      4352
Ile Ala Arg Ala Ser Gly Gly Gly Gly Asp Val Ser Glu Ile Gly Ala
            265                 270                 275 gtg gct gct att aga atg ccg atg ctt cgt gtt tcg gat ttt aat gga      4400
Val Ala Ala Ile Arg Met Pro Met Leu Arg Val Ser Asp Phe Asn Gly
        280                 285                 290 gag cta agt tat gcg ata ctt gtt tgt gtt tta ccg ggc ggg acc cgt      4448
Glu Leu Ser Tyr Ala Ile Leu Val Cys Val Leu Pro Gly Gly Thr Arg
    295                 300                 305 cgg gat tgg act tat cag gag att gag att gtt aaa gtt gtg gcg gat      4496
Arg Asp Trp Thr Tyr Gln Glu Ile Glu Ile Val Lys Val Val Ala Asp
310                 315                 320                 325 caa gta acc gtt gcg tta gat cat gca gcg gtt ctt gaa gag tct cag      4544
Gln Val Thr Val Ala Leu Asp His Ala Ala Val Leu Glu Glu Ser Gln
                330                 335                 340 ctt atg agg gag aag ctg gcg gaa cag aac agg gcg ttg cag atg gcg      4592
Leu Met Arg Glu Lys Leu Ala Glu Gln Asn Arg Ala Leu Gln Met Ala
            345                 350                 355 aag aga gac gcg ttg aga gcg agc caa gcg agg aat gcg ttt cag aaa      4640
Lys Arg Asp Ala Leu Arg Ala Ser Gln Ala Arg Asn Ala Phe Gln Lys
        360                 365                 370 acg atg agc gaa ggg atg agg cgt cct atg cat tcg ata ctc ggt ctt      4688
Thr Met Ser Glu Gly Met Arg Pro Met His Ser Ile Leu Gly Leu
    375                 380                 385 ttg tcg atg att cag gac gag aag ttg agt gac gag cag aaa atg att      4736
Leu Ser Met Ile Gln Asp Glu Lys Leu Ser Asp Glu Gln Lys Met Ile
390                 395                 400                 405 gtt gat acg atg gtt aaa aca ggg aat gtt atg tcg aat ttg gtg ggg      4784
Val Asp Thr Met Val Lys Thr Gly Asn Val Met Ser Asn Leu Val Gly
                410                 415                 420 gac tct atg gat gtg cct gac ggt aga ttt ggt acg gag atg aaa ccg      4832
Asp Ser Met Asp Val Pro Asp Gly Arg Phe Gly Thr Glu Met Lys Pro
            425                 430                 435 ttt agt ctg cat cgt acg atc cat gaa gca gct tgt atg gcg aga tgt      4880
Phe Ser Leu His Arg Thr Ile His Glu Ala Ala Cys Met Ala Arg Cys
        440                 445                 450 ttg tgt cta tgc aat gga att agg ttc ttg gtt gac gcg gag aag tct      4928
Leu Cys Leu Cys Asn Gly Ile Arg Phe Leu Val Asp Ala Glu Lys Ser
    455                 460                 465
```

```
cta cct gat aat gta gta ggt gat gaa aga agg gtc ttt caa gtg ata   4976
Leu Pro Asp Asn Val Val Gly Asp Glu Arg Arg Val Phe Gln Val Ile
470             475                 480                 485 ctt cat atg gtt ggt agt tta gta aag cct aga aaa cgt caa gaa gga   5024
Leu His Met Val Gly Ser Leu Val Lys Pro Arg Lys Arg Gln Glu Gly
            490                 495                 500 tct tca ttg atg ttt aag gtt ttg aaa gaa aga gga agc ttg gat agg   5072
Ser Ser Leu Met Phe Lys Val Leu Lys Glu Arg Gly Ser Leu Asp Arg
        505                 510                 515 agt gat cat aga tgg gct gct tgg aga tca ccg gct tct tca gca gat   5120
Ser Asp His Arg Trp Ala Ala Trp Arg Ser Pro Ala Ser Ser Ala Asp
    520                 525                 530 gga gat gtg tat ata aga ttt gaa atg aat gta gag aat gat gat tca   5168
Gly Asp Val Tyr Ile Arg Phe Glu Met Asn Val Glu Asn Asp Asp Ser
535                 540                 545 agt tct caa tca ttt gct tct gtt tcc tcc aga gat caa gaa gtt ggt   5216
Ser Ser Gln Ser Phe Ala Ser Val Ser Ser Arg Asp Gln Glu Val Gly
550                 555                 560                 565 gat gtt aga ttc tcc ggc ggc tat ggg tta gga caa gat cta agc ttt   5264
Asp Val Arg Phe Ser Gly Gly Tyr Gly Leu Gly Gln Asp Leu Ser Phe
            570                 575                 580 ggt gtt tgt aag aaa gtg gtg cag gtgagtttcc ttacatatct ctttctaaag   5318
Gly Val Cys Lys Lys Val Val Gln
        585 ttcctgtcat tagtctgagt ttctgtttag gagttctttg ataatgtgtg cag ttg     5374
                                                             Leu
                                                             590 att cat ggg aat atc tcg gtg gtc cct ggc tcg gat ggt tca ccg gag   5422
Ile His Gly Asn Ile Ser Val Val Pro Gly Ser Asp Gly Ser Pro Glu
                595                 600                 605 acc atg tcg ttg ctc ctt cgg ttt cga cgt aga ccc tcc ata tct gtc   5470
Thr Met Ser Leu Leu Leu Arg Phe Arg Arg Arg Pro Ser Ile Ser Val
            610                 615                 620 cat gga tcc agc gag tcg cca gct cct gac cac cac gct cac cca cat   5518
His Gly Ser Ser Glu Ser Pro Ala Pro Asp His His Ala His Pro His
        625                 630                 635 tcg aat tct ctg tta cgt ggc tta caa gtt tta ttg gta gac acc aac   5566
Ser Asn Ser Leu Leu Arg Gly Leu Gln Val Leu Leu Val Asp Thr Asn
    640                 645                 650 gat tcg aac cgg gca gtt aca cgt aaa ctc tta gag aaa ctc ggg tgc   5614
Asp Ser Asn Arg Ala Val Thr Arg Lys Leu Leu Glu Lys Leu Gly Cys
655                 660                 665                 670 gat gta acc gcg gtt tcc tct gga ttc gat tgc ctt acc gcc att gct   5662
Asp Val Thr Ala Val Ser Ser Gly Phe Asp Cys Leu Thr Ala Ile Ala
            675                 680                 685 ccc ggc tcg tcc tcg cct tct act tcg ttt caa gtg gtg gtg ctt gat   5710
Pro Gly Ser Ser Ser Pro Ser Thr Ser Phe Gln Val Val Val Leu Asp
        690                 695                 700 ctt caa atg gca gag atg gac ggt tat gaa gtg gcc atg agg atc agg   5758
Leu Gln Met Ala Glu Met Asp Gly Tyr Glu Val Ala Met Arg Ile Arg
    705                 710                 715 agt cga tct tgg ccg ttg att gtg gcg acg aca gtg agc ttg gat gaa   5806
Ser Arg Ser Trp Pro Leu Ile Val Ala Thr Thr Val Ser Leu Asp Glu
720                 725                 730 gaa atg tgg gac aag tgt gca cag att gga atc aat gga gtt gtg aga   5854
Glu Met Trp Asp Lys Cys Ala Gln Ile Gly Ile Asn Gly Val Val Arg
735                 740                 745                 750 aag cca gtg gtg tta aga gct atg gag agt gag ctc cga aga gta ttg   5902
Lys Pro Val Val Leu Arg Ala Met Glu Ser Glu Leu Arg Arg Val Leu
            755                 760                 765
```

-continued

```
ttg caa gct gac caa ctt ctc taa gttgttatct caacttctct tctacattca    5956
Leu Gln Ala Asp Gln Leu Leu
            770 aaattttttac accatagatt tatgtcaaat atatcaaaat gaaatttcga aattgttatt    6016
atatatacca cccatatctc tatgatttgt acatcctgtt ttttttttgtt cttttctca    6076 ttttgaaccc cacgaaattg cattgaatct tagtatttcg tagggtcaag aaggagtcag    6136
tttcgtagtt ttttgttttc tttatgttac gaacttacga aactgaatat ggcattatag    6196
agtttt                                                               6202
```

<210> SEQ ID NO 42
<211> LENGTH: 773
<212> TYPE: PRT
<213> ORGANISM: Arabidopsis thaliana

<400> SEQUENCE: 42

```
Met Val Lys Glu Ile Ala Ser Trp Leu Leu Ile Leu Ser Met Val Val
 1               5                  10                  15

Phe Val Ser Pro Val Leu Ala Ile Asn Gly Gly Tyr Pro Arg Cys
            20                  25                  30

Asn Cys Glu Asp Glu Gly Asn Ser Phe Trp Ser Thr Glu Asn Ile Leu
        35                  40                  45

Glu Thr Gln Arg Val Ser Asp Phe Leu Ile Ala Val Ala Tyr Phe Ser
     50                  55                  60

Ile Pro Ile Glu Leu Leu Tyr Phe Val Ser Cys Ser Asn Val Pro Phe
 65                  70                  75                  80

Lys Trp Val Leu Phe Glu Phe Ile Ala Phe Ile Val Leu Cys Gly Met
                85                  90                  95

Thr His Leu Leu His Gly Trp Thr Tyr Ser Ala His Pro Phe Arg Leu
            100                 105                 110

Met Met Ala Phe Thr Val Phe Lys Met Leu Thr Ala Leu Val Ser Cys
        115                 120                 125

Ala Thr Ala Ile Thr Leu Ile Thr Leu Ile Pro Leu Leu Lys Val
    130                 135                 140

Lys Val Arg Glu Phe Met Leu Lys Lys Ala His Glu Leu Gly Arg
145                 150                 155                 160

Glu Val Gly Leu Ile Leu Ile Lys Lys Glu Thr Gly Phe His Val Arg
                165                 170                 175

Met Leu Thr Gln Glu Ile Arg Lys Ser Leu Asp Arg His Thr Ile Leu
            180                 185                 190

Tyr Thr Thr Leu Val Glu Leu Ser Lys Thr Leu Gly Leu Gln Asn Cys
        195                 200                 205

Ala Val Trp Met Pro Asn Asp Gly Gly Thr Glu Met Asp Leu Thr His
    210                 215                 220

Glu Leu Arg Gly Arg Gly Gly Tyr Gly Gly Cys Ser Val Ser Met Glu
225                 230                 235                 240

Asp Leu Asp Val Val Arg Ile Arg Glu Ser Asp Glu Val Asn Val Leu
                245                 250                 255

Ser Val Asp Ser Ser Ile Ala Arg Ala Ser Gly Gly Gly Asp Val
            260                 265                 270

Ser Glu Ile Gly Ala Val Ala Ala Ile Arg Met Pro Met Leu Arg Val
        275                 280                 285

Ser Asp Phe Asn Gly Glu Leu Ser Tyr Ala Ile Leu Val Cys Val Leu
    290                 295                 300
```

-continued

```
Pro Gly Gly Thr Arg Arg Asp Trp Thr Tyr Gln Glu Ile Glu Ile Val
305                 310                 315                 320

Lys Val Val Ala Asp Gln Val Thr Val Ala Leu Asp His Ala Ala Val
                325                 330                 335

Leu Glu Glu Ser Gln Leu Met Arg Glu Lys Leu Ala Glu Gln Asn Arg
            340                 345                 350

Ala Leu Gln Met Ala Lys Arg Asp Ala Leu Arg Ala Ser Gln Ala Arg
        355                 360                 365

Asn Ala Phe Gln Lys Thr Met Ser Glu Gly Met Arg Arg Pro Met His
    370                 375                 380

Ser Ile Leu Gly Leu Leu Ser Met Ile Gln Asp Glu Lys Leu Ser Asp
385                 390                 395                 400

Glu Gln Lys Met Ile Val Asp Thr Met Val Lys Thr Gly Asn Val Met
                405                 410                 415

Ser Asn Leu Val Gly Asp Ser Met Asp Val Pro Asp Gly Arg Phe Gly
            420                 425                 430

Thr Glu Met Lys Pro Phe Ser Leu His Arg Thr Ile His Glu Ala Ala
        435                 440                 445

Cys Met Ala Arg Cys Leu Cys Leu Cys Asn Gly Ile Arg Phe Leu Val
    450                 455                 460

Asp Ala Glu Lys Ser Leu Pro Asp Asn Val Val Gly Asp Glu Arg Arg
465                 470                 475                 480

Val Phe Gln Val Ile Leu His Met Val Gly Ser Leu Val Lys Pro Arg
                485                 490                 495

Lys Arg Gln Glu Gly Ser Ser Leu Met Phe Lys Val Leu Lys Glu Arg
            500                 505                 510

Gly Ser Leu Asp Arg Ser Asp His Arg Trp Ala Ala Trp Arg Ser Pro
        515                 520                 525

Ala Ser Ser Ala Asp Gly Asp Val Tyr Ile Arg Phe Glu Met Asn Val
    530                 535                 540

Glu Asn Asp Asp Ser Ser Ser Gln Ser Phe Ala Ser Val Ser Ser Arg
545                 550                 555                 560

Asp Gln Glu Val Gly Asp Val Arg Phe Ser Gly Gly Tyr Gly Leu Gly
                565                 570                 575

Gln Asp Leu Ser Phe Gly Val Cys Lys Lys Val Val Gln Leu Ile His
            580                 585                 590

Gly Asn Ile Ser Val Val Pro Gly Ser Asp Gly Ser Pro Glu Thr Met
        595                 600                 605

Ser Leu Leu Leu Arg Phe Arg Arg Pro Ser Ile Ser Val His Gly
    610                 615                 620

Ser Ser Glu Ser Pro Ala Pro Asp His His Ala His Pro His Ser Asn
625                 630                 635                 640

Ser Leu Leu Arg Gly Leu Gln Val Leu Leu Val Asp Thr Asn Asp Ser
                645                 650                 655

Asn Arg Ala Val Thr Arg Lys Leu Leu Glu Lys Leu Gly Cys Asp Val
            660                 665                 670

Thr Ala Val Ser Ser Gly Phe Asp Cys Leu Thr Ala Ile Ala Pro Gly
        675                 680                 685

Ser Ser Ser Pro Ser Thr Ser Phe Gln Val Val Leu Asp Leu Gln
    690                 695                 700

Met Ala Glu Met Asp Gly Tyr Glu Val Ala Met Arg Ile Arg Ser Arg
705                 710                 715                 720
```

```
Ser Trp Pro Leu Ile Val Ala Thr Thr Val Ser Leu Asp Glu Glu Met
            725                 730                 735

Trp Asp Lys Cys Ala Gln Ile Gly Ile Asn Gly Val Val Arg Lys Pro
            740                 745                 750

Val Val Leu Arg Ala Met Glu Ser Glu Leu Arg Arg Val Leu Leu Gln
            755                 760                 765

Ala Asp Gln Leu Leu
        770

<210> SEQ ID NO 43
<211> LENGTH: 2404
<212> TYPE: DNA
<213> ORGANISM: Arabidopsis thaliana
<220> FEATURE:
<221> NAME/KEY: CDS
<222> LOCATION: (1)..(2322)

<400> SEQUENCE: 43 atg gtt aaa gaa ata gct tct tgg tta ttg ata cta tca atg gtg gtg     48
Met Val Lys Glu Ile Ala Ser Trp Leu Leu Ile Leu Ser Met Val Val
 1               5                  10                  15 ttt gtt tct ccg gtt tta gct ata aac ggc ggt ggt tat cca cga tgt     96
Phe Val Ser Pro Val Leu Ala Ile Asn Gly Gly Gly Tyr Pro Arg Cys
                20                  25                  30 aac tgc gaa gac gaa gga aac agt ttc tgg agt aca gag aac att cta    144
Asn Cys Glu Asp Glu Gly Asn Ser Phe Trp Ser Thr Glu Asn Ile Leu
            35                  40                  45 gaa act caa aga gta agc gat ttc tta atc gca gta gct tat ttc tca    192
Glu Thr Gln Arg Val Ser Asp Phe Leu Ile Ala Val Ala Tyr Phe Ser
     50                  55                  60 atc cct att gag tta ctt tac ttc gtg agt tgt tcc aat gtt cca ttc    240
Ile Pro Ile Glu Leu Leu Tyr Phe Val Ser Cys Ser Asn Val Pro Phe
 65                  70                  75                  80 aaa tgg gtt ctc ttt gag ttt atc gcc ttc att gtt ctt tgt ggt atg    288
Lys Trp Val Leu Phe Glu Phe Ile Ala Phe Ile Val Leu Cys Gly Met
                85                  90                  95 act cat ctt ctt cat ggt tgg act tac tct gct cat cca ttt aga tta    336
Thr His Leu Leu His Gly Trp Thr Tyr Ser Ala His Pro Phe Arg Leu
                100                 105                 110 atg atg gcg ttt act gtt ttc aag atg ttg act gct tta gtc tct tgt    384
Met Met Ala Phe Thr Val Phe Lys Met Leu Thr Ala Leu Val Ser Cys
            115                 120                 125 gct act gcg att acg ctt att act ttg att cct ctg ctt tgt aaa gtt    432
Ala Thr Ala Ile Thr Leu Ile Thr Leu Ile Pro Leu Leu Lys Val
    130                 135                 140 aaa gtt aga gag ttt atg ctt aag aag aaa gct cat gag ctt ggt cgt    480
Lys Val Arg Glu Phe Met Leu Lys Lys Lys Ala His Glu Leu Gly Arg
145                 150                 155                 160 gaa gtt ggt ttg att ttg att aag aaa gag act ggc ttt cat gtt cgt    528
Glu Val Gly Leu Ile Leu Ile Lys Lys Glu Thr Gly Phe His Val Arg
                165                 170                 175 atg ctt act caa gag att cgt aag tct ttg gat cgt cat acg att ctt    576
Met Leu Thr Gln Glu Ile Arg Lys Ser Leu Asp Arg His Thr Ile Leu
            180                 185                 190 tat act act ttg gtt gag ctt tcg aag act tta ggg ttg cag aat tgt    624
Tyr Thr Thr Leu Val Glu Leu Ser Lys Thr Leu Gly Leu Gln Asn Cys
        195                 200                 205 gcg gtt tgg atg ccg aat gac ggt gga acg gag atg gat ttg act cat    672
Ala Val Trp Met Pro Asn Asp Gly Gly Thr Glu Met Asp Leu Thr His
    210                 215                 220
```

| | | |
|---|---|---|
| gag ttg aga ggg aga ggt ggt tat ggt ggt tgt tct gtt tct atg gag<br>Glu Leu Arg Gly Arg Gly Gly Tyr Gly Gly Cys Ser Val Ser Met Glu<br>225                      230                      235                  240 | 720 |
| gat ttg gat gtt gtt agg att agg gag agt gat gaa gtg aat gtg ttg<br>Asp Leu Asp Val Val Arg Ile Arg Glu Ser Asp Glu Val Asn Val Leu<br>                      245                      250                      255 | 768 |
| agt gtt gac tcg tcc att gct cga gct agt ggt ggt ggt ggg gat gtt<br>Ser Val Asp Ser Ser Ile Ala Arg Ala Ser Gly Gly Gly Gly Asp Val<br>            260                      265                      270 | 816 |
| agt gag att ggt gcc gtg gct gct att aga atg ccg atg ctt cgt gtt<br>Ser Glu Ile Gly Ala Val Ala Ala Ile Arg Met Pro Met Leu Arg Val<br>                275                      280                      285 | 864 |
| tcg gat ttt aat gga gag cta agt tat gcg ata ctt gtt tgt gtt tta<br>Ser Asp Phe Asn Gly Glu Leu Ser Tyr Ala Ile Leu Val Cys Val Leu<br>            290                      295                      300 | 912 |
| ccg ggc ggg acc cgt cgg gat tgg act tat cag gag att gag att gtt<br>Pro Gly Gly Thr Arg Arg Asp Trp Thr Tyr Gln Glu Ile Glu Ile Val<br>305                      310                      315                  320 | 960 |
| aaa gtt gtg gcg gat caa gta acc gtt gcg tta gat cat gca gcg gtt<br>Lys Val Val Ala Asp Gln Val Thr Val Ala Leu Asp His Ala Ala Val<br>                      325                      330                      335 | 1008 |
| ctt gaa gag tct cag ctt atg agg gag aag ctg gcg gaa cag aac agg<br>Leu Glu Glu Ser Gln Leu Met Arg Glu Lys Leu Ala Glu Gln Asn Arg<br>                340                      345                      350 | 1056 |
| gcg ttg cag atg gcg aag aga gac gcg ttg aga gcg agc caa gcg agg<br>Ala Leu Gln Met Ala Lys Arg Asp Ala Leu Arg Ala Ser Gln Ala Arg<br>            355                      360                      365 | 1104 |
| aat gcg ttt cag aaa acg atg agc gaa ggg atg agg cgt cct atg cat<br>Asn Ala Phe Gln Lys Thr Met Ser Glu Gly Met Arg Arg Pro Met His<br>370                      375                      380 | 1152 |
| tcg ata ctc ggt ctt ttg tcg atg att cag gac gag aag ttg agt gac<br>Ser Ile Leu Gly Leu Leu Ser Met Ile Gln Asp Glu Lys Leu Ser Asp<br>385                      390                      395                  400 | 1200 |
| gag cag aaa atg att gtt gat acg atg gtt aaa aca ggg aat gtt atg<br>Glu Gln Lys Met Ile Val Asp Thr Met Val Lys Thr Gly Asn Val Met<br>                      405                      410                      415 | 1248 |
| tcg aat ttg gtg ggg gac tct atg gat gtg cct gac ggt aga ttt ggt<br>Ser Asn Leu Val Gly Asp Ser Met Asp Val Pro Asp Gly Arg Phe Gly<br>            420                      425                      430 | 1296 |
| acg gag atg aaa ccg ttt agt ctg cat cgt acg atc cat gaa gca gct<br>Thr Glu Met Lys Pro Phe Ser Leu His Arg Thr Ile His Glu Ala Ala<br>                435                      440                      445 | 1344 |
| tgt atg gcg aga tgt ttg tgt cta tgc aat gga att agg ttc ttg gtt<br>Cys Met Ala Arg Cys Leu Cys Leu Cys Asn Gly Ile Arg Phe Leu Val<br>450                      455                      460 | 1392 |
| gac gcg gag aag tct cta cct gat aat gta gta ggt gat gaa aga agg<br>Asp Ala Glu Lys Ser Leu Pro Asp Asn Val Val Gly Asp Glu Arg Arg<br>465                      470                      475                  480 | 1440 |
| gtc ttt caa gtg ata ctt cat atg gtt ggt agt tta gta aag cct aga<br>Val Phe Gln Val Ile Leu His Met Val Gly Ser Leu Val Lys Pro Arg<br>                      485                      490                      495 | 1488 |
| aaa cgt caa gaa gga tct tca ttg atg ttt aag gtt ttg aaa gaa aga<br>Lys Arg Gln Glu Gly Ser Ser Leu Met Phe Lys Val Leu Lys Glu Arg<br>            500                      505                      510 | 1536 |
| gga agc ttg gat agg agt gat cat aga tgg gct gct tgg aga tca ccg<br>Gly Ser Leu Asp Arg Ser Asp His Arg Trp Ala Ala Trp Arg Ser Pro<br>                515                      520                      525 | 1584 |
| gct tct tca gca gat gga gat gtg tat ata aga ttt gaa atg aat gta<br>Ala Ser Ser Ala Asp Gly Asp Val Tyr Ile Arg Phe Glu Met Asn Val<br>            530                      535                      540 | 1632 |

```
gag aat gat gat tca agt tct caa tca ttt gct tct gtt tcc tcc aga      1680
Glu Asn Asp Asp Ser Ser Ser Gln Ser Phe Ala Ser Val Ser Ser Arg
545                 550                 555                 560 gat caa gaa gtt ggt gat gtt aga ttc tcc ggc ggc tat ggg tta gga      1728
Asp Gln Glu Val Gly Asp Val Arg Phe Ser Gly Gly Tyr Gly Leu Gly
                565                 570                 575 caa gat cta agc ttt ggt gtt tgt aag aaa gtg gtg cag ttg att cat      1776
Gln Asp Leu Ser Phe Gly Val Cys Lys Lys Val Val Gln Leu Ile His
            580                 585                 590 ggg aat atc tcg gtg gtc cct ggc tcg gat ggt tca ccg gag acc atg      1824
Gly Asn Ile Ser Val Val Pro Gly Ser Asp Gly Ser Pro Glu Thr Met
        595                 600                 605 tcg ttg ctc ctt cgg ttt cga cgt aga ccc tcc ata tct gtc cat gga      1872
Ser Leu Leu Leu Arg Phe Arg Arg Arg Pro Ser Ile Ser Val His Gly
    610                 615                 620 tcc agc gag tcg cca gct cct gac cac cac gct cac cca cat tcg aat      1920
Ser Ser Glu Ser Pro Ala Pro Asp His His Ala His Pro His Ser Asn
625                 630                 635                 640 tct ctg tta cgt ggc tta caa gtt tta ttg gta gac acc aac gat tcg      1968
Ser Leu Leu Arg Gly Leu Gln Val Leu Leu Val Asp Thr Asn Asp Ser
                645                 650                 655 aac cgg gca gtt aca cgt aaa ctc tta gag aaa ctc ggg tgc gat gta      2016
Asn Arg Ala Val Thr Arg Lys Leu Leu Glu Lys Leu Gly Cys Asp Val
            660                 665                 670 acc gcg gtt tcc tct gga ttc gat tgc ctt acc gcc att gct ccc ggc      2064
Thr Ala Val Ser Ser Gly Phe Asp Cys Leu Thr Ala Ile Ala Pro Gly
        675                 680                 685 tcg tcc tcg cct tct act tcg ttt caa gtg gtg gtg ctt gat ctt caa      2112
Ser Ser Ser Pro Ser Thr Ser Phe Gln Val Val Val Leu Asp Leu Gln
    690                 695                 700 atg gca gag atg gac ggt tat gaa gtg gcc atg agg atc agg agt cga      2160
Met Ala Glu Met Asp Gly Tyr Glu Val Ala Met Arg Ile Arg Ser Arg
705                 710                 715                 720 tct tgg ccg ttg att gtg gcg acg aca gtg agc ttg gat gaa gaa atg      2208
Ser Trp Pro Leu Ile Val Ala Thr Thr Val Ser Leu Asp Glu Glu Met
                725                 730                 735 tgg gac aag tgt gca cag att gga atc aat gga gtt gtg aga aag cca      2256
Trp Asp Lys Cys Ala Gln Ile Gly Ile Asn Gly Val Val Arg Lys Pro
            740                 745                 750 gtg gtg tta aga gct atg gag agt gag ctc cga aga gta ttg ttg caa      2304
Val Val Leu Arg Ala Met Glu Ser Glu Leu Arg Arg Val Leu Leu Gln
        755                 760                 765 gct gac caa ctt ctc taa gttgttatct caacttctct tctacattca            2352
Ala Asp Gln Leu Leu
    770 aaattttac accatagatt tatgtcaaat atatcaaaat gaaatttcga aa            2404

<210> SEQ ID NO 44
<211> LENGTH: 773
<212> TYPE: PRT
<213> ORGANISM: Arabidopsis thaliana

<400> SEQUENCE: 44

Met Val Lys Glu Ile Ala Ser Trp Leu Leu Ile Leu Ser Met Val Val
1               5                   10                  15

Phe Val Ser Pro Val Leu Ala Ile Asn Gly Gly Gly Tyr Pro Arg Cys
                20                  25                  30

Asn Cys Glu Asp Glu Gly Asn Ser Phe Trp Ser Thr Glu Asn Ile Leu
            35                  40                  45
```

-continued

```
Glu Thr Gln Arg Val Ser Asp Phe Leu Ile Ala Val Ala Tyr Phe Ser
     50                  55                  60
Ile Pro Ile Glu Leu Leu Tyr Phe Val Ser Cys Ser Asn Val Pro Phe
 65                  70                  75                  80
Lys Trp Val Leu Phe Glu Phe Ile Ala Phe Ile Val Leu Cys Gly Met
                     85                  90                  95
Thr His Leu Leu His Gly Trp Thr Tyr Ser Ala His Pro Phe Arg Leu
                    100                 105                 110
Met Met Ala Phe Thr Val Phe Lys Met Leu Thr Ala Leu Val Ser Cys
                115                 120                 125
Ala Thr Ala Ile Thr Leu Ile Thr Leu Ile Pro Leu Leu Leu Lys Val
    130                 135                 140
Lys Val Arg Glu Phe Met Leu Lys Lys Ala His Glu Leu Gly Arg
145                 150                 155                 160
Glu Val Gly Leu Ile Leu Ile Lys Lys Glu Thr Gly Phe His Val Arg
                    165                 170                 175
Met Leu Thr Gln Glu Ile Arg Lys Ser Leu Asp Arg His Thr Ile Leu
                180                 185                 190
Tyr Thr Thr Leu Val Glu Leu Ser Lys Thr Leu Gly Leu Gln Asn Cys
            195                 200                 205
Ala Val Trp Met Pro Asn Asp Gly Thr Glu Met Asp Leu Thr His
    210                 215                 220
Glu Leu Arg Gly Arg Gly Gly Tyr Gly Gly Cys Ser Val Ser Met Glu
225                 230                 235                 240
Asp Leu Asp Val Val Arg Ile Arg Glu Ser Asp Glu Val Asn Val Leu
                    245                 250                 255
Ser Val Asp Ser Ser Ile Ala Arg Ala Ser Gly Gly Gly Gly Asp Val
                260                 265                 270
Ser Glu Ile Gly Ala Val Ala Ile Arg Met Pro Met Leu Arg Val
            275                 280                 285
Ser Asp Phe Asn Gly Glu Leu Ser Tyr Ala Ile Leu Val Cys Val Leu
    290                 295                 300
Pro Gly Gly Thr Arg Arg Asp Trp Thr Tyr Gln Glu Ile Glu Ile Val
305                 310                 315                 320
Lys Val Val Ala Asp Gln Val Thr Val Ala Leu Asp His Ala Val
                325                 330                 335
Leu Glu Glu Ser Gln Leu Met Arg Glu Lys Leu Ala Glu Gln Asn Arg
                340                 345                 350
Ala Leu Gln Met Ala Lys Arg Asp Ala Leu Arg Ala Ser Gln Ala Arg
            355                 360                 365
Asn Ala Phe Gln Lys Thr Met Ser Glu Gly Met Arg Arg Pro Met His
    370                 375                 380
Ser Ile Leu Gly Leu Leu Ser Met Ile Gln Asp Glu Lys Leu Ser Asp
385                 390                 395                 400
Glu Gln Lys Met Ile Val Asp Thr Met Val Lys Thr Gly Asn Val Met
                    405                 410                 415
Ser Asn Leu Val Gly Asp Ser Met Asp Val Pro Asp Gly Arg Phe Gly
                420                 425                 430
Thr Glu Met Lys Pro Phe Ser Leu His Arg Thr Ile His Glu Ala Ala
            435                 440                 445
Cys Met Ala Arg Cys Leu Cys Leu Cys Asn Gly Ile Arg Phe Leu Val
450                 455                 460
```

```
Asp Ala Glu Lys Ser Leu Pro Asp Asn Val Val Gly Asp Glu Arg Arg
465                 470                 475                 480

Val Phe Gln Val Ile Leu His Met Val Gly Ser Leu Val Lys Pro Arg
            485                 490                 495

Lys Arg Gln Glu Gly Ser Ser Leu Met Phe Lys Val Leu Lys Glu Arg
                500                 505                 510

Gly Ser Leu Asp Arg Ser Asp His Arg Trp Ala Ala Trp Arg Ser Pro
            515                 520                 525

Ala Ser Ser Ala Asp Gly Asp Val Tyr Ile Arg Phe Glu Met Asn Val
530                 535                 540

Glu Asn Asp Asp Ser Ser Ser Gln Ser Phe Ala Ser Val Ser Ser Arg
545                 550                 555                 560

Asp Gln Glu Val Gly Asp Val Arg Phe Ser Gly Gly Tyr Gly Leu Gly
                565                 570                 575

Gln Asp Leu Ser Phe Gly Val Cys Lys Lys Val Val Gln Leu Ile His
            580                 585                 590

Gly Asn Ile Ser Val Val Pro Gly Ser Asp Gly Ser Pro Glu Thr Met
            595                 600                 605

Ser Leu Leu Leu Arg Phe Arg Arg Pro Ser Ile Ser Val His Gly
610                 615                 620

Ser Ser Glu Ser Pro Ala Pro Asp His His Ala His Pro His Ser Asn
625                 630                 635                 640

Ser Leu Leu Arg Gly Leu Gln Val Leu Leu Val Asp Thr Asn Asp Ser
                645                 650                 655

Asn Arg Ala Val Thr Arg Lys Leu Leu Glu Lys Leu Gly Cys Asp Val
                660                 665                 670

Thr Ala Val Ser Ser Gly Phe Asp Cys Leu Thr Ala Ile Ala Pro Gly
            675                 680                 685

Ser Ser Ser Pro Ser Thr Ser Phe Gln Val Val Leu Asp Leu Gln
            690                 695                 700

Met Ala Glu Met Asp Gly Tyr Glu Val Ala Met Arg Ile Arg Ser Arg
705                 710                 715                 720

Ser Trp Pro Leu Ile Val Ala Thr Thr Val Ser Leu Asp Glu Glu Met
                725                 730                 735

Trp Asp Lys Cys Ala Gln Ile Gly Ile Asn Gly Val Val Arg Lys Pro
                740                 745                 750

Val Val Leu Arg Ala Met Glu Ser Glu Leu Arg Arg Val Leu Leu Gln
            755                 760                 765

Ala Asp Gln Leu Leu
    770

<210> SEQ ID NO 45
<211> LENGTH: 3010
<212> TYPE: DNA
<213> ORGANISM: Arabidopsis thaliana
<220> FEATURE:
<221> NAME/KEY: CDS
<222> LOCATION: (564)..(1469)
<221> NAME/KEY: CDS
<222> LOCATION: (1565)..(1933)
<221> NAME/KEY: CDS
<222> LOCATION: (2014)..(2280)
<221> NAME/KEY: CDS
<222> LOCATION: (2359)..(2487)
<221> NAME/KEY: CDS
<222> LOCATION: (2579)..(2749)

<400> SEQUENCE: 45
```

```
acttttaaaa tttctttatt tcattgtcag aaaaagagag ctaataatat tattatttaa      60
atgtaacaag taggcctata acacgtgaac ttccctcttt gcaaaaaaaa aatcatcaaa     120
aacttttacc tctcattggt ttcttcttta tcacactgtt acgcttggat tctcatttct     180
tcaagttcat aacgctcgga tcaatcagga agacgaactt gaactttctt tttttcatca     240
ttacccaaag ctatgaggct cacaccacca atacgtccgc cgtcatgaat ccttctcttc     300
caggtactgt gccgtctcgg gataacaaac tttctattta ttctcttctg atcggatcta     360
tctatcgatg aagattgatt tcactacttt agtaacattt catctgatcg atctgtgttg     420
tgttatcgag gaatcaatct cattttgtag attcaatttt ctggatagat tttgtatctc     480
ttttccatag ctctagtcca aatctagtct ccactgatat ctgagttttg ttgaccaggt     540
caacacaagt cagagctcca aaa atg gag tca tgc gat tgt ttt gag acg cat     593
                          Met Glu Ser Cys Asp Cys Phe Glu Thr His
                            1               5                  10 gtg aat caa gat gat ctg tta gtg aag tac caa tac atc tca gat gcg     641
Val Asn Gln Asp Asp Leu Leu Val Lys Tyr Gln Tyr Ile Ser Asp Ala
            15                  20                  25 ttg att gct ctt gca tac ttc tca atc cca ctc gag ctt atc tat ttc     689
Leu Ile Ala Leu Ala Tyr Phe Ser Ile Pro Leu Glu Leu Ile Tyr Phe
            30                  35                  40 gtg caa aag tct gct ttc ttc cct tac aaa tgg gtg ctt atg cag ttt     737
Val Gln Lys Ser Ala Phe Phe Pro Tyr Lys Trp Val Leu Met Gln Phe
        45                  50                  55 gga gcc ttt atc att ctc tgt gga gct acg cat ttc atc aac cta tgg     785
Gly Ala Phe Ile Ile Leu Cys Gly Ala Thr His Phe Ile Asn Leu Trp
    60                  65                  70 atg ttc ttc atg cat tcc aaa gcc gtt gcc att gtc atg act att gct     833
Met Phe Phe Met His Ser Lys Ala Val Ala Ile Val Met Thr Ile Ala
75                  80                  85                  90 aaa gtc tct tgc gcg gtt gtg tcg tgt gct acc gcg ttg atg ttg gtt     881
Lys Val Ser Cys Ala Val Val Ser Cys Ala Thr Ala Leu Met Leu Val
                95                  100                 105 cat att att cct gat ctt ctc agt gtt aag aac agg gaa ttg ttt ctc     929
His Ile Ile Pro Asp Leu Leu Ser Val Lys Asn Arg Glu Leu Phe Leu
            110                 115                 120 aag aag aaa gct gat gag tta gat aga gaa atg ggt ctt att tta aca     977
Lys Lys Lys Ala Asp Glu Leu Asp Arg Glu Met Gly Leu Ile Leu Thr
        125                 130                 135 caa gag gag act ggt agg cat gtt agg atg ctt act cat gga att aga    1025
Gln Glu Glu Thr Gly Arg His Val Arg Met Leu Thr His Gly Ile Arg
    140                 145                 150 aga act ctt gat agg cat act att tta aga acc act ctt gtt gag ctt    1073
Arg Thr Leu Asp Arg His Thr Ile Leu Arg Thr Thr Leu Val Glu Leu
155                 160                 165                 170 ggt aaa act ctt tgt ctt gag gaa tgt gcg ttg tgg atg cct tct caa    1121
Gly Lys Thr Leu Cys Leu Glu Glu Cys Ala Leu Trp Met Pro Ser Gln
                175                 180                 185 agt ggt tta tat ttg cag ctt tct cat act ttg agt cat aaa ata caa    1169
Ser Gly Leu Tyr Leu Gln Leu Ser His Thr Leu Ser His Lys Ile Gln
            190                 195                 200 gtt gga agc agt gtg ccg ata aat ctc ccg att att aat gaa ctc ttc    1217
Val Gly Ser Ser Val Pro Ile Asn Leu Pro Ile Ile Asn Glu Leu Phe
        205                 210                 215 aat agc gct caa gct atg cac ata cct cat tct tgt cct ttg gct aag    1265
Asn Ser Ala Gln Ala Met His Ile Pro His Ser Cys Pro Leu Ala Lys
    220                 225                 230 att ggg cct ccg gtt ggg aga tat tca cct cct gag gtt gtt tct gtc    1313
```

```
Ile Gly Pro Pro Val Gly Arg Tyr Ser Pro Pro Glu Val Val Ser Val
235                 240                 245                 250 cgt gtt cct ctt tta cat ctc tct aat ttc caa ggc agt gac tgg tcg    1361
Arg Val Pro Leu Leu His Leu Ser Asn Phe Gln Gly Ser Asp Trp Ser
                255                 260                 265 gat ctc tct ggc aaa ggt tac gct atc atg gtc ctg att ctc cca acc    1409
Asp Leu Ser Gly Lys Gly Tyr Ala Ile Met Val Leu Ile Leu Pro Thr
            270                 275                 280 gat ggt gca aga aaa tgg aga gac cat gag tta gag ctt gta gaa aac    1457
Asp Gly Ala Arg Lys Trp Arg Asp His Glu Leu Glu Leu Val Glu Asn
        285                 290                 295 gtg gcg gat cag gtccatctct ttacttgtat atgtttggtt gtgtgtcaag        1509
Val Ala Asp Gln
    300 ttgctttacc agcttttagt gttttgtttt gtcccctgac tctcacttca ttcag gtg   1567
                                                              Val gct gtg gct ctc tca cat gct gca att ttg gaa gaa tcc atg cac gct    1615
Ala Val Ala Leu Ser His Ala Ala Ile Leu Glu Glu Ser Met His Ala
    305                 310                 315 cgt gac cag ctt atg gag cag aat ttt gct tta gac aag gct cgt caa    1663
Arg Asp Gln Leu Met Glu Gln Asn Phe Ala Leu Asp Lys Ala Arg Gln
320                 325                 330                 335 gag gct gag atg gca gta cat gct cga aat gat ttc cta gct gtt atg    1711
Glu Ala Glu Met Ala Val His Ala Arg Asn Asp Phe Leu Ala Val Met
                340                 345                 350 aac cac gag atg agg aca ccg atg cat gcc atc atc tct ctt tct tct    1759
Asn His Glu Met Arg Thr Pro Met His Ala Ile Ile Ser Leu Ser Ser
            355                 360                 365 ctt ctc ctt gag act gag ctg tct cca gag caa aga gtt atg atc gag    1807
Leu Leu Leu Glu Thr Glu Leu Ser Pro Glu Gln Arg Val Met Ile Glu
        370                 375                 380 aca ata ctg aaa agc agc aat ctt gtg gct aca cta atc agc gac gtt    1855
Thr Ile Leu Lys Ser Ser Asn Leu Val Ala Thr Leu Ile Ser Asp Val
    385                 390                 395 ctg gat ctt tcg aga ttg gaa gat ggg agc tta ctc ttg gaa aat gaa    1903
Leu Asp Leu Ser Arg Leu Glu Asp Gly Ser Leu Leu Leu Glu Asn Glu
400                 405                 410                 415 cca ttc agt cta caa gcg atc ttt gaa gag gtaactaaat cccctgatt       1953
Pro Phe Ser Leu Gln Ala Ile Phe Glu Glu
                420                 425 aaccagtgaa gtccattata tatgtcttac atgaataaca tgggcgcttt gaatctgcag  2013 gtc atc tct ttg ata aag cca atc gca tca gtg aag aaa cta tca acg    2061
Val Ile Ser Leu Ile Lys Pro Ile Ala Ser Val Lys Lys Leu Ser Thr
                430                 435                 440 aat ctg att ctg tct gca gac tta cca act tat gct att ggt gat gag    2109
Asn Leu Ile Leu Ser Ala Asp Leu Pro Thr Tyr Ala Ile Gly Asp Glu
            445                 450                 455 aaa cgt ctg atg caa aca att ctt aac atc atg ggc aac gct gtg aaa    2157
Lys Arg Leu Met Gln Thr Ile Leu Asn Ile Met Gly Asn Ala Val Lys
        460                 465                 470 ttt act aag gaa ggc tac atc tcc ata ata gcc tct atc atg aaa ccc    2205
Phe Thr Lys Glu Gly Tyr Ile Ser Ile Ile Ala Ser Ile Met Lys Pro
    475                 480                 485 gag tcc tta caa gaa tta cca tct cca gaa ttt ttt cca gtt ctc agt    2253
Glu Ser Leu Gln Glu Leu Pro Ser Pro Glu Phe Phe Pro Val Leu Ser
490                 495                 500                 505 gac agt cac ttc tac cta tgt gtg cag gttagaccca atctacaaat          2300
Asp Ser His Phe Tyr Leu Cys Val Gln
                510
```

```
tactaaacta caaagttaag cttcttactg tgttcttact gttataatca tggtgcag         2358 gtg aag gac aca ggg tgt gga att cac aca caa gac att cct ttg ctc        2406
Val Lys Asp Thr Gly Cys Gly Ile His Thr Gln Asp Ile Pro Leu Leu
515                 520                 525                 530 ttt acc aaa ttt gta cag cct cgg acc gga act cag agg aac cat tcc        2454
Phe Thr Lys Phe Val Gln Pro Arg Thr Gly Thr Gln Arg Asn His Ser
                535                 540                 545 ggt gga gga ctc ggg cta gct ctc tgt aaa cga gtaacaaccc aaaagtatat      2507
Gly Gly Gly Leu Gly Leu Ala Leu Cys Lys Arg
                550                 555 ataagttata agcagatggt gttacaaata gctaaaaggc aagtttctgt tgatggatgt      2567
ctctggttag g ttt gtc ggg cta atg gga gga tac atg tgg ata gaa agt       2617
             Phe Val Gly Leu Met Gly Gly Tyr Met Trp Ile Glu Ser
                             560                 565                 570 gaa ggc cta gag aaa ggc tgc aca gct tcg ttc atc atc agg ctt ggt        2665
Glu Gly Leu Glu Lys Gly Cys Thr Ala Ser Phe Ile Ile Arg Leu Gly
                575                 580                 585 atc tgc aac ggt cca agc agt agc agt ggt tca atg gcg cta cat ctt        2713
Ile Cys Asn Gly Pro Ser Ser Ser Ser Gly Ser Met Ala Leu His Leu
                590                 595                 600 gca gct aaa tca caa acc aga ccg tgg aac tgg tga tacttacgtt             2759
Ala Ala Lys Ser Gln Thr Arg Pro Trp Asn Trp
                605                 610 ggaaagactt gtattgaggt gagcttttt aactacacag cagcaagaga agaagaaaa        2819 tacatgaccg gacggtgtga tctaacttat tggattttgt tggatgtaat atgtaaaata     2879
aaaatcctat atacggggag aggtacctta tctgttctca ctatatttta ttgaacatta     2939
ctttagagaa tatgttttgg aattcactac taaataaacg atataaatct tcacgaaaag     2999
agcaacattt t                                                           3010

<210> SEQ ID NO 46
<211> LENGTH: 613
<212> TYPE: PRT
<213> ORGANISM: Arabidopsis thaliana

<400> SEQUENCE: 46

Met Glu Ser Cys Asp Cys Phe Glu Thr His Val Asn Gln Asp Asp Leu
1               5                   10                  15

Leu Val Lys Tyr Gln Tyr Ile Ser Asp Ala Leu Ile Ala Leu Ala Tyr
            20                  25                  30

Phe Ser Ile Pro Leu Glu Leu Ile Tyr Phe Val Gln Lys Ser Ala Phe
        35                  40                  45

Phe Pro Tyr Lys Trp Val Leu Met Gln Phe Gly Ala Phe Ile Ile Leu
    50                  55                  60

Cys Gly Ala Thr His Phe Ile Asn Leu Trp Met Phe Phe Met His Ser
65                  70                  75                  80

Lys Ala Val Ala Ile Val Met Thr Ile Ala Lys Val Ser Cys Ala Val
                85                  90                  95

Val Ser Cys Ala Thr Ala Leu Met Leu Val His Ile Ile Pro Asp Leu
            100                 105                 110

Leu Ser Val Lys Asn Arg Glu Leu Phe Leu Lys Lys Ala Asp Glu
        115                 120                 125

Leu Asp Arg Glu Met Gly Leu Ile Leu Thr Gln Glu Thr Gly Arg
    130                 135                 140

His Val Arg Met Leu Thr His Gly Ile Arg Arg Thr Leu Asp Arg His
```

```
                145                 150                 155                 160
Thr Ile Leu Arg Thr Thr Leu Val Glu Leu Gly Lys Thr Leu Cys Leu
                    165                 170                 175

Glu Glu Cys Ala Leu Trp Met Pro Ser Gln Ser Gly Leu Tyr Leu Gln
                180                 185                 190

Leu Ser His Thr Leu Ser His Lys Ile Gln Val Gly Ser Ser Val Pro
                195                 200                 205

Ile Asn Leu Pro Ile Ile Asn Glu Leu Phe Asn Ser Ala Gln Ala Met
            210                 215                 220

His Ile Pro His Ser Cys Pro Leu Ala Lys Ile Gly Pro Pro Val Gly
225                 230                 235                 240

Arg Tyr Ser Pro Pro Glu Val Val Ser Val Arg Val Pro Leu Leu His
                245                 250                 255

Leu Ser Asn Phe Gln Gly Ser Asp Trp Ser Asp Leu Ser Gly Lys Gly
                260                 265                 270

Tyr Ala Ile Met Val Leu Ile Leu Pro Thr Asp Gly Ala Arg Lys Trp
                275                 280                 285

Arg Asp His Glu Leu Glu Leu Val Glu Asn Val Ala Asp Gln Val Ala
            290                 295                 300

Val Ala Leu Ser His Ala Ala Ile Leu Glu Glu Ser Met His Ala Arg
305                 310                 315                 320

Asp Gln Leu Met Glu Gln Asn Phe Ala Leu Asp Lys Ala Arg Gln Glu
                325                 330                 335

Ala Glu Met Ala Val His Ala Arg Asn Asp Phe Leu Ala Val Met Asn
                340                 345                 350

His Glu Met Arg Thr Pro Met His Ala Ile Ile Ser Leu Ser Ser Leu
                355                 360                 365

Leu Leu Glu Thr Glu Leu Ser Pro Gln Arg Val Met Ile Glu Thr
370                 375                 380

Ile Leu Lys Ser Ser Asn Leu Val Ala Thr Leu Ile Ser Asp Val Leu
385                 390                 395                 400

Asp Leu Ser Arg Leu Glu Asp Gly Ser Leu Leu Leu Glu Asn Glu Pro
                405                 410                 415

Phe Ser Leu Gln Ala Ile Phe Glu Glu Val Ile Ser Leu Ile Lys Pro
                420                 425                 430

Ile Ala Ser Val Lys Lys Leu Ser Thr Asn Leu Ile Leu Ser Ala Asp
            435                 440                 445

Leu Pro Thr Tyr Ala Ile Gly Asp Glu Lys Arg Leu Met Gln Thr Ile
        450                 455                 460

Leu Asn Ile Met Gly Asn Ala Val Lys Phe Thr Lys Glu Gly Tyr Ile
465                 470                 475                 480

Ser Ile Ile Ala Ser Ile Met Lys Pro Glu Ser Leu Gln Glu Leu Pro
                485                 490                 495

Ser Pro Glu Phe Phe Pro Val Leu Ser Asp Ser His Phe Tyr Leu Cys
                500                 505                 510

Val Gln Val Lys Asp Thr Gly Cys Gly Ile His Thr Gln Asp Ile Pro
            515                 520                 525

Leu Leu Phe Thr Lys Phe Val Gln Pro Arg Thr Gly Thr Gln Arg Asn
        530                 535                 540

His Ser Gly Gly Gly Leu Gly Leu Ala Leu Cys Lys Arg Phe Val Gly
545                 550                 555                 560

Leu Met Gly Gly Tyr Met Trp Ile Glu Ser Glu Gly Leu Glu Lys Gly
                565                 570                 575
```

```
Cys Thr Ala Ser Phe Ile Ile Arg Leu Gly Ile Cys Asn Gly Pro Ser
            580                 585                 590

Ser Ser Ser Gly Ser Met Ala Leu His Leu Ala Ala Lys Ser Gln Thr
        595                 600                 605

Arg Pro Trp Asn Trp
    610

<210> SEQ ID NO 47
<211> LENGTH: 2314
<212> TYPE: DNA
<213> ORGANISM: Arabidopsis thaliana
<220> FEATURE:
<221> NAME/KEY: CDS
<222> LOCATION: (224)..(2065)

<400> SEQUENCE: 47
```

| | |
|---|---:|
| aaaaaaatca tcaaaaactt ttacctctca ttggtttctt ctttatcaca ctgttacgct | 60 |
| tggattctca tttcttcaag ttcataacgc tcggatcaat caggaagacg aacttgaact | 120 |
| ttctttttt catcattacc caaagctatg aggctcacac caccaatacg tccgccgtca | 180 |

```
tgaatccttc tcttccaggt caacacaagt cagagctcca aaa atg gag tca tgc     235
                                              Met Glu Ser Cys
                                                1 gat tgt ttt gag acg cat gtg aat caa gat gat ctg tta gtg aag tac     283
Asp Cys Phe Glu Thr His Val Asn Gln Asp Asp Leu Leu Val Lys Tyr
 5                  10                  15                  20 caa tac atc tca gat gcg ttg att gct ctt gca tac ttc tca atc cca     331
Gln Tyr Ile Ser Asp Ala Leu Ile Ala Leu Ala Tyr Phe Ser Ile Pro
                25                  30                  35 ctc gag ctt atc tat ttc gtg caa aag tct gct ttc ttc cct tac aaa     379
Leu Glu Leu Ile Tyr Phe Val Gln Lys Ser Ala Phe Phe Pro Tyr Lys
            40                  45                  50 tgg gtg ctt atg cag ttt gga gcc ttt atc att ctc tgt gga gct acg     427
Trp Val Leu Met Gln Phe Gly Ala Phe Ile Ile Leu Cys Gly Ala Thr
        55                  60                  65 cat ttc atc aac cta tgg atg ttc ttc atg cat tcc aaa gcc gtt gcc     475
His Phe Ile Asn Leu Trp Met Phe Phe Met His Ser Lys Ala Val Ala
    70                  75                  80 att gtc atg act att gct aaa gtc tct tgc gcg gtt gtg tcg tgt gct     523
Ile Val Met Thr Ile Ala Lys Val Ser Cys Ala Val Val Ser Cys Ala
85                  90                  95                 100 acc gcg ttg atg ttg gtt cat att att cct gat ctt ctc agt gtt aag     571
Thr Ala Leu Met Leu Val His Ile Ile Pro Asp Leu Leu Ser Val Lys
                105                 110                 115 aac agg gaa ttg ttt ctc aag aag aaa gct gat gag tta gat aga gaa     619
Asn Arg Glu Leu Phe Leu Lys Lys Lys Ala Asp Glu Leu Asp Arg Glu
            120                 125                 130 atg ggt ctt att tta aca caa gag gag act ggt agg cat gtt agg atg     667
Met Gly Leu Ile Leu Thr Gln Glu Glu Thr Gly Arg His Val Arg Met
        135                 140                 145 ctt act cat gga att aga aga act ctt gat agg cat act att tta aga     715
Leu Thr His Gly Ile Arg Arg Thr Leu Asp Arg His Thr Ile Leu Arg
    150                 155                 160 acc act ctt gtt gag ctt ggt aaa act ctt tgt ctt gag gaa tgt gcg     763
Thr Thr Leu Val Glu Leu Gly Lys Thr Leu Cys Leu Glu Glu Cys Ala
165                 170                 175                 180 ttg tgg atg cct tct caa agt ggt tta tat ttg cag ctt tct cat act     811
Leu Trp Met Pro Ser Gln Ser Gly Leu Tyr Leu Gln Leu Ser His Thr
                185                 190                 195
```

```
ttg agt cat aaa ata caa gtt gga agc agt gtg ccg ata aat ctc ccg    859
Leu Ser His Lys Ile Gln Val Gly Ser Ser Val Pro Ile Asn Leu Pro
        200                 205                 210 att att aat gaa ctc ttc aat agc gct caa gct atg cac ata cct cat    907
Ile Ile Asn Glu Leu Phe Asn Ser Ala Gln Ala Met His Ile Pro His
            215                 220                 225 tct tgt cct ttg gct aag att ggg cct ccg gtt ggg aga tat tca cct    955
Ser Cys Pro Leu Ala Lys Ile Gly Pro Pro Val Gly Arg Tyr Ser Pro
    230                 235                 240 cct gag gtt gtt tct gtc cgt gtt cct ctt tta cat ctc tct aat ttc   1003
Pro Glu Val Val Ser Val Arg Val Pro Leu Leu His Leu Ser Asn Phe
245                 250                 255                 260 caa ggc agt gac tgg tcg gat ctc tct ggc aaa ggt tac gct atc atg   1051
Gln Gly Ser Asp Trp Ser Asp Leu Ser Gly Lys Gly Tyr Ala Ile Met
                265                 270                 275 gtc ctg att ctc cca acc gat ggt gca aga aaa tgg aga gac cat gag   1099
Val Leu Ile Leu Pro Thr Asp Gly Ala Arg Lys Trp Arg Asp His Glu
            280                 285                 290 tta gag ctt gta gaa aac gtg gcg gat cag gtg gct gtg gct ctc tca   1147
Leu Glu Leu Val Glu Asn Val Ala Asp Gln Val Ala Val Ala Leu Ser
    295                 300                 305 cat gct gca att ttg gaa gaa tcc atg cac gct cgt gac cag ctt atg   1195
His Ala Ala Ile Leu Glu Glu Ser Met His Ala Arg Asp Gln Leu Met
310                 315                 320 gag cag aat ttt gct tta gac aag gct cgt caa gag gct gag atg gca   1243
Glu Gln Asn Phe Ala Leu Asp Lys Ala Arg Gln Glu Ala Glu Met Ala
325                 330                 335                 340 gta cat gct cga aat gat ttc cta gct gtt atg aac cac gag atg agg   1291
Val His Ala Arg Asn Asp Phe Leu Ala Val Met Asn His Glu Met Arg
                345                 350                 355 aca ccg atg cat gcc atc atc tct ctt tct tct ctt ctc ctt gag act   1339
Thr Pro Met His Ala Ile Ile Ser Leu Ser Ser Leu Leu Leu Glu Thr
            360                 365                 370 gag ctg tct cca gag caa aga gtt atg atc gag aca ata ctg aaa agc   1387
Glu Leu Ser Pro Glu Gln Arg Val Met Ile Glu Thr Ile Leu Lys Ser
    375                 380                 385 agc aat ctt gtg gct aca cta atc agc gac gtt ctg gat ctt tcg aga   1435
Ser Asn Leu Val Ala Thr Leu Ile Ser Asp Val Leu Asp Leu Ser Arg
390                 395                 400 ttg gaa gat ggg agc tta ctc ttg gaa aat gaa cca ttc agt cta caa   1483
Leu Glu Asp Gly Ser Leu Leu Leu Glu Asn Glu Pro Phe Ser Leu Gln
405                 410                 415                 420 gcg atc ttt gaa gag gtc atc tct ttg ata aag cca atc gca tca gtg   1531
Ala Ile Phe Glu Glu Val Ile Ser Leu Ile Lys Pro Ile Ala Ser Val
                425                 430                 435 aag aaa cta tca acg aat ctg att ctg tct gca gac tta cca act tat   1579
Lys Lys Leu Ser Thr Asn Leu Ile Leu Ser Ala Asp Leu Pro Thr Tyr
            440                 445                 450 gct att ggt gat gag aaa cgt ctg atg caa aca att ctt aac atc atg   1627
Ala Ile Gly Asp Glu Lys Arg Leu Met Gln Thr Ile Leu Asn Ile Met
    455                 460                 465 ggc aac gct gtg aaa ttt act aag gaa ggc tac atc tcc ata ata gcc   1675
Gly Asn Ala Val Lys Phe Thr Lys Glu Gly Tyr Ile Ser Ile Ile Ala
470                 475                 480 tct atc atg aaa ccc gag tcc tta caa gaa tta cca tct cca gaa ttt   1723
Ser Ile Met Lys Pro Glu Ser Leu Gln Glu Leu Pro Ser Pro Glu Phe
485                 490                 495                 500 ttt cca gtt ctc agt gac agt cac ttc tac cta tgt gtg cag gtg aag   1771
Phe Pro Val Leu Ser Asp Ser His Phe Tyr Leu Cys Val Gln Val Lys
                505                 510                 515
```

-continued

```
gac aca ggg tgt gga att cac aca caa gac att cct ttg ctc ttt acc        1819
Asp Thr Gly Cys Gly Ile His Thr Gln Asp Ile Pro Leu Leu Phe Thr
            520                 525                 530 aaa ttt gta cag cct cgg acc gga act cag agg aac cat tcc ggt gga        1867
Lys Phe Val Gln Pro Arg Thr Gly Thr Gln Arg Asn His Ser Gly Gly
        535                 540                 545 gga ctc ggg cta gct ctc tgt aaa cgg ttt gtc ggg cta atg gga gga        1915
Gly Leu Gly Leu Ala Leu Cys Lys Arg Phe Val Gly Leu Met Gly Gly
    550                 555                 560 tac atg tgg ata gaa agt gaa ggc cta gag aaa ggc tgc aca gct tcg        1963
Tyr Met Trp Ile Glu Ser Glu Gly Leu Glu Lys Gly Cys Thr Ala Ser
565                 570                 575                 580 ttc atc atc agg ctt ggt atc tgc aac ggt cca agc agt agc agt ggt        2011
Phe Ile Ile Arg Leu Gly Ile Cys Asn Gly Pro Ser Ser Ser Ser Gly
                585                 590                 595 tca atg gcg cta cat ctt gca gct aaa tca caa acc aga ccg tgg aac        2059
Ser Met Ala Leu His Leu Ala Ala Lys Ser Gln Thr Arg Pro Trp Asn
            600                 605                 610 tgg tga tacttacgtt ggaaagactt gtattgaggt gagactttt aactacacag         2115
Trp cagcaagaga aagaagaaaa tacatgaccg gacggtgtga tctaacttat tggattttgt    2175
tggatgtaat atgtaaaata aaaatcctat atacggggag aggtaccta tctgttctca     2235 ctatatttta ttgaacatta ctttagagaa tatgttttgg aattcactac taaataaacg    2295
atataaatct tcacgaaaa                                                   2314

<210> SEQ ID NO 48
<211> LENGTH: 613
<212> TYPE: PRT
<213> ORGANISM: Arabidopsis thaliana

<400> SEQUENCE: 48

Met Glu Ser Cys Asp Cys Phe Glu Thr His Val Asn Gln Asp Asp Leu
  1               5                  10                  15

Leu Val Lys Tyr Gln Tyr Ile Ser Asp Ala Leu Ile Ala Leu Ala Tyr
             20                  25                  30

Phe Ser Ile Pro Leu Glu Leu Ile Tyr Phe Val Gln Lys Ser Ala Phe
         35                  40                  45

Phe Pro Tyr Lys Trp Val Leu Met Gln Phe Gly Ala Phe Ile Ile Leu
     50                  55                  60

Cys Gly Ala Thr His Phe Ile Asn Leu Trp Met Phe Phe Met His Ser
 65                  70                  75                  80

Lys Ala Val Ala Ile Val Met Thr Ile Ala Lys Val Ser Cys Ala Val
                 85                  90                  95

Val Ser Cys Ala Thr Ala Leu Met Leu Val His Ile Ile Pro Asp Leu
            100                 105                 110

Leu Ser Val Lys Asn Arg Glu Leu Phe Leu Lys Lys Ala Asp Glu
        115                 120                 125

Leu Asp Arg Glu Met Gly Leu Ile Leu Thr Gln Glu Thr Gly Arg
    130                 135                 140

His Val Arg Met Leu Thr His Gly Ile Arg Arg Thr Leu Asp Arg His
145                 150                 155                 160

Thr Ile Leu Arg Thr Thr Leu Val Glu Leu Gly Lys Thr Leu Cys Leu
                165                 170                 175

Glu Glu Cys Ala Leu Trp Met Pro Ser Gln Ser Gly Leu Tyr Leu Gln
            180                 185                 190
```

```
-continued

Leu Ser His Thr Leu Ser His Lys Ile Gln Val Gly Ser Ser Val Pro
            195                 200                 205
Ile Asn Leu Pro Ile Ile Asn Glu Leu Phe Asn Ser Ala Gln Ala Met
            210                 215                 220
His Ile Pro His Ser Cys Pro Leu Ala Lys Ile Gly Pro Pro Val Gly
225                 230                 235                 240
Arg Tyr Ser Pro Pro Glu Val Val Ser Val Arg Val Pro Leu Leu His
                245                 250                 255
Leu Ser Asn Phe Gln Gly Ser Asp Trp Ser Asp Leu Ser Gly Lys Gly
                260                 265                 270
Tyr Ala Ile Met Val Leu Ile Leu Pro Thr Asp Gly Ala Arg Lys Trp
            275                 280                 285
Arg Asp His Glu Leu Glu Leu Val Glu Asn Val Ala Asp Gln Val Ala
290                 295                 300
Val Ala Leu Ser His Ala Ala Ile Leu Glu Glu Ser Met His Ala Arg
305                 310                 315                 320
Asp Gln Leu Met Glu Gln Asn Phe Ala Leu Asp Lys Ala Arg Gln Glu
            325                 330                 335
Ala Glu Met Ala Val His Ala Arg Asn Asp Phe Leu Ala Val Met Asn
            340                 345                 350
His Glu Met Arg Thr Pro Met His Ala Ile Ile Ser Leu Ser Ser Leu
            355                 360                 365
Leu Leu Glu Thr Glu Leu Ser Pro Glu Gln Arg Val Met Ile Glu Thr
            370                 375                 380
Ile Leu Lys Ser Ser Asn Leu Val Ala Thr Leu Ile Ser Asp Val Leu
385                 390                 395                 400
Asp Leu Ser Arg Leu Glu Asp Gly Ser Leu Leu Leu Glu Asn Glu Pro
                405                 410                 415
Phe Ser Leu Gln Ala Ile Phe Glu Glu Val Ile Ser Leu Ile Lys Pro
                420                 425                 430
Ile Ala Ser Val Lys Lys Leu Ser Thr Asn Leu Ile Leu Ser Ala Asp
            435                 440                 445
Leu Pro Thr Tyr Ala Ile Gly Asp Glu Lys Arg Leu Met Gln Thr Ile
450                 455                 460
Leu Asn Ile Met Gly Asn Ala Val Lys Phe Thr Lys Glu Gly Tyr Ile
465                 470                 475                 480
Ser Ile Ile Ala Ser Ile Met Lys Pro Glu Ser Leu Gln Glu Leu Pro
            485                 490                 495
Ser Pro Glu Phe Phe Pro Val Leu Ser Asp Ser His Phe Tyr Leu Cys
            500                 505                 510
Val Gln Val Lys Asp Thr Gly Cys Gly Ile His Thr Gln Asp Ile Pro
            515                 520                 525
Leu Leu Phe Thr Lys Phe Val Gln Pro Arg Thr Gly Thr Gln Arg Asn
            530                 535                 540
His Ser Gly Gly Gly Leu Gly Leu Ala Leu Cys Lys Arg Phe Val Gly
545                 550                 555                 560
Leu Met Gly Gly Tyr Met Trp Ile Glu Ser Glu Gly Leu Glu Lys Gly
                565                 570                 575
Cys Thr Ala Ser Phe Ile Ile Arg Leu Gly Ile Cys Asn Gly Pro Ser
                580                 585                 590
Ser Ser Ser Gly Ser Met Ala Leu His Leu Ala Ala Lys Ser Gln Thr
            595                 600                 605
```

-continued

```
Arg Pro Trp Asn Trp
    610

<210> SEQ ID NO 49
<211> LENGTH: 2405
<212> TYPE: DNA
<213> ORGANISM: Lycopersicon esculentum
<220> FEATURE:
<221> NAME/KEY: CDS
<222> LOCATION: (288)..(2195)

<400> SEQUENCE: 49 ttttttttt  gtcaaaagct cgatgtaaaa atccgatggc cacaagcaaa acgacaggtt      60
ccaacttcac ggagattgtg aaatggagt agtagttcag tgaagtagta gatactgaga     120
tcgcattctc cggcgtcgtt tttcacatcg aaatagtcgt gtaaaaaaat gaaaaaattg     180
ctgcgagaca ggtatgtgtc gcagcaggaa atagcatctt aaaggaagga aggaaggaaa     240
ctcgaaagtt actaaaaatt tttgattctt tgggacgaaa cgagata atg gaa tcc       296
                                                      Met Glu Ser
                                                       1
```

| | | | | | | | | | | | | | | | | |
|---|---|---|---|---|---|---|---|---|---|---|---|---|---|---|---|---|
| tgt | gat | tgc | att | gag | gct | tta | ctg | cca | act | ggt | gac | ctg | ctg | gtt | aaa | 344 |
| Cys | Asp | Cys | Ile | Glu | Ala | Leu | Leu | Pro | Thr | Gly | Asp | Leu | Leu | Val | Lys | |
| | 5 | | | | | 10 | | | | | 15 | | | | | |

```
tac caa tac ctc tca gat ttc ttc att gct gta gcc tac ttt tcc att      392
Tyr Gln Tyr Leu Ser Asp Phe Phe Ile Ala Val Ala Tyr Phe Ser Ile
 20                  25                  30                  35 ctg ttg gag ctt att tat ttt gtc cac aaa tct gca tgc ttc cca tac      440
Leu Leu Glu Leu Ile Tyr Phe Val His Lys Ser Ala Cys Phe Pro Tyr
                 40                  45                  50 aga tgg gtc ctc atg caa ttt ggt gct ttt att gtg ctc tgt gga gca      488
Arg Trp Val Leu Met Gln Phe Gly Ala Phe Ile Val Leu Cys Gly Ala
     55                  60                  65 aca cac ttt att agc ttg tgg acc ttc ttt atg cac tct aag acg gtc      536
Thr His Phe Ile Ser Leu Trp Thr Phe Phe Met His Ser Lys Thr Val
 70                  75                  80 gct gtg gtt atg acc ata tca aaa atg ttg aca gct gcc gtg tcc tgt      584
Ala Val Val Met Thr Ile Ser Lys Met Leu Thr Ala Ala Val Ser Cys
     85                  90                  95 atc aca gct ttg atg ctt gtt cac att att cct gat ttg cta agt gtt      632
Ile Thr Ala Leu Met Leu Val His Ile Ile Pro Asp Leu Leu Ser Val
100                 105                 110                 115 aaa acg cga gag ttg ttc ttg aaa act cga gct gaa gag ctt gac aag      680
Lys Thr Arg Glu Leu Phe Leu Lys Thr Arg Ala Glu Glu Leu Asp Lys
                 120                 125                 130 gaa atg ggc cta ata ata aga caa gaa gaa act ggc aga cat gtc agg      728
Glu Met Gly Leu Ile Ile Arg Gln Glu Glu Thr Gly Arg His Val Arg
     135                 140                 145 atg ctg act cat gag ata aga agc aca ctc gac aga cac aca atc ttg      776
Met Leu Thr His Glu Ile Arg Ser Thr Leu Asp Arg His Thr Ile Leu
150                 155                 160 aag act act ctt gtg gag cta ggt agg acc tta gac ctg gca gaa tgt      824
Lys Thr Thr Leu Val Glu Leu Gly Arg Thr Leu Asp Leu Ala Glu Cys
                 165                 170                 175 gct ttg tgg atg cca tgc caa gga ggc ctg act ttg caa ctt tcc cat      872
Ala Leu Trp Met Pro Cys Gln Gly Gly Leu Thr Leu Gln Leu Ser His
180                 185                 190                 195 aat tta aac aat cta ata cct ctg gga tct act gtg cca att aat ctt      920
Asn Leu Asn Asn Leu Ile Pro Leu Gly Ser Thr Val Pro Ile Asn Leu
                 200                 205                 210 cct att atc aat gaa att ttt agt agc cct gaa gca ata caa att cca      968
```

```
                Pro Ile Ile Asn Glu Ile Phe Ser Ser Pro Glu Ala Ile Gln Ile Pro
                            215                 220                 225 cat aca aat cct ttg gca agg atg agg aat act gtt ggt aga tat att         1016
His Thr Asn Pro Leu Ala Arg Met Arg Asn Thr Val Gly Arg Tyr Ile
            230                 235                 240 cca cca gaa gta gtt gct gtt cgt gta ccg ctt tta cac ctc tca aat         1064
Pro Pro Glu Val Val Ala Val Arg Val Pro Leu Leu His Leu Ser Asn
        245                 250                 255 ttt act aat gac tgg gct gaa ctg tct act aga agt tat gcg gtt atg         1112
Phe Thr Asn Asp Trp Ala Glu Leu Ser Thr Arg Ser Tyr Ala Val Met
260                 265                 270                 275 gtt ctg gtt ctc ccg atg aat ggc tta aga aag tgg cgt gaa cat gag         1160
Val Leu Val Leu Pro Met Asn Gly Leu Arg Lys Trp Arg Glu His Glu
                280                 285                 290 tta gaa ctt gtg caa gtt gtc gca gat cag gtt gct gtc gct ctt tca         1208
Leu Glu Leu Val Gln Val Val Ala Asp Gln Val Ala Val Ala Leu Ser
            295                 300                 305 cat gct gca att tta gaa gat tcc atg cga gcc cat gat cag ctc atg         1256
His Ala Ala Ile Leu Glu Asp Ser Met Arg Ala His Asp Gln Leu Met
        310                 315                 320 gaa cag aat att gct ttg gat gta gct cga caa gaa gca gag atg gcc         1304
Glu Gln Asn Ile Ala Leu Asp Val Ala Arg Gln Glu Ala Glu Met Ala
325                 330                 335 atc cgt gca cgt aac gac ttc ctt gct gtg atg aac cat gaa atg aga         1352
Ile Arg Ala Arg Asn Asp Phe Leu Ala Val Met Asn His Glu Met Arg
340                 345                 350                 355 acg ccc atg cat gca gtt att gct ctg tgc tct ctg ctt tta gaa aca         1400
Thr Pro Met His Ala Val Ile Ala Leu Cys Ser Leu Leu Leu Glu Thr
                360                 365                 370 gac tta act cca gag cag aga gtt atg att gag acc ata ttg aag agc         1448
Asp Leu Thr Pro Glu Gln Arg Val Met Ile Glu Thr Ile Leu Lys Ser
            375                 380                 385 agc aat ctt ctt gca aca ctg ata aat gat gtt cta gat ctt tct aga         1496
Ser Asn Leu Leu Ala Thr Leu Ile Asn Asp Val Leu Asp Leu Ser Arg
        390                 395                 400 ctt gaa gat ggt att ctt gaa cta gaa aac gga aca ttc aat ctt cat         1544
Leu Glu Asp Gly Ile Leu Glu Leu Glu Asn Gly Thr Phe Asn Leu His
405                 410                 415 ggc atc tta aga gag gcc gtt aat ttg ata aag cca att gca tct ttg         1592
Gly Ile Leu Arg Glu Ala Val Asn Leu Ile Lys Pro Ile Ala Ser Leu
420                 425                 430                 435 aag aaa tta tct ata act ctt gct ttg gct ctg gat tta cct att ctt         1640
Lys Lys Leu Ser Ile Thr Leu Ala Leu Ala Leu Asp Leu Pro Ile Leu
                440                 445                 450 gct gtg ggt gat gca aaa cgt ctt atc caa act ctc tta aac gtg gtg         1688
Ala Val Gly Asp Ala Lys Arg Leu Ile Gln Thr Leu Leu Asn Val Val
            455                 460                 465 gga aat gct gtg aag ttc act aaa gaa gga cat att tca att gag gct         1736
Gly Asn Ala Val Lys Phe Thr Lys Glu Gly His Ile Ser Ile Glu Ala
        470                 475                 480 tca gtt gcc aaa cca gag tat gcg aga gat tgt cat cct cct gaa atg         1784
Ser Val Ala Lys Pro Glu Tyr Ala Arg Asp Cys His Pro Pro Glu Met
485                 490                 495 ttc cct atg cca agt gat ggc cag ttt tat ttg cgt gtc cag gtt aga         1832
Phe Pro Met Pro Ser Asp Gly Gln Phe Tyr Leu Arg Val Gln Val Arg
500                 505                 510                 515 gat act ggg tgt gga att agc cca caa gat ata cca cta gta ttc acc         1880
Asp Thr Gly Cys Gly Ile Ser Pro Gln Asp Ile Pro Leu Val Phe Thr
                520                 525                 530
```

-continued

```
aaa ttt gca gag tca cgg cct acg tca aat cga agt act gga ggg gaa    1928
Lys Phe Ala Glu Ser Arg Pro Thr Ser Asn Arg Ser Thr Gly Gly Glu
        535                 540                 545 ggt cta ggg ctt gcc att tgg aga cga ttt att caa ctt atg aaa ggt    1976
Gly Leu Gly Leu Ala Ile Trp Arg Arg Phe Ile Gln Leu Met Lys Gly
    550                 555                 560 aac att tgg att gag agt gag ggc cct gga aag gga acc act gtc acg    2024
Asn Ile Trp Ile Glu Ser Glu Gly Pro Gly Lys Gly Thr Thr Val Thr
565                 570                 575 ttt gta gtg aaa ctc gga atc tgt cac cat cca aat gca tta cct ctg    2072
Phe Val Val Lys Leu Gly Ile Cys His His Pro Asn Ala Leu Pro Leu
580                 585                 590                 595 cta cct atg cct ccc aga ggc aga ttg aac aaa ggt agc gat gat ctc    2120
Leu Pro Met Pro Pro Arg Gly Arg Leu Asn Lys Gly Ser Asp Asp Leu
            600                 605                 610 ttc agg tat aga cag ttc cgt gga gat gat ggt ggg atg tct gtg aat    2168
Phe Arg Tyr Arg Gln Phe Arg Gly Asp Asp Gly Gly Met Ser Val Asn
        615                 620                 625 gct caa cgc tat caa aga agt atg taa atgacaaaag gacattggtg          2215
Ala Gln Arg Tyr Gln Arg Ser Met
    630                 635 tgacaaagaa cattaaatca tgactagtga atttgagatt tcttcactgt tctgtacact  2275
ccaaatggca cagtttgtct tgtaactaac ctaattcaat gctcgtaaag tgagtactgg  2335
agtatcttga aaatgtaact atcgaattta tacatcgagc ttttgacaaa aaaaaaaaa   2395 aaaaaaaaaa                                                        2405

<210> SEQ ID NO 50
<211> LENGTH: 635
<212> TYPE: PRT
<213> ORGANISM: Lycopersicon esculentum

<400> SEQUENCE: 50

Met Glu Ser Cys Asp Cys Ile Glu Ala Leu Leu Pro Thr Gly Asp Leu
  1               5                  10                  15

Leu Val Lys Tyr Gln Tyr Leu Ser Asp Phe Ile Ala Val Ala Tyr
             20                  25                  30

Phe Ser Ile Leu Leu Glu Leu Ile Tyr Phe Val His Lys Ser Ala Cys
         35                  40                  45

Phe Pro Tyr Arg Trp Val Leu Met Gln Phe Gly Ala Phe Ile Val Leu
     50                  55                  60

Cys Gly Ala Thr His Phe Ile Ser Leu Trp Thr Phe Phe Met His Ser
 65                  70                  75                  80

Lys Thr Val Ala Val Met Thr Ile Ser Lys Met Leu Thr Ala Ala
                 85                  90                  95

Val Ser Cys Ile Thr Ala Leu Met Leu Val His Ile Ile Pro Asp Leu
            100                 105                 110

Leu Ser Val Lys Thr Arg Glu Leu Phe Leu Lys Thr Arg Ala Glu Glu
        115                 120                 125

Leu Asp Lys Glu Met Gly Leu Ile Ile Arg Gln Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Asp Leu
                165                 170                 175

Ala Glu Cys Ala Leu Trp Met Pro Cys Gln Gly Gly Leu Thr Leu Gln
            180                 185                 190
```

```
Leu Ser His Asn Leu Asn Asn Leu Ile Pro Leu Gly Ser Thr Val Pro
        195                 200                 205

Ile Asn Leu Pro Ile Ile Asn Glu Ile Phe Ser Ser Pro Glu Ala Ile
        210                 215                 220

Gln Ile Pro His Thr Asn Pro Leu Ala Arg Met Arg Asn Thr Val Gly
225                 230                 235                 240

Arg Tyr Ile Pro Pro Glu Val Val Ala Val Arg Val Pro Leu Leu His
                245                 250                 255

Leu Ser Asn Phe Thr Asn Asp Trp Ala Glu Leu Ser Thr Arg Ser Tyr
                260                 265                 270

Ala Val Met Val Leu Val Leu Pro Met Asn Gly Leu Arg Lys Trp Arg
        275                 280                 285

Glu His Glu Leu Glu Leu Val Gln Val Ala Asp Gln Val Ala Val
290                 295                 300

Ala Leu Ser His Ala Ala Ile Leu Glu Asp Ser Met Arg Ala His Asp
305                 310                 315                 320

Gln Leu Met Glu Gln Asn Ile Ala Leu Asp Val Ala Arg Gln Glu Ala
                325                 330                 335

Glu Met Ala Ile Arg Ala Arg Asn Asp Phe Leu Ala Val Met Asn His
                340                 345                 350

Glu Met Arg Thr Pro Met His Ala Val Ile Ala Leu Cys Ser Leu Leu
                355                 360                 365

Leu Glu Thr Asp Leu Thr Pro Glu Gln Arg Val Met Ile Glu Thr Ile
        370                 375                 380

Leu Lys Ser Ser Asn Leu Leu Ala Thr Leu Ile Asn Asp Val Leu Asp
385                 390                 395                 400

Leu Ser Arg Leu Glu Asp Gly Ile Leu Glu Leu Glu Asn Gly Thr Phe
                405                 410                 415

Asn Leu His Gly Ile Leu Arg Glu Ala Val Asn Leu Ile Lys Pro Ile
                420                 425                 430

Ala Ser Leu Lys Lys Leu Ser Ile Thr Leu Ala Leu Ala Leu Asp Leu
        435                 440                 445

Pro Ile Leu Ala Val Gly Asp Ala Lys Arg Leu Ile Gln Thr Leu Leu
450                 455                 460

Asn Val Val Gly Asn Ala Val Lys Phe Thr Lys Glu Gly His Ile Ser
465                 470                 475                 480

Ile Glu Ala Ser Val Ala Lys Pro Glu Tyr Ala Arg Asp Cys His Pro
                485                 490                 495

Pro Glu Met Phe Pro Met Pro Ser Asp Gly Gln Phe Tyr Leu Arg Val
                500                 505                 510

Gln Val Arg Asp Thr Gly Cys Gly Ile Ser Pro Gln Asp Ile Pro Leu
                515                 520                 525

Val Phe Thr Lys Phe Ala Glu Ser Arg Pro Thr Ser Asn Arg Ser Thr
        530                 535                 540

Gly Gly Glu Gly Leu Gly Leu Ala Ile Trp Arg Arg Phe Ile Gln Leu
545                 550                 555                 560

Met Lys Gly Asn Ile Trp Ile Glu Ser Glu Gly Pro Gly Lys Gly Thr
                565                 570                 575

Thr Val Thr Phe Val Val Lys Leu Gly Ile Cys His His Pro Asn Ala
                580                 585                 590

Leu Pro Leu Leu Pro Met Pro Arg Gly Arg Leu Asn Lys Gly Ser
        595                 600                 605
```

```
Asp Asp Leu Phe Arg Tyr Arg Gln Phe Arg Gly Asp Asp Gly Gly Met
    610                 615                 620
Ser Val Asn Ala Gln Arg Tyr Gln Arg Ser Met
625             630             635

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: synthetic.

<400> SEQUENCE: 51
ataataataa                                                              10

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: synthetic.

<400> SEQUENCE: 52
ggagcctttt tcattattat c                                                 21

<210> SEQ ID NO 53
<211> LENGTH: 32
<212> TYPE: DNA
<213> ORGANISM: Arabidopsis thaliana

<400> SEQUENCE: 53
cccggatcca tagtgtaaaa aattcataat gg                                     32

<210> SEQ ID NO 54
<211> LENGTH: 32
<212> TYPE: DNA
<213> ORGANISM: Arabidopsis thaliana

<400> SEQUENCE: 54
ccggatccgt tgaagacttc catcttctaa cc                                     32

<210> SEQ ID NO 55
<211> LENGTH: 30
<212> TYPE: DNA
<213> ORGANISM: Lycopersicon esculentum

<400> SEQUENCE: 55
ccggatccat ggaatcctgt gattgcattg                                        30

<210> SEQ ID NO 56
<211> LENGTH: 22
<212> TYPE: DNA
<213> ORGANISM: Lycopersicon esculentum

<400> SEQUENCE: 56
gataatagga agattaattg gc                                                22
```

PLANTS HAVING MODIFIED RESPONSE TO ETHYLENE BY TRANSFORMATION WITH AN ETR NUCLEIC ACID

This is a continuation of application Ser. No. 08/263,480 filed Jun. 28, 1994, now abandoned which is a continuation-in-part of application Ser. No. 08/086,555 filed Jul. 1, 1993, now abandoned.

The U.S. Government has certain rights in this invention pursuant to Department of Energy Contract No. DE-FG03-88ER13873.

TECHNICAL FIELD OF THE INVENTION

The invention generally relates to modified ETR nucleic acid and plants transformed with such nucleic acid which have a phenotype characterized by a modification in the normal response to ethylene.

BACKGROUND OF THE INVENTION

Ethylene has been recognized as a plant hormone since the turn of the century when its effect on pea seedling development was first described. Neljubow (1901), *Pflanzen Beih. Bot. Zentralb.* 10:128–139. Since then, numerous reports have appeared which demonstrate that ethylene is an endogenous regulator of growth and development in higher plants. For example, ethylene has been implicated in seed dormancy, seedling growth, flower initiation, leaf abscission, senescence and fruit ripening. Ethylene is a plant hormone whose biosynthesis is induced by environmental stress such as oxygen deficiency, wounding, pathogen invasion and flooding.

Recently, genes encoding some of the enzymes involved in ethylene biosynthesis have been cloned. Sato, et al. (1989) *Proc. Natl. Acad. Sci. U.S.A.* 86:6621–6625; Nakajima, et al. (1990) *Plant Cell Phys. Physiol.* 29:989–996; Van Der Straeten, et al. (1990) *Proc. Natl. Acad. Sci U.S.A.* 87:4859–4963; Hamilton, et al. (1991) *Proc. Natl. Acad. Sci. U.S.A.* 88:7434–7437; and Spanu, et al. (1991) *EMBO J.* 10:2007–2013. The pathway for ethylene biosynthesis is shown in FIG. 1. As can be seen the amino acid methionine is converted to S-adenosyl-methionine (SAM) by SAM synthetase which in turn is converted to 1-aminocyclopropane-1-carboxylic acid (ACC) by ACC synthase. Adams, et al. (1979) *Proc. Natl. Acad. Sci. U.S.A.* 76:170–174. The ACC is then converted to ethylene by way of the enzyme ACC oxidase. Yang, et al. (1984) *Annu. Rev. Plant. Physiol.* 35:155–189.

A number of approaches have been taken in an attempt to control ethylene biosynthesis to thereby control fruit ripening. Oeller, et al. (1991) *Science* 254:437–439 report that expression of an antisense RNA to ACC synthase inhibits fruit ripening in tomato plants. Hamilton, et al. (1990) *Nature* 346:284–287 report the use of an antisense TOM13 (ACC oxidase) gene in transgenic plants. Picton et al. (1993) *Plant Journal* 3:469–481, report altered fruit ripening and leaf senesence in tomatoes expressing an antisense ethylene-forming enzyme.

In a second approach, ethylene biosynthesis was reportedly modulated by expressing an ACC deaminase in plant tissue to lower the level of ACC available for conversion to ethylene. See PCT publication No. WO92/12249 published Jul. 23, 1992, and Klee et al. (1991) *Plant Cell* 3:1187–1193.

While a substantial amount of information has been gathered regarding the biosynthesis of ethylene, very little is known about how ethylene controls plant development. Although several reports indicate that a high affinity binding site for ethylene is present in plant tissues, such receptors have not been identified. Jerie, et al. (1979) *Planta* 144:503; Sisler (1979) *Plant Physiol.* 64:538; Sisler, et al. (1990) *Plant Growth Reg.* 9:157–164, and Sisler (1990) "Ethylene-Binding Component in Plants", *The Plant Hormone Ethylene*, A. K. Mattoo and J. C. Suttle, eds. (Boston) C.R.C. Press, Inc., pp. 81–90. In Arabidopsis, several categories of mutants have been reported. In the first two categories, mutants were reported which produce excess ethylene or reduced ethylene as compared to the wild-type. Guzman, et al. (1990) *The Plant Cell* 2:513–523. In a third category, mutants failed to respond to ethylene. Id.; Bleecker, et al. (1988) *Science* 241:1086–1089, Harpham, et al. (1991) *Ann. of Botany* 68:55–61. The observed insensitivity to ethylene was described as being either a dominant or recessive mutation. Id.

Based upon the foregoing, it is clear that the genetic basis and molecular mechanism of ethylene interaction with plants has not been clearly delineated. Given the wide range of functions regulated by ethylene and the previous attempts to control ethylene function by regulating its synthesis, it would be desirable to have an alternate approach to modulate growth and development in various plant tissues such as fruits, vegetables and flowers by altering the interaction of ethylene with plant tissue.

Accordingly, it is an object of the invention to provide isolated nucleic acids comprising an ethylene response (ETR) nucleic acid.

In addition, it is an object to provide modifications to such ETR nucleic acids to substitute, insert and/or delete one or more nucleotides so as to substitute, insert and/or delete one or more amino acid residues in the protein encoded by the ETR nucleic acid.

Still further, it is an object to provide plant cells transformed with one or more modified ETR nucleic acids. Such transformed plant cells can be used to produce transformed plants wherein the phenotype vis-a-vis the response of one or more tissues of the plant to ethylene is modulated.

SUMMARY OF THE INVENTION

In accordance with the foregoing objects, the invention includes transformed plants having at least one cell transformed with a modified ETR nucleic acid. Such plants have a phenotype characterized by a decrease in the response of at least one transformed plant cell to ethylene as compared to a plant not containing the transformed plant cell.

The invention also includes vectors capable of transforming a plant cell to alter the response to ethylene. In one embodiment, the vector comprises a modified ETR nucleic acid which causes a decrease in cellular response to ethylene. Tissue and/or temporal specificity for expression of the modified ETR nucleic acid is controlled by selecting appropriate expression regulation sequences to target the location and/or time of expression of the transformed nucleic acid.

The invention also includes methods for producing plants having a phenotype characterized by a decrease in the response of at least one transformed plant cell to ethylene as compared to a wild-type plant not containing such a transformed cell. The method comprises transforming at least one plant cell with a modified ETR nucleic acid, regenerating plants from one or more of the transformed plant cells and selecting at least one plant having the desired phenotype.

BRIEF DESCRIPTION OF THE DRAWINGS

FIGS. 2A–2C depict the genomic nucleic acid sequence (SEQ ID NO:1) for the ETR gene from *Arabidopsis thaliana*.

FIGS. 3A–3D depict the cDNA nucleic acid (SEQ ID NO:2) and deduced amino acid sequence (SEQ ID NO:3) for the ETR gene from *Arabidopsis thaliana*.

FIGS. 4A, 4B, 4C and 4D depict the cDNA nucleic acid (SEQ ID NO:8) and deduced amino acid sequence (SEQ ID NO:9) of the etr1-3 mutation of the ETR gene from *Arabidopsis thaliana* which confers ethylene insensitivity. The sequences depicted in FIG. 4 differ from the wild-type sequence set forth in FIG. 3 by the substitution of alanine-31 with valine.

FIGS. 5A, 5B, 5C and 5D depict the cDNA nucleic acid (SEQ ID NO:10) and deduced amino acid sequence (SEQ ID NO:11) of the etr1-4 mutation of the ETR gene from *Arabidopsis thaliana* which confers ethylene insensitivity. The sequences depicted in FIG. 5 differ from the wild-type sequence set forth in FIG. 3 by the substitution of isoleucine-62 with phenylalanine.

FIGS. 6A, 6B, 6C and 6D depict the cDNA nucleic acid (SEQ ID NO:4) and deduced amino acid sequence (SEQ ID NO:5) of the etr1-1 mutation of the ETR gene from *Arabidopsis thaliana* which confers ethylene insensitivity. The sequences depicted in FIG. 6 differ from the wild-type sequence set forth in FIG. 3 by the substitution of cysteine-65 with tyrosine.

FIGS. 7A, 7B, 7C and 7D depict the cDNA nucleic acid (SEQ ID NO:6) and deduced amino acid sequence (SEQ ID NO:6) of the etr1-2 mutation of the ETR gene from *Arabidopsis thaliana* which confers ethylene insensitivity. The sequences depicted in FIG. 7 differ from the wild-type sequence set forth in FIG. 3 by the substitution of alanine-102 with threonine.

FIGS. 9A–9B depict the amino acid sequence alignments of the predicted ETR1 protein and the conserved domains of several bacterial histidine kinases and response regulators. Amino acids are shown in boldface type at positions where there are at least two identities with ETR1. In FIG. 9A, the deduced ETR1 amino acid sequence (SEQ ID NOs:12 and 27) (residues 326 to 562) aligned with the histidine kinase domains of *E. coli* BarA (SEQ ID NOs:13 and 28), *P. syringae* LemA (SEQ ID NOs:14 and 29) and *X. campestris* RpfC(SEQ ID NOs:15 and 30). Boxes surround the five conserved motifs characteristic of the bacterial histidine kinase domain as compiled by Parkinson and Kofoid (Parkinson et al. (1992) *Annu. Rev. Genet.* 26:71). The conserved histidine residue that is the supposed site of autophosphorylation is indicated by an asterisk. Numbers and positions of amino acids not shown are given in parentheses. In FIG. 9B, the deduced ETR1 amino acid sequence (residues 610 to 729) (SEQ ID NOs:15 and 31) are aligned with the response regulator domains of *B. parapertussis* BvgS (SEQ ID NOs:17 and 32), *P. syringae* LemA (SEQ ID NOs:19 and 34) and *E. coli* RscC (SEQ ID NOs:18 and 33). Amino acids are shown in boldface type where there are at least two identities with ETR1. Boxes surround the four highly conserved residues in bacterial response regulators. The conserved aspartate residue that is the site of phosphorylation is indicated by an asterisk. Numbers and positions of amino acids not shown are given in parentheses. For alignment purposes, a gap (_) was introduced in the ETR1 sequence.

FIGS. 10A and 10B depict specific DNA sequences for ETR nucleic acids from tomato and *Arabidopsis thaliana*. FIG. 10A compares the DNA sequence encoding amino acid residues 1 through 123 (SEQ ID NOs:20 and 21). FIG. 10B compares the ETR nucleic acid sequence encoding amino acids 306 through 403 (SEQ ID NOs:22 and 23). The vertical lines in each figure identify homologous nucleotides.

FIGS. 11A–11B compare partial amino acid sequences (using single letter designation) for an ETR protein from tomato and *Arabidopsis thaliana*. FIG. 11A compares the amino acid sequence for the ETR protein for amino acids 1 through 123 (SEQ ID NOs:24 and 25). FIG. 11B compares the amino acid sequence for the ETR protein for residues 306 through 403 (SEQ ID NOs:26 and 27). The vertical lines indicate exact sequence homology. Two vertical dots indicate that the amino acid residues are functionally conserved. One dot indicates weak functional conservation as between amino acid residues.

FIGS. 12A–12D depict the genomic nucleic acid sequence (SEQ ID NO:45) and deduced amino acid sequence (SEQ ID NO:46) for the QITR ETR gene from *Arabidopsis thaliana*.

FIGS. 13A–13C depict the cDNA nucleic acid sequence and deduced protein sequence for the QITR ETR gene from *Arabidopsis thaliana*.

FIGS. 14A–14F depict the genomic nucelic acid sequence (SEQ ID NO:41) and deduced amino acid sequence (SEQ ID NO:42) for the Q8 ETR gene from *Arabidopsis thaliana*.

FIGS. 15A–15D depict the cDNA nucleic acid sequence (SEQ ID NO:43) and deduced amino acid sequence (SEQ ID NO:44) for the Q8 ETR gene from *Arabidopsis thaliana*.

FIGS. 16A–16C depict the nucleic acid sequence (SEQ ID NO:35) and deduced amino acid sequence (SEQ ID NO:36) for the TETR nucleic acid from tomato.

FIG. 17 is a comparison of the amino terminal portions of the TETR and ETR1 proteins from tomato and Arabidopsis respectively. The top line is the TETR sequence and extends through amino acid residue 315. The lower line represents the ETR1 protein sequence and extends through amino acid residue 316. The vertical lines and single and double vertical dots have the same meaning as set forth in the description of FIGS. 11A and 11B. The percent identity between these sequence portions is 73.33%. The percent similarity is 84.76%.

FIGS. 18A–18E depict the nucleic acid (SEQ ID NO:37) and deduced amino acid sequence (SEQ ID NO:38) for the TGETR1 ETR nucleic acid from tomato.

FIG. 19 depicts the nucleic acid (SEQ ID NO:39) and deduced amino acid sequence (SEQ ID NO:40) for a partial sequence of the TGETR2 ETR nucleic acid from tomato.

FIG. 20 is a comparison of the amino terminal portions for the TGETR1 and ETR1 proteins from tomato and Arabidopsis respectively. The top line is the TGETR1 sequence through amino acid residue 316. The bottom line represents the ETR1 protein sequence through amino acid residue 316. The identity as between these two sequences is 91.75%. The percent similarity is 95.87%. The vertical lines and single and double dots have the same meaning as for FIGS. 11A and 11B.

FIG. 21 is a comparison of an amino terminal portion of the TGETR2 protein with the corresponding ETR1 sequence. The top line is the TGETR2 sequence from amino acid residue 11 through amino acid residue 245. The lower line is the ETR1 sequence from amino acid residue 1 through amino acid residue 235. The sequence identity is 85.11% as between these two sequences. The sequence similarity is 92.34%. The vertical lines and single and double dots have the same meaning as for FIGS. 11A and 11B.

FIGS. 22A–22C depict the nucleic acid (SEQ ID NO:50) and deduced amino acid sequence (SEQ ID NO:51) for the Nr (Never-ripe) ETR nucleic acid from Never-ripe tomato. The amino acid sequence in FIG. 22 differs from the TETR sequence in FIG. 16 in that the amino acid residue proline at residue 36 is replaced with leucine.

DETAILED DESCRIPTION OF THE INVENTION

Figure 1:
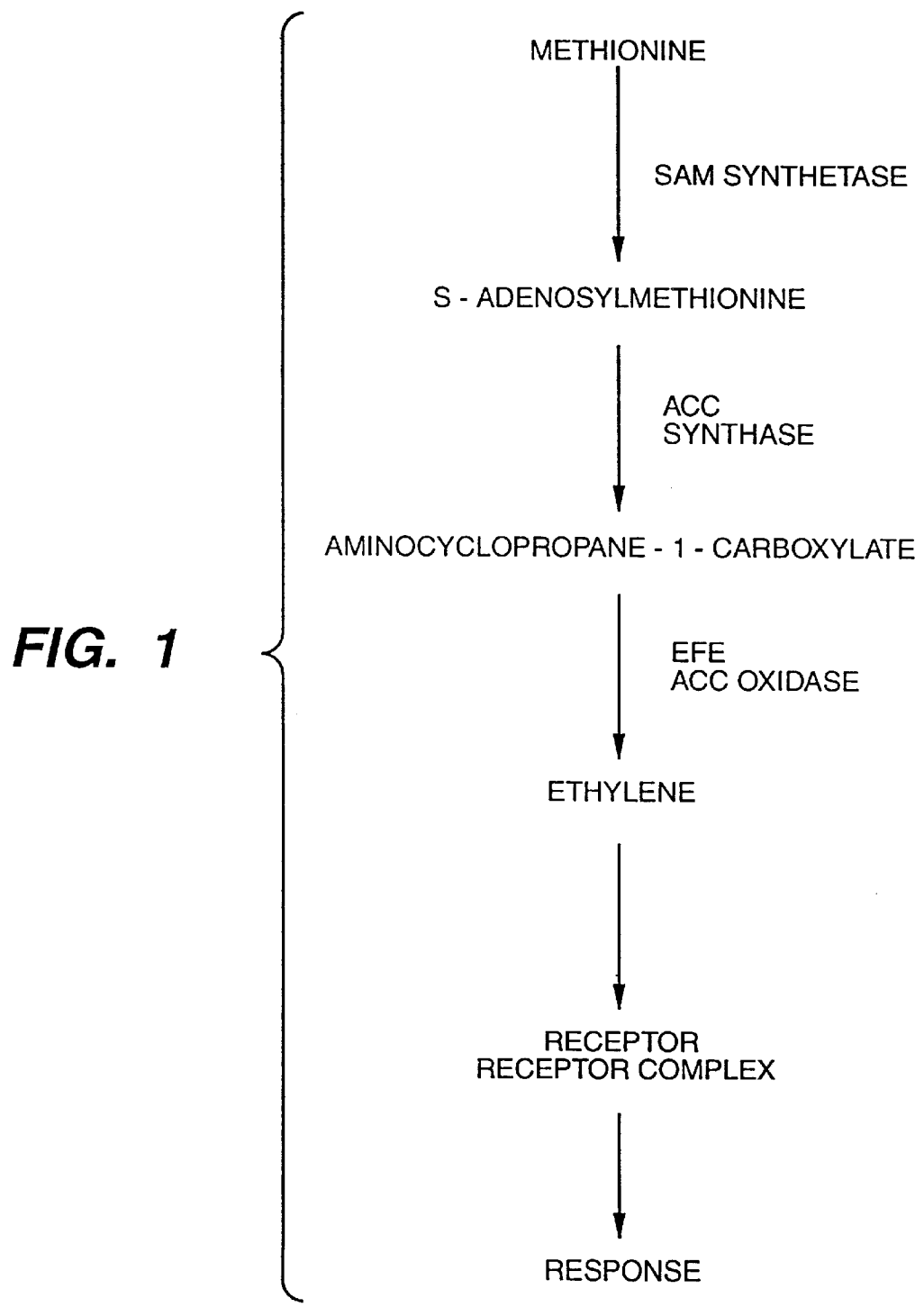
FIG. 1 depicts the biosynthetic pathway for ethylene.

The invention provides, in part, plants having cells transformed with a vector comprising an ETR nucleic acid or a modified ETR nucleic acid. Such transformed plant cells have a modulated response to ethylene. In a preferred embodiment, the expression of a modified ETR nucleic acid confers a phenotype on the plant characterized by a decrease in the response to ethylene for at least for those cells expressing the modified ETR nucleic acid as compared to a corresponding non-transformed plant. Thus, for example, when the modified ETR nucleic acid is expressed in fruit such as tomato, the fruit ripening process is retarded thereby reducing spoilage and extending the shelf life and/or harvesting season for the fruit. The invention is similarly useful to prevent spoilage of vegetative tissue and to enhance the longevity of cut flowers.

As used herein, a "plant ETR nucleic acid" refers to nucleic acid encoding all or part of a "plant ETR protein". ETR nucleic acids can initially be identified by homology to the ETR nucleic acid sequences disclosed herein but can also be identified by homology to any identified ETR nucleic acid or amino acid sequence. Examples of ETR nucleic acids include ETR1, QITR and Q8 from Arabidopsis and TETR, TGETR1 and TGETR2 from tomato. ETR nucleic acids, however, are also defined functionally by their ability to confer a modulated ethylene response upon transformation into plant tissue. For example, an antisense construct of an ETR nucleic acid or modified ETR nucleic acid is capable of reducing the ethylene response in plant tissue expressing the antisense or modified ETR nucleic acid. In addition, transformation with an ETR nucleic acid or modified ETR nucleic acid can result in co-suppression of the endogenous ETR alleles which in turn modifies the ethylene response. Furthermore, ETR nucleic acids can be modified as described herein to produce modified ETR nucleic acids which when used to transform plant tissue result in varying degrees of ethylene insensitivity in the tissue expressing such modified ETR nucleic acids. When evaluating a putative ETR nucleic acid for the ability of a modified form of the ETR nucleic acid to confer ethylene insensitivity, it is preferred that a codon or combination of codons encoding the amino acid residues equivalent to Ala-31, Ile-62, Cys-65 or Tyr-102 in the ETR1 protein of *Arabidopsis thaliana* or Pro-36 in the TETR protein in tomato be modified so as to substitute a different amino acid residue such as those disclosed herein for the specified residues.

Plant ETR nucleic acids include genomic DNA, cDNA and oligonucleotides including sense and anti-sense nucleic acids as well as RNA transcripts thereof. The genomic DNA sequence (SEQ ID NO:1) for the ETR1 gene from *Arabidopsis thaliana* is shown in FIG. 2. The corresponding cDNA sequence (SEQ ID NO:2) and deduced ETR amino acid sequence (SEQ ID NO:3) are shown in FIG. 3. An amino terminal domain (i.e., resides 1 through about 316) of the predicted ETR protein sequence has no homology to known protein sequences. Approximately midway in the ETR protein (i.e., residues 295 through 313) is a putative transmembrane domain followed by a putative intracellular domain (i.e., residues 314 through 738). A substantial portion of this putative intracellular domain unexpectedly has sequence homology to the two component environmental sensor-regulators known in bacteria. These two families in bacteria form a conserved sensor-regulator system that allows the bacteria to respond to a broad range of environmental fluctuations. It is believed that the amino terminal portion of the ETR protein interacts either directly with ethylene or indirectly (e.g., with an ethylene binding protein or another protein) and that upon such interaction, signal transduction through the intracellular domain occurs.

An ETR nucleic acid or ETR protein can be identified by substantial nucleic acid and/or amino acid sequence homology to a known ETR sequence. Such homology can be based upon the overall nucleic acid or amino acid sequence in which case the overall homology of the protein sequence is preferably greater than about 50%, preferably greater than 60%, still more preferably greater than 75% and most preferably greater than 90% homologous. Notwithstanding overall sequence homology, it is preferred that the unique amino-terminal portion of an ETR protein sequence or the nucleic acid sequence encoding this portion of the molecule (i.e., the 5' terminal portion) be used to identify an ETR protein or ETR nucleic acid. When using this amino terminal sequence portion, it is preferred that the amino acid sequence homology with the known ETR sequence be greater than about 55%, more preferably about 60%, still more preferably about 70%, more preferably greater than 85% and most preferably greater than 95% homologous. Homology based on nucleic acid sequence is commensurate with amino acid homology but takes into account the degeneracy in the genetic code and codon bias in different plants. Accordingly, the nucleic acid sequence homology may be substantially lower than that based on protein sequence. Thus, an ETR protein is any protein which has an amino-terminal portion which is substantially homologous to the amino-terminal domain of a known ETR protein. One such known ETR protein is the ETR1 protein (see FIG. 3) from *Arabidopsis thaliana*. An ETR nucleic acid by analogy also encodes at least the amino-terminal domain of an ETR protein.

An ETR nucleic acid from a plant species other than *Arabidopsis thaliana* can be readily identified by standard methods utilizing known ETR nucleic acid. For example, labelled probes corresponding to a known ETR nucleic acid or encoding the unique amino-terminal domain can be used for in situ hybridization to detect the presence of an ETR gene in a particular plant species. In addition, such probes can be used to screen genomic or cDNA libraries of a different plant species or to identify one or more bands containing all or part of an ETR gene by hybridization to an electrophoretically separated preparation of genomic DNA digested with one or more restriction endo-nucleases.

The hybridization conditions will vary depending upon the probe used. When a unique nucleotide sequence of an ETR nucleic acid is used, e.g., an oligonucleotide encoding all or part of the amino terminal domain, relatively high stringency, e.g., about 0.1×SSPE at 65° C. is used. When the hybridization probe covers a region which has a potentially lower sequence homology to known ETR nucleic acids, e.g., a region covering a portion of the unique amino terminal domain and a portion covering a transmembrane domain, the hybridization is preferably carried out under moderate stringency conditions, e.g., about 5×SSPE at 50° C.

For example, using the above criteria, a ripening tomato cDNA library (Stratagene, LaJolla, Calif., Catalog No. 936004) was screened with a labeled probe comprising a nucleic acid sequence encoding an amino terminal portion of the Arabidopsis ETR protein sequence disclosed herein in FIGS. 3A, B, C and D. Several clones were identified and sequenced by standard techniques. The DNA sequences for this ETR nucleic acid from tomato (TETR) and *Arabidopsis thaliana* (ETR1) encoding amino acid residues 1 through 123 (SEQ ID NOs:20 and 21) and amino acids 306 through 403 (SEQ ID NOs:22 and 23) are set forth in FIGS. 10A and 10B, respectively.

The amino acid sequences for the ETR1 protein from *Arabidopsis thaliana* and tomato (TETR) for residues 1 through 123 (SEQ ID NOs:25 and 24) and 306 through 403 (SEQ ID NOs:27 and 26) are set forth in FIGS. 11A and 11B, respectively.

The complete ETR nucleic acid (SEQ ID NO:35) and amino acid sequence (SEQ ID NO:36) for TETR is shown in FIG. 16. A direct comparison of the amino acid sequence between the TETR and ETR1 proteins for the amino terminal 316 amino acid residues is shown in FIG. 17.

As can be seen, there is substantial homology between these particular Arabidopsis and tomato ETR sequences both on the level of DNA sequence and amino acid sequence. In particular, the homology on the DNA level for the sequence encoding amino acids 1 through 45 is slightly greater than 72%. The homology on the amino acid level for amino acid residues 1 through 123 is approximately 79%. For the amino terminal portion (residues 1 through 316) the overall homology is approximately 73%. In the case of amino acid sequence homology, when the differences between the amino acids at equivalent residues are compared and such differences comprise the substitution of a conserved residue, i.e., amino acid residues which are functionally equivalent, the amino acid sequence similarity rises to about 90% for the first 123 residues. The sequence similarity for the amino terminal 316 amino acids rises to almost 85%. Such sequence similarity was determined using a Best Fit sequence program as described by Devereux et al. (1984) *Nucl. Acids Res.* 12:387–395. Functionally equivalent (i.e., conserved) residues are identified by double and single data in the comparative sequences. Similarly, the nucleic acid sequence homology between Arabidopsis and tomato for the sequence encoding amino acid residues 306 to 403 is approximately 75%. The sequence homology on the amino acid level for identical amino acids is almost 86% whereas the similarity is almost 96%.

In addition to ETR1 from Arabidopsis and TETR (sometimes referred to TXTR) from tomato, a number of other ETR nucleic acids have been identified in Arabidopsis and tomato. In Arabidopsis, the QITR and Q8 ETR nucleic acids and proteins have been identified. See FIGS. 12, 13, 14 and 15 and Seq. ID Nos. 41 through 48. For QITR, the overall nucleic acid homology with ETR1 is approximately 69%. With regard to the amino terminal portion between residues 1 and 316, the homology is approximately 71% identical for amino acid sequence and approximately 72% identical in terms of nucleic acid sequence. With regard to Q8, the overall sequence homology to ETR1 from Arabidopsis is approximately 69% for the overall nucleic acid sequence as compared to approximately 81% homology for that portion of the Q8 encoding the amino terminal 316 amino acids. The homology on the amino acid level for the amino terminal portion is between Q8 and ETR1 is approximatley 72%.

The other ETR nucleic acids identified in tomato include TGETR1 (SEQ ID NO:37) and TGETR2 (SEQ ID NO:39). the deduced protein sequence for TGETR1 (SEQ ID NO:38) and TGETR2 (SEQ ID NO:40) are set forth in FIGS. 18 and 19 respectively. The sequence of TGETR2 is incomplete. A comparison of the sequence homology for the first 316 amino acid residues of the TGETR1 protein and the ETR1 protein is shown in FIG. 20. The sequence identity is just under 92%. The sequence similarity rises to almost 96% between this portion of these two proteins. With regard to TGETR2, FIG. 21 sets forth a comparison of the amino terminal portion of this molecule (through amino acid residue 245) with the corresponding portion of the ETR1 protein. The identity of sequences between these two sequence portions is approximately 85%. The sequence similarity rises to just above 92%.

The cloning and sequencing of the ETR nucleic acids from Arabidopsis is described in the examples herein. However, given the extensive disclosure of the sequences for these ETR nucleic acids, one skilled in the art can readily construct oligonucleotide probes, perform PCR amplification or utilize other standard protocols known to those skilled in the art to isolate the disclosed genes as well as other ETR nucleic acids having homology thereto from other species. When screening the same plant species, relatively moderate to high stringency conditions can be used for hybridization which would vary from between 55° C. to 65° C. in 5×SSPE. When it is desirable to probe for lower homology or in other plant species, lower stringency conditions such as 50° C. at 5×SSPE can be used. Washing conditions however required 0.2×SSPE.

The isolation of the TETR1 ETR nucleic acid from tomato is described in the examples. The isolation of this sequence utilized the amino terminal portion of the ETR1 gene from Arabidopsis. The other tomato ETR nucleic acids disclosed herein (TGETR1 and TGETR2) were identified by probing a tomato genomic library with an ETR1 probe. The genomic library was made from EMBL 3 to which was ligated a partially Sau3A digested genomic DNA extract of tomato. Conditions were 65° C. 5×SSC with washes at 2×SSC.

In reviewing the overall structure of the various ETR nucleic acids and proteins identified to date, it appears that at least one class of ETR protein contains a unique amino terminal portion followed by a histine-kinase domain followed by a response regulatory region. This is the ETR1 protein in Arabidopsis. A second class of ETR protein does not contain the response regulatory region. Examples of such ETR proteins include QITR in Arabidopsis and TETR in tomato. The significance of this is not understood at this time. However, as described hereinafter, mutations in the ETR nucleic acids encoding members from each class can confer a dominate ethylene insensitivity to transgenic plants containing such nucleic acids.

As described hereinafter, substitution of amino acid residues Ala-31, Ile-62, Cys-65 and Tyr-102 with a different amino acid results in modified Arabidopsis ETR nucleic acid which are capable of conferring ethylene insensitivity in a transformed plant. Each of these residues are identical as between the ETR protein of tomato (TETR) and *Arabidopsis thaliana* (ETR1).

Once the ETR nucleic acid is identified, it can be cloned and, if necessary, its constituent parts recombined to form the entire ETR nucleic acid. Once isolated from its natural source, e.g., contained within a plasmid or other vector or excised therefrom as a linear nucleic acid segment, the ETR nucleic acid can be further used as a probe to identify and isolate other ETR nucleic acids. It can also be used as a "precursor" nucleic acid to make modified ETR nucleic acids and proteins.

As used herein, the term "modified ETR nucleic acid" refers to an ETR nucleic acid containing the substitution, insertion or deletion of one or more nucleotides of a precursor ETR nucleic acid. The precursor ETR nucleic acids include naturally-occurring ETR nucleic acids as well as other modified ETR nucleic acids. The naturally-occurring ETR nucleic acid from *Arabidopsis thaliana* can be used as a precursor nucleic acid which can be modified by standard techniques, such as site-directed mutagenesis, cassette mutagenesis and the like, to substitute one or more nucleotides at a codon such as that which encodes alanine at residue 31 in the Arabidopsis ETR nucleic acid. Such in vitro codon modification can result in the generation of a codon at position 31 which encodes any one of the other naturally occurring amino acid residues. Such modification results in a modified ETR nucleic acid.

For example, the mutation responsible for the pheno-type observed in the Never-ripe mutant is disclosed in the examples. As described, a single point mutation changes the proline normally present at residue 36 in the TETR protein to leucine. This single mutation is sufficient to confer a dominant ethylene insensitivity phenotype on the wild-type plant. The transformation of tomato and other plants with this modified ETR nucleic acid is expected to confer the dominant ethylene insensitivity phenotype on such transformed plant cells.

Alternatively, the precursor nucleic acid can be one wherein one or more of the nucleotides of a wild-type ETR nucleic acid have already been modified. Thus, for example, the *Arabidopsis thaliana* ETR nucleic acid can be modified at codon 31 to form a modified nucleic acid containing the substitution of that codon with a codon encoding an amino acid other than alanine, e.g., valine. This modified ETR nucleic acid can also act as a precursor nucleic acid to introduce a second modification. For example, the codon encoding Ala-102 can be modified to encode the substitution of threonine in which case the thus formed modified nucleic acid encodes the substitution of two different amino acids at residues 31 and 102.

Deletions within the ETR nucleic acid are also contemplated. For example, an ETR nucleic acid can be modified to delete that portion encoding the putative transmembrane or intracellular domains. The thus formed modified ETR nucleic acid when expressed within a plant cell produces only an amino-terminal portion of the ETR protein which is potentially capable of binding ethylene, either directly or indirectly, to modulate the effective level of ethylene in plant tissue.

In addition, the modified ETR nucleic acid can be identified and isolated from a mutant plant having a dominant or recessive phenotype characterized by an altered response to ethylene. Such mutant plants can be spontaneously arising or can be induced by well known chemical or radiation mutagenesis techniques followed by the determination of the ethylene response in the progeny of such plants. Examples of such mutant plants which occur spontaneously include the Never ripe mutant of tomato and the ethylene insensitive mutant of carnation. Thus, modified ETR nucleic acids can be obtained by recombinant modification of wild-type ETR nucleic acids or by the identification and isolation of modified ETR alleles from mutant plant species.

It is preferred that the modified ETR nucleic acid encode the substitution, insertion and/or deletion of one or more amino acid residues in the precursor ETR protein. Upon expression of the modified nucleic acid in host plant cells, the modified ETR protein thus produced is capable of modulating at least the host cell's response to ethylene. In connection with the generation of such a phenotype, a number of codons have been identified in the ETR nucleic acid from *Arabidopsis thaliana* which when modified and reintroduced into a wild-type plant result in a decrease in the ethylene response by the transformed plant. These codons encode amino acid residues Ala-31, Ile-62, Cys-65 and Tyr-102 in the ETR protein of *Arabidopsis thaliana*. The ETR gene and each of these particular modified amino acid residues were identified by cloning the wild-type ETR gene from *Arabidopsis thaliana* and chemically modified alleles from four different varieties (etr1-1, etr1-2, etr1-3 and etr1-4) of *Arabidopsis thaliana* (each of which exhibited a dominant phenotype comprising insensitivity to ethylene) and comparing the nucleotide and deduced amino acid sequences. The invention, however, is not limited to modified ETR nucleic acids from *Arabidopsis thaliana* as described in the examples. Rather, the invention includes other readily identifiable modified ETR nucleic acids which modulate ethylene sensitivity.

The above four varieties exhibiting dominant ethylene insensitivity were generated by chemical modification of seedlings of *Arabidopsis thaliana* and identified by observing plant development from such modified seedlings with the addition of exogenous ethylene. Using a similar approach either with or without the addition of exogenous ethylene, the skilled artisan can readily generate other variants of any selected plant species which also have a modulated response to ethylene. Then, using ETR probes based upon the wild-type or modified ETR nucleic acid sequences disclosed herein, other modified ETR nucleic acids can be isolated by probing appropriate genomic or cDNA libraries of the modified selected plant species. The nucleotide and/or encoded amino acid sequence of such newly generated modified ETR nucleic acids is then preferably compared with the wild-type ETR nucleic acid from the selected plant species to determine which modifications, if any, in the ETR nucleic acid are responsible for the observed phenotype. If the wild-type sequence of the selected plant species is not available, the wild-type or modified ETR sequences disclosed herein for *Arabidopsis thaliana* or other ETR sequences which have been identified can be used for comparison. In this manner, other modifications to ETR proteins can be identified which can confer the ethylene insensitivity phenotype. Such modifications include the identification of amino acids other than those disclosed herein which can be substituted at residues equivalent to Ala-31,Ile-62, Cys-65 and Ala-102 in the *Arabidopsis thaliana* ETR protein and the identification of other amino acid residues which can be modified by substitution, insertion and/or deletion of one or more amino acid residues to produce the desired phenotype.

Alternatively, a cloned precursor ETR nucleic acid can be systematically modified such that it encodes the substitution, insertion and/or deletion of one or more amino acid residues and tested to determine the effect of such modification on a plant's ethylene response. Such modifications are preferably made within that portion of the ETR nucleic acid which encodes the amino-terminal portion of the ETR protein. However, modifications to the carboxy-terminal or putative transmembrane domains to modulate signal transduction are also contemplated (e.g., modifications of the conserved histidine of the histidine kinase domain which is the supposed site of autophosphorylation or the conserved aspartate of the response regulator domain which is the supposed site of phosphorylation). One method which may be used for identifying particular amino acid residues involved in the direct or indirect interaction with ethylene is the sequential substitution of the codons of an ETR nucleic acid with codons encoding a scanning amino acid such as glycine or alanine (See, e.g., PCT Publication WO90/04788 published May 3, 1990) followed by transformation of each of the thus formed modified nucleic acids into a plant to determine the effect of such sequential substitution on the ethylene response. Other approaches include random modifications or predetermined targeted modifications of the cloned ETR nucleic (See, e.g., PCT Publication No. WO92/07090 published Apr. 30, 1992) followed by transformation of plant cells and the identification of progeny having an altered ethylene response. The ETR nucleic acid from those plants having the desired phenotype is isolated and sequenced to confirm or identify the modification responsible for the observed phenotype.

Amino acid residues equivalent to those specifically identified in an ETR protein which can be modified to alter the ethylene response can also be readily identified in ETR proteins from other plant species. For example, equivalent amino acid residues to those identified in the ETR protein from*Arabidopsis thaliana* can be readily identified in other FTR proteins. An amino acid residue in a precursor ETR protein is equivalent to a particular residue in the ETR protein of *Arabidopsis thaliana* if it is homologous in position in either primary or tertiary structure to the specified residue of the Arabidopsis ETR protein.

In order to establish homology by way of primary structure, the primary amino acid sequence of a precursor ETR protein is directly compared by alignment with the primary sequence of the ETR protein from *Arabidopsis thaliana*. Such alignment is preferably of the amino-terminal domain and will take into account the potential insertion or deletion of one or more amino acid residues as between the two sequences so as to maximize the amino acid sequence homology. A comparison of a multiplicity of ETR protein sequences with that of *Arabidopsis thaliana* provides for the identification of conserved residues among such sequences which conservation is preferably maintained for further comparison of primary amino acid sequence. Based on the alignment of such sequences, the skilled artisan can readily identify amino acid residues in other ETR proteins which are equivalent to Ala-31, Ile-62, Cys-65, Ala-102 and other residues in *Arabidopsis thaliana* ETR protein. Such equivalent residues are selected for modifications analogous to those of other modified ETR proteins which confer the desired ethylene responsive phenotype. Such modified ETR proteins are preferably made by modifying a precursor ETR nucleic acid to encode the corresponding substitution, insertion and/or deletion at the equivalent amino acid residue.

In addition to homology at the primary sequence level, equivalent residues can be identified based upon homology at the level of tertiary structure. The determination of equivalency at this level will generally require three-dimensional crystal structures for an ETR protein or modified ETR protein from Arabidopsis (or crystal structure of another ETR protein having defined equivalent residues) and the crystal structure of a selected ETR protein. Equivalent residues at the level of tertiary structure are defined as those for which the atomic coordinates of two or more of the main chain atoms of a particular amino acid residue of the selected ETR protein, as compared to the ETR protein from Arabidopsis, are within 0.13 nm and preferably 0.10 nm after alignment. Alignment is achieved after the best model has been oriented and positioned to give the maximum overlap of atomic coordinates of non-hydrogen protein atoms of the ETR proteins in question.

ETR nucleic acids can be derived from any of the higher plants which are responsive to ethylene. Particularly suitable plants include tomato, banana, kiwi fruit, avocado, melon, mango, papaya, apple, peach and other climacteric fruit plants. Non-climacteric species from which ETR nucleic acids can be isolated include strawberry, raspberry, blackberry, blueberry, lettuce, cabbage, cauliflower, onion, broccoli, brussel sprout, cotton, canola, grape, soybean and oil seed rape. In addition, ETR nucleic acids can be isolated from flowering plants within the Division Magnoliophyta which comprise the angiosperms which include dicotyledons (Class Magnoliopsida and Dicotyledoneae) and monocotyledons (Class Liliopsida). Particularly preferred Orders of angiosperm according to "Taxonomy of Flowering Plants", by A. M. Johnson, The Century Co., NY, 1931 include Rosales, Cucurbitales, Rubiales, Campanulatae, Contortae, Tubiflorae, Plantaginales, Ericales, Primulales, Ebenales, Diapensiales, Primulales, Plumbaginales, Opuntiales, Parietales, Myritiflorae, Umbelliflorae, Geraniales, Sapindales, Rhamnales, Malvales, Pandales, Rhoendales, Sarraceniales, Ramales, Centrospermae, Santalales, Euphorbiales, Capparales, Aristolochiales, Julianiales, Juglandales, Fagales, Urticales, Myricales, Polygonales, Batidales, Balanopsidales, Proteales, Salicales, Leitneriales, Garryales, Verticillatae and Piperales. Particularly preferred plants include lily, carnation, chrysanthemum, petunia, rose, geranium, violet, gladioli, orchid, lilac, crabapple, sweetgum, maple, poinsettia, locust, ash and linden tree.

In addition to providing a source for ETR nucleic acids which can be modified or isolated according to the teachings herein, the foregoing plants can be used as recipients of the modified nucleic acid to produce chimeric or transgenic plants which exhibit an ethylene resistance phenotype in one or more tissue types of the transformed plant.

Once a modified ETR nucleic acid has been cloned, it is used to construct vectors for transforming plant cells. The construction of such vectors is facilitated by the use of a shuttle vector which is capable of manipulation and selection in both plant and a convenient cloning host such as a prokaryote. Such shuttle vectors thus can include an antibiotic resistance gene for selection in plant cells (e.g., kanamycin resistance) and an antibiotic resistance gene for selection in a bacterial host (e.g. actinomycin resistance). Such shuttle vectors also contain an origin of replication appropriate for the prokaryotic host used and preferably at least one unique restriction site or a polylinker containing unique restriction sites to facilitate vector construction. Examples of such shuttle vectors include pMON530 (Rogers et al. (1988) *Methods in Enzymology* 153:253–277) and pCGN1547 (McBride et al. (1990) Plant *Molecular Biology* 14:269–276).

In the preferred embodiments, which comprise the best mode for practicing the invention, a promoter is used to drive expression of an ETR or a modified ETR nucleic acid within at least a portion of the tissues of a transformed plant. Expression of an ETR nucleic acid is preferably in the antisense orientation to modulate the ethylene response by reduction in translation of the endogenous ETR RNA transcript. Expression of a modified ETR nucleic acid results in the production of a modified ETR protein which is capable of conferring ethylene insensitivity. Such promoters may be obtained from plants, plant pathogenic bacteria or plant viruses. Constitutive promoters include the 35S and 19S promoters of cauliflower mosaic virus (CaMV35S and CaMV19S), the full-length transcript promoter from the Figwort mosaic virus (FMV35S) (See PCT Publication No. WO92/12249 published Jul. 23, 1992) and promoters associated with Agrobacterium genes such as nopaline, synthase (NOS), mannopine synthase (MOS) or octopine synthase (OCS). Other constitutive promoters include the $\alpha$-1 and -$\beta$1 tubulin promoters (Silflow et al. (1987) *Devel. Genet.* 8:435–460), the histone promoters (Chaubet (1987) *Devl. Genet.* 8:461–473) and the promoters which regulate transcription of ETR nucleic acids.

In some embodiments, tissue and/or temporal-specific promoters can be used to control expression of ETR and modified ETR nucleic acids. Examples of fruit specific promoters include the E8, E4, E17 and J49 promoters from tomato (Lincoln et al. (1988) *Mol. Gen. Genet.* 212:71–75) and the 2A11, Z130 and Z70 promoters from tomato as described in U.S. Pat. Nos. 4,943,674, 5,175,095 and 5,177,307. In addition, preferential expression in rapidly dividing tissue can be obtained utilizing the plant EF-1$\alpha$ promoter as described in U.S. Pat. No. 5,177,011. Examples of floral specific promoters include the leafy promoter and promoters from the apetala, pistillata and agamous genes. A promoter system for targeting expression in the leaves of a transformed plant is a chimeric promoter comprising the CaMV35S promoter ligated to the portion of the ssRUBISCO gene which represses the expression of ssRUBISCO in the absence of light. In addition, pollen-specific promoters can also be used. Such promoters are well known to those skilled in the art and are readily available. A example of such a promoter is Zn13 (Hamilton et al. (1992) *Plant Mol. Biol.* 18:211–218). This promoter was cloned from corn (Monocot) but functions as a strong and pollen-specific promoter when used in tobacco (Dicot).

Examples of inducible promoters which can be used for conditional expression of ETR nucleic acids include those from heat-shock protein genes such as the PHS1 heat-shock protein gene (Takahashi et al. (1989) *Mol. Gen. Genet.* 219:365–372) and light-inducible promoters including the three chlorophyll a/b light harvesting protein promoters (Leutwiler et al. (1986) *Nucl. Acids. Res.* 14:4051–4064) and the pre-ferredoxin promoter (Vorst et al. (1990) *Plant Mol. Biol.* 14:491–499).

In a further embodiment of the invention, the vector used to transform plant cells is constructed to target the insertion of the ETR nucleic acid into an endogenous promoter within a plant cell. One type of vector which can be used to target the integration of a modified ETR nucleic acid to an endogenous promoter comprises a positive-negative selection vector analogous to that set forth by Monsour, et al. *Nature* 336:348–352 (1988) which describes the targeting of exogenous DNA to a predetermined endogenous locus in mammalian ES cells. Similar constructs utilizing positive and negative selection markers functional in plant cells can be readily designed based upon the identification of the endogenous plant promoter and the sequence surrounding it. When such an approach is used, it is preferred that a replacement-type vector be used to minimize the likelihood of reversion to the wild-type genotype.

The vectors of the invention are designed such that the promoter sequence contained in the vector or the promoter sequence targeted in the plant cell genome are operably linked to the nucleic acid encoding the ETR or modified ETR nucleic acid. When the positive strand of the ETR nucleic acid is used, the term "operably linked" means that the promoter sequence is positioned relative to the coding sequence of the ETR nucleic acid such that RNA polymerase is capable of initiating transcription of the ETR nucleic acid from the promoter sequence. In such embodiments it is also preferred to provide appropriate ribosome binding sites, transcription initiation and termination sequences, translation initiation and termination sequences and polyadenylation sequences to produce a functional RNA transcript which can be translated into ETR protein. When an antisense orientation of the ETR nucleic acid is used, all that is required is that the promoter be operably linked to transcribe the ETR antisense strand. Thus, in such embodiments, only transcription start and termination sequences are needed to provide an RNA transcript capable of hybridizing with the mRNA or other RNA transcript from an endogenous ETR gene or modified ETR nucleic acid contained within a transformed plant cell. In addition to promoters, other expression regulation sequences, such as enhancers, can be added to the vector to facilitate the expression of ETR nucleic acid in vivo.

Once a vector is constructed, the transformation of plants can be carried out in accordance with the invention by essentially any of the various transformation methods known to those skilled in the art of plant molecular biology. Such methods are generally described in *Methods and Enzymology*, Vol. 153 ("Recombinant DNA Part D") 1987, Wu and Grossman, Academic Press, eds. As used herein, the term "transformation" means the alteration of the genotype of a plant cell by the introduction of exogenous nucleic acid. Particular methods for transformation of plant cells include the direct microinjection of the nucleic acid into a plant cell by use of micropipettes. Alternatively, the nucleic acid can be transferred into a plant cell by using polyethylene glycol (Paszkowski et al. *EMBO J.* 3:2717–2722 (1984)). Other transformation methods include electroporation of protoplasts (Fromm, et al. Proc. Natl. Acad. Sci. U.S.A. 82:5824 (1985); infection with a plant specific virus, e.g., cauliflower mosaic virus (Hohn et al. "Molecular Biology of Plant Tumors", Academic Press, New York (1982), pp. 549–560) or use of transformation sequences from plant specific bacteria such as Agrobacterium tumefaciens, e.g., a Ti plasmid transmitted to a plant cell upon infection by agrobacterium tumefaciens (Horsch et al. Science 233:496–498 (1984); Fraley et al. *Proc. Natl. Acad. Sci. U.S.A.* 80:4803 (1983)). Alternatively, plant cells can be transformed by introduction of nucleic acid contained within the matrix or on the surface of small beads or particles by way of high velocity ballistic penetration of the plant cell (Klein et al. *Nature* 327:70–73 (1987)).

After the vector is introduced into a plant cell, selection for successful transformation in typically carried out prior to regeneration of a plant. Such selection for transformation is not necessary, but facilitates the selection of regenerated plants having the desired phenotype by reducing wild-type background. Such selection is conveniently based upon the antibiotic resistance and/or herbicide resistance genes which may be incorporated into the transformation vector.

Practically all plants can be regenerated from cultured cells or tissues. As used herein, the term "regeneration" refers to growing a whole plant from a plant cell, a group of plant cells or a plant part. The methods for plant regeneration are well known to those skilled in the art. For example, regeneration from cultured protoplasts is described by Evans et al. "Protoplasts Isolation and Culture", *Handbook of Plant Cell Cultures* 1:124–176 (MacMillan Publishing Co., New York (1983); M. R. Davey, "Recent Developments in the Culture and Regeneration of Plant Protoplasts", *Protoplasts* (1983) *Lecture Proceedings*, pp. 12–29 (Birkhauser, Basil 1983); and H. Binding "Regeneration of Plants", *Plant Protoplasts*, pp. 21–73 (CRC Press, Bocaraton 1985). When transformation is of an organ part, regeneration can be from the plant callus, explants, organs or parts. Such methods for regeneration are also known to those skilled in the art. See, e.g., *Methods in Enzymology*, supra.; *Methods in Enzymology*, Vol. 118; and Klee et al. *Annual Review of Plant Physiology* 38:467–486.

A preferred method for transforming and regenerating petunia with the vectors of the invention is described by Horsch, R. B. et al. (1985) *Science* 227:1229–1231. A preferred method for transforming cotton with the vectors of the invention and regenerating plants therefrom is described by Trolinder et al. (1987) *Plant Cell Reports* 6:231–234.

Tomato plant cells are preferably transformed utilizing Agrobacterium strains by the method as described in McCormick et al., *Plant Cell Reports* 5:81–84 (1986). In particular, cotyledons are obtained from 7–8 day old seedlings. The seeds are surface sterilized for 20 minutes in 30% Clorox bleach and germinated in Plantcons boxes on Davis germination media. Davis germination media is comprised of 4.3 g/l MS salts, 20 g/l sucrose and 10 mls/l Nitsch vitamins, pH 5.8. The Nitsch vitamin solution is comprised of 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine. The seeds are allowed to germinate for 7–8 days in the growth chamber at 25° C., 40% humidity under cool white lights with an intensity of 80 einsteins $M^2$–$s^{-1}$. The photoperiod is 16 hours of light and 8 hours of dark.

Once germination occurs, the cotyledons are explanted using a #15 feather blade by cutting away the apical meristem and the hypocotyl to create a rectangular explant. These cuts at the short ends of the germinating cotyledon increase the surface area for infection. The explants are bathed in sterile Davis regeneration liquid to prevent desiccation. Davis regeneration media is composed of 1xMS salts, 3% sucrose, 1x Nitsch vitamins, 2.0 mg/l zeatin, pH 5.8. This solution was autoclaved with 0.8% Noble Agar.

The cotyledons are pre-cultured on "feeder plates" composed of media containing no antibiotics. The media is composed of 4.3 g/l MS salts, 30 g/l sucrose, 0.1 g/l myo-inositol, 0.2 g/l $KH_2PO_4$, 1.45 mls/l of a 0.9 mg/ml solution of thiamine HCl, 0.2 mls of a 0.5 mg/ml solution of kinetin and 0.1 ml of a 0.2 mg/ml solution of 2,4 D. This solution is adjusted to pH 6.0 with KOH. These plates are overlaid with 1.5–2.0 mls of tobacco suspension cells (TXD's) and a sterile Whitman filter soaked in 2C005K media. 2C005K media is composed of 4.3 g/l Gibco MS salt mixture, 1 ml B5 vitamins (1000x stock), 30 g/l sucrose, 2 mls/l PCPA from 2 mg/ml stock, and 10 µl/l kinetin from 0.5 mg/ml stock. The cotyledons were cultured for 1 day in a growth chamber at 25° C. under cool white lights with a light intensity of 40–50 einsteins $m^2s^{-1}$ with a continuous light photoperiod.

Cotyledons are then inoculated with a log phase solution of Agrobacterium containing the modified or wild type ETR nucleic acid. The concentration of the Agrobacterium is approximately $5 \times 10^8$ cells/ml. The cotyledons are allowed to soak in the bacterial solution for six minutes and are then blotted to remove excess solution on sterile Whatman filter disks and subsequently replaced to the original feeder plate where they are allowed to co-culture for 2 days. After the two days, cotyledons are transferred to selection plates containing Davis regeneration media with 2 mg/l zeatin riboside, 500 µg/ml carbenicillin, and 100 µg/ml kanamycin. After 2–3 weeks, cotyledons with callus and/or shoot formation are transferred to fresh Davis regeneration plates containing carbenicillin and kanamycin at the same levels. The experiment is scored for transformants at this time. The callus tissue is subcultured at regular 3 week intervals and any abnormal structures are trimmed so that the developing shoot buds continue to regenerate. Shoots develop within 3–4 months.

Once shoots develop, they are excised cleanly from callus tissue and planted on rooting selection plates. These plates contain 0.5×MSO containing 50 µg/ml kanamycin and 500 µg/ml carbenicillin. These shoots form roots on the selection media within two weeks. If no roots appear after 2 weeks, shoots are trimmed and replanted on the selection media. Shoot cultures are incubated in percivals at a temperature of 22° C. Shoots with roots are then potted when roots were about 2 cm in length. The plants are hardened off in a growth chamber at 21° C. with a photoperiod of 18 hours light and 6 hours dark for 2–3 weeks prior to transfer to a greenhouse. In the greenhouse, the plants are grown at a temperature of 26° C. during the day and 21° C. during the night. The photoperiod is 13 hours light and 11 hours dark and the plants are allowed to mature.

Once plants have been regenerated, one or more plants are selected based upon a change in the ethylene response phenotype. For example, when a modified ETR nucleic acid is used with its native promoter, selection can be based upon an alteration in any of one of the "triple responses" of seedlings from such plants. Guzman et al. (1990) *The Plant Cell* 2:523. Alternatively, or when constitutive promoters are used, various other ethylene responses can be assayed and compared to the wild type plant. Such other ethylene responses include epinasty (which is observed primarily in tomato), epsision, abscission, flower petal senescence and fruit ripening. In addition to overt changes in the ethylene response, the levels of various enzymes can be determined followed by exposure to ethylene to determine the response time for the typical increase or decrease in the level of a particular protein such as an enzyme. Examples of various ethylene responses which can be used to determine whether a particular plant has a decreased response to ethylene are set forth in Chapter 7, The Mechanisms of Ethylene Action in "Ethylene in Plant Biology" 2d Ed. F. B. Abels, P. W. Morgan and M. E. Salveit, Jr., eds., San Diego, Academic Press, Inc. (1992). When a tissue and/or temporal-specific promoter or inducible promoter is used, the determination of a modulation in the ethylene response is determined in the appropriate tissue at the appropriate time and if necessary under the appropriate conditions to activate/inactivate an inducible promoter. In each case, the ethylene response is preferably compared to the same ethylene response from a wild-type plant.

The following are particularly preferred embodiments for modulating the ethylene response in fruit. However, such embodiments can be readily modified to modulate the ethylene response in vegetative tissue and flowers.

In one approach, a modified ETR nucleic acid operably linked to a constitutive promoter of moderate strength is used to reduce the ethylene response. This results in a lengthening of the time for fruit ripening.

In an alternate embodiment, a modified ETR nucleic acid operably linked to a regulatable (inducible) promoter is used so that the condition that turns on the expression of the modified ETR nucleic acid can be maintained to prevent fruit ripening. The condition that turns off the expression of the modified ETR nucleic acid can then be maintained to obtain ripening. For example, a heat-inducible promoter can be used which is active in high (field) temperatures, but not in low temperatures such as during refrigeration. A further example utilizes an auxin or gibberellin-induced promoter such that transformed plants can be treated with commercial auxin analogs such as 2, 4-D or with commercial gibberellin analogs such as Pro-Gibb to prevent early ripening.

Alternatively, a strong constitutive promoter can be operably linked to a modified ETR nucleic acid to prevent fruit ripening. So as to allow eventual fruit ripening, the plant is also transformed with a wild-type ETR nucleic acid operably linked to an inducible promoter. Expression of the wild-type ETR nucleic acid is increased by exposing the plant to the appropriate condition to which the inducible promoter responds. When the wild-type ETR nucleic acid expression is increased, the effect of expression of the modified ETR nucleic acid is reduced such that fruit ripening occurs.

Particular constructs which are desirable for use in transforming plants to confer ethylene insensitivity include the CaMV35S promoter operably linked to any other mutant Arabidopsis ETR genomic or cDNA clones including the corresponding modification at residue 36 to convert proline to leucine. Such constructs are expected to confer a dominant ethylene insensitivity phenotype tp cells and plants transformed with and expressing such constructs.

In addition, a preferred construct includes operably linking the FMV promoter to drive expression of the tomato TETR cDNA which has been engineered to contain a mutation analogous to any of those identified in the ETR genes from Arabidopsis as well as the Nr mutation found in the tomato ETR gene. Such constructs are expected to confer a dominant ethylene insensitivity phenotype to cells and plants which are transformed with and express such constructs.

Other preferred constructs include the operable linking the FMV promoter to ETR antisense cDNAs including TETR and ETR1. Such constructs are expected to confer a dominant ethylene insensitivity phenotype to cells and plants which are transformed with and express such constructs.

The invention can be practiced in a wide variety of plants to obtain useful phenotypes. For example, the invention can be used to delay or prevent floral senescence and abscission during growth or during transport or storage as occurs in flower beds or cotton crops (Hall, et al. (1957) *Physiol. Plant* 10:306–317) and in ornamental flowers (e.g., carnations, roses) that are either cut (Halevy, et al. (1981) *Hort. Rev.* 3:59–143) or not cut. In addition, the invention can be practiced to delay or prevent senescence and abscission of leaves and fruits in cucumber (Jackson, et al. (1972) *Can. J. Bot.* 50:1465–1471), legumes and other crops (Heck et al. (1962) *Texas Agric. Expt. Sta. Misc. Publ.* MP 613:1–13) and ornamental plants (e.g., holly wreaths) (Curtis et al. (1952) *Proc. Am. Soc. Hort. Sci.* 560:104–108). Other uses include the reduction or prevention of bitter-tasting phenolic compounds (isocoumarins) which are induced by ethylene for example in sweet potatoes (Kitinoja (1978) "Manipulation of Ethylene Responses in Horticulture", Reid, ed.,*Acta. Hort.* Vol 201, 377–42) carrots (Coxon et al. (1973) *Phyto. Chem. Istry.* 12:1881–1885), parsnip (Shattuck et al. (1988) *Hort. Sci.* 23:912) and Brassica. Other uses include the prevention of selective damage to reproductive tissues as occurs in oats and canola (Reid et al. (1985) in "Ethylene in Plant Development", Roberts, Tucker, eds. (London), Butterworths, pp. 277–286), the loss of flavor, firmness and/or texture as occurs in stored produce such as apples and watermelons (Risse et al. (1982) *Hort. Sci.* 17:946–948), russet spotting (a post-harvest disorder) which is ethylene induced in crisphead lettuce (Hyodo et al. (1978) *Plant Physiol.* 62:31–35), to promote male flower production (Jaiswal et al. (1985) *Proc. Indian Acad. Sci.* (Plantg Sci. 95:453–459) and to increase plant size, e.g., by delaying the formation of flowers in ornamental bromeliads (Mekers et al. (9183) *Acta Hortic* 137:217–223). Furthermore, a decrease in ethylene response can be used to delay disease developments such as the preventing of lesions and senescence in cucumbers infected with *Colletotrichum lagenarium* and to reduce diseases in plants in which ethylene causes an increase in disease development, e.g., in barley, citrus, Douglas fir seedlings, grapefruit, plum, rose, carnation, strawberry, tobacco, tomato, wheat, watermelon and ornamental plants. In addition, the invention can be used to reduce the effect of ethylene found in the environment and indirectly the effect of various environmental stresses which result in the biosynthesis of ethylene in plant tissue. For example, ethylene exists at biologically detrimental levels in localized atmospheres due to fires, automobile exhaust and industry. See, e.g., Chapter 8, Ethylene in the Environment in "Ethylene in Plant Biology", supra. In addition, the invention can be used to minimize the effect of ethylene synthesized in response to environmental stresses such as flooding, drought, oxygen deficiency, wounding (including pressure and bruising), chilling, pathogen invasion (by viruses, bacteria, fungi, insects, nematodes and the like), chemical exposure (e.g., ozone salt and heavy metal ions) and radiation.

The following is presented by way of example and is not to be construed as a limitation on the scope of the invention. Further, all references referred to herein are expressly incorporated by reference.

EXAMPLE 1

Cloning of the ETR1 Gene etr1-1 plants were crossed with two lines carrying the recessive visible markers ap1 and clv2 respectively. The $F_1$ progeny were allowed to self-pollinate. Phenotypes were scored in the $F_2$. The recombination percentages (using the Kosambi mapping function (D. D. Kosambi (1944) *Ann. Eugen.* 12:172)) were determined in centimorgans. The ETR1 locus mapped to the lower portion of chromosome 1 between the visible genetic markers ap1 and clv2 (6.5+/−1.0 cM from AP1 and 2.8+/−1.1 cM from CLV2).

etr1-1 was crossed to tester line W100 (ecotype Landsberg (Koornneef et al. (1987) *Arabidopsis Inf. Serv.* 23:46) and the $F_1$ plants were allowed to self-pollinate. Linkage of RFLP markers to the ETR1 locus was analyzed in 56 $F_2$ plants as described in Chang, et al. (1988) *Proc. Natl. Acad. Sci. U.S.A.* 85:6856. Of the RFLP markers that reside in this region of chromosome 1, one marker, 1bAt315, completely cosegregated with the etr1-1 mutant phenotype out of 112 chromosomes. The 1bAt315 clone was therefore used as a probe to initiate a chromosome walk in the ETR1 gene region. Various genomic DNA cosmid libraries were utilized. One library contained subclones of two yeast artificial chromosomes (YACs EG4E4 and EG2G11 (Grill et al.

Figure 8:
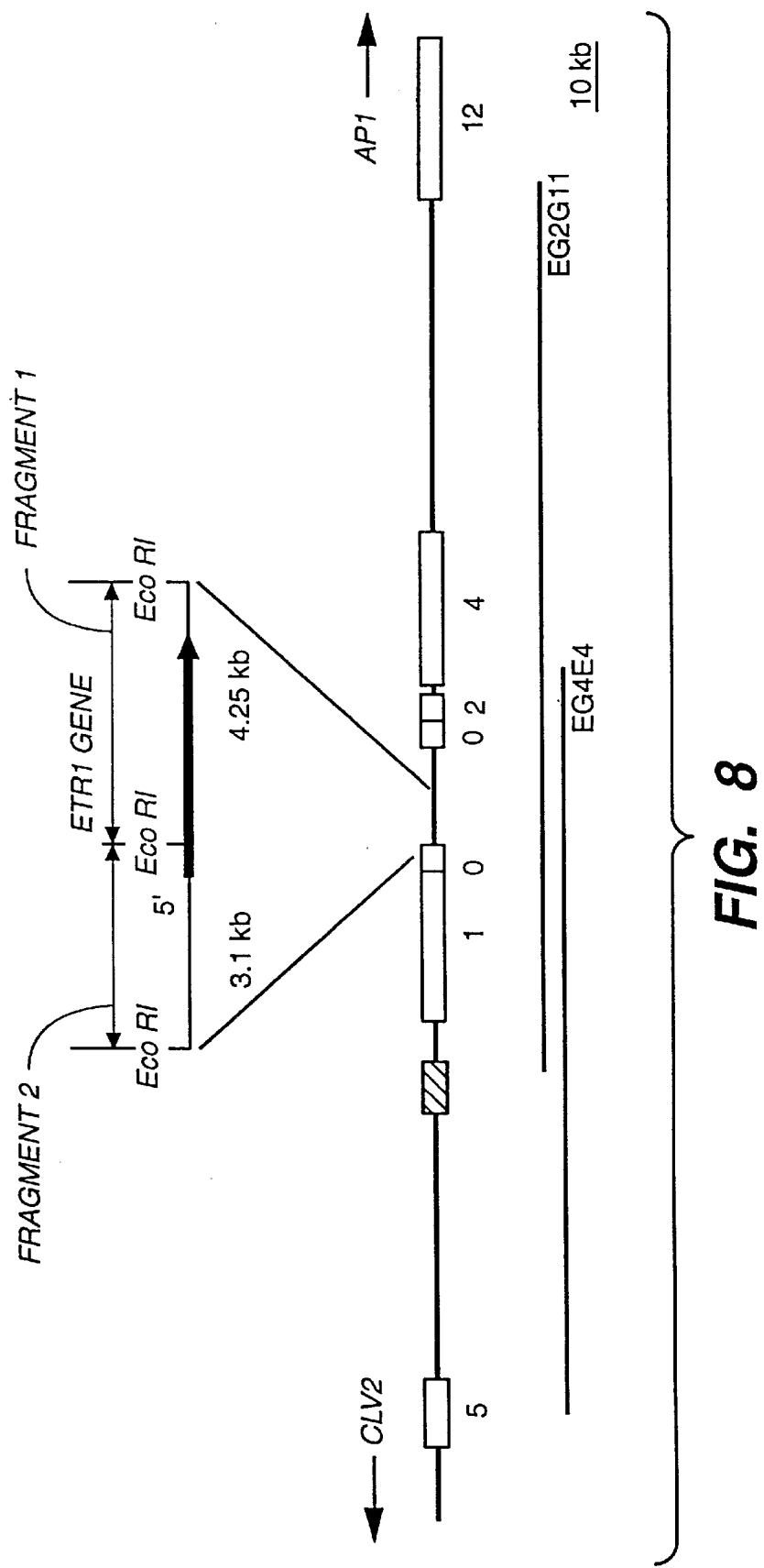
FIG. 8 depicts the structure of the cosmid insert used to localize the ETR1 gene from *Arabidopsis thaliana*. The starting position for the chromosome walk is indicated by a hatched bar. The open bars give the location and length of DNA segments used as probes to detect recombination break points. The maximum number of break points detected by each probe is shown. The numbers to the right of the ETR1 gene are out of 74 F2 recombinants between etr1-1 and ap-1, and those to the left of the ETR-1 gene are out of 25 F2 recombinants between etr1-1 and clv2. Overlapping YAC clones EG4E4 and EG2G11 are also shown.

(1991) *Mol. Gen. Genet.* 226:484)) that hybridized to 1bAt315. To subclone the YACs, total DNA from yeast cells harboring EG4E4 or EG2G11 was partially digested with Sau3AI, and cloned into the BglII site of cosmid vector pCIT30 (Ma et al. (1992) Gene 117:161). Standard cloning and screening methods were used (Sambrook et al, *Molecular Cloning: A Laboratory Manual* (Cold Spring Harbor Laboratory, Cold Spring Harbor, N.Y., 1989)). A library from the etr1-1 mutant was similarly constructed in pCIT30. The wild type library was constructed previously (Yanofsky et al. (1990) *Nature* 346:35). By restriction analysis and sequential hybridization to these libraries, overlapping cosmids (a contig) were obtained that spanned a distance of approximately 230 kb. See FIG. 8.

The ETR1 gene was localized to a subregion of approximately 47 kb using fine structure RFLP mapping.

To create the fine structure map, meiotic recombinants were isolated based on phenotype from the F2 self-progeny of the above crosses between the etr1-1 mutant (ecotype Columbia) and two lines (both ecotype Landsberg) carrying ap1 and clv2. Recombinants were identified in the F2 progeny as plants that were either wild type at both loci or mutant at both loci. ETR1 was scored in dark grown seedlings (Bleecker et al. (1988) *Science* 241:1086). Seventy-four (74) recombinants between ETR1 and AP1 were obtained, and 25 recombinants between ETR1 and CLV2. The recombination break points were mapped using DNA fragments from the chromosome walk as RFLP probes. Given the number of recombinants isolated, the calculated average distance between break points was roughly 20 kb for each cross. Over the 230 kb contig, the actual density of break points found was consistent with the calculated density on the CLV2 side (with 5 break points in approximately 120 kb). The nearest break points flanking the ETR1 gene defined a DNA segment of approximately 47 kb.

To search for transcripts derived from this 47 kb region, cDNA libraries were screened using DNA fragments. One cDNA clone was designated λC4 and was detected with the 4.25 kb EcoRI fragment 1 shown in FIG. 8. Because λC4 potentially represented the ETR1 gene, this clone was further characterized.

EXAMPLE 2

ETR Gene Characterization

The nucleotide sequences of the λC4 cDNA and the corresponding genomic DNA (FIG. 2) (SEQ ID NO:1) was determined using sequenase version 2.0 (United States Biochemical Co., Cleveland, Ohio) and synthetic oligonucleotide primers having a length of 17 nucleotides. The primer sequences were chosen from existing ETR1 sequences in order to extend the sequence until the entire sequence was determined. The initial sequence was obtained using primers that annealed to the cloning vector. Templates were double-stranded plasmids. Both strands of the genomic DNA were sequenced, including 225 bp upstream of the presumed transcriptional start site, and 90 bp downstream of the polyadenylation site. λC4 was sequenced on a single strand.

λC4 was 1812 base pairs long, including a polyA tail of 18 bases. From the DNA sequences and RNA blots (described below), it was determined that λC4 lacked approximately 1000 base pairs of the 5' end.

To obtain longer cDNAs, first strand cDNA was synthesized (RiboClone cDNA Synthesis System, Promega, Madison Wis.) from seedling polyA+RNA using sequence-specific primers internal to λC4. The cDNA was then amplified by PCR (Saiki, R. K. et al. (1985) *Science* 230:1350) using various pairs of primers: 3' PCR primers were chosen to anneal to different exons as deduced from the cDNA and genomic DNA sequences, and 5' PCR primers were chosen to anneal to various 5' portions of genomic DNA sequences. Six different primers at the 5' end were used. The farthest upstream primer which amplified the cDNA was primer Q (5'AGTAAGAACGAAGAAGAAGTG) (SEQ ID NO:26). An overlapping primer, which was shifted twelve bases downstream, also amplified the cDNA. The cDNA could not be amplified using a 5' end primer that was 98 base pairs farther upstream. Genomic DNA templates were used for PCR controls. The longest cDNA was considered to extend to the 5' end of primer Q. The amplified cDNAs were sequenced directly with Sequenase Version 2.0 as follows: after concentrating the PCR reactions by ethanol precipitation, the amplified products were separated by electrophoresis in 0.8% LMP agarose gels. The DNA fragments were excised, and a mixture of 10 μl excised gel (melted at 70° C.), 1 ml 10 mM primer and 1.2 ml 5% Nonidet P-40 was heated at 90° C. for two minutes to denature the DNA. The mixture was then cooled to 37° C. prior to proceeding with sequencing reactions.

The longest cDNA, which was 2786 bases (not including the polyA tail), was consistent with the estimated size of 2800 bases from RNA blots, and was presumed to be close to full length. A potential TATA box (5' ATAATAATAA) (SEQ ID NO:51) lies 33 bp upstream of the 5' end in the genomic sequence. Based on comparison of the cDNA and the genomic DNA sequences, the gene has six introns, one of which is in the 5' untranslated leader. The exons contain a single open reading frame of 738 amino acids. See FIG. 3.

The determination that this gene is, in fact, ETR1 was established by comparing the nucleotide sequences of the wild type allele and the four mutant alleles. For each mutant allele, an EcoRI size-selected library was constructed in the vector lambda ZAPII (Stratagene, LaJolla, Calif.). Clones of the 4.25 kb EcoRI fragment were isolated by hybridization with the wild type fragment. These clones were converted into plasmids (pBluescript vector) by in vivo excision according to the supplier (Stratagene) and sequenced. Two independent clones were sequenced on a single strand for each mutant allele. The 5' ends (535 bp not contained on the 4.25 kb EcoRI fragment) were amplified by PCR and directly sequenced as previously described. Codon differences were as follows: Codon 65 TGT to TAT in etr1-1 (FIGS. 6A, B, C and D), Codon 102 GCG to ACG in etr1-2 (FIGS. 7A, B, C and D), Codon 31 GCG to GTG in etr1-3 (FIGS. 4A, B, C and D), Codon 62 ATC to TTC in etr1-4 (FIGS. 5A, B, C and D). All four mutations are clustered in the amino-terminal region of the deduced protein sequence.

The ETR1 message was examined in standard RNA electrophoresis (formaldehyde) gel blots. The 2.8 kb ETR1 transcript was present in all plant parts examined—leaves, roots, stems, flowers and seedlings (data not shown). In addition, no differences were observed between ETR1 transcripts of the wild type and the mutant alleles (data not shown). Treatment with ethylene did not detectably alter the amount of ETR1 mRNA in dark-grown wild type seedlings (data not shown).

When the ETR1 gene was hybridized to Arabidopsis genomic DNA blots at normal stringency (i.e., overnight in 5×SSPE (0.9 M NaCl, 50 mM $NaH_2PO_4$, 40 mM NaOH, 4.5 mM EDTA, pH 7.4 at 65° C., with the most stringent wash in 0.1×SSPE at 65° C. for 30 minutes), only the expected fragments of the ETR1 locus were observed (data not shown). At reduced stringency (i.e., hybridization in 5×SSPE at 50° C. and washs in 5×SSPE at 50° C.), however, numerous fragments were detected, which suggests that a family of similar genes exists in Arabidopsis.

The predicted amino terminal sequence of ETR1 (residues 1–316) has no similarity to sequences in the GenBank database (version 77.0). The carboxy-terminal portion, however, is highly similar to the conserved domains of both the sensor and the response regulator of the prokaryotic two-component system of signal transduction. In bacteria, the histidine protein kinase domain of the sensor is characterized by five sequence motifs arranged in a specific order with loosely conserved spacing (Parkinson (1992) *Annu. Rev. Genet.* 26:71). The deduced ETR1 sequence contains all five motifs with the same relative order and spacing found in the bacterial proteins (FIG. 9A). The deduced sequence is most similar to the sequences of *Escherichia coli* Bar A (Nagasawa et al. (1992) *Mol. Microbiol.* 6:3011) and *Pseudomonas syringae* LemA (Harbak et al. (1992) *J. Bact.* 174:3011); over the entire histidine kinase domain (the 241 amino acids from residues 336 through 566), there are 43% and 41% amino acid identities with BarA and LemA respectively, and 72% and 71% similarities respectively. The function of BarA is unknown, although it was cloned based on its ability to complement a deletion in the *E. coli* osmotic sensor protein, EnvZ (Nagasawa, supra.). LemA is required for pathogenicity of *P. syringae* on bean plants (Hrabak, supra.). Other bacterial proteins with sequences highly similar to this putative ETR1 domain are: *Xanthomonas campestris* RpfC (35% identity) which is possibly involved in host recognition for pathogenicity in cruciferous plants (Tang et al (1991) *Mol. Gen. Genet.* 226:409), *E. coli* RcsC (34% identity) which is involved in regulation of capsule synthesis (Stout et al. (1990) *J. Bacteriol.* 172:659) and *E. coli* ArcB (25% identity) which is responsible for repression of anaerobic enzymes (Luchi et al. (1990) *Mol. Microbiol.* 4:715).

Adjacent to the putative histidine kinase domain, the deduced ETR1 sequence exhibits structural characteristics and conserved residues of bacterial response regulators. Structural characteristics of response regulators are based on the known three-dimensional structure of CheY (the response regulator for chemotaxis) in *Salmonella typhimurium* and *E. coli*, which consists of five parallel β-strands surrounded by five a-helices (Stock et al. (1989) *Nature* 337:745; Volz et al. (1991) *J. Biol. Chem.* 266:15511). Sequences of bacterial response regulators have been aligned to this structure based on residues that are compatible with the hydrophobic core of the CheY (Stock et al. (1989) *Microbiological Rev.* 53:450). The deduced ETR1 sequence can be similarly aligned (data not shown). At four specific positions, response regulators contain highly conserved residues—three aspartates and a lysine (Parkinson et al. (1992) *Annu. Rev. Genet.* 26:71; Stock et al., supra.); the three aspartates form an acidic pocket into which protrudes the side chain of the conserved lysine (Stock et al. (1989) *Nature* 337:745; Volz et al. (1991) *J. Biol. Chem.* 266:15511) and the third aspartate is the receiver of the phosphate from phosphohistidine (Stock et al. (1989), supra.). Except for the conservative substitution of glutamate for the second aspartate, these conserved amino acids are found in the same positions in the deduced ETR1 sequence (FIG. 9B). The deduced sequence in this domain (a stretch of 121 amino acids from residues 609 through 729 in ETR1) is most similar to the sequences of *Bordetella parapertussis* BvgS (29% identity, 60% similarity) which controls virulence-associated genes for pathogenicity in humans (Aricò et al. (1991) *Mol. Microbiol.* 5:2481), *E. coli* RcsC (29% identity, 64% similarity), *P. syringae* LemA (26% identity, 57% similarity), *X. campestris* RpfC (25% identity) and *E. coli* BarA (20% identity). All of the bacterial proteins that are similar to ETR1 in sequence are also structurally similar to ETR1 in that they contain both the histidine kinase domain and the response regulator domain. Although these features are shared, the sensing functions are clearly diverged.

A potential membrane spanning domain (residues 295–313) exists in the deduced ETR1 sequence based on hydropathy analysis (Kyte et al. (1982) *J. Mol. Biol.* 157:105), but it is unclear whether ETR1 is actually a transmembrane protein since there is no clear signal sequence. There are also no N-linked glycosylation sites. While all of the bacterial proteins to which the deduced ETR1 sequence is similar have two potential membrane spanning domains flanking the amino terminal domain, a few bacterial sensors (those which lack the response regulator) do not.

EXAMPLE 3

An etr1 Mutant Gene Confers Ethylene Insensitivity to Wild Type Plants

Dominant ethylene insensitivity was conferred to wild type Arabidopsis plants when the etr1-1 mutant gene was stably introduced using Agrobacterium-mediated transformation. The gene was carried on a 7.3 kb genomic DNA fragment (fragments 1 and 2 in FIG. 8 which included approximately 2.7 kb upstream of the transcription initiation site, and approximately 1 kb downstream of the polyadenylation site). It was cloned into binary transformation vector pCGN1547 obtained from Calgene, Inc., Davis, Calif. The vector also carried a selectable marker for kanamycin resistance in plants.

For the etr1-1 construct, the 4.25 kb EcoRI plasmid clone containing the etr1-1 mutation was linearized by partial EcoRI digestion and ligated with the 3.1 kb EcoRI fragment which was agarose gel-purified from cosmid clone theta8 (a subclone of YAC EG4E4 in the walk). The resulting plasmid, containing the two EcoRI fragments in the correct relative orientation, was linearized at polylinker site Asp718, the ends were filled in using Klenow enzyme, and BamHI linkers were ligated to the blunt ends. Finally, the 7.3 kb insert was removed from the plasmid at the polylinker site BamHI, and ligated into the BamHI site of binary transformation vector pCGN1547 (McBride, K. E. et al. (1990) *Plant Molecular Biology* 14:269). For the control construct, the wild type 7.3 kb fragment was agarose gel-purified from EcoRI partially digested cosmid theta8, and subcloned into the EcoRI site of pBluescript. The fragment was then removed using the BamHI and KpnI sites of the polylinker, and ligated into pCGN1547 that had been digested with BamHI and KpnI. The mutant and wild type constructs were transformed into Agrobacterium (Holsters et al. (1978) *Mol. Gen. Genet.* 163:181) strain ASE (Monsanto) (Rogers et al. (1988) *Meth. Enzymol.* 153:253). Arabidopsis ecotype Nossen was transformed (Valvekens, D. et al. (1988) *Natl. Proc. Acad. Sci. U.S.A.* 85:5536) using root-tissue cultured in liquid rather than on solid medium. Triploid plants having one mutant copy of the ETR1 gene were obtained as the progeny of crosses between the etr1-1 homozygote (diploid) and a tetraploid wild type in ecotype Bensheim which has the same triple response phenotype as ecotype Columbia. Triploid wild type plants were similarly obtained by crossing the diploid wild type to the tetraploid. Ethylene sensitivity was assayed in dark-grown seedlings treated with either ethylene (Bleecker et al., supra.) or 0.5 mM ACC. For ACC treatment, plants were germinated and grown on Murashige and Skoog basal salt mixture (MS, Sigma), pH 5.7, 0.5 mM ACC (Sigma), 1% Bacto-agar (Difco). Kanamycin resistance was measured by the extent of root elongation in one week old seedlings grown on MS pH 5.7 µg/ml Kanamycin, 1% Bacto-agar.

Ten kanamycin resistant plants were produced. Eight of the ten exhibited ethylene insensitive self-progeny as evaluated by the dark-grown seedling response to ethylene. In each line, ethylene insensitivity cosegregated with kanamycin resistance. As a control, transformations were performed using the corresponding 7.3 kb genomic DNA fragment of the wild type from which six kanamycin resistant plants were obtained. These lines gave rise to only ethylene sensitive self-progeny which did not appear to be different from the wild type.

The etr1-1 transformants displayed different levels of ethylene insensitivity. Thus, the wild type gene is capable of attenuating the mutant phenotype and the etr1-1 mutation is not fully dominant in the transformed plants. Of the ten kanamycin resistant lines, six gave completely dominant ethylene insensitivity, indicating the presence of multiple copies of the mutant gene. Two other lines displayed partial dominance, and two lines appeared to be wild type. Reduced ethylene insensitivity was presumably due to low expression levels which can be caused by position effects (e.g., DNA methylation) or possibly by truncation of the transferred DNA.

EXAMPLE 4

Vector Constructs Containing Heterologous Promoter

This example describes the construction of a plant transformation vector containing a heterologous promoter to control expression of wild type and mutant ETR1 nucleic acids.

The cauliflower mosaic virus 35S protein promoter (Guilley et al. (1982) Cell 30:763–773; Odell, et al. (1985) Nature 313:810–812 and Sanders et al. (1987) Nucl. Acids Res. 15:1543–1558) and the 3' end of the Nopaline synthase (NOS) gene were cloned into the pCGN1547 vector to create pCGN18. The 35S promoter, on a HindIII-BamHI fragment of approximately 1.6 kb, was cloned into the unique HindIII-BamHI site of pCGN1547. The 1 kb BamHI-KpnI NOS fragment was cloned into the unique BamHI-KpnI site of pCGN1547.

The 4.25 kb EcoRI fragment of both the wild type and mutant ETR1-1 allele were independently cloned into the unique BamHI site of the above pCGN18 vector using BamHI linkers. This 4.25 kb EcoRI genomic fragment contains the entire coding sequence including five introns and approximately 1 kb genomic DNA downstream of the polyadenylation site. It does not contain the ETR1 promoter which is on the 3.1 EcoRI fragment 2 in FIG. 5.

These vectors were used to transform root explants as described in Example 3. Kanamycin resistant plants containing the mutant ETR1-1 gene were obtained and demonstrated an ethylene insensitivity phenotype similar to that found in Example 3. Control plants transformed with the wild type ETR1 gene produced only ethylene sensitive self-progeny.

EXAMPLE 5

Vector Construct Utilizing Antisense ETR1

Ethylene insensitivity was- conferred to wild-type Arabidopsis by expression of an ETR1 antisense nucleic acid which was introduced using standard Agrobacterium root transformation procedure. Valvekens et al. (1988) Proc. Natl. Acad. Sci. U.S.A. 85:5536. The antisense nucleic acid consisted of a 1.9 kb ETR1 cDNA fragment. Expression of this fragment, which extended from the MscI restriction site at nucleotide 220 to the first SmaI site at nucleotide 2176 in FIGS. 3A, 3B, 3C and 3D was driven in the reverse orientation by the CaMV 35S promoter. To construct the antisense nucleic acid, BamHI linkers were ligated to the ends of the 1.9 kb MscI-SmaI DNA fragment and the thus formed fragment was ligated into the BamHI site of pCGN 18 transformation vector. Jack et al. (1994) Cell 76:703. The construct was transformed into Agrobacterium strain ASE as described above and then into Arabidopsis.

Seedlings derived from this transformation experiment were tested for sensitivity to ethylene as previously described. Seedlings containing the antisense construct were ethylene insensitive.

EXAMPLE 6

Identification of QITR, a Second ETR Nucleic Acid in Arabidopsis

Genomic DNA from Arabidopsis thaliana was partially digested with Sau3A and cloned into a λGEM11 (half-site arms) obtained from Promega, Madison, Wis. The genomic digest was partial end filled prior to cloning with λGEM11 and plated on media as suggested by the manufacturer.

The thus cloned library was screened with a $^{32}$P-labeled cDNA XbaI fragment extending from nucleotides 993–2308 as set forth in FIGS. 3B, 3C and 3D. Hybridization conditions were 50° C. and 5×SSPE. Washes were made at 50° C. 0.2×SSPE. Several positively hybridizing clones were identified, replated and rescreened. Positively hybridizing clones were digested with SacI (which cleaves within the arms of the cloning phage and within the insert). The multiple fragments obtained therefrom were subcloned into bacterial plasmids for sequencing. The genomic DNA sequence (SEQ ID NO.:45) together with the deduced amino acid sequence (SEQ ID NO.:46 and 48) is set forth in FIG. 12. This ETR nucleic acid and amino acid sequence is referred to as the QITR nucleic or amino acid sequence respectively. The QITR cDNA sequence (SEQ ID NO.:47) and the QITR amino acid sequence (SEQ ID NOs:46 and 48) are shown in FIG. 13.

By comparison to the ETR1 Arabidopsis nucleic acid and amino acid sequence (see FIGS. 2 and 3), the QITR protein appears to contain an amino terminal portion having a relatively high level of homology to the amino terminal portion of the ETR1 protein and a histidine kinase portion with a moderate level of homology to the same sequence in ETR1. The response regulatory region found in ETR1 is not present in the QITR protein. The overall nucleic acid homology is approximately 69%. With regard to the amino terminal portion (i.e., between residues 1 through 316) the homology is approximately 71% identical in terms of amino acid sequence and 72% identical in terms of nucleic acid sequence.

EXAMPLE 7

Modification of QITR Nucleic Acid to Confer Ethylene Insensitivity

An amino acid substitution was made in a 5 kb QITR genomic clone which was analogous to that for the ETR1-4 mutation, namely the substitution of the isoleucine at position 62 with phenylalanine. Compare FIG. 3A with FIG. 5A at residue 62. As further indicated at FIGS. 12 and 13, residue 62 in the QITR protein is also isoleucine as in the ETR1 protein.

The amino acid substitution was made to the QITR nucleic acid using oligonucleotide-directed in vitro mutagenesis. Kunkel et al. (1987) *Methods in Enzymology* 154:367–382. A Muta-gene kit from Bio-Rad Laboratories, Hercules, Calif., was used in connection with this particular mutation. The sequence of the oligonucleotide used was 5' GGA GCC TTT TTC ATT CTC (SEQ ID NO:52). Replacement of nucleotide A with T in the codon ATC changed the amino acid Ile at residue 62 to Phe in the deduced protein sequence.

The QITR nucleic acid spanning approximately 5 kb from the first HindIII site to the second KpnI site contained approximately 2.4 kb of nucleotides upstream from the start codon. This 5 kb fragment was ligated into the pCGN1547 transformation vector (supra.). This construct was then transformed into Agrobacterium strain ASE as described supra and then into Arabidopsis.

Seedlings derived from this transformation experiment were tested for sensitivity to ethylene as previously described. Seedlings containing the QITR nucleic acid containing the modification at residue 62 were ethylene insensitive.

EXAMPLE 8

Identification of Arabidopsis ETR Nucleic Acid Q8

The ETR nucleic acid Q8 (SEQ ID NOs:41 and 43) was identified by direct sequence comparison with the ETR1 nucleic acid from Arabidopsis. The Arabidopsis Q8 nucleic acid was identified in connection with a chromosome walk on chromosome 3 of *Arabidopsis thaliana*.

Briefly, overlapping YAC clones were generated which were thereafter subcloned into plasmids. The genomic inserts in such plasmids were extricated by digesting with restriction endonuclease and hybridized to a cDNA library from Arabidopsis floral tissue.

Positively hybridizing inserts were sequenced to produce the overall genomic sequence (SEQ ID NO.:41) together with the deduced amino acid sequence (SEQ ID NOs:42 and 44) as set forth in FIG. 14. The cDNA sequence (SEQ ID NO:43) and deduced amino acid sequence (SEQ ID NOs:42 and 44) is set forth in FIG. 15.

The overall nucleic acid homology as between the Q8 nucleic acid and the ETR1 nucleic acid is approximately 69%. With regard to the amino terminal portion extending from residues 1 through 316, the overall amino sequence homology is approximately 72% whereas the nucleic acid encoding this sequence is approximately has a sequence homology of approximately 71% as between the Q8 and ETR1 nucleic acids.

EXAMPLE 9

Isolation of the TETR cDNA

A $^{32}$P-labeled hybridization probe was prepared by random-primer labeling of a 1.3 kb PCR fragment generated by PCR amplification of the Arabidopsis ETR1 gene with the PCR primers "5'BamHI" (CCCGGATCCATAGTGTAAAAAATTCATAATGG) (SEQ ID NO:54) and "3'BamHIB" (CCGGATCCGTTGAAGACTTCCATCTTCTAACC) (SEQ ID NO:54).

This probe was used to screen a cDNA library of red tomato fruit mRNA cloned in the EcoRI site of lambda ZAP II vector from Stratagene, LaJolla, Calif. Twenty (20) positive primary plaques were identified that hybridized to this probe (2×SSC at 65° C. wash conditions) and secondary screens were performed on these to obtain pure plaques. In vivo excision was then performed with resultant recombinant phage and 19 independent plasmid clones were obtained.

Complementary DNAs, from plasmid clones containing the largest fragments that hybridized to the ETR1 probe, were sequenced and the nucleotide sequence and predicted amino acid sequences of the longest tomato cDNA (TETR14, also referred to as TXTR) were compared to the ETR1 and QITR sequences. The nucleotide sequence of TETR14 predicted that the encoded peptide was more similar to the QITR peptide than the ETR1 peptide. This conclusion was based on the fact that the response regulatory domain (which is present in ETR1) is absent in both TETR14 and QITR. The sequence (or partial sequence) of several of the other cDNA clones was determined and they were found to correspond to the same gene.

EXAMPLE 10

Analysis of TETR14 Gene Expression

Northern analysis was performed with mRNA from developing fruits of normal, or mutant tomato (Ripening inhibitor (rin), Non-ripening (nor) or Never-ripe (Nr)) fruit. Stages of developing fruits used were mature green, breaker, breaker plus 7 days, and mature green fruit treated with ethylene. Messenger RNA that hybridized to the TETR14 gene probe was not present at the mature green stage, but was present in breaker, breaker plus 7 days, and ethylene treated mature green fruit. Thus, it was concluded that accumulation of the ETR14 mRNA was regulated by ethylene. Accumulation of the TETR14 mRNA was attenuated in all three ripening mutants, further supporting the finding that mRNA accumulation is ethylene regulated.

EXAMPLE 11

Analysis of the TETR14 Gene from Pearson and Never-ripe DNA

PCR primers were obtained that would specifically amplify the N-terminal region of the TETR14 gene. The amplified portion was between Met1 and Ile214 in FIGS. 16A and 16B. The primers were (CCGGATCCATGGAATCCTGTGATTGCATTG) (SEQ ID NO:55)

and TETR4A (GATAATAGGAAGATTAATTGGC) (SEQ ID NO:56). PCR conditions (Perkin-Elmer Cetus): 1 µg of tomato genomic DNA, 40 picomole of each primer, 1 min 94° C., 2 min 45° C., 2 min 72° C., 35 cycles. PCR products, obtained with these primers, resulting from two independent amplification reactions of pearson and Nr DNA were agarose gel purified and subcloned into either the T/A vector (Invitrogen) or digested with BamHI and XhoI and subcloned into Bluescript KS–that had been linearized with BamHI and SalI. Single stranded template DNA was prepared from the resultant plasmids and sequenced. The sequence of the PCR products from the pearson DNA were identical to the sequence of the TETR14 clone. Sequence analysis revealed that the PCR fragments resulting from PCR of the Nr DNA (TETR14-Nr) were not identical to those obtained from the Pearson DNA. The cytosine nucleotide at position 395 of the TETR14 gene is a thymine in the gene amplified from the Nr DNA. This nucleotide substitution in TETR14-Nr changes the proline at amino acid position 36 of the predicted peptide to a leucine. See FIG. 22 and Seq. ID Nos. 49 and 50 for the overall nucleic acid and amino acid sequence respectively. This Pro-36 of the TETR14 corresponds to the Pro-36 of the ETR1 peptide and to the Pro-36 of the QITR peptide. This results indicates that a mutation in the tomato TETR14 gene confers dominant ethylene-insensitivity. And thus, it is possible to predict that other changes in the TETR14 gene and other tomato ETR1 homologues will result in ethylene insensitivity in tomato.

Having described the preferred embodiments of the invention, it will appear to those of ordinary skill in the art that various modifications may be made to the disclosed embodiments, and that such modifications are intended to be within the scope of the invention.

All references are expressly incorporated herein by reference.

What is claimed is:

1. An isolated nucleic acid comprising a plant ETR nucleic acid encoding an ETR protein, said ETR protein having at least 50% overall similarity to the ETR protein sequence of *Arabidopsis thaliana* as set forth in SEQ ID NO:3, and at least 55% similarity to the N-terminal 316 amino acids of said ETR protein sequence of *Arabidopsis thaliana*, wherein the expression of said ETR protein encoded by said ETR nucleic acid in a plant cell results in an increased or decreased response to ethylene by said cell.

2. The isolated nucleic acid of claim 1 wherein said ETR protein has at least 70% similarity to the N-terminal 316 amino acids of said ETR protein sequence of *Arabidopsis thaliana*.

3. The isolated nucleic acid of claim 2 wherein said ETR protein has at least 85% similarity to the N-terminal 316 amino acids of said ETR protein sequence of *Arabidopsis thaliana*.

4. An isolated nucleic acid comprising a plant ETR nucleic acid encoding an ETR protein, said ETR protein having at least 50% overall similarity to the ETR protein sequence of *Arabidopsis thaliana* as set forth in SEQ ID NO:3, and at least 55% similarity to the N-terminal 316 amino acids of said ETR protein sequence of *Arabidopsis thaliana*, wherein the expression of said ETR protein encoded by said ETR nucleic acid in a plant cell results in an increased response to ethylene by said cell.

5. An isolated modified plant ETR nucleic acid comprising a precursor ETR nucleic acid which has been modified to encode a modified ETR protein comprising the substitution, insertion or deletion of an amino acid residue in the N-terminal 316 amino acids of the ETR protein encoded by said precursor ETR nucleic acid, wherein said modified ETR protein has at least 50% overall similarity to the ETR protein sequence of *Arabidopsis thaliana* as set forth in SEQ ID NO:3, and at least 55% similarity to the N-terminal 316 amino acids of said ETR protein sequence of *Arabidopsis thaliana*, wherein the expression of said modified ETR protein encoded by said isolated modified plant ETR nucleic acid in a plant cell results in an increased or decreased response to ethylene by said cell.

6. The isolated modified plant ETR nucleic acid according to claim 5 wherein said modified ETR protein comprises the substitution of a selected amino acid residue in said precursor ETR protein with a different amino acid and wherein said selected amino acid residue in said precursor ETR protein is equivalent to an amino acid residue selected from the group consisting of Ala-31, Pro-36, Ile-62, Cys-65 and Ala-102 in the ETR protein sequence of *Arabidopsis thaliana*.

7. The isolated modified plant ETR nucleic acid of claim 5 wherein said ETR protein has at least 70% similarity to the N-terminal 316 amino acids of said ETR protein sequence of *Arabidopsis thaliana*.

8. The isolated modified plant ETR nucleic acid of claim 5 wherein said ETR protein has at least 85% similarity to the N-terminal 316 amino acids of said ETR protein sequence of *Arabidopsis thaliana*.

9. An isolated modified plant ETR nucleic acid comprising a precursor ETR nucleic acid which has been modified to encode a modified ETR protein comprising the substitution or deletion of an amino acid residue in the N-terminal 316 amino acids of the ETR protein encoded by said precursor ETR nucleic acid, wherein said modified ETR protein has at least 50% overall similarity to the ETR protein sequence of *Arabidopsis thaliana* as set forth in SEQ ID NO:3, and at least 55% similarity to the N-terminal 316 amino acids of said ETR protein sequence of *Arabidopsis thaliana*, wherein the expression of said modified ETR protein encoded by said isolated modified plant ETR nucleic acid in a plant cell results in a decreased response to ethylene by said cell.

10. The isolated modified plant ETR nucleic acid of claim 9 wherein the modified ETR protein has a single amino acid substitution in the N-terminal 316 amino acids.

11. The isolated modified plant ETR nucleic acid of claim 9 wherein the modified ETR protein has a single amino acid deletion in the N-terminal 316 amino acids.

12. A recombinant nucleic acid comprising a promoter operably linked to the modified plant ETR nucleic acid of claim 5.

13. The recombinant nucleic acid according to claim 12 wherein said promoter is heterologous to said modified plant ETR nucleic acid and causes expression of said modified plant ETR nucleic acid in a plant cell.

14. The recombinant nucleic acid according to claim 13 wherein said promoter is a tissue-specific promoter or temporal-specific promoter.

15. The recombinant nucleic acid according to claim 13 wherein said promoter is inducible.

16. A recombinant nucleic acid comprising a promoter operably linked to an ETR nucleic acid, wherein said ETR nucleic acid hybridizes with a probe having the sequence represented in SEQ ID NO:2 at hybridization conditions of 50° C. in 5×SSPE and washing conditions of 50° C. in 0.2×SSPE, wherein the expression of an ETR protein encoded by said ETR nucleic acid in a plant cell results in an increased or decreased response to ethylene by said cell.

17. A method of producing a plant comprising transformed plant cells having a detectable increased or decreased response to ethylene as compared to untransformed cells of a corresponding wild-type plant, said method comprising the steps of:
   a) transforming at least one plant cell with a modified ETR nucleic acid comprising a precursor ETR nucleic acid which has been modified to encode a modified ETR protein comprising the substitution, insertion or deletion of an amino acid residue in the N-terminal 316 amino acids of the ETR protein encoded by said precursor ETR nucleic acid, wherein said modified ETR protein has at least about 50% overall similarity to the ETR protein sequence of *Arabidopsis thaliana* as set forth in SEQ ID NO:3, and at least about 55% similarity to the N-terminal 316 amino acids of said ETR protein sequence of *Arabidopsis thaliana*;
   b) regenerating plants from one or more of the thus transformed plant cells; and
   c) selecting a plant comprising said transformed plant cells having a detectable increased or decreased response to ethylene.

18. The method according to claim 17 wherein said modified ETR nucleic acid is operably linked to a tissue-specific promoter.

19. A method of producing a plant comprising transformed plant cells having a detectable decrease in response to ethylene as compared to untransformed cells of a corresponding wild-type plant, said method comprising the steps of:
   a) transforming at least one plant cell with a modified ETR nucleic acid comprising a precursor ETR nucleic acid which has been modified to encode a modified ETR protein comprising a substitution, insertion or deletion of an amino acid residue in the N-terminal 316 amino acids of the ETR protein encoded by said precursor ETR nucleic acid, wherein said modified ETR protein has at least about 50% overall similarity to the ETR protein sequence of *Arabidopsis thaliana* as set forth in SEQ ID NO:3, and at least about 55% similarity to the N-terminal 316 amino acids of said ETR protein sequence of *Arabidopsis thaliana*;
   b) regenerating plants from one or more of the thus transformed plant cells; and
   c) selecting a plant comprising said transformed plant cells having a detectable decrease in response to ethylene.

20. The method of claim 19 wherein the modified ETR protein has a single amino acid substitution in the N-terminal 316 amino acids.

21. The method of claim 19 wherein the modified ETR protein has a single amino acid deletion in the N-terminal 316 amino acids.

22. A plant cell transformed with the recombinant nucleic acid of claim 13.

23. A plant comprising the plant cell of claim 22.

24. A plant comprising plant cells transformed with the isolated modified plant ETR nucleic acid of claim 5 wherein said plant cells have an increased or decreased response to ethylene as compared to untransformed cells of a corresponding wild-type plant.

25. The plant according to claim 23 wherein said modified ETR protein comprises the substitution of a selected amino acid residue with a different amino acid, wherein said selected amino acid residue is equivalent to an amino acid residue selected from the group consisting of Ala-31, Pro-36, Ile-62, Cys-65 and Ala-102 in the ETR protein sequence of *Arabidopsis thaliana*.

26. The plant according to claim 24 wherein a tissue-specific promoter is operably linked to said modified ETR nucleic acid.

27. The plant according to claim 26 wherein said plant is fruit-bearing and said tissue specific promoter is a fruit-specific promoter.

28. The plant according to claim 27 wherein said plant has a decrease in the rate of fruit ripening.

29. Fruit from the plant according to claim 28.

30. The fruit according to claim 29 wherein said fruit is tomato.

31. A plant produced by the method of claim 17.

32. A plant comprising plant cells transformed with the isolated modified plant ETR nucleic acid of claim 9, said plant cells having a detectable decrease in response to ethylene as compared too untransformed cells of a corresponding wild-type plant.

* * * * *